(12) United States Patent
Kim et al.

(10) Patent No.: US 10,008,675 B2
(45) Date of Patent: Jun. 26, 2018

(54) ORGANIC COMPOUND AND ORGANIC ELECTROLUMINESCENT ELEMENT COMPRISING SAME

(71) Applicant: DOOSAN CORPORATION, Seoul (KR)

(72) Inventors: Young Bae Kim, Hwaseong-si (KR); Hyunjong Jo, Seoul (KR); Chang Jun Lee, Ansan-si (KR); Jinyong Shin, Yongin-si (KR); Hoe Moon Kim, Suwon-si (KR); Youngmi Beak, Yongin-si (KR); Tae Hyung Kim, Seongnam-si (KR)

(73) Assignee: DOOSAN CORPORATION, Seoul (KR)

( * ) Notice: Subject to any disclaimer, the term of this patent is extended or adjusted under 35 U.S.C. 154(b) by 42 days.

(21) Appl. No.: 15/039,315

(22) PCT Filed: Dec. 16, 2014

(86) PCT No.: PCT/KR2014/012386
§ 371 (c)(1),
(2) Date: May 25, 2016

(87) PCT Pub. No.: WO2015/093812
PCT Pub. Date: Jun. 25, 2015

(65) Prior Publication Data
US 2016/0351825 A1 Dec. 1, 2016

(30) Foreign Application Priority Data
Dec. 17, 2013 (KR) .................... 10-2013-0157627

(51) Int. Cl.
| | | |
|---|---|---|
| H01L 51/00 | (2006.01) |
| C07D 487/04 | (2006.01) |
| C09K 11/06 | (2006.01) |
| C07D 491/044 | (2006.01) |
| C07D 495/04 | (2006.01) |
| C07D 471/14 | (2006.01) |
| C07D 495/14 | (2006.01) |
| C09K 11/02 | (2006.01) |
| H01L 51/50 | (2006.01) |

(52) U.S. Cl.
CPC ........ *H01L 51/0072* (2013.01); *C07D 471/14* (2013.01); *C07D 487/04* (2013.01); *C07D 491/044* (2013.01); *C07D 495/04* (2013.01); *C07D 495/14* (2013.01); *C09K 11/025* (2013.01); *C09K 11/06* (2013.01); *H01L 51/0054* (2013.01); *H01L 51/0057* (2013.01); *H01L 51/0067* (2013.01); *H01L 51/0071* (2013.01); *H01L 51/0073* (2013.01); *H01L 51/0074* (2013.01); *H01L 51/0052* (2013.01); *H01L 51/5012* (2013.01); *H01L 51/5072* (2013.01)

(58) Field of Classification Search
CPC ............. H01L 51/0072; H01L 51/0074; H01L 51/0054; H01L 51/0067; H01L 51/0071; H01L 51/0073; H01L 51/0057; H01L 51/005; C07D 471/14; C07D 495/14; C07D 495/04; C07D 491/044; C07D 487/04; C09K 11/025; C09K 11/06
See application file for complete search history.

(56) References Cited

FOREIGN PATENT DOCUMENTS

KR 2014-0119642 A 10/2014

OTHER PUBLICATIONS

R. Rodrigo, et al., "Cancentrine. IV. Acetolysis Products of Cancertrine Methiodide", Canadian Journal of Chemistry, Aug. 2, 1972, p. 3900-3910, vol. 50.
A. Nováček, et al., "Reaction of 8-Chloro-10-Phenylhydrazono-10,11-Dihydro-Dibenzo[b, f]Thiepine With Aromatic Aldehydes", Collection Czechoslov. Chem. Commun, 1976, pp. 785-787, vol. 41.
Luca Vaghi, et al., "A Structurally Diverse Heterocyclic Library by Decoration of Oxcarbazepine Scaffold", Molecules, 2013, pp. 13705-13722, vol. 18.
International Searching Authority, International Search Report for PCT/KR2014/012386 dated Mar. 27, 2015 [PCT/ISA/210].
International Searching Authority, Written Opinion for PCT/KR2014/012386 dated Mar. 27, 2015 [PCT/ISA/237].

*Primary Examiner* — Alexander Kollias
(74) *Attorney, Agent, or Firm* — Sughrue Mion, PLLC

(57) ABSTRACT

The present disclosure relates to a novel compound and an organic electroluminescent element including the same, and the compound according to the present disclosure is used for an organic material layer of the organic electroluminescent element, thereby improving the light emitting efficiency, driving voltage, lifetime, and the like of the organic electroluminescent element.

15 Claims, No Drawings

ORGANIC COMPOUND AND ORGANIC ELECTROLUMINESCENT ELEMENT COMPRISING SAME

CROSS REFERENCE TO RELATED APPLICATIONS

This application is a National Stage of International Application No. PCT/KR2014/012386 filed Dec. 16, 2014, claiming priority based on Korean Patent Application No. 10-2013-0157627 filed Dec. 17, 2013, the contents of all of which are incorporated herein by reference in their entirety.

TECHNICAL FIELD

The present disclosure relates to a novel organic compound and an organic electroluminescent element comprising the same, and more particularly, to a novel compound which is excellent in carrier transporting capability, light emitting capability, and the like, and an organic electroluminescent element including the compound as a material for an organic material layer, thereby improving characteristics, such as light emitting efficiency, driving voltage, lifetime, and the like.

BACKGROUND ART

Studies on an organic electroluminescent (EL) element (hereinafter, simply referred to as 'organic EL element') have continued from the start point of observing an organic thin film light emission by Bernanose in the 1950s to blue electric light emission using an anthracene single crystal in 1965, and then an organic EL element having a laminated structure which is divided into functional layers of a hole layer and a light emitting layer was proposed by Tang in 1987. Since then, the organic EL element has been developed in a form in which a specific organic material layer is introduced into the element and a specialized material used therefor has been developed in order to improve the efficiency and lifetime of an organic EL element.

In the organic EL element, when voltage is applied between two electrodes, holes are injected into the organic material layer at the anode, and electrons are injected into the organic material layer at the cathode. When the injected holes and electrons meet each other, an exciton is formed, and then the exciton falls down to a bottom state to emit light. Materials used as the organic material layer may be classified into a light emitting material, a hole injection material, a hole transporting material, an electron transporting material, an electron injection material, and the like according to the function.

Light emitting materials may be divided into blue, green, and red light emitting materials according to the light emitting color. In addition, the light emitting materials may be classified into yellow and orange light emitting materials which are necessary for implementing a more natural color. Furthermore, a host/dopant system may be used as a light emitting material for the purpose of enhancing color purity and light emitting efficiency through energy transfer.

Dopant materials may be divided into a fluorescent dopant using an organic material and a phosphorescent dopant using a metal complex compound including heavy atoms such as Ir and Pt. Since the development of the phosphorescent material may theoretically improve light emitting efficiency up to 4 times compared to the fluorescent material, interests in not only phosphorescent dopants, but also phosphorescent host materials have been focused.

As materials used as a hole injection layer, a hole transporting layer, a hole blocking layer, and an electron transporting layer, NPB, BCP, $Alq_3$ and the like represented by the following Formulae have been widely known until now, and for a light emitting material, anthracene derivatives have been reported as a fluorescent dopant/host material. In particular, for the phosphorescent material having a great advantage in terms of improving the efficiency among the light emitting materials, there are metal complex compounds including Ir, such as Firpic, $Ir(ppy)_3$, and $(acac)Ir(btp)_2$, and the compounds are used as blue, green and red dopant materials. Until now, CBP exhibits excellent characteristics as a phosphorescent host material.

However, since the light emitting materials in the related art have a low glass transition temperature and thus are very poor in thermal stability, the materials fail to reach a level which is satisfactory in terms of lifetime for an organic EL element, and need to be improved even in terms of light emitting characteristics. Therefore, there is a need for developing a light emitting material having excellent performance.

DISCLOSURE

Technical Problem

An object of the present disclosure is to provide a novel compound which is excellent in heat resistance, carrier transporting capability, light emitting capability, and the like, and thus may be used as a material for an organic material layer of an organic electroluminescent element, particularly, a light emitting layer material, a lifetime enhancement layer material, a light emitting auxiliary layer material, or an electron transporting layer material, and the like.

Further, another object of the present disclosure is to provide an organic electroluminescent element which includes the novel compound to have a low driving voltage, a high light emitting efficiency, and an improved lifetime.

Technical Solution

The present disclosure provides a compound represented by the following Chemical Formula 1:

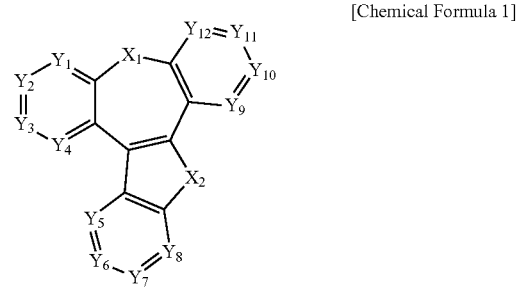

[Chemical Formula 1]

in Chemical Formula 1, $X_1$ and $X_2$ are the same as or different from each other, and are each independently selected from the group consisting of O, S, $N(Ar_1)$, $C(Ar_2)(Ar_3)$, and $Si(Ar_4)(Ar_5)$, and in this case, at least one of $X_1$ and $X_2$ is $N(Ar_1)$;

$Y_1$ to $Y_{12}$ are the same as or different from each other, and are each independently N or $C(R_1)$, and in this case, when $R_1$ is present in a plural number, these are the same as or different from each other;

$Ar_1$ to $Ar_5$ are the same as or different from each other, and are each independently selected from the group consisting of a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group, or may combine with an adjacent group to form a fused ring, $R_1$ is selected from the group consisting of hydrogen, deuterium, halogen, a cyano group, a nitro group, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group, or may combine with an adjacent group to form a fused ring, and the alkyl group, the cycloalkyl group, the heterocycloalkyl group, the aryl group, the heteroaryl group, the alkyloxy group, the aryloxy group, the alkylsilyl group, the arylsilyl group, the alkylboron group, the arylboron group, the arylphosphine group, the arylphosphine oxide group, and the arylamine group of $Ar_1$ to $Ar_5$ and $R_1$ may be each independently unsubstituted or substituted with one or more substituents selected from the group consisting of deuterium, halogen, a cyano group, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group, and in this case, the substituent may combine with an adjacent group to form a fused ring, provided that when the substituent is present in a plural number, these are the same as or different from each other.

Further, the present disclosure provides an organic electroluminescent element including an anode, a cathode, and one or more organic material layers interposed between the anode and the cathode, in which at least one of the organic material layers includes the above-described compound represented by Chemical Formula 1.

Here, according to an exemplary embodiment of the present disclosure, the one or more organic material layers include a hole injection layer, a hole transporting layer, a light emitting layer, an electron transporting layer, and an electron injection layer, and in this case, the one or more organic material layers including the compound represented by Chemical Formula 1 are a light emitting layer or an electron transporting layer.

Further, according to another exemplary embodiment of the present disclosure, the one or more organic material layers may include a hole injection layer, a hole transporting layer, a light emitting auxiliary layer, a light emitting layer, an electron transporting layer, and an electron injection layer. In this case, the one or more organic material layers including the compound represented by Chemical Formula 1 is a light emitting auxiliary layer.

Furthermore, according to still another exemplary embodiment of the present disclosure, the one or more organic material layers may include a hole injection layer, a hole transporting layer, a light emitting layer, a lifetime enhancement layer, an electron transporting layer, and an electron injection layer. In this case, the one or more organic material layers including the compound represented by Chemical Formula 1 are a lifetime enhancement layer.

Advantageous Effects

Since the compound represented by Chemical Formula 1 according to the present disclosure is excellent in heat resistance, carrier transporting capability, light emitting capability, and the like, the compound may be used as a material for an organic material layer of an organic electroluminescent element.

Further, for the organic electroluminescent element including the compound according to the present disclosure, the aspects such as light emitting performance, driving voltage, lifetime, and efficiency may be significantly improved, and accordingly, the organic electroluminescent element may be effectively applied to a full-color display panel, and the like.

BEST MODE

Hereinafter, the present disclosure will be described.
1. Novel Compound

A novel organic compound according to the present disclosure forms a basic structure from the fusion of a benzene fused 5-membered heteroaromatic ring moiety, an indene moiety, or an indole moiety with dibenzoazepine (5H-dibenzo[b,f]azepine), dibenzooxepine (dibenzo[b,f]oxepine), dibenzothiepine (dibenzo[b,f]thiepine), dibenzosilepine (5H-dibenzo[b,f]silepine), or dibenzocycloheptene (5H-dibenzo[a,d]cycloheptene), and is represented by Chemical Formula 1. Since the compound represented by Chemical Formula 1 has a higher molecular weight than a material for an organic EL element in the related art [for example: 4,4-dicarbazolybiphenyl (hereinafter, referred to as 'CBP'), the compound has excellent thermal stability due to a high glass transition temperature, and carrier transporting capability, light emitting capability, and the like. Accordingly, when an organic electroluminescent element includes the compound of Chemical Formula 1, the driving voltage, efficiency, lifetime, and the like of the element may be improved.

In general, in the phosphorescent light emitting layer of an organic electroluminescent element, a host material needs to have a triplet energy gap greater than a triplet energy gap of the dopant. That is, when the lowest excitation state of the host has a greater energy than the lowest emission state of the dopant, the phosphorescent light emitting efficiency may be improved. The compound of Chemical Formula 1 has a high triplet energy of 2.3 eV or more. Further, the compound represented by Chemical Formula 1 may be used as a host material because a specific substituent is introduced into the basic structure in which an indole derivative having a wide singlet energy level and a high triplet energy level is fused, and thus, the energy level may be adjusted to a higher level than that of the dopant.

Further, the compound of the present disclosure has a high triplet energy as described above, and thus may prevent excitons produced from a light emitting layer from diffusing into an electron transporting layer or a hole transporting layer adjacent to the light emitting layer. Accordingly, when the compound of Chemical Formula 1 is used to form an organic material layer (hereinafter, referred to as a 'light emitting auxiliary layer') between a hole transporting layer and a light emitting layer, the diffusion of excitons is prevented by the compound such that the number of excitons substantially contributing to light emission in the light emitting layer is increased, and thus the light emitting efficiency of the element may be improved unlike an organic electroluminescent element in the related art, which does not include the light emitting auxiliary layer. Further, even when the compound of Chemical Formula 1 is used to form an organic material layer (hereinafter, referred to as a 'lifetime enhancement layer') between a light emitting layer and an electron transporting layer, the diffusion of excitons is prevented by the compound of Chemical Formula 1, and thus, the durability and stability of the organic electroluminescent element may be improved, thereby efficiently increasing the half-lifetime of the element. As described above, the compound represented by Chemical Formula 1 may be used as a material for the light emitting auxiliary layer or a material for the lifetime enhancement layer, in addition to the host of the light emitting layer.

In addition, the compound of Chemical Formula 1 may have a wide bandgap and may have high carrier transporting capability because the HOMO and LUMO energy levels may be adjusted according to the type of substituent to be introduced into the basic structure. For example, in the compound, when an electron withdrawing group (EWG) having large electron absorption properties, such as a nitrogen-containing hetero ring (for example, a pyridine group, a pyrimidine group, a triazine group, and the like) is bonded to the basic structure, the entire molecule has bipolar characteristics, thereby increasing the binding force between holes and electrons. As described above, the compound of Chemical Formula 1, in which the EWG is introduced into the basic structure, has excellent carrier transporting capability and light emitting characteristics, and thus, may also be used as an electron injection/transporting layer material, or a lifetime enhancement layer material in addition to a light emitting layer material of an organic electroluminescent element. Meanwhile, when an electron donor group (EDG) having great electron donor properties, such as an arylamine group, a carbazole group, a terphenyl group, and a triphenylene group is bonded to the basic structure, holes are smoothly injected and transported, so that the compound of Chemical Formula 1 may be usefully used as a hole injection/transporting layer material or a light emitting auxiliary layer material in addition to a light emitting layer material.

As described above, the compound represented by Chemical Formula 1 may improve the light emitting efficiency of the organic electroluminescent element, and simultaneously improve hole injection/transporting capability, electron injection/transporting capability, light emitting efficiency, driving voltage, lifetime characteristics, and the like. Accordingly, the compound of Chemical Formula 1 according to the present disclosure may be used as an organic material layer material, preferably a light emitting layer material (blue, green, and/or red phosphorescent host material), an electron transporting/injection layer material and a hole transporting/injection layer material, a light emitting auxiliary layer material, a lifetime enhancement layer material, and more preferably, a light emitting layer material, an electron injection layer material, a light emitting auxiliary layer material, and a lifetime enhancement layer material, of the organic electroluminescent element.

Further, in the compound of Chemical Formula 1, various substituents, particularly an aryl group and/or a heteroaryl group are/is introduced into the basic structure to significantly increase the molecular weight of the compound and improve the glass transition temperature, and accordingly, the compound may have higher thermal stability than the light emitting material in the related art (for example, CBP). In addition, the compound represented by Chemical Formula 1 is also effective for suppressing crystallization of the organic material layer. Accordingly, in the organic electroluminescent element including the compound of Chemical Formula 1 according to the present disclosure, performance and lifetime characteristics may be greatly improved, and even in a full-color organic light emitting panel to which the organic electroluminescent element is applied, performance may be maximized.

In the compound represented by Chemical Formula 1 according to the present disclosure, $X_1$ and $X_2$ are the same as or different from each other, and are each independently selected from the group consisting of O, S, N(Ar$_1$), C(Ar$_2$)(Ar$_3$), and Si(Ar$_4$)(Ar$_5$), preferably are each independently selected from the group consisting of O, S, and N(Ar$_1$). In this case, at least one of $X_1$ and $X_2$ is N(Ar$_1$).

The compound represented by Chemical Formula 1 may be embodied as any one of the following Chemical Formulae 2 to 10.

[Chemical Formula 2]

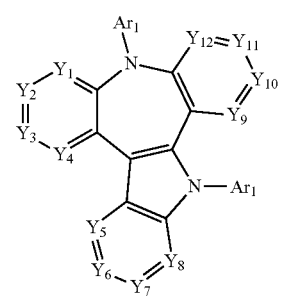

[Chemical Formula 3]

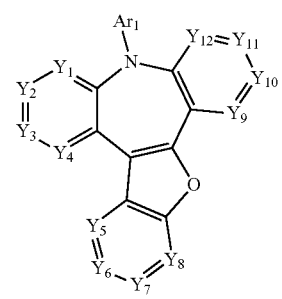

[Chemical Formula 4]

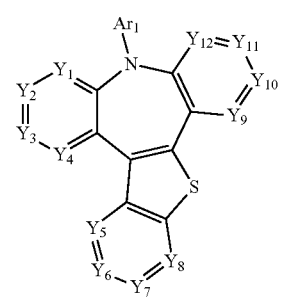

[Chemical Formula 5]

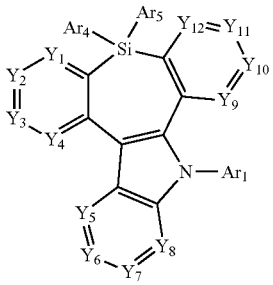

[Chemical Formula 6]

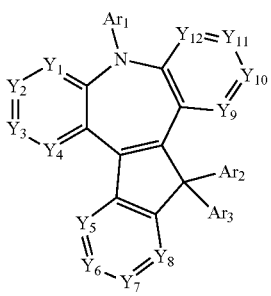

[Chemical Formula 7]

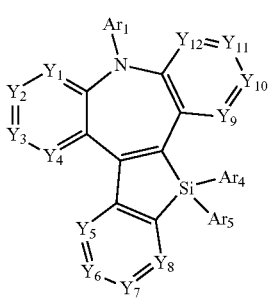

[Chemical Formula 8]

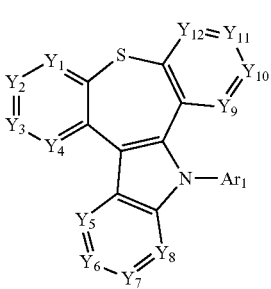

[Chemical Formula 9]

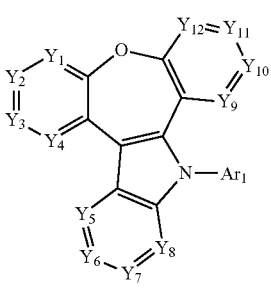

[Chemical Formula 10]

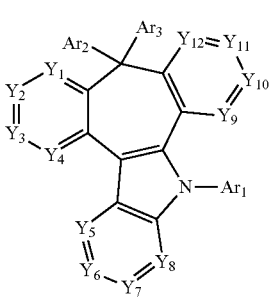

in Chemical Formulae 2 to 10, $Ar_1$ to $Ar_5$ and $Y_1$ to $Y_{12}$ are each the same as those defined in Chemical Formula 1.

In Chemical Formulae 1 to 10, $Ar_1$ to $Ar_5$ are the same as or different from each other, and are each independently selected from the group consisting of a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group, or may combine with an adjacent group to form a fused ring.

Preferably, $Ar_1$ may be selected from the group consisting of a $C_6$ to $C_{60}$ aryl group, and a heteroaryl group having 5 to 60 nuclear atoms.

Preferably, $Ar_2$ to $Ar_5$ are the same as or different from each other, and may be each independently selected from the group consisting of a $C_1$ to $C_{40}$ alkyl group and a $C_6$ to $C_{60}$ aryl group, and more preferably, $Ar_2$ to $Ar_5$ are the same as or different from each other, and may be each independently a methyl group or a phenyl group.

Further, $Y_1$ to $Y_{12}$ are the same as or different from each other, and are each independently N or $C(R_1)$, and preferably, all of $Y_1$ to $Y_{12}$ are $C(R_1)$, or one of $Y_1$ to $Y_{12}$ may be N, and the others may be $C(R_1)$. In this case, when $R_1$ is present in a plural number, these are the same as or different from each other.

$R_1$ is selected from the group consisting of hydrogen, deuterium, halogen, a cyano group, a nitro group, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group, or may combine with an adjacent group to form a fused ring.

The alkyl group, the cycloalkyl group, the heterocycloalkyl group, the aryl group, the heteroaryl group, the alkyloxy group, the aryloxy group, the alkylsilyl group, the arylsilyl group, the alkylboron group, the arylboron group, the arylphosphine group, the arylphosphine oxide group, and the arylamine group of $Ar_1$ to $Ar_5$ and $R_1$ may be each independently unsubstituted or substituted with one or more substituents selected from the group consisting of deuterium (D), halogen, a cyano group, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group, and in this case, the substituent may combine with an adjacent group to form a fused ring. Provided that when the substituent is present in a plural number, these are the same as or different from each other.

Further, $Ar_1$ to $Ar_5$ and $R_1$ are the same as or different from each other, and may be each independently selected from hydrogen (provided that $Ar_1$ to $Ar_5$ are excluded) or the group consisting of the following substituents S1 to S204, but the substituents are not limited thereto.

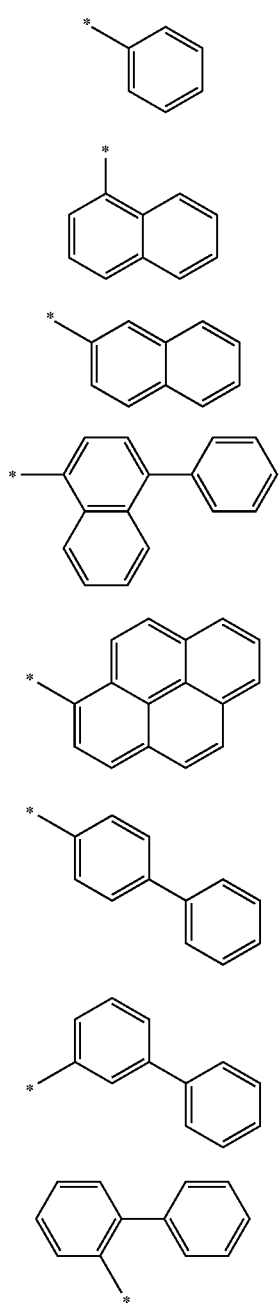

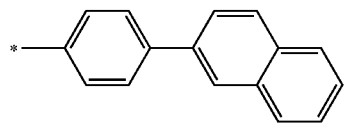

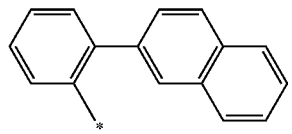

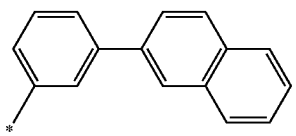

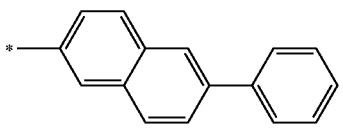

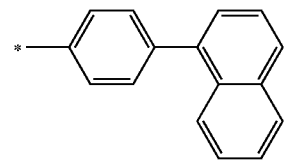

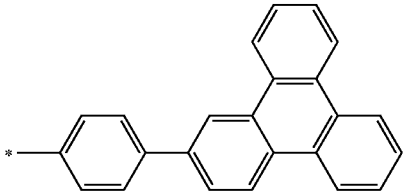

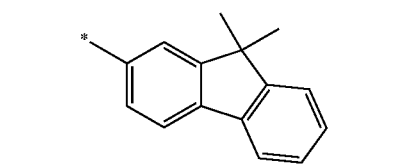

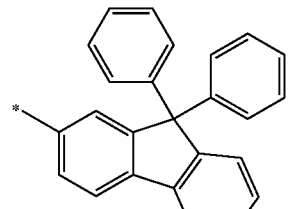

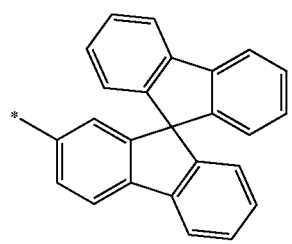

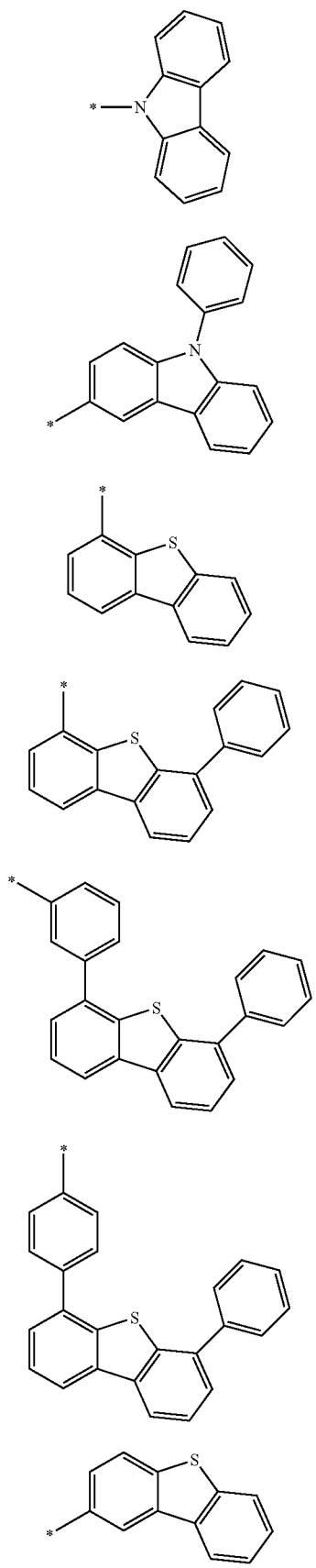
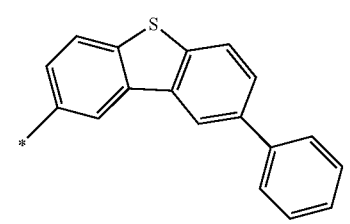
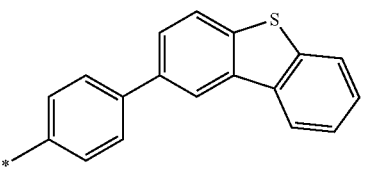
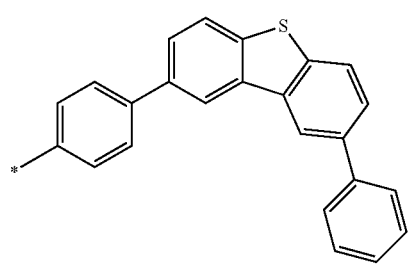
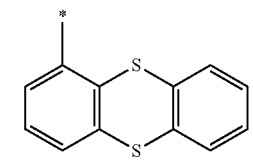
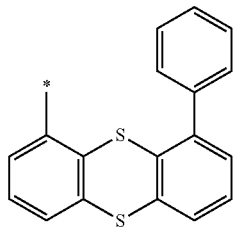
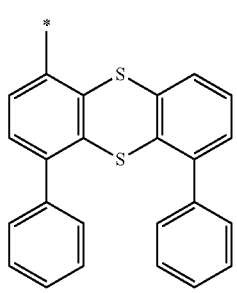

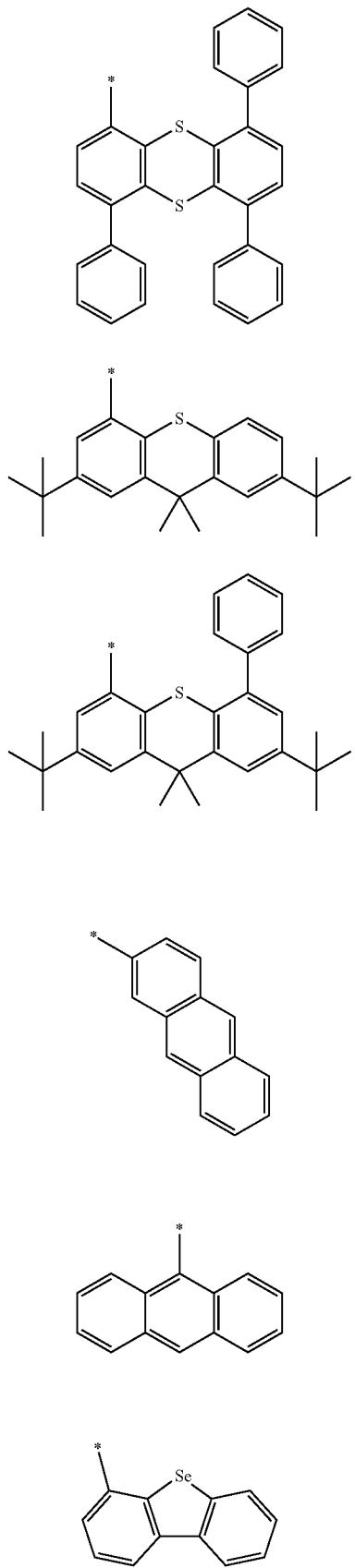
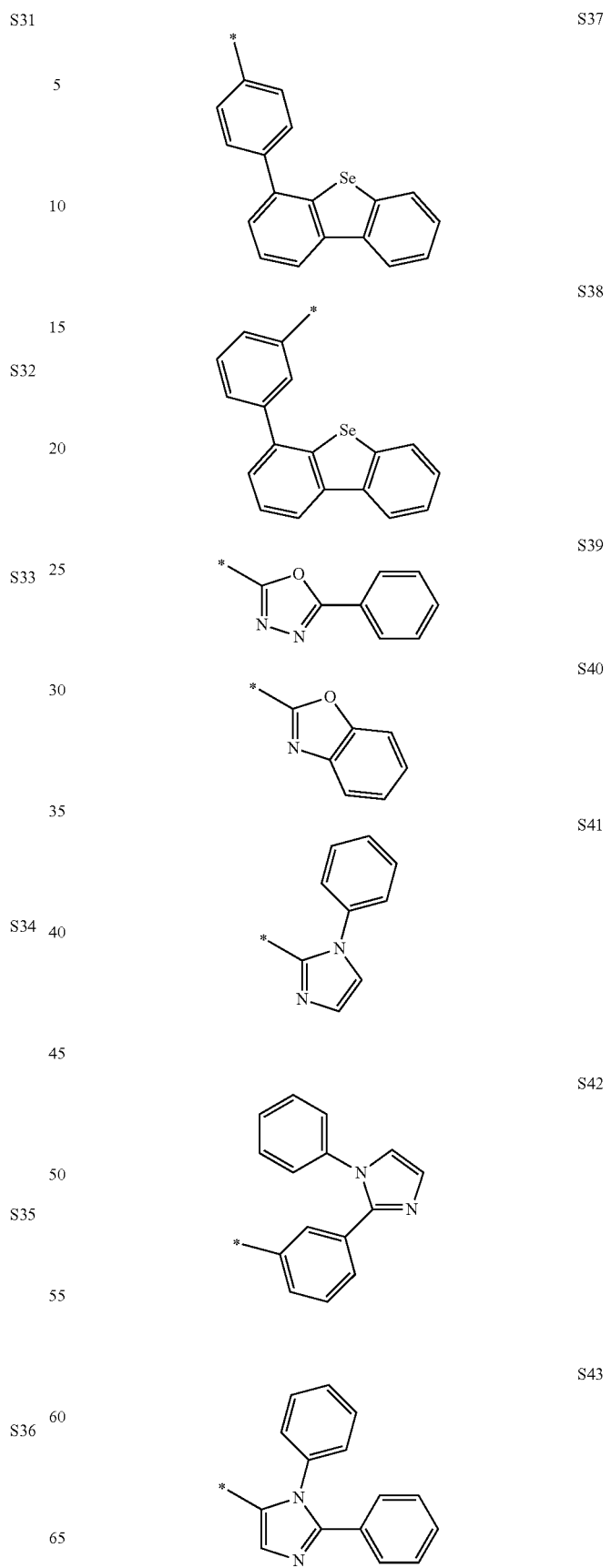

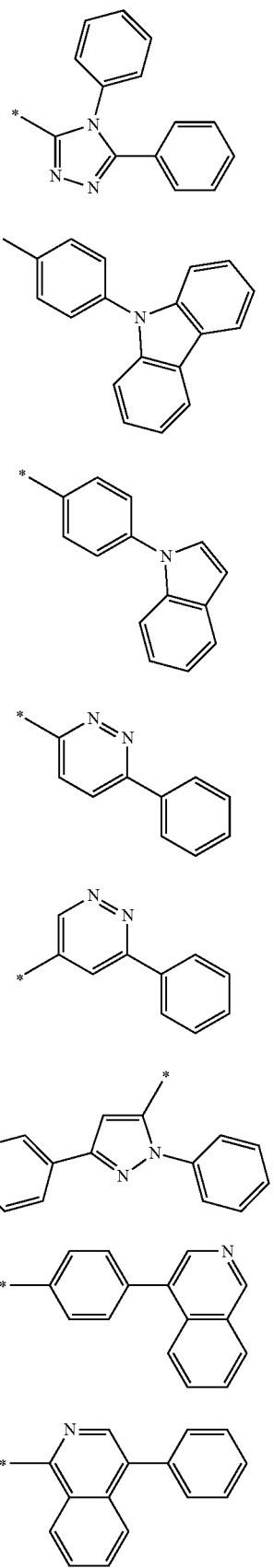
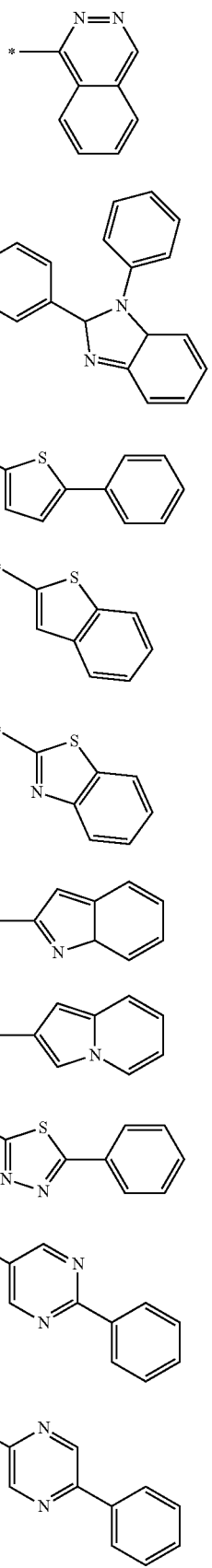

| | |
|---|---|
| S62 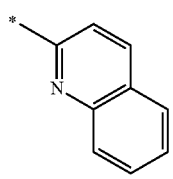 | S71 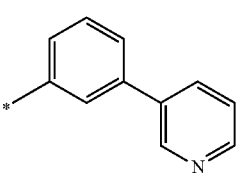 |
| S63 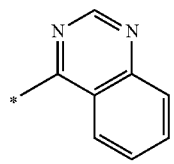 | S72 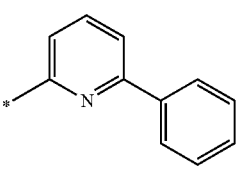 |
| S64 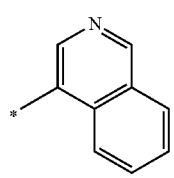 | S73 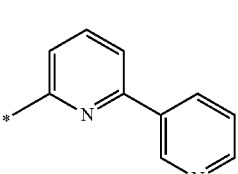 |
| S65 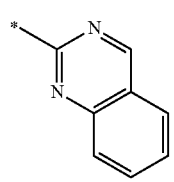 | S74 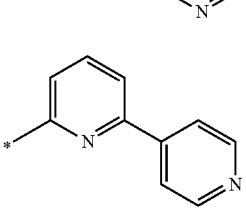 |
| S66 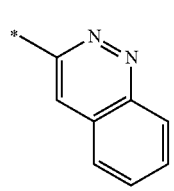 | S75  |
| S67 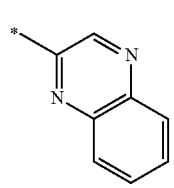 | S76 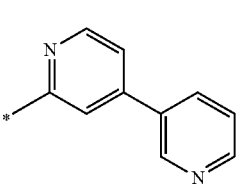 |
| S68 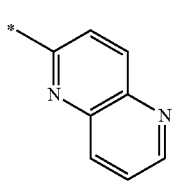 | S77 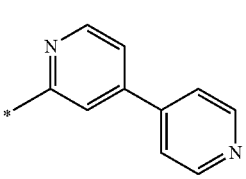 |
| S69 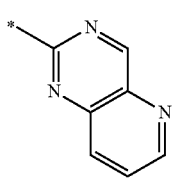 | S78 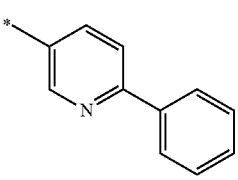 |
| S70 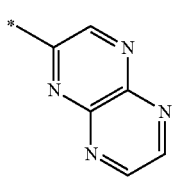 | S79 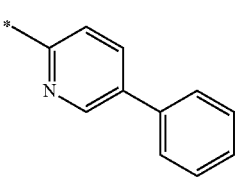 |

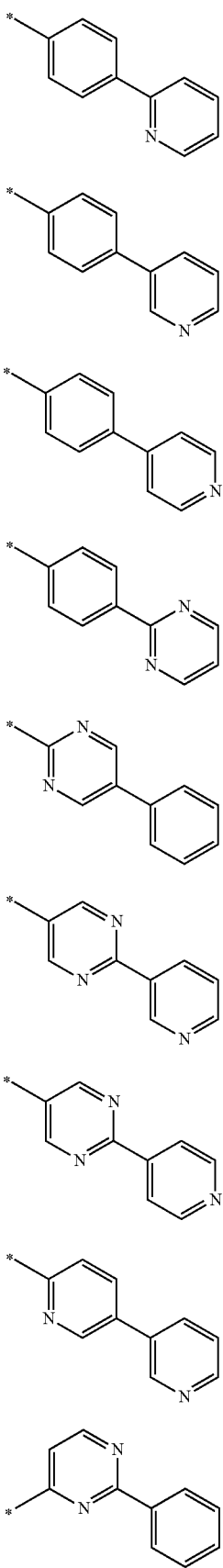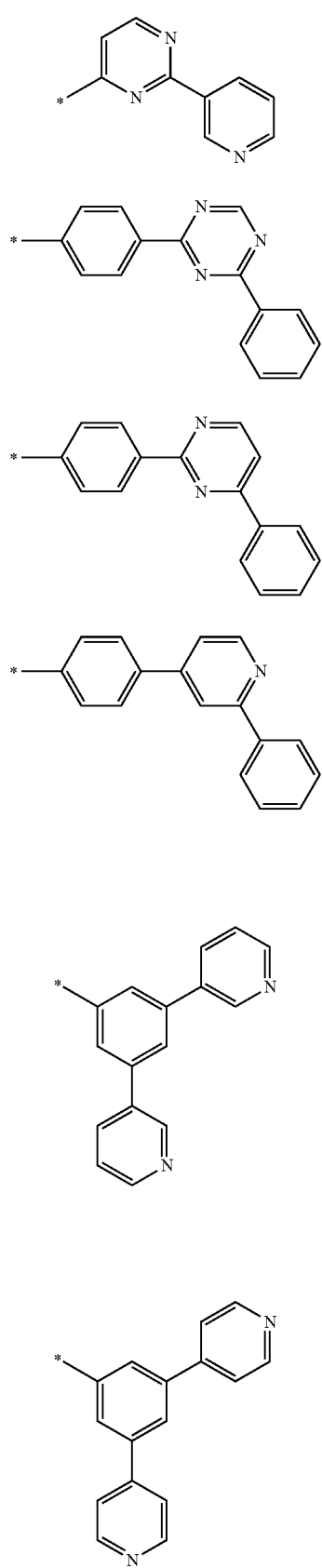

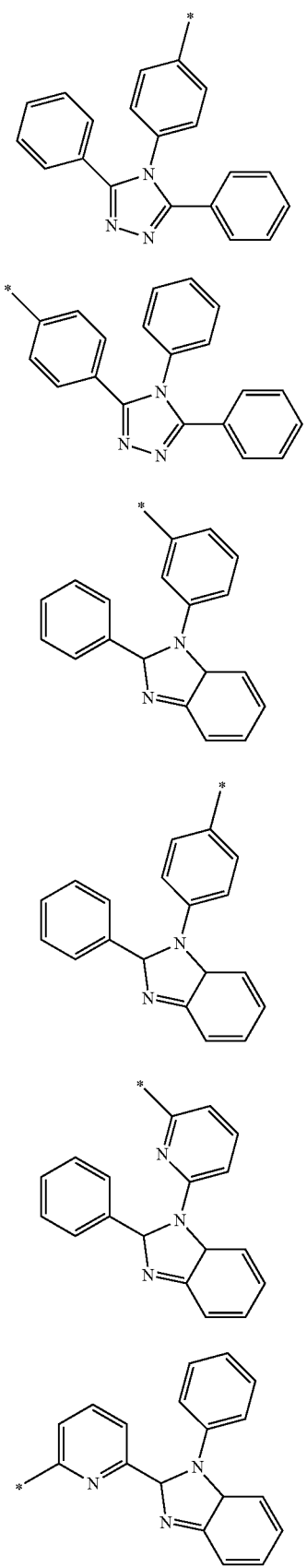
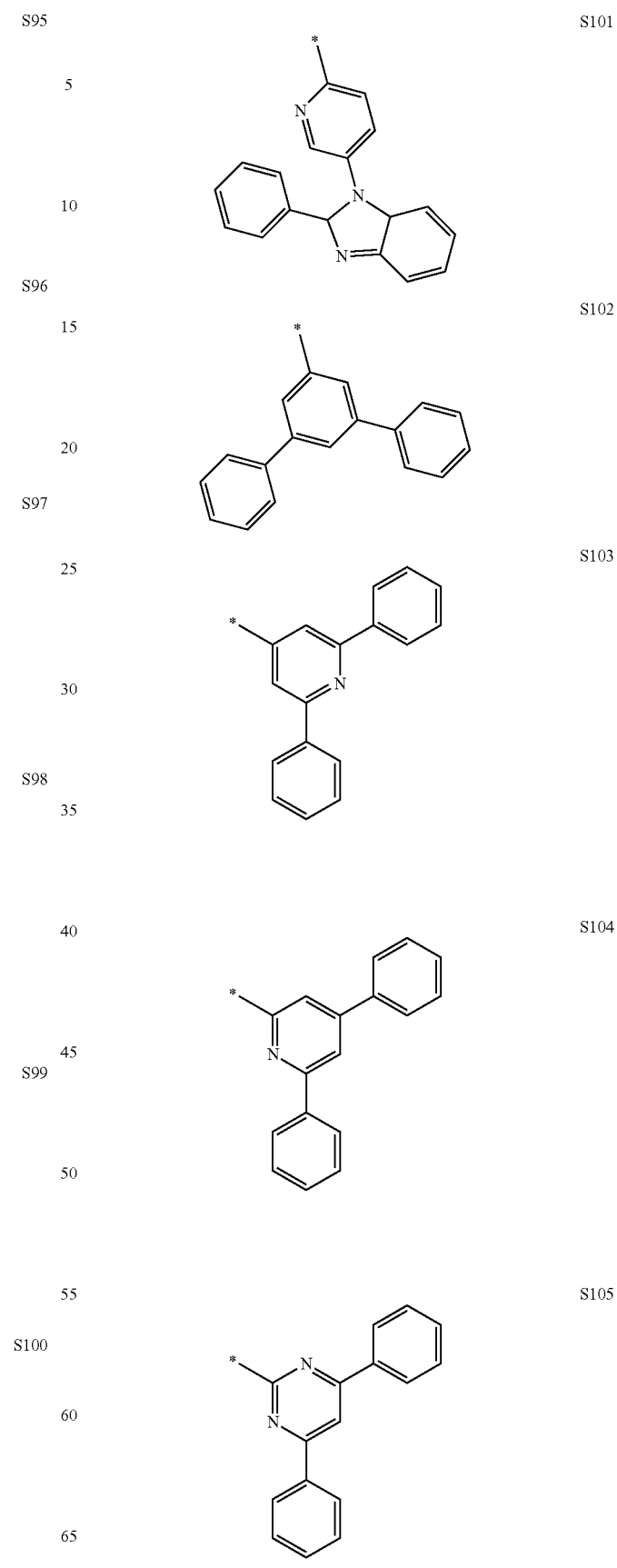

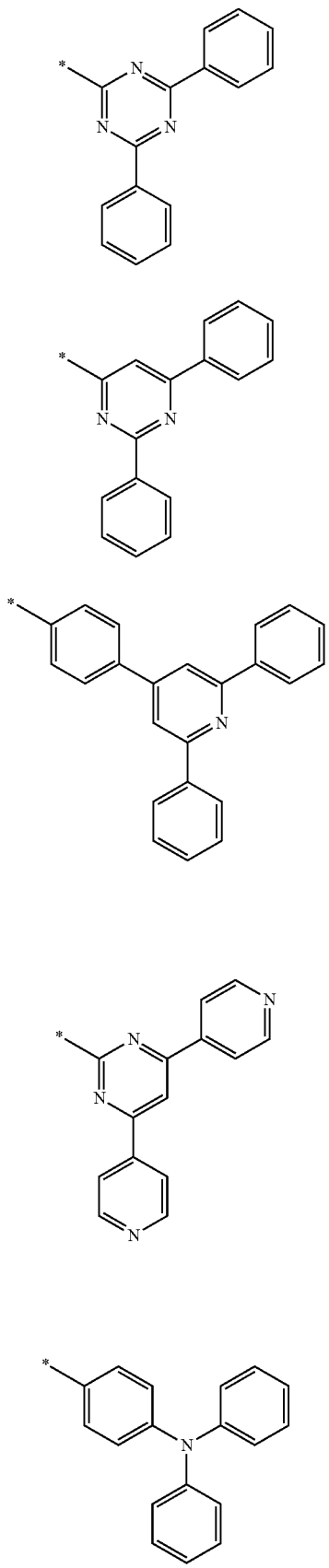
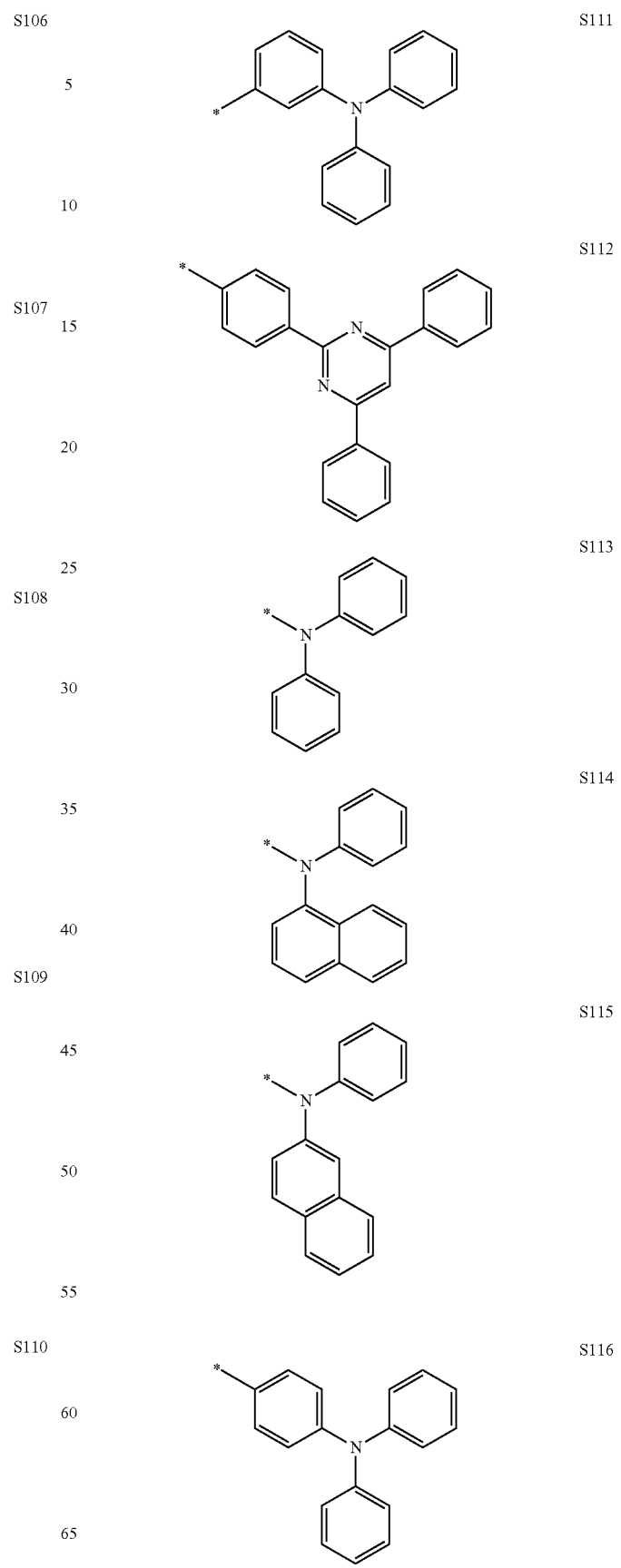

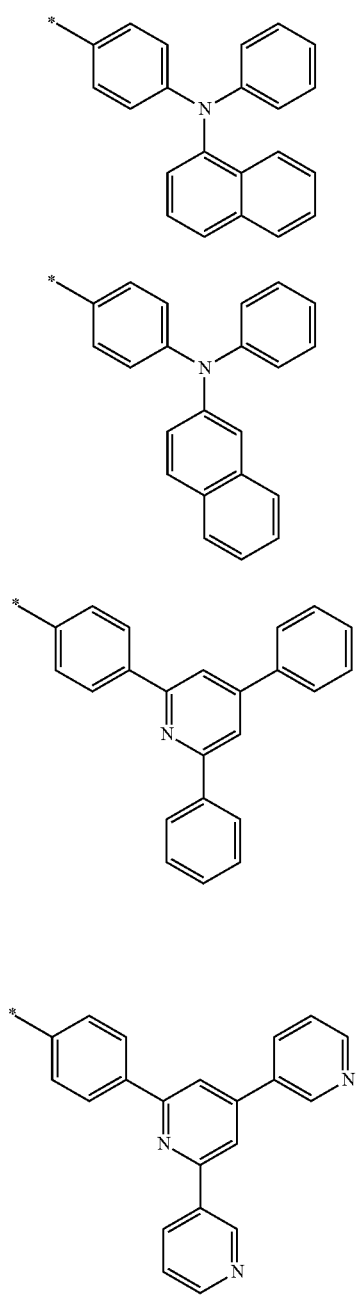
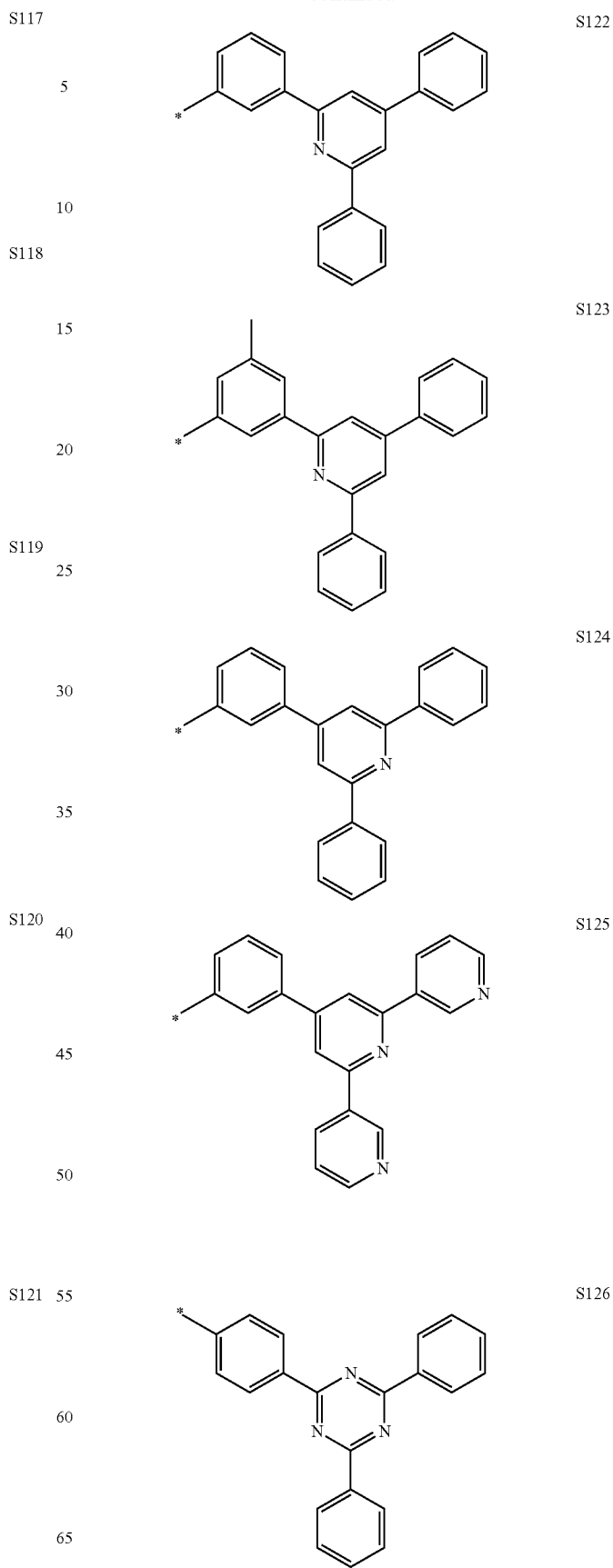

S127
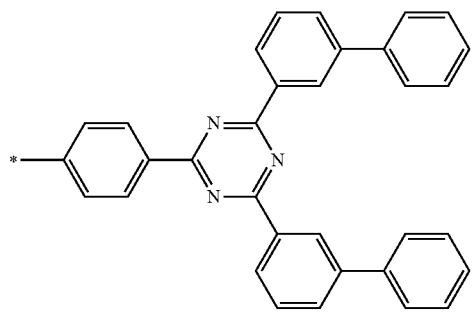
S128
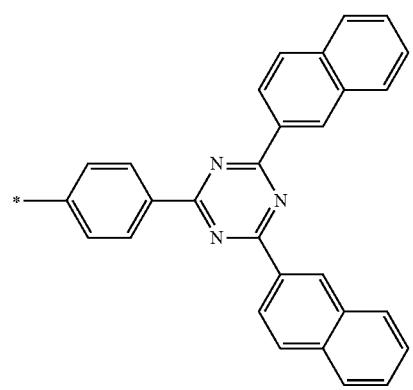
S129
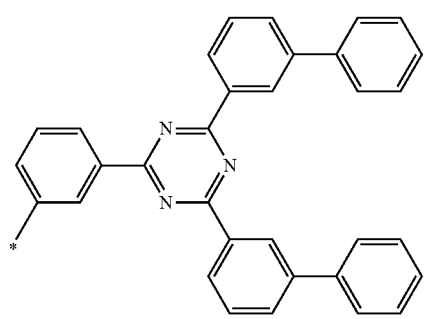
S130
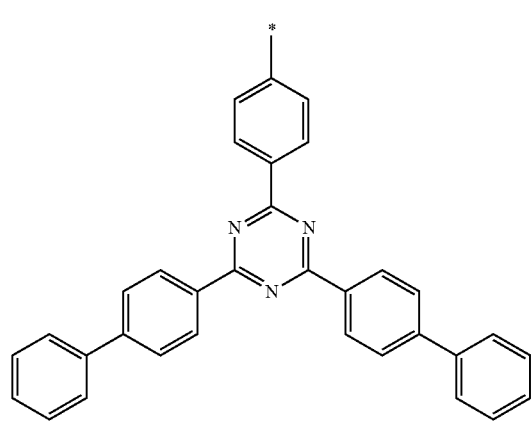
S131
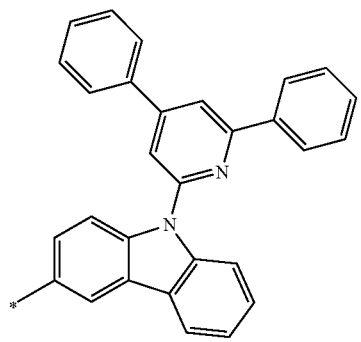
S132
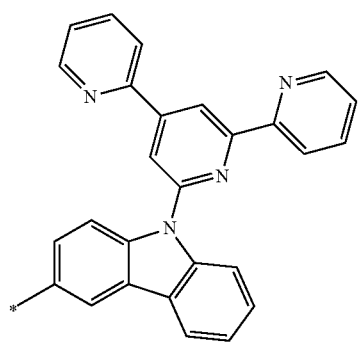
S133
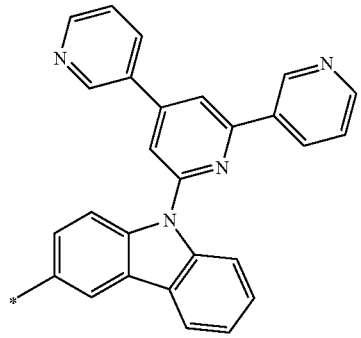
S134
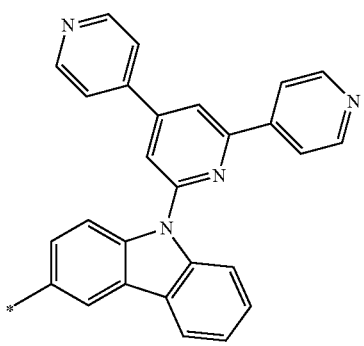

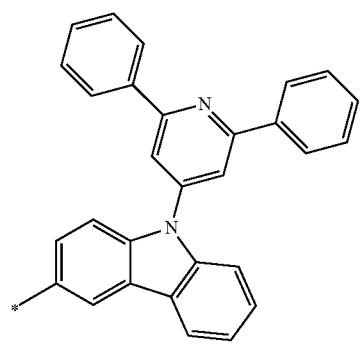
S135
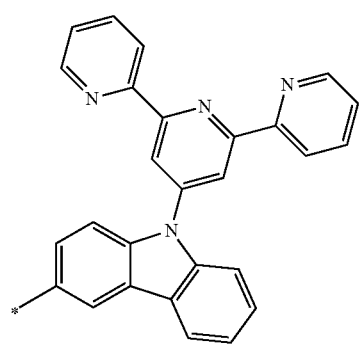
S136
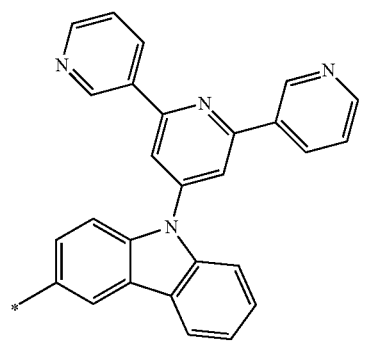
S137
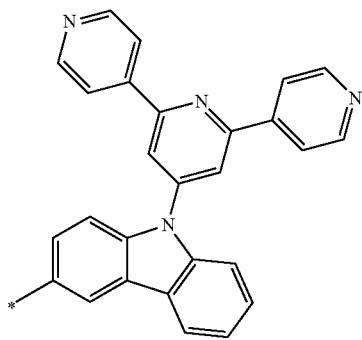
S138
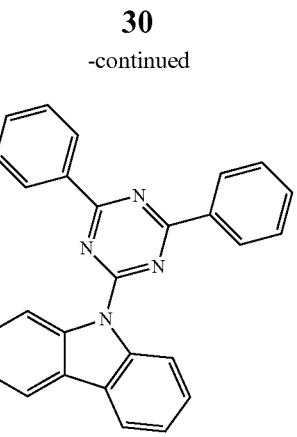
S139
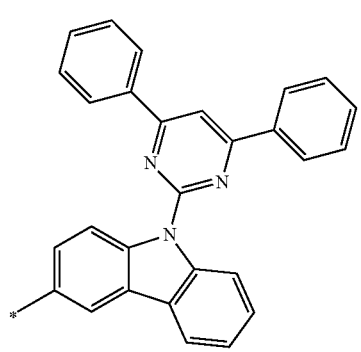
S140
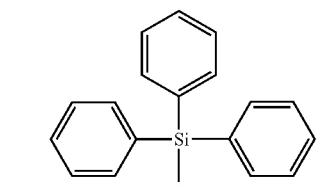
S141
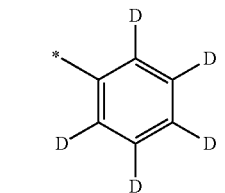
S142
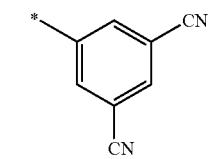
S143
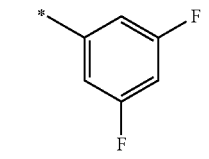
S144
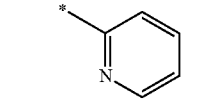
S145

S146
S147
S148
S149
S150
S151
S152
S153
S154
S155
S156
S157
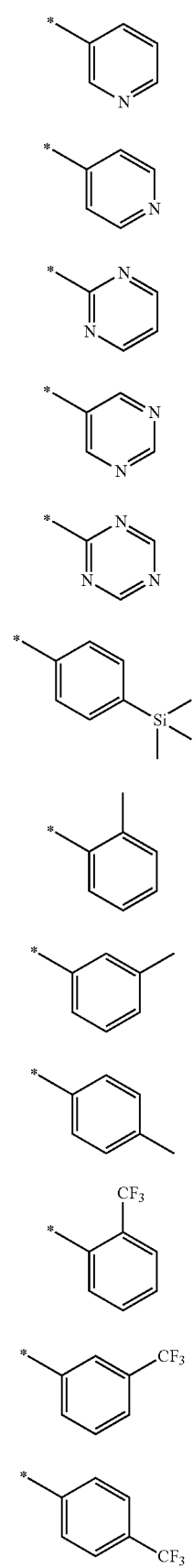
S158
S159
S160
S161
S162
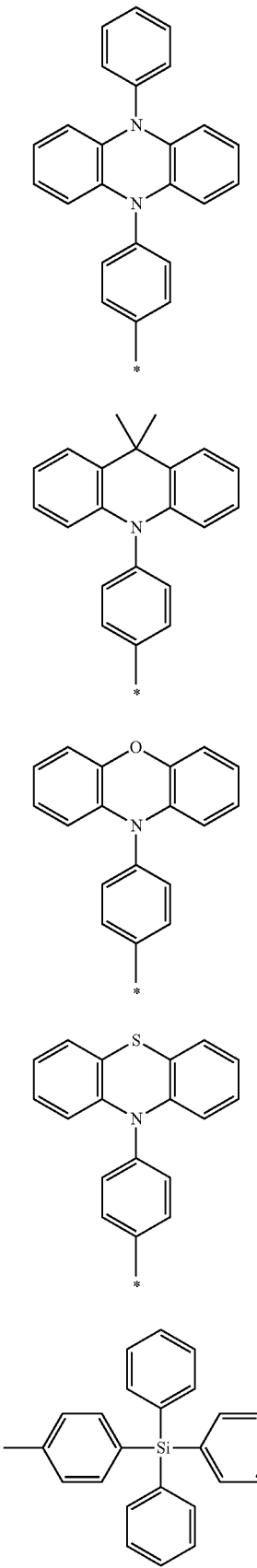

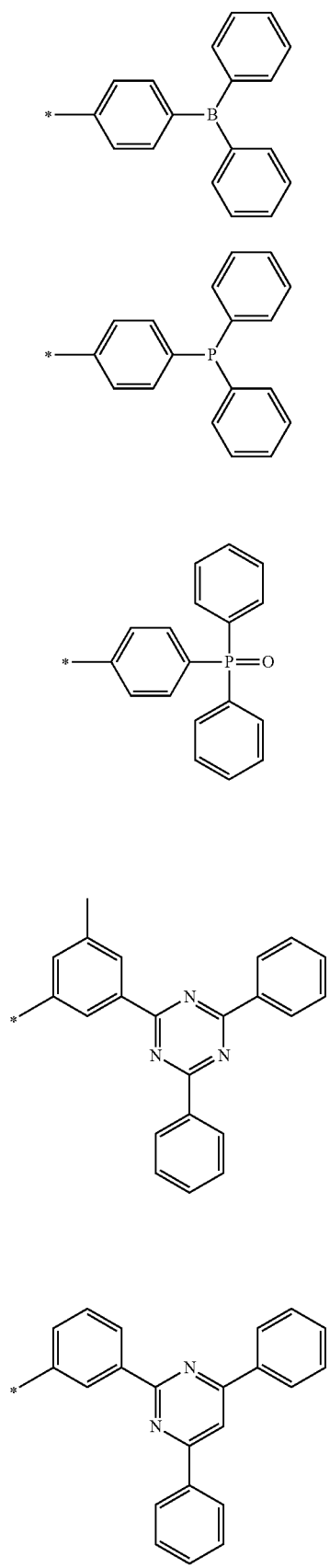
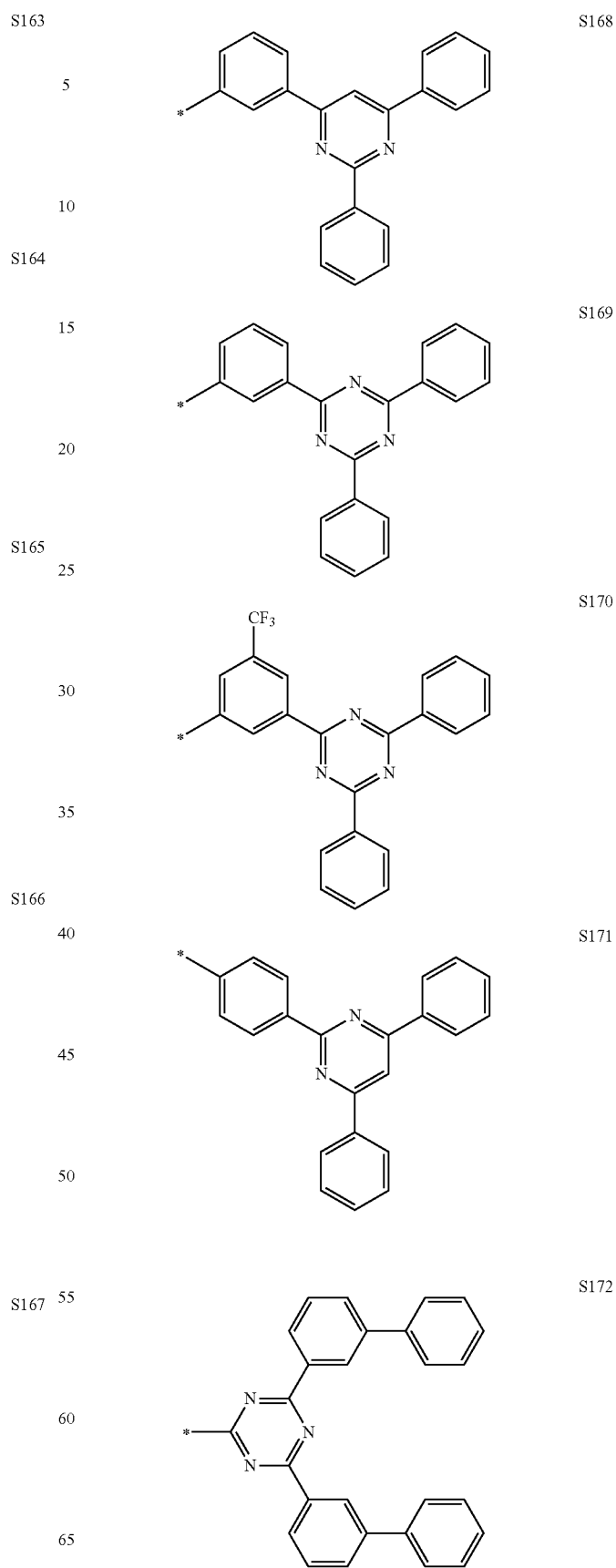

-continued
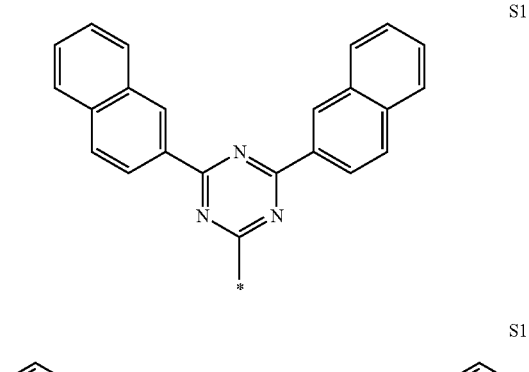
S173
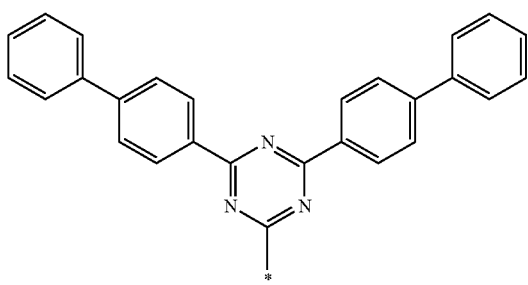
S174
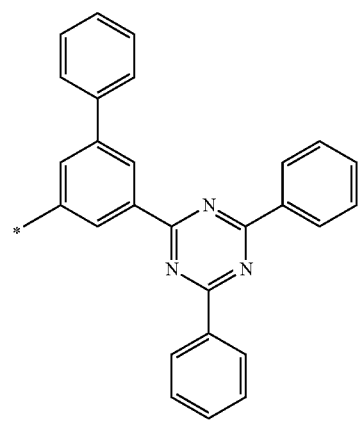
S175
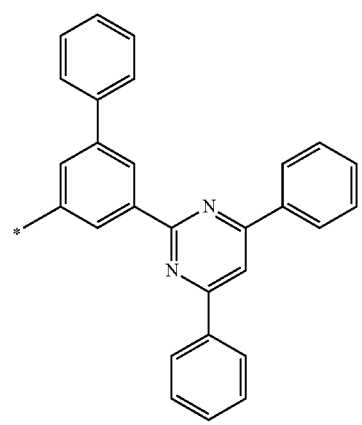
S176
-continued
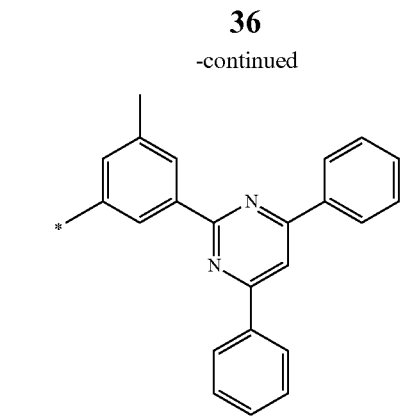
S177
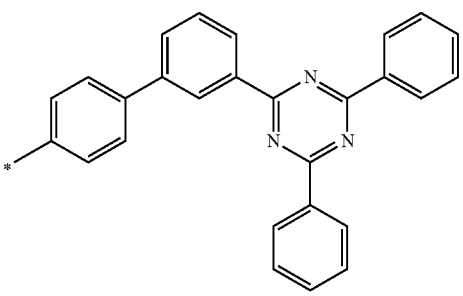
S178
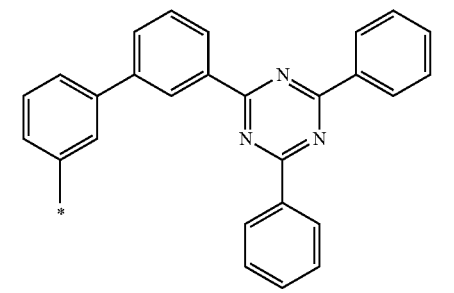
S179
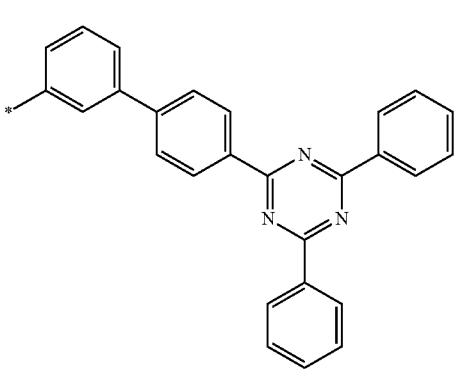
S180
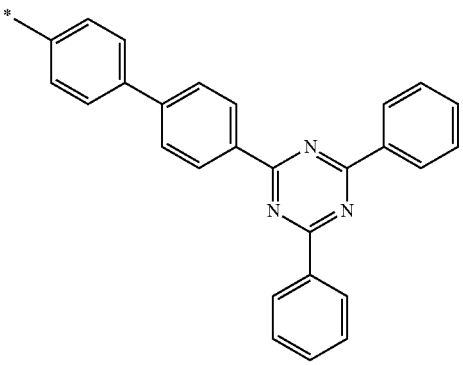
S181

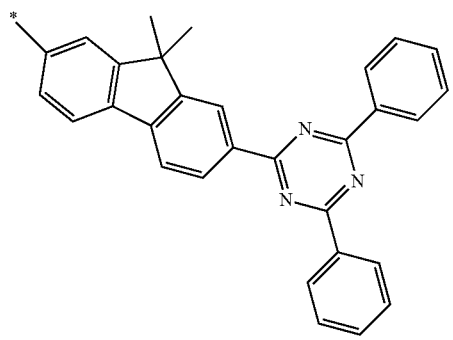
S182
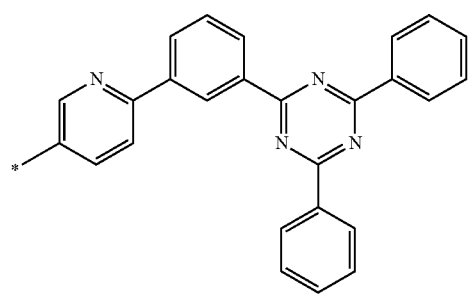
S183
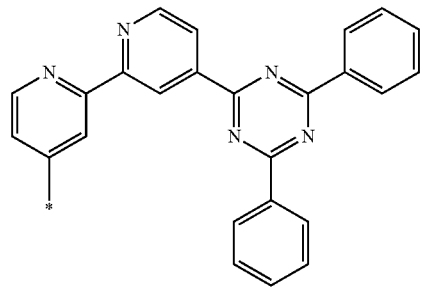
S184
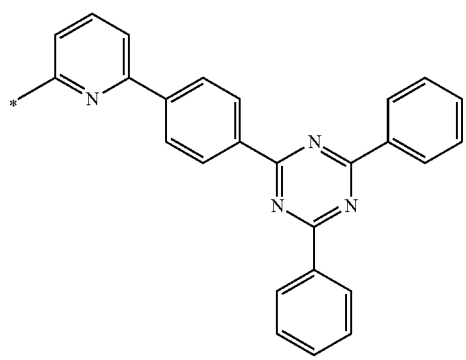
S185
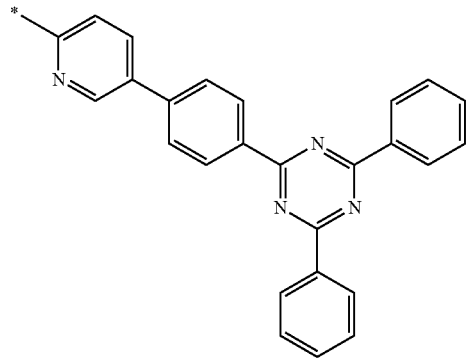
S186
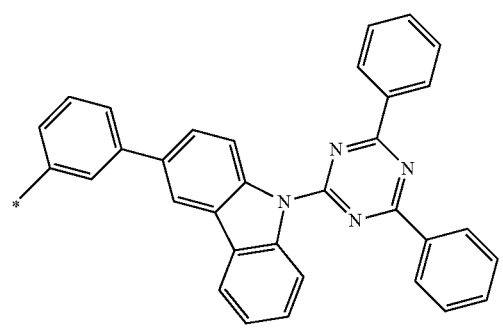
S187
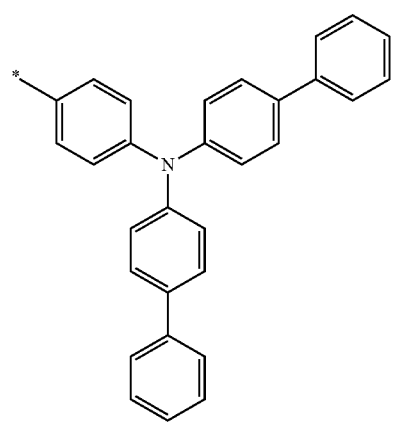
S188
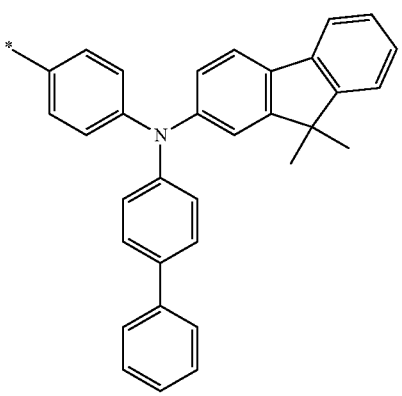
S189

S190 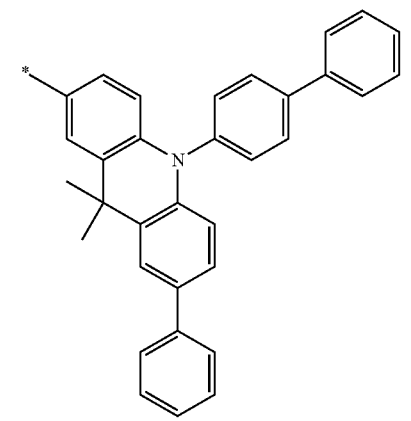
S191 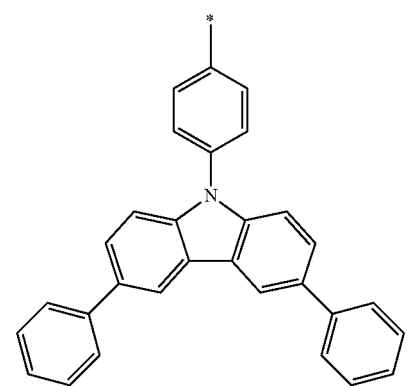
S192 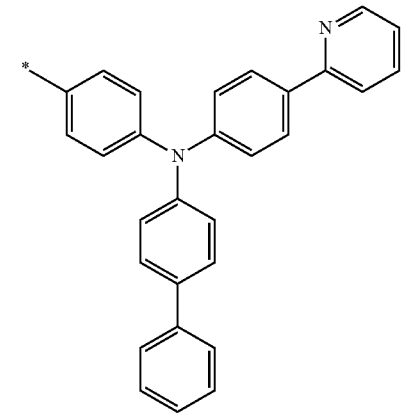
S193 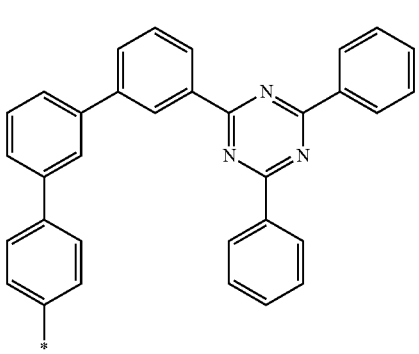
S194 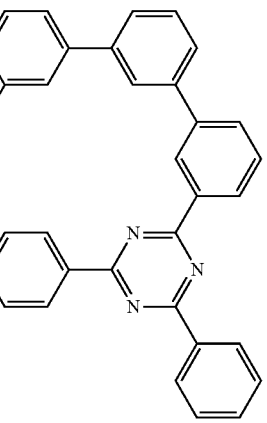
S195 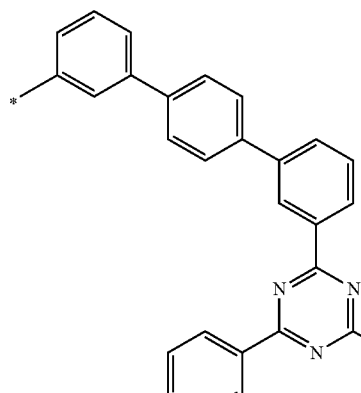
S196 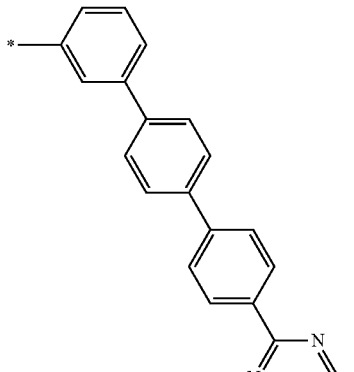
S197 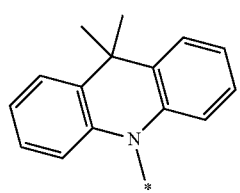

S198 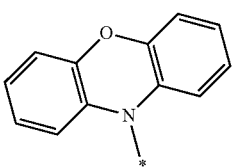

S199 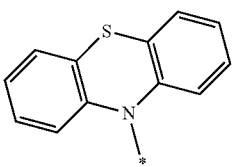

S200 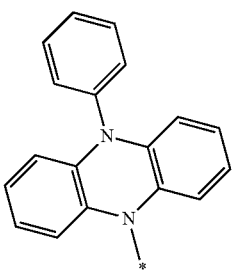

S201 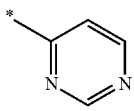

S202

S203 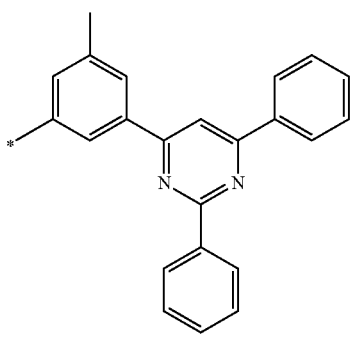

S204 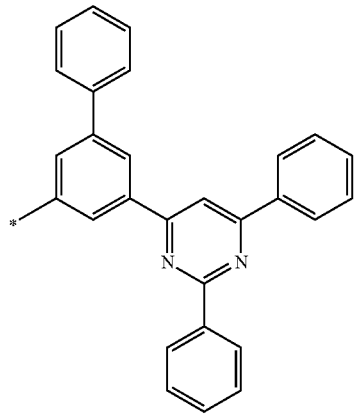

Further, in Chemical Formulae 1 to 10, $Ar_1$ and $R_1$ are the same as or different from each other, and are each independently a substituent represented by the following Chemical Formula 11, or a $C_6$ to $C_{60}$ aryl group (for example, a phenyl group, a biphenyl group, a terphenyl group, a fluorene group, and the like), and in this case, the aryl group of $Ar_1$ and $R_1$ may be unsubstituted or substituted with one or more substituents selected from the group consisting of deuterium (D), halogen, a cyano group, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group, and in this case, the substituent may combine with an adjacent group to form a fused ring, provided that when the substituent is present in a plural number, these are the same as or different from each other.

[Chemical Formula 11]

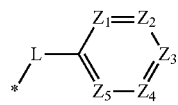

in Chemical Formula 11,

L is a single bond, or is selected from the group consisting of a $C_6$ to $C_{18}$ arylene group and a heteroarylene group having 5 to 18 nuclear atoms, and may be preferably a single bond or may be a phenylene group or a biphenylene group;

$Z_1$ to $Z_5$ are the same as or different from each other, and are each independently N or $C(R_{11})$, provided that at least one of $Z_1$ to $Z_5$ is N, and in this case, when $C(R_{11})$ is present in a plural number, these are the same as or different from each other;

$R_{11}$ is selected from the group consisting of hydrogen, deuterium (D), halogen, a cyano group, a $C_1$ to $C_{40}$ alkyl group, a $C_6$ to $C_{40}$ aryl group, a heteroaryl group having 5 to 40 nuclear atoms, a $C_6$ to $C_{40}$ aryloxy group, a $C_1$ to $C_{40}$ alkyloxy group, a $C_6$ to $C_{40}$ arylamine group, a $C_1$ to $C_{40}$ alkylsilyl group, a $C_1$ to $C_{40}$ alkylboron group, a $C_6$ to $C_{40}$ arylboron group, a $C_6$ to $C_{40}$ arylphosphine group, a $C_6$ to $C_{40}$ arylphosphine oxide group, and a $C_6$ to $C_{40}$ arylsilyl group, or may combine with an adjacent group to form a fused ring;

in this case, the alkyl group, the aryl group, the heteroaryl group, the aryloxy group, the alkyloxy group, the arylamine group, the alkylsilyl group, the alkylboron group, the arylboron group, the arylphosphine group, the arylphospine oxide group, and the arylsilyl group of $R_{11}$ may be each independently unsubstituted or substituted with one or more substituents selected from the group consisting of deuterium (D), halogen, a cyano group, a $C_1$ to $C_{40}$ alkyl group, a $C_2$ to $C_{40}$ alkenyl group, a $C_2$ to $C_{40}$ alkynyl group, a $C_6$ to $C_{40}$ aryl group, a heteroaryl group having 5 to 40 nuclear atoms, a $C_6$ to $C_{40}$ aryloxy group, a $C_1$ to $C_{40}$ alkyloxy group, a $C_6$ to $C_{40}$ arylamine group, a $C_3$ to $C_{40}$ cycloalkyl group, a heterocycloalkyl group having 3 to 40 nuclear atoms, a $C_1$ to $C_{40}$ alkylsilyl group, a $C_1$ to $C_{40}$ alkylboron group, a $C_6$ to $C_{40}$ arylboron group, a $C_6$ to $C_{40}$ arylphosphine group, a $C_6$ to $C_{40}$ arylphosphine oxide group, and a $C_6$ to $C_{40}$ arylsilyl group, and in this case, when the substituent is present in a plural number, these are the same as or different from each other.

Examples of the substituent represented by Chemical Formula 11 include a substituent represented by any one of the following Chemical Formulae A-1 to A-15, and the examples are not limited thereto.

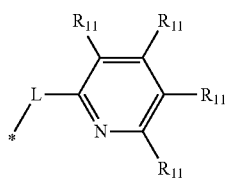

A-1

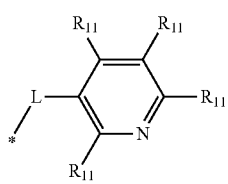

A-2

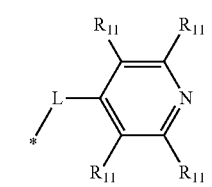

A-3

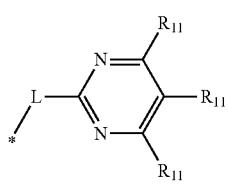

A-4

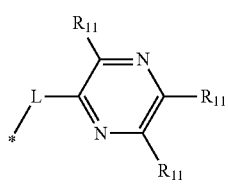

A-5

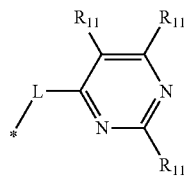

A-6

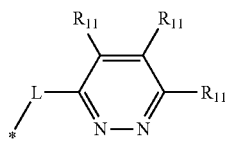

A-7

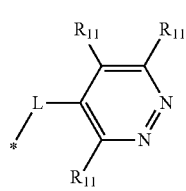

A-8

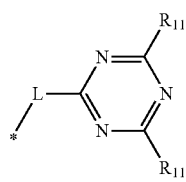

A-9

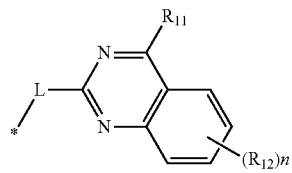

A-10

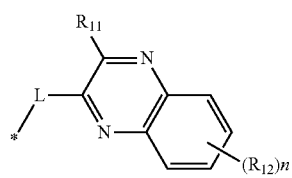

A-11

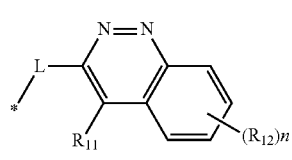

A-12

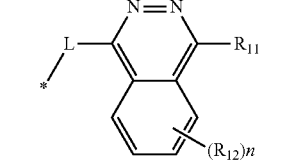

A-13

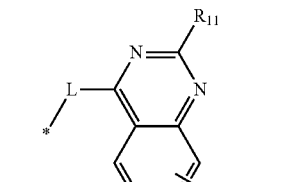

A-14

-continued

[A-15]

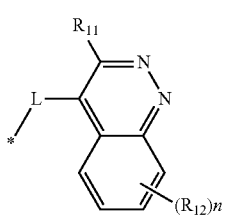

In Chemical Formulae A-1 to A-15,

L and $R_{11}$ are each the same as those defined in Chemical Formula 11,

A plurality of $R_{12}$ is the same as or different from each other, $R_{12}$ is selected from the group consisting of hydrogen, deuterium (D), halogen, a cyano group, a $C_1$ to $C_{40}$ alkyl group, a $C_6$ to $C_{40}$ aryl group, a heteroaryl group having 5 to 40 nuclear atoms, a $C_6$ to $C_{40}$ aryloxy group, a $C_1$ to $C_{40}$ alkyloxy group, a $C_6$ to $C_{40}$ arylamine group, a $C_1$ to $C_{40}$ alkylsilyl group, a $C_1$ to $C_{40}$ alkylboron group, a $C_6$ to $C_{40}$ arylboron group, a $C_6$ to $C_{40}$ arylphosphine group, a $C_6$ to $C_{40}$ arylphosphine oxide group, and a $C_6$ to $C_{40}$ arylsilyl group, or may combine with an adjacent group to form a fused ring, n is an integer of 1 to 4, in this case, the alkyl group, the aryl group, the heteroaryl group, the aryloxy group, the alkyloxy group, the arylamine group, the alkylsilyl group, the alkylboron group, the arylboron group, the arylphosphine group, the arylphospine oxide group, and the arylsilyl group of $R_{12}$ may be each independently unsubstituted or substituted with one or more substituents selected from the group consisting of deuterium (D), halogen, a cyano group, a $C_1$ to $C_{40}$ alkyl group, a $C_2$ to $C_{40}$ alkenyl group, a $C_2$ to $C_{40}$ alkynyl group, a $C_6$ to $C_{40}$ aryl group, a heteroaryl group having 5 to 40 nuclear atoms, a $C_6$ to $C_{40}$ aryloxy group, a $C_1$ to $C_{40}$ alkyloxy group, a $C_6$ to $C_{40}$ arylamine group, a $C_3$ to $C_{40}$ cycloalkyl group, a heterocycloalkyl group having 3 to 40 nuclear atoms, a $C_1$ to $C_{40}$ alkylsilyl group, a $C_1$ to $C_{40}$ alkylboron group, a $C_6$ to $C_{40}$ arylboron group, a $C_6$ to $C_{40}$ arylphosphine group, a $C_6$ to $C_{40}$ arylphosphine oxide group, and a $C_6$ to $C_{40}$ arylsilyl group, and in this case, when the substituent is present in a plural number, these are the same as or different from each other.

The compound represented by Chemical Formula 1 according to the present disclosure may be embodied by any one of the following Chemical Formulae 12 to 20, but is not limited thereto.

[Chemical Formula 12]

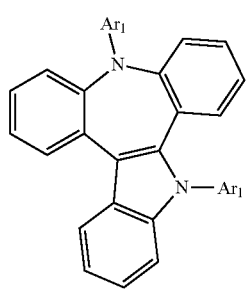

[Chemical Formula 13]

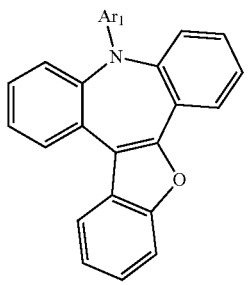

[Chemical Formula 14]

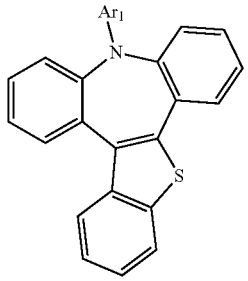

[Chemical Formula 15]

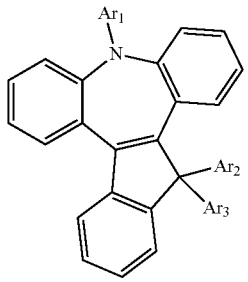

[Chemical Formula 16]

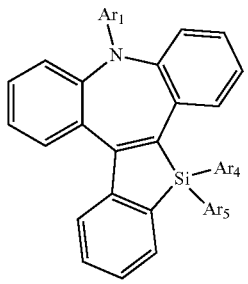

[Chemical Formula 17]

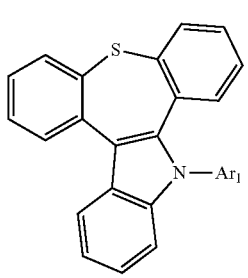

[Chemical Formula 18]

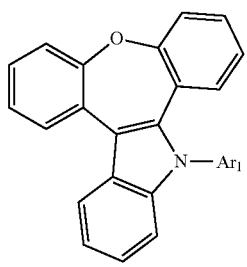

[Chemical Formula 19]

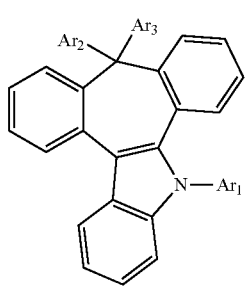

[Chemical Formula 20]

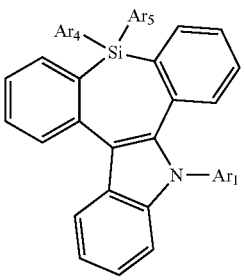

In Chemical Formulae 12 to 20,

Ar$_1$ to Ar$_5$ are each the same as those defined in Chemical Formula 1, and a plurality of Ar$_1$ is the same as or different from each other.

Examples of the compound represented by Chemical Formula 1 according to the present disclosure include Compounds A-1 to A-23, Compounds B-1 to B-23, Compounds C-1 to C-23, Compounds D-1 to D-23, Compounds E-1 to E-23, Compounds F-1 to F-23, Compounds G-1 to G-23, Compounds H-1 to H-23, Compounds I-1 to I-23, Compounds J-1 to J-10, Compounds K-1 to K-10, Compounds L-1 to L-3, Compounds M-1 to M-3, Compounds N-1 to N-3, Compounds O-1 to O-3, Compounds P-1 to P-16, Compounds Q-1 to Q41, but the examples are not limited thereto.

A-1

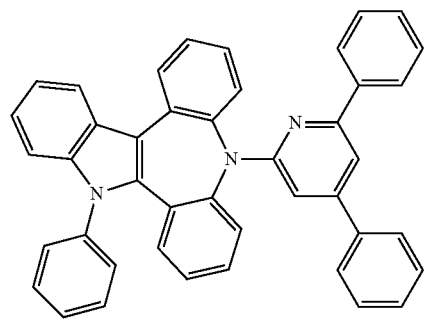

A-2

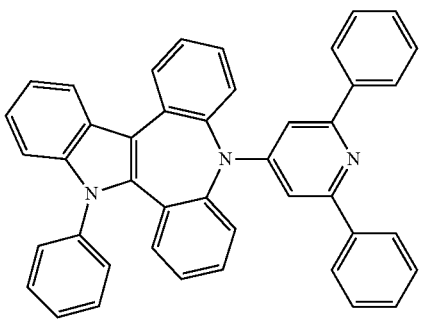

A-3

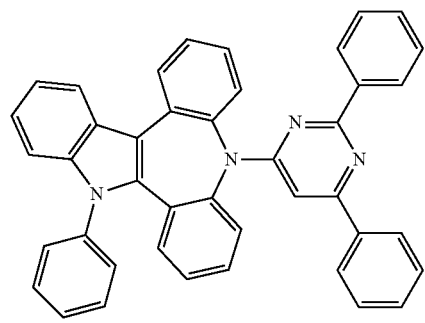

A-4

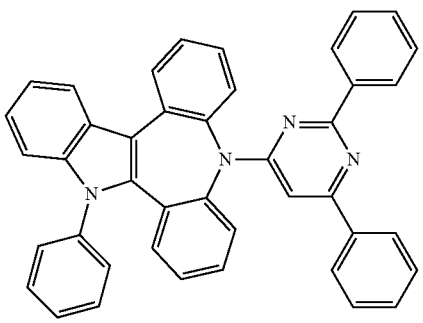

-continued
A-5
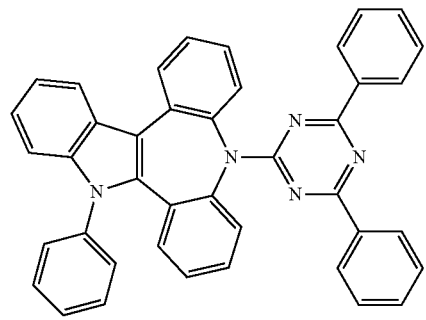
A-6
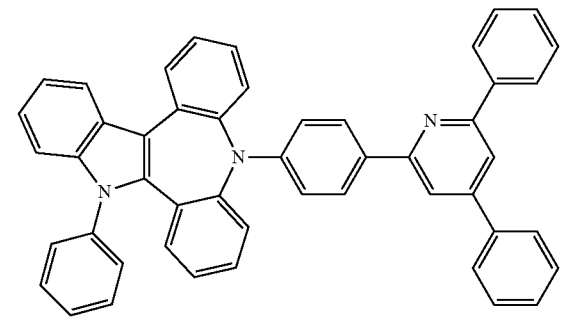
A-7
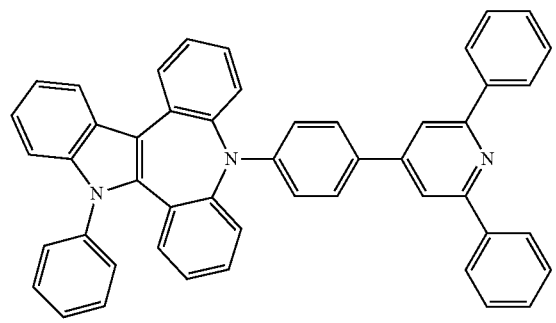
A-8
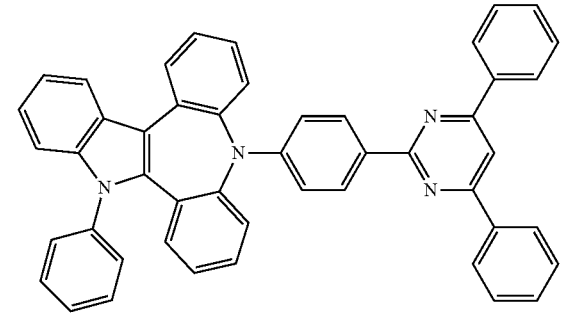
A-9
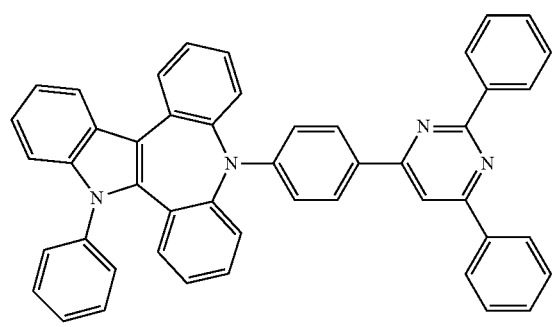
A-10
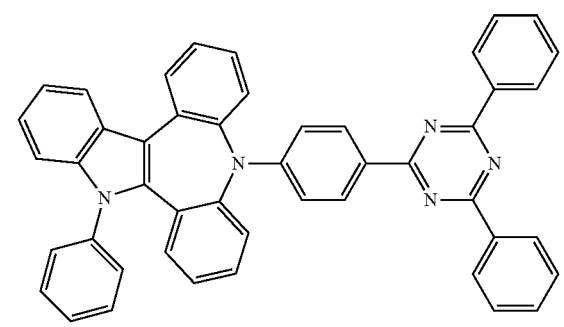
A-11
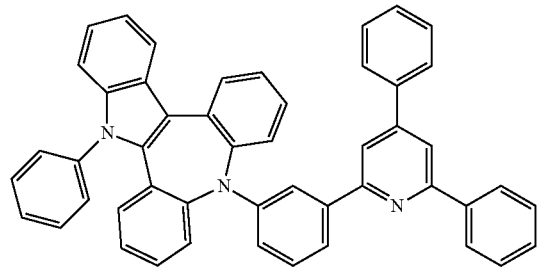
A-12
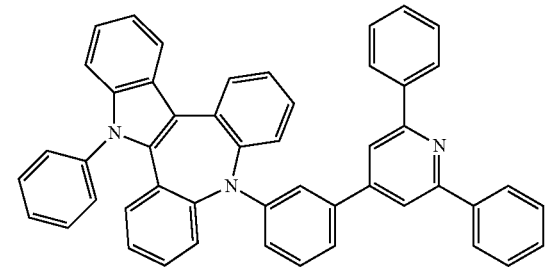
A-13
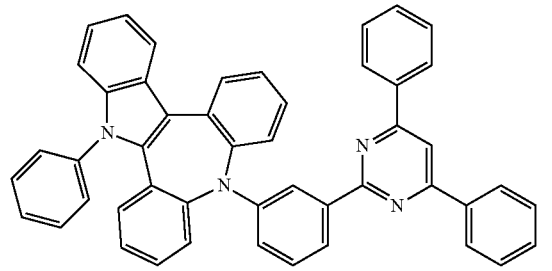
A-14
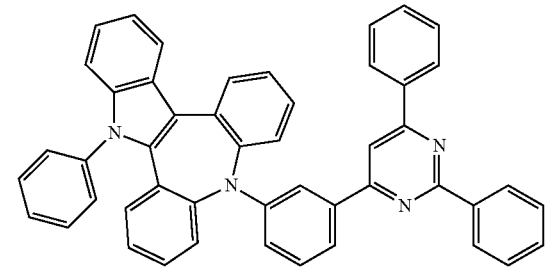

-continued
A-15
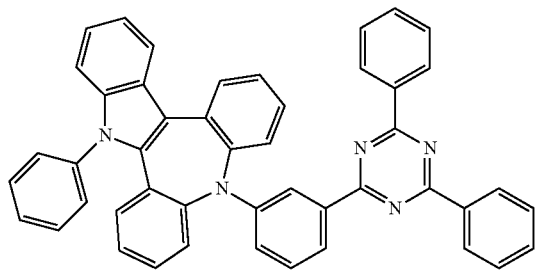
A-16
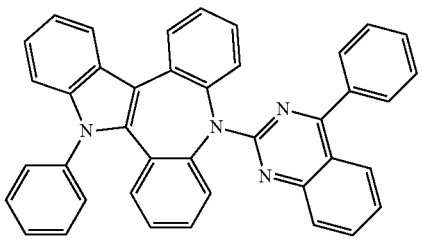
A-17
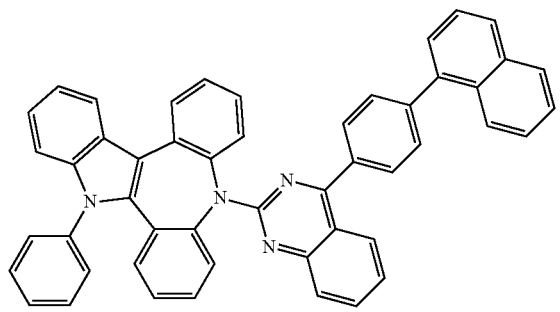
A-18
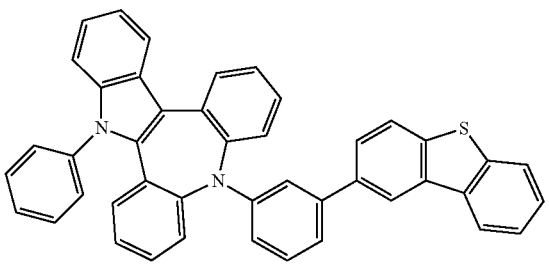
A-19
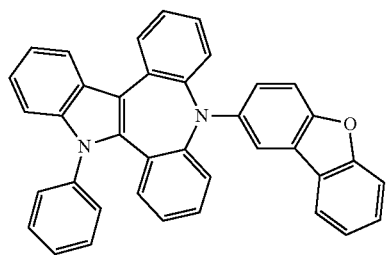
A-20
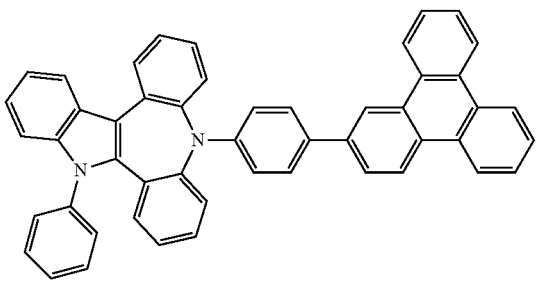
A-21
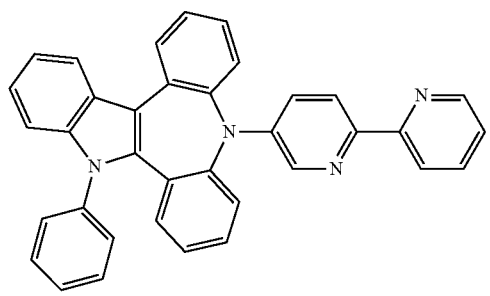
A-22
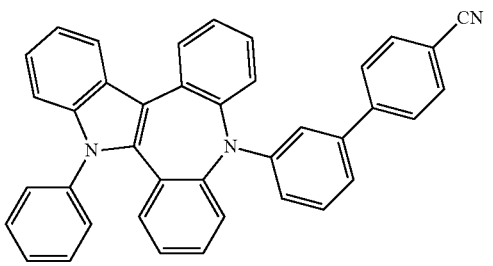
A-23
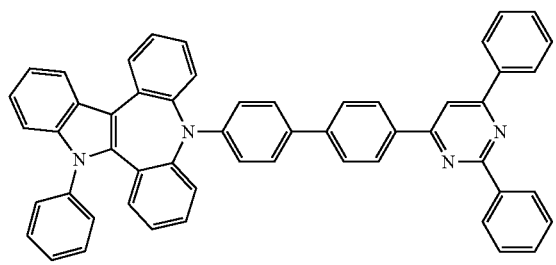
B-1
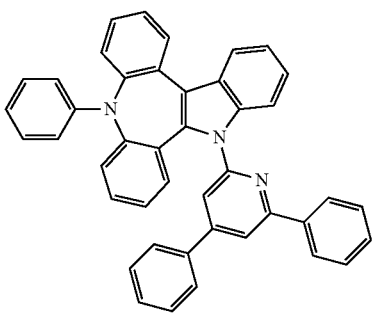

-continued
B-2
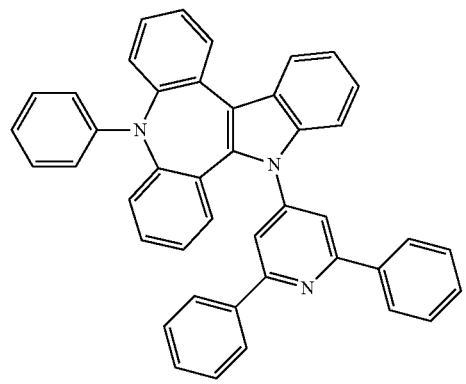
B-3
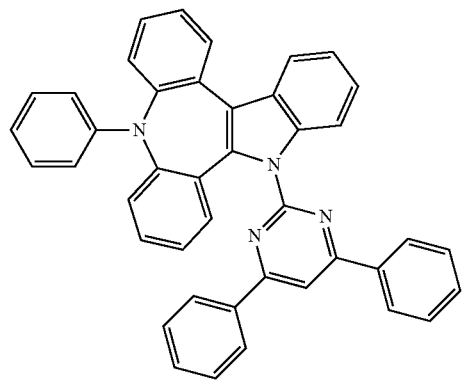
B-4
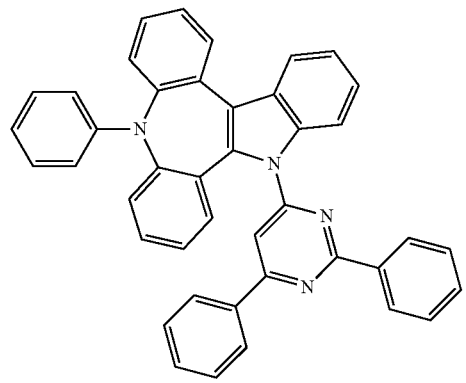
B-5
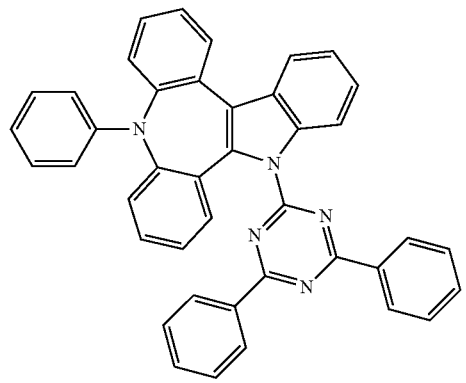
B-6
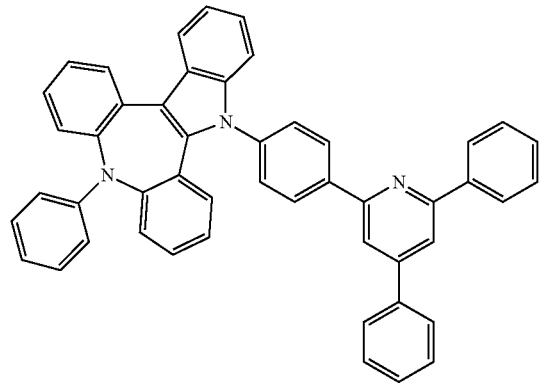
B-7
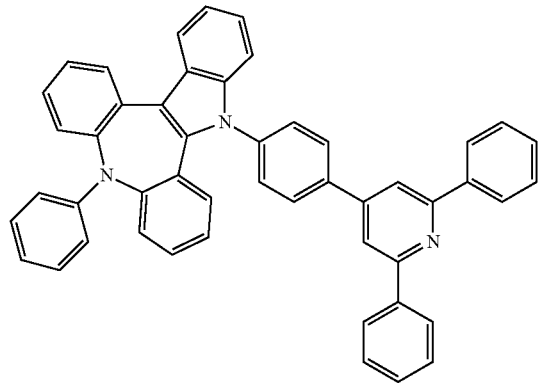
B-8
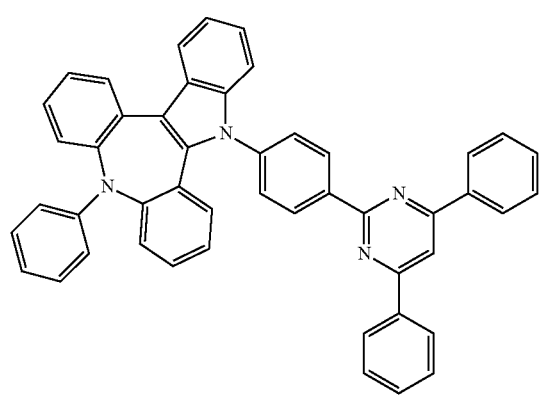
B-9
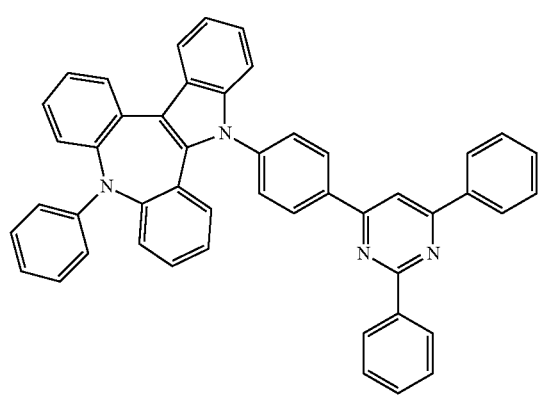

-continued
B-10
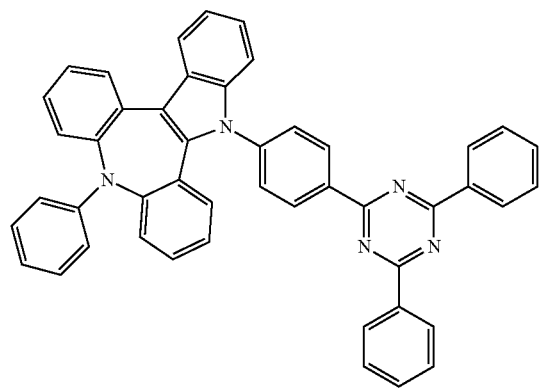
B-11
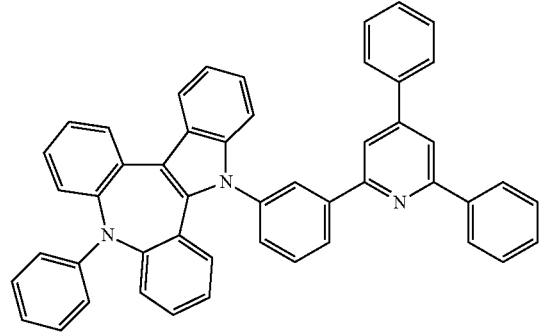
B-12
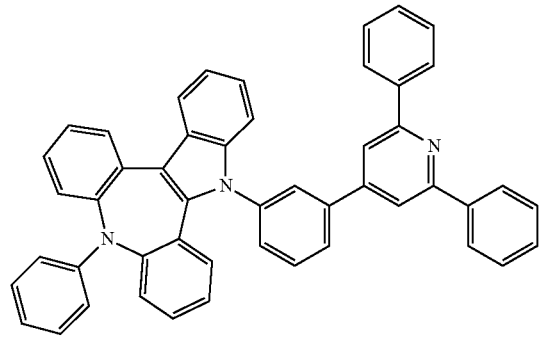
B-13
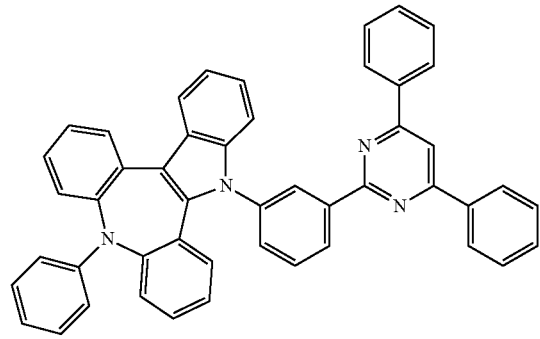
B-14
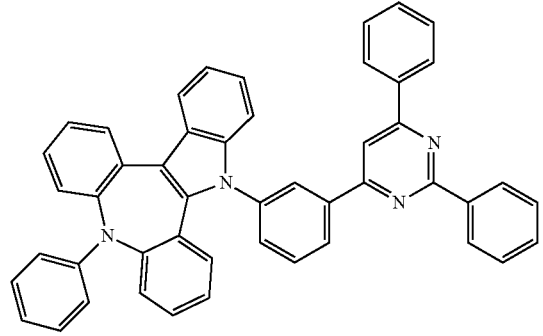
B-15
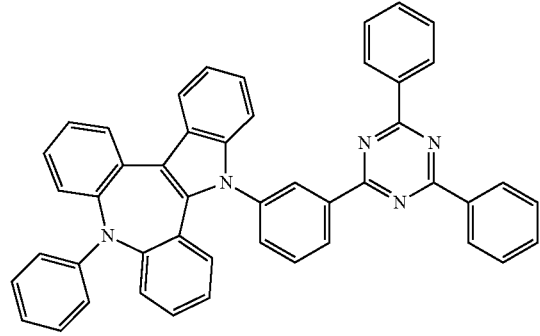
B-16
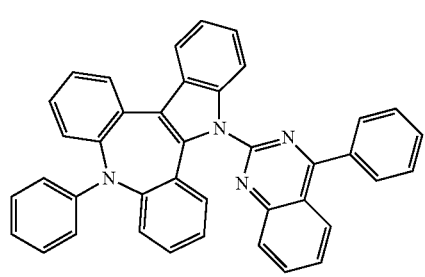
B-17
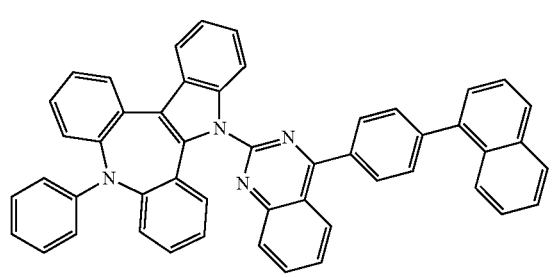

-continued
B-18
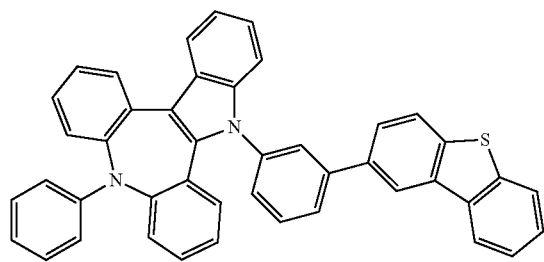
B-19
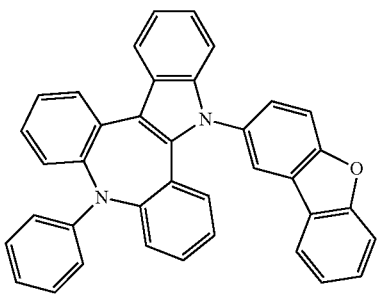
B-20
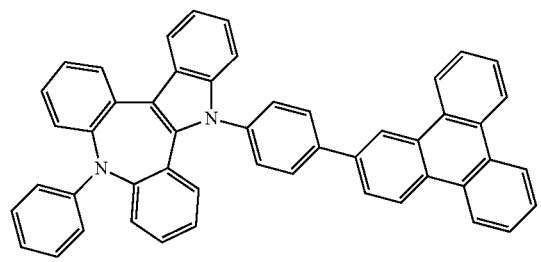
B-21
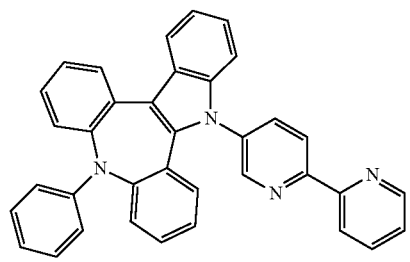
B-22
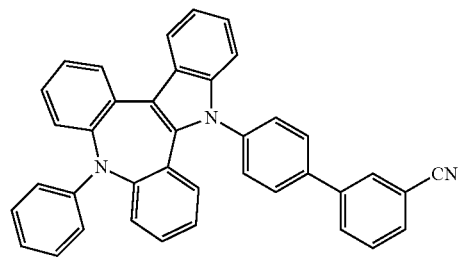
B-23
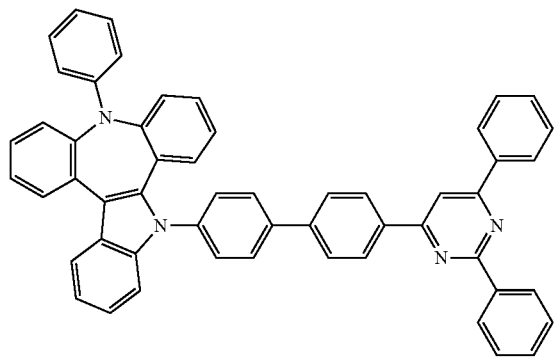
C-1
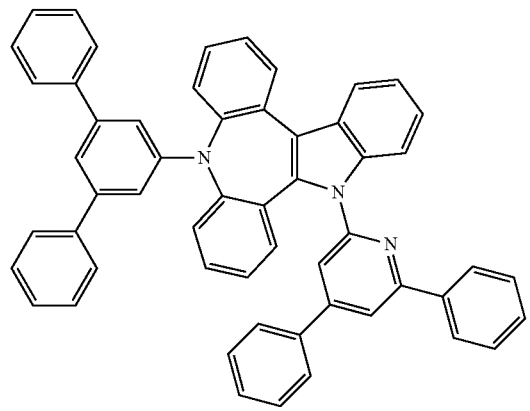
C-2
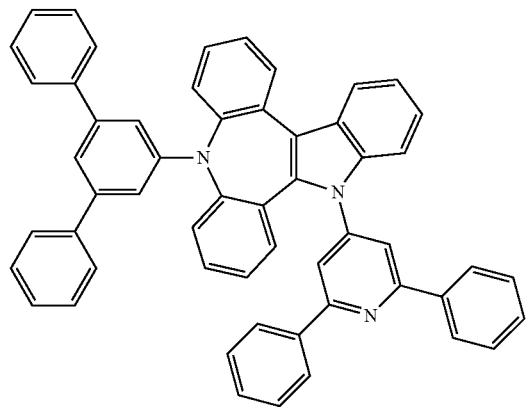

-continued
C-3
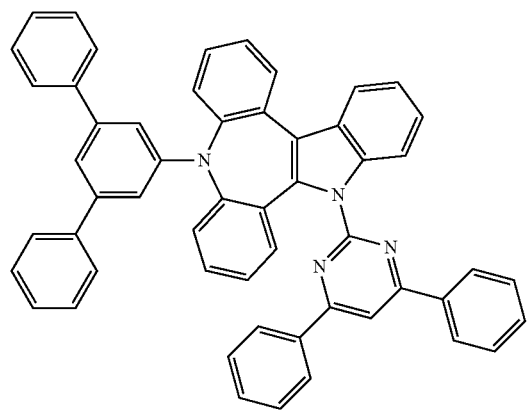
C-4
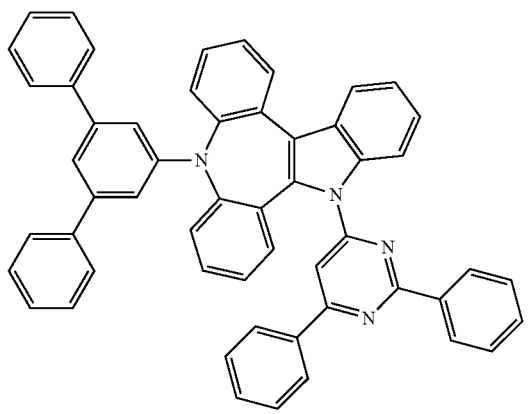
C-5
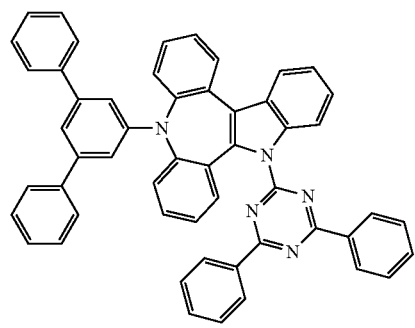
C-6
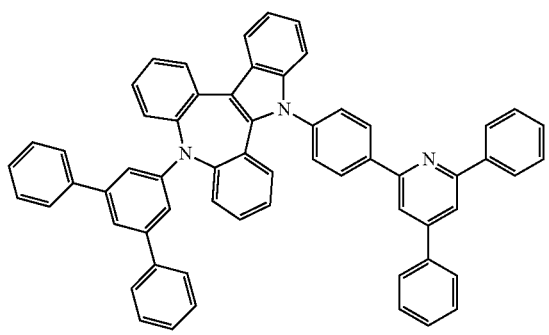
C-7
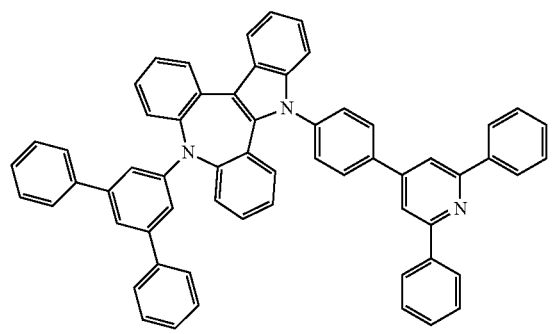
C-8
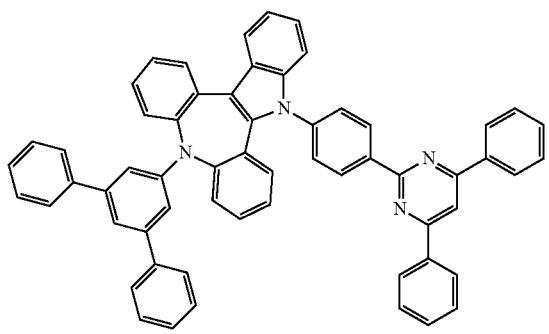
C-9
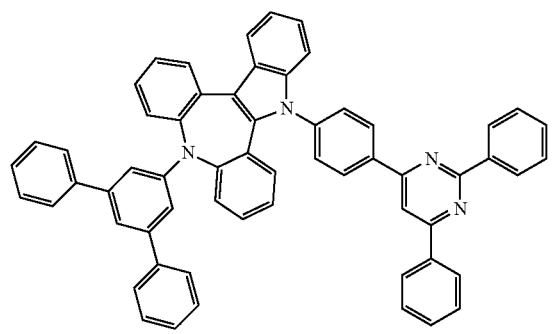
C-10
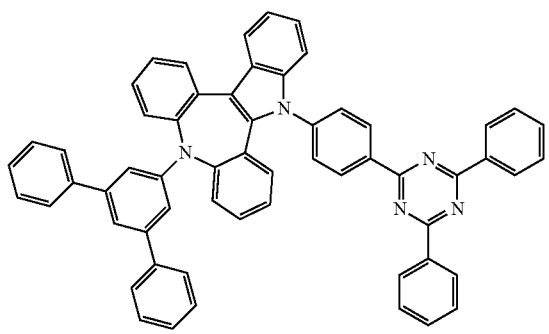

-continued
C-11
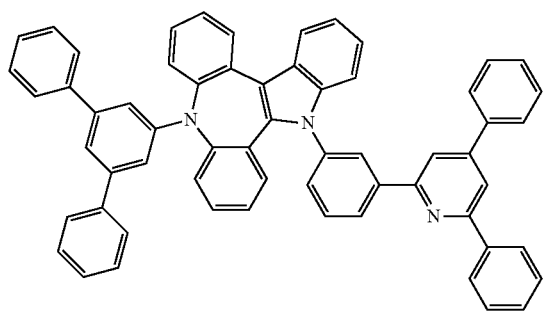
C-12
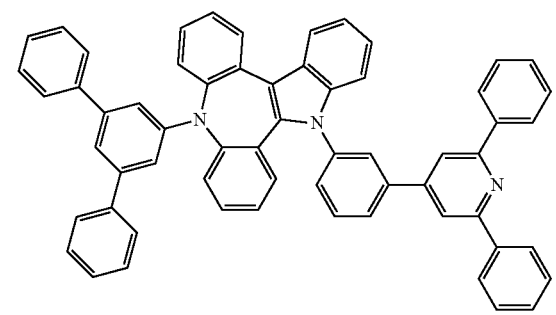
C-13
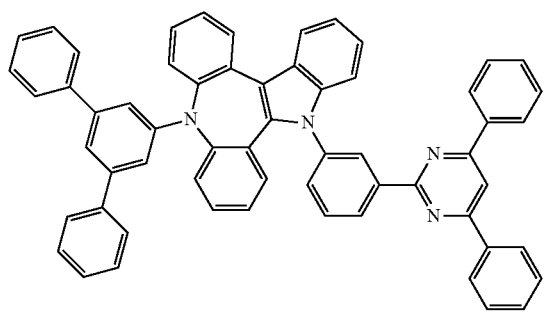
C-14
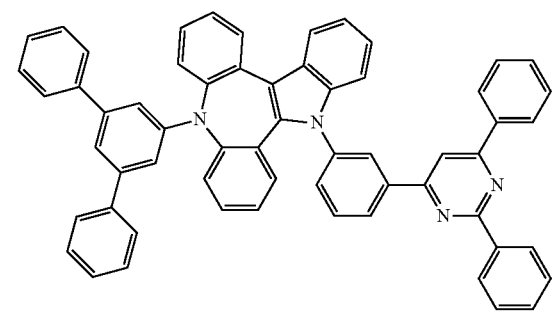
C-15
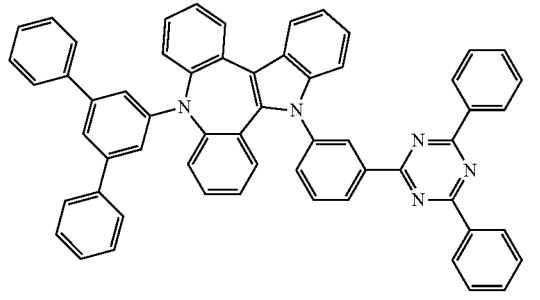
C-16
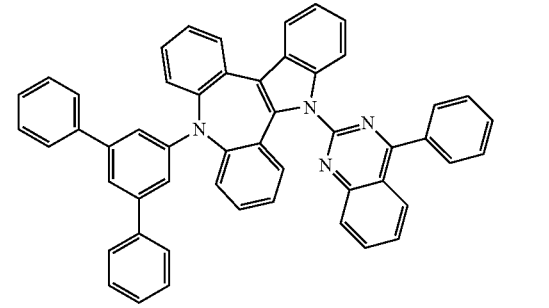
C-17
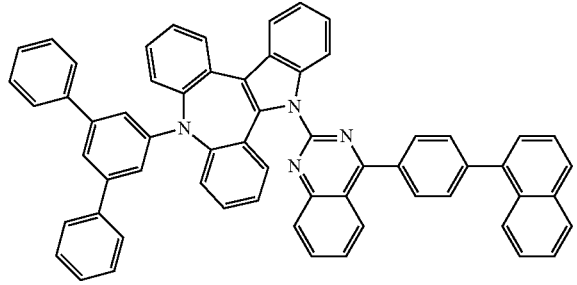
C-18
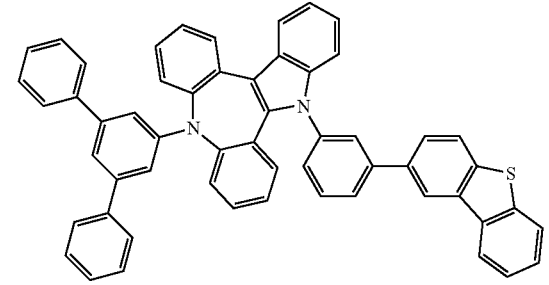
C-19
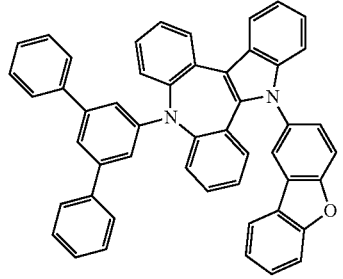
C-20
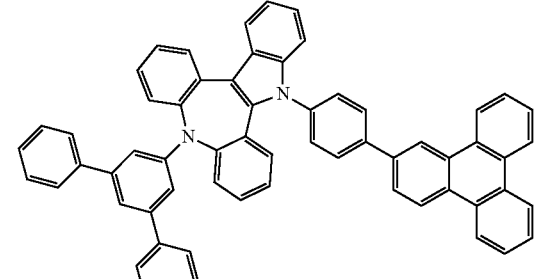

-continued
C-21
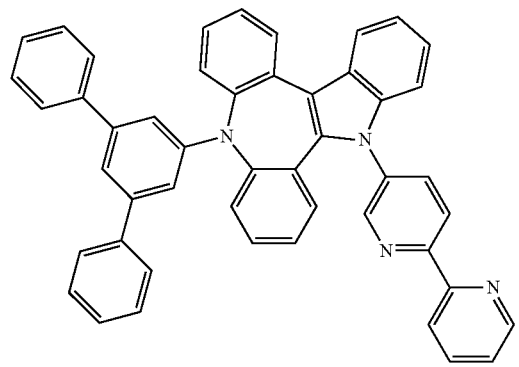
C-22
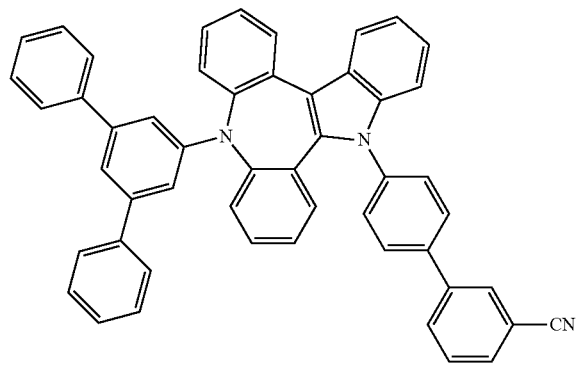
C-23
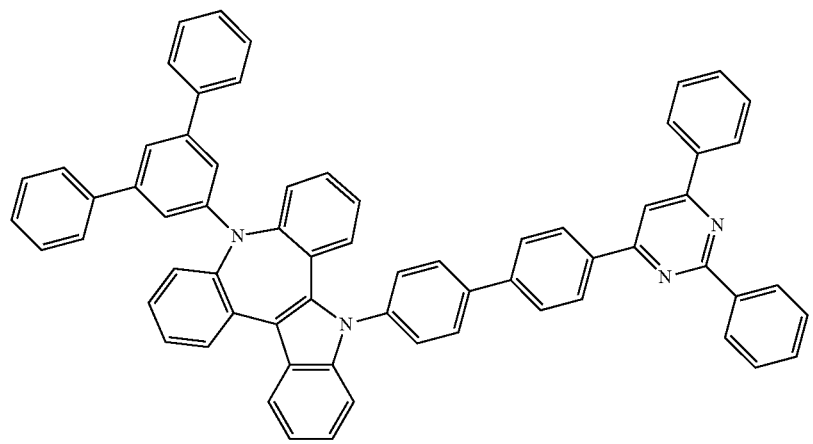
D-1
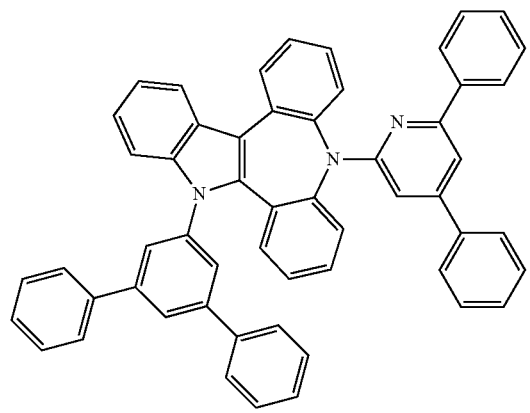
D-2
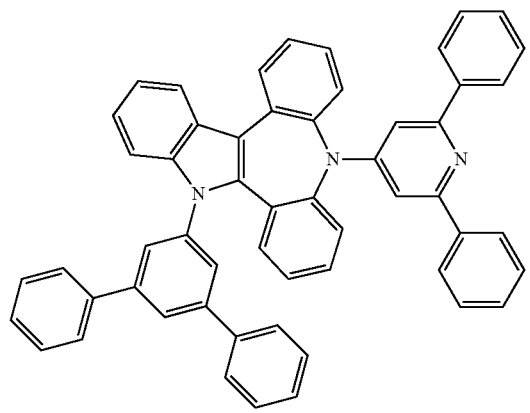
D-3
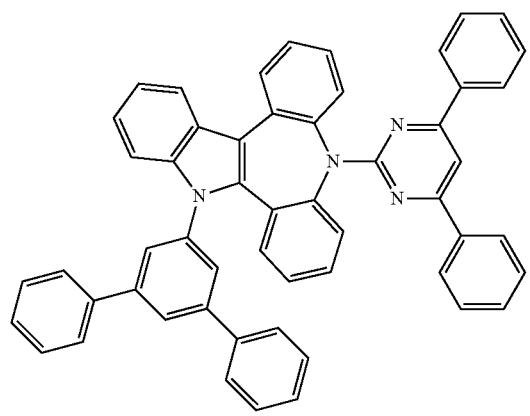
D-4
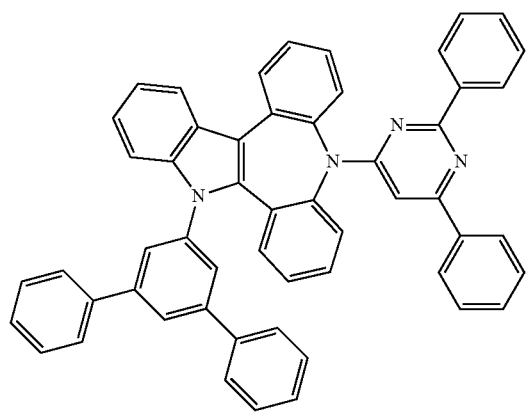

-continued
D-5
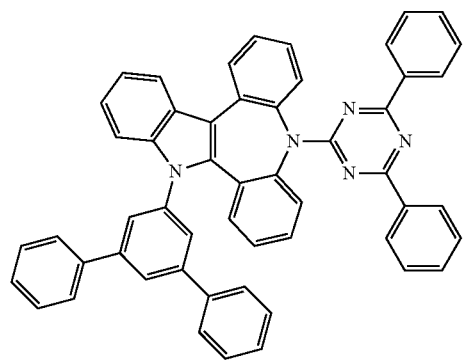
D-6
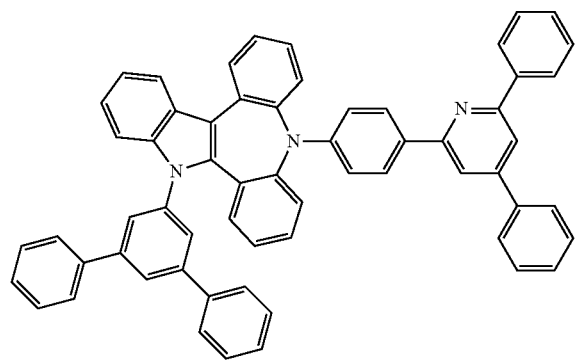
D-7
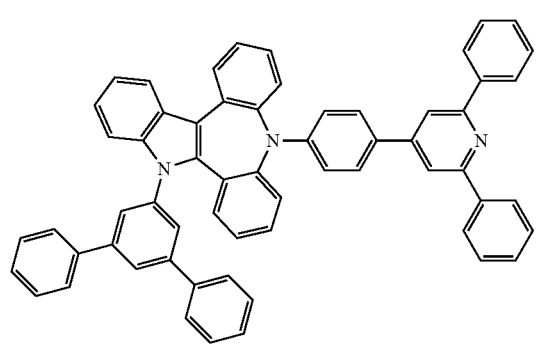
D-8
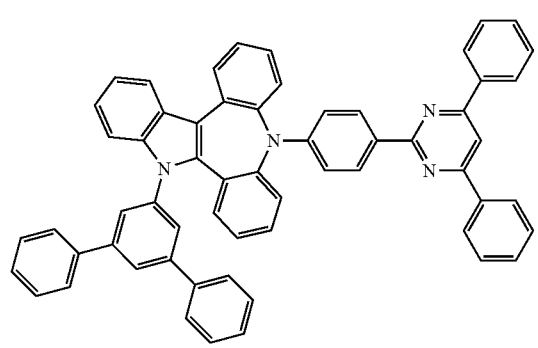
D-9
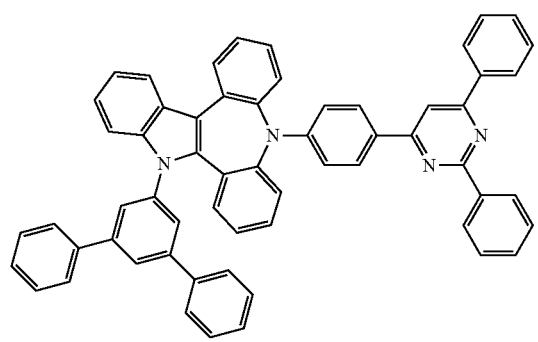
D-10
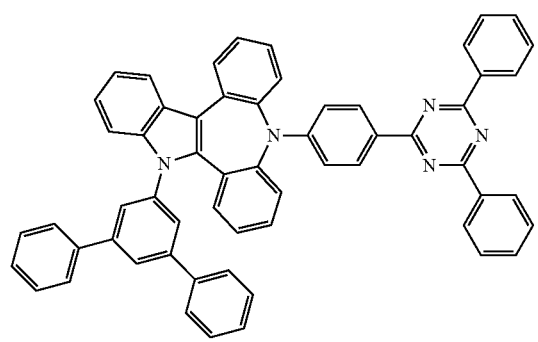
D-11
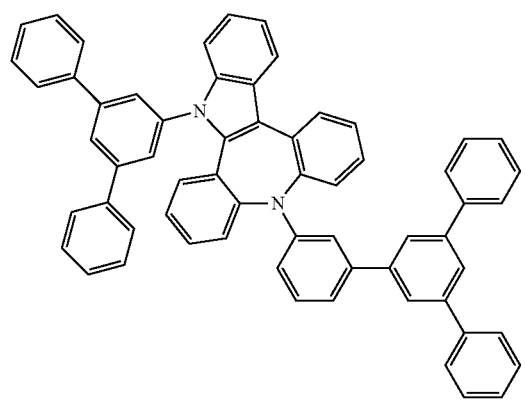
D-12
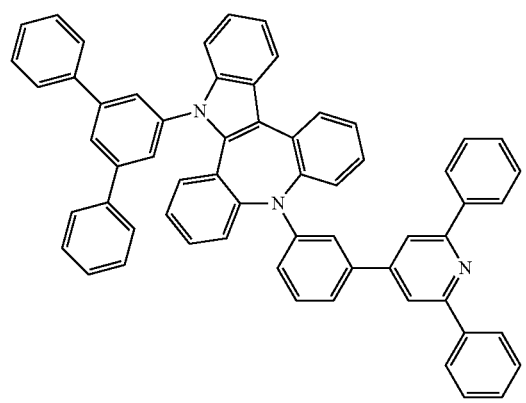

-continued
D-13
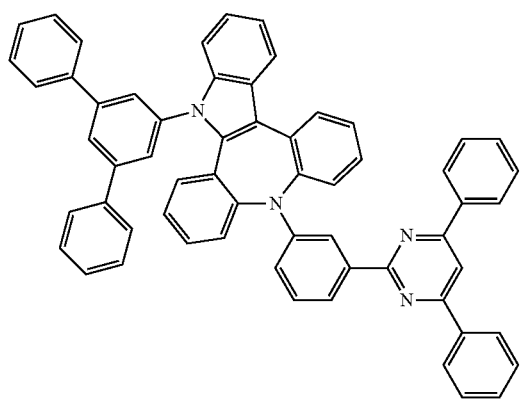
D-14
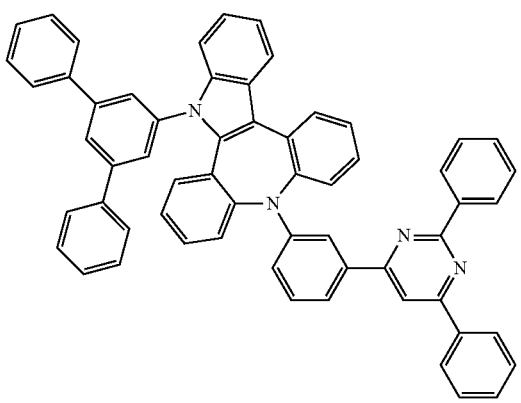
D-15
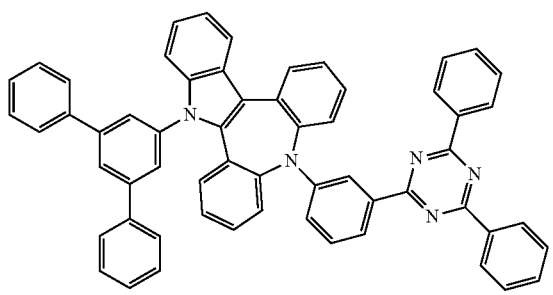
D-16
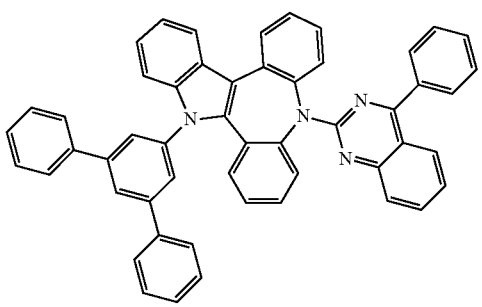
D-17
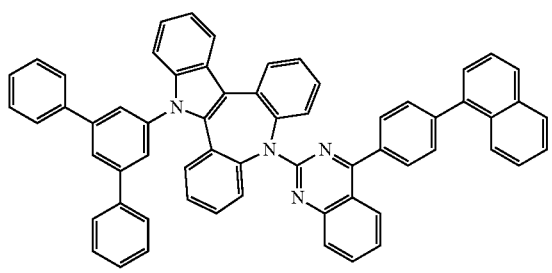
D-18
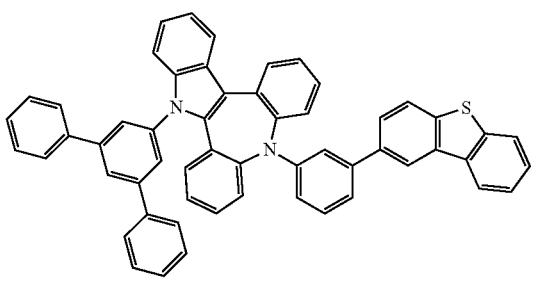
D-19
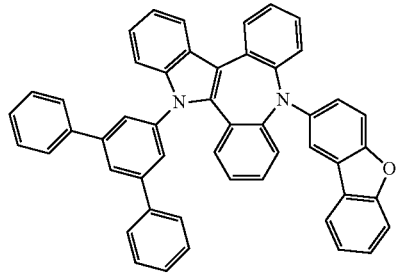
D-20
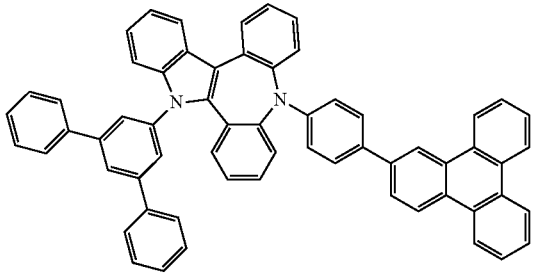
D-21
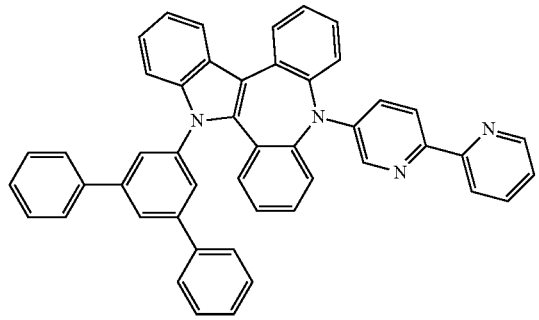
D-22
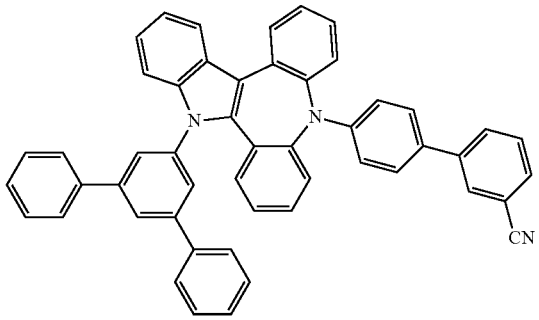

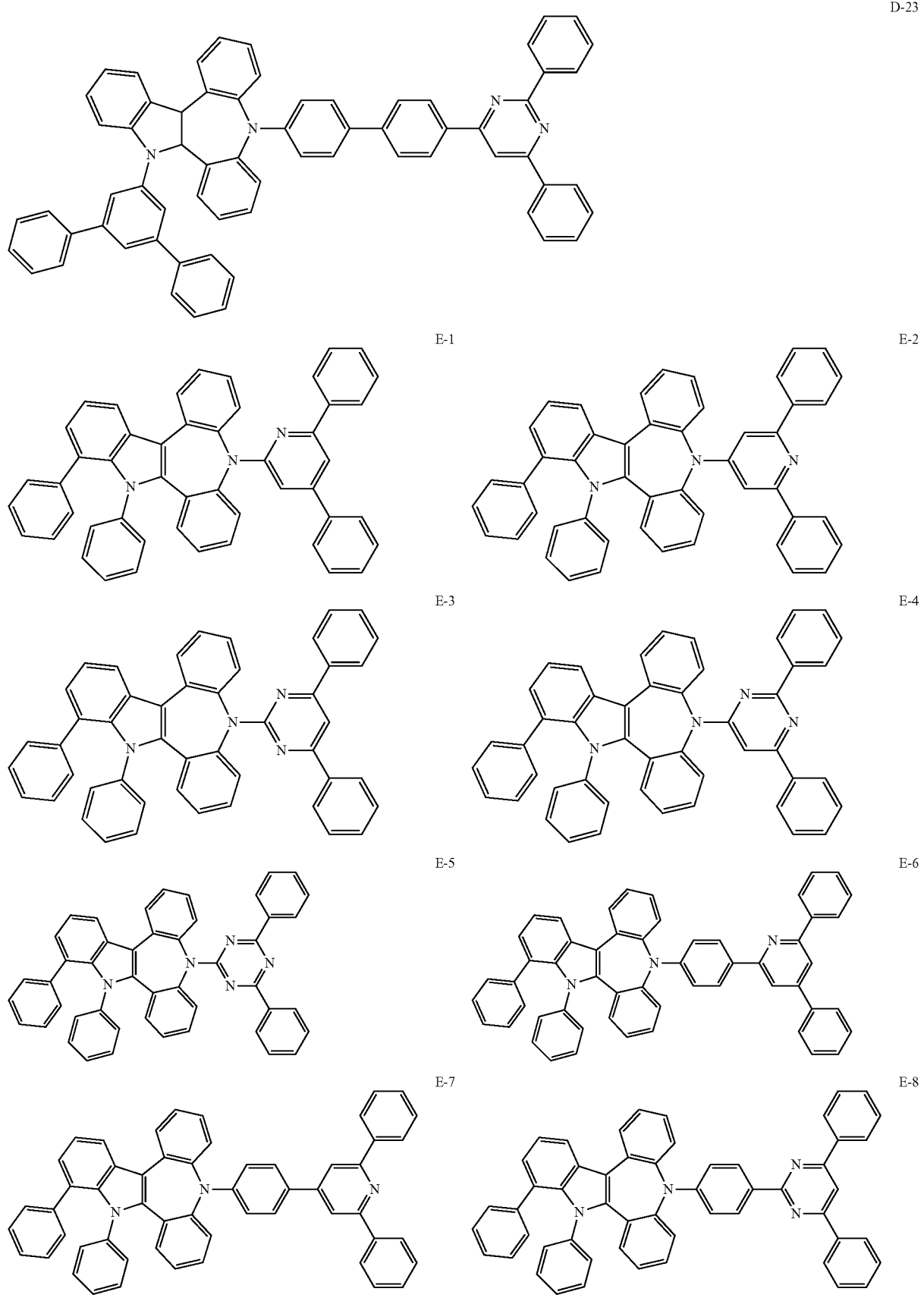

-continued
E-9
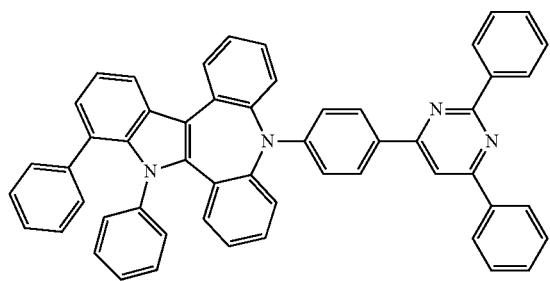
E-10
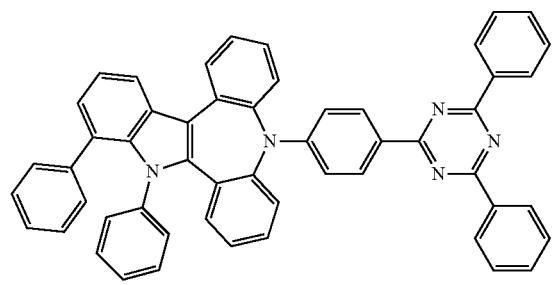
E-11
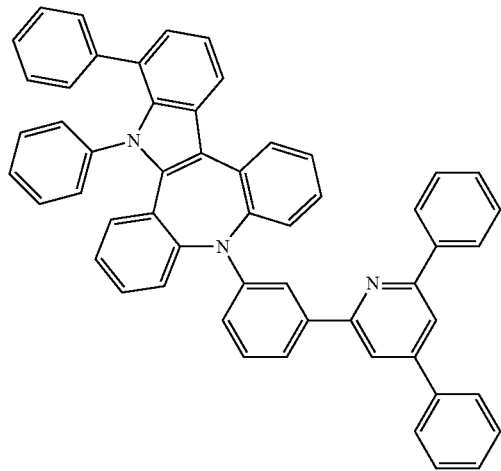
E-12
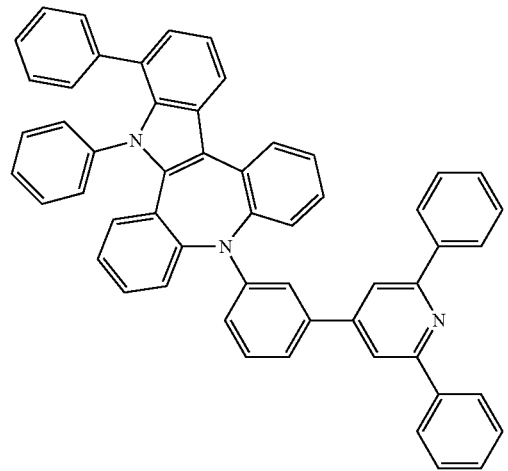
E-13
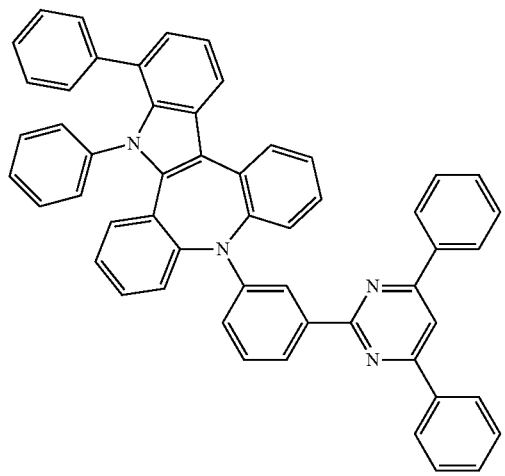
E-14
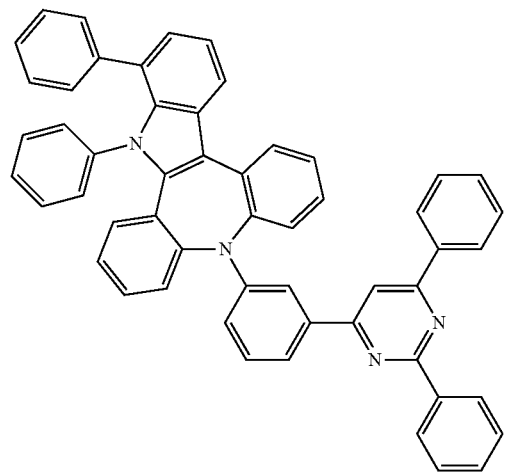

-continued
E-15
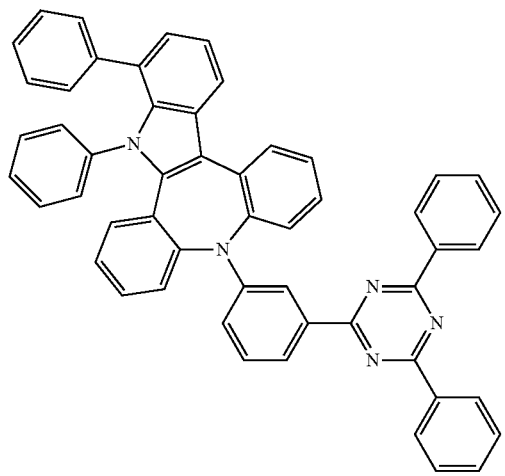
E-16
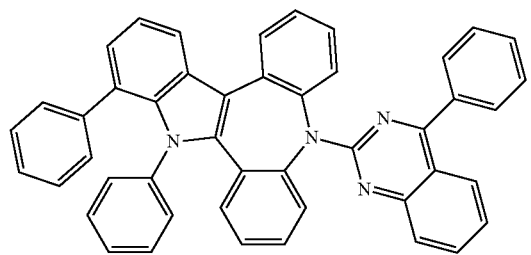
E-17
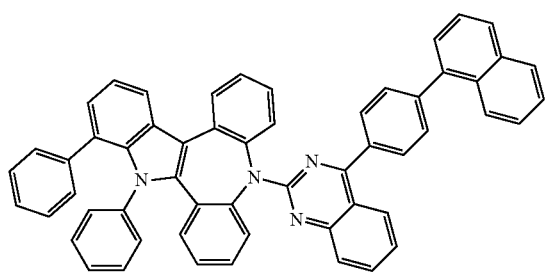
E-18
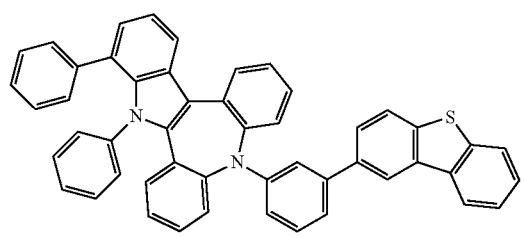
E-19
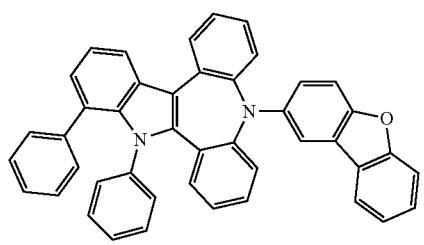
E-20
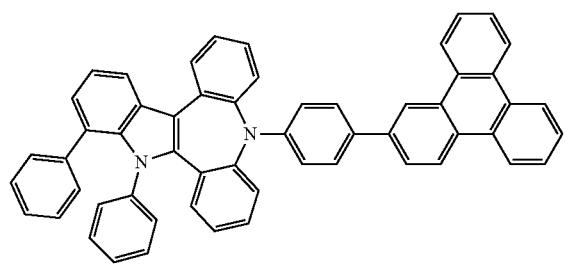
E-21
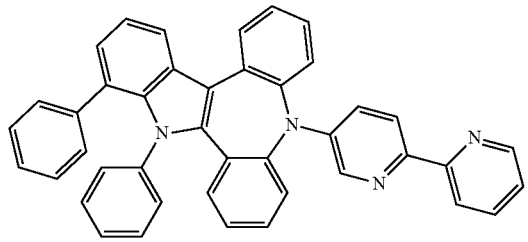
E-22
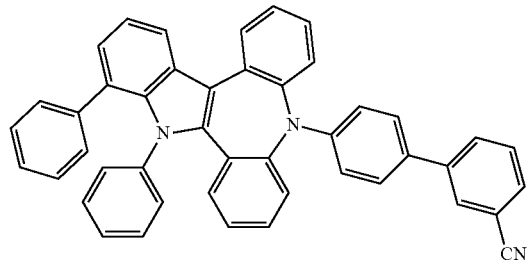
E-23
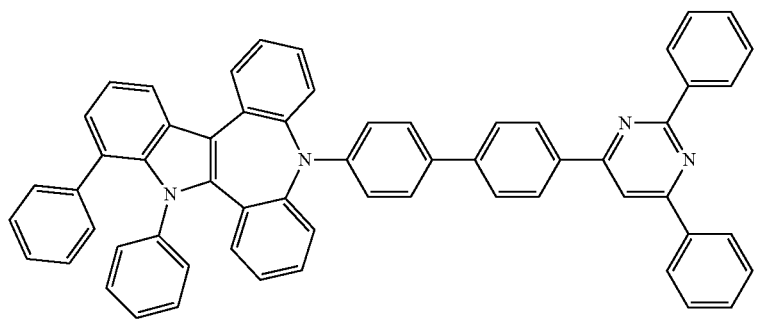

-continued
F-1
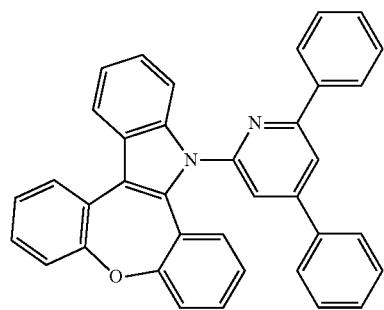
F-2
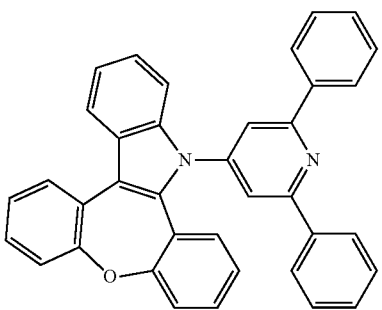
F-3
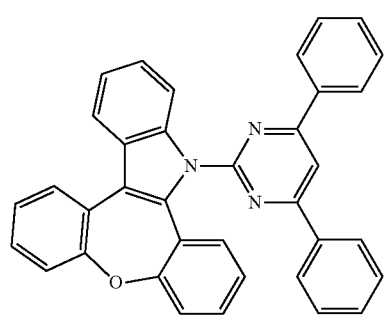
F-4
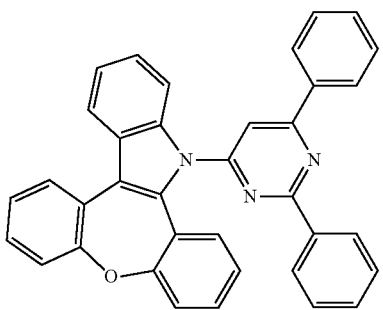
F-5
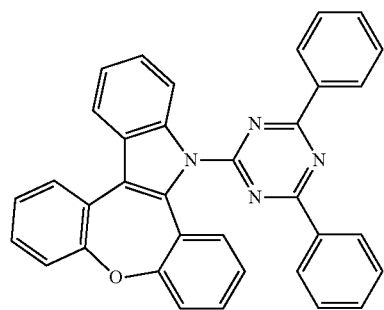
F-6
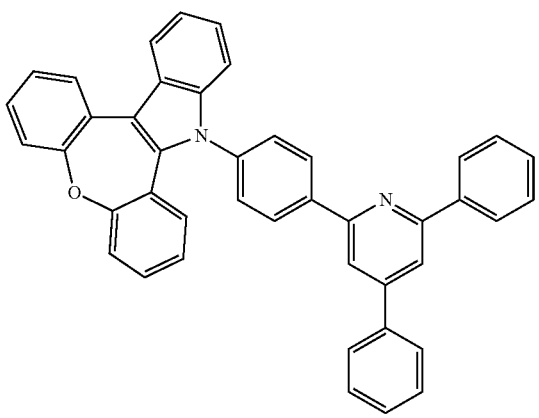
F-7
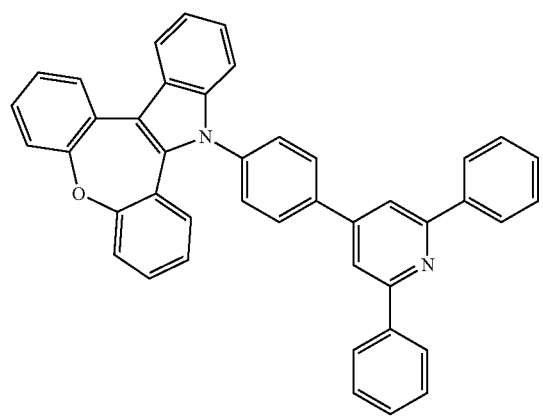
F-8
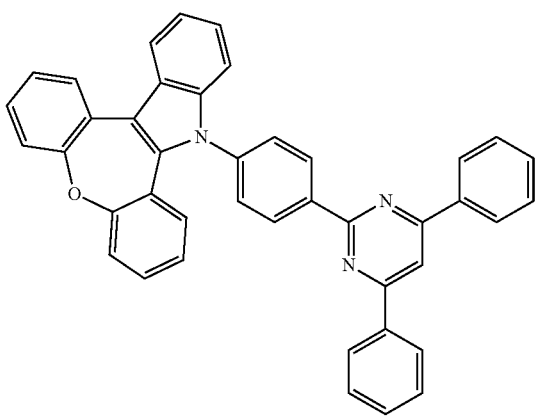

-continued
F-9
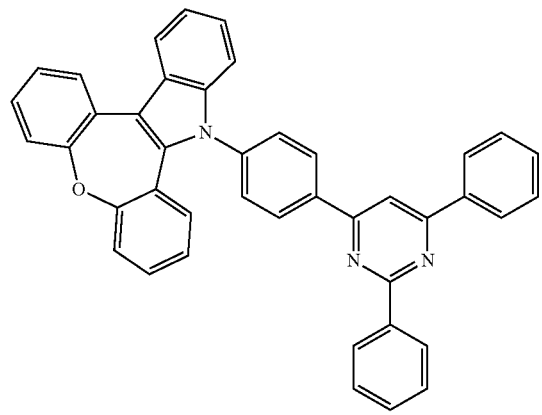
F-10
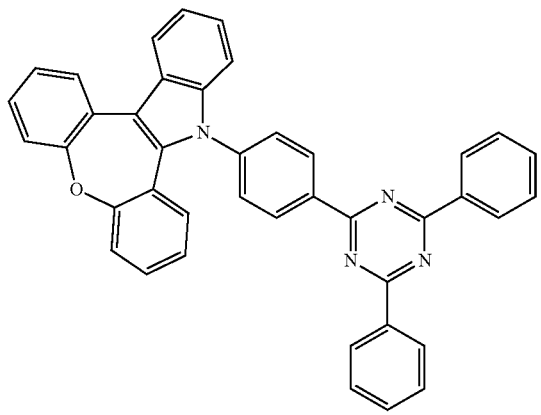
F-11
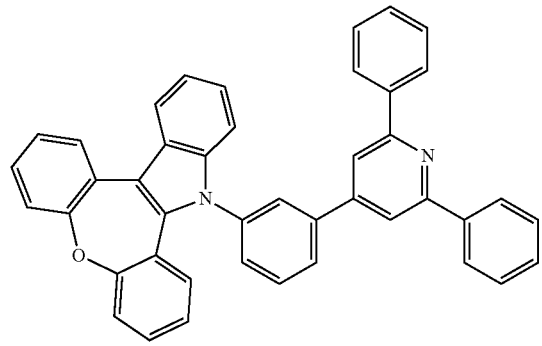
F-12
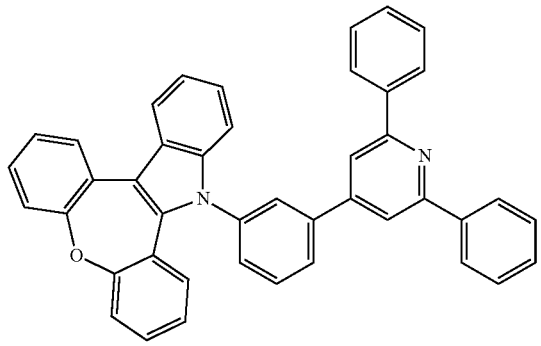
F-13
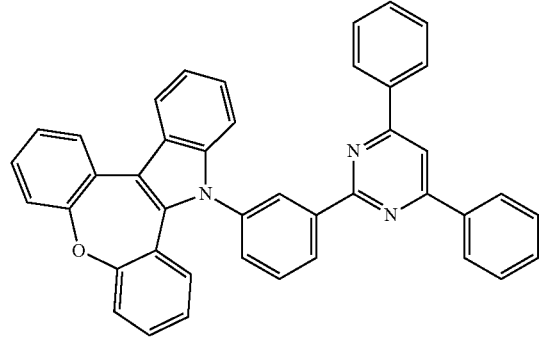
F-14
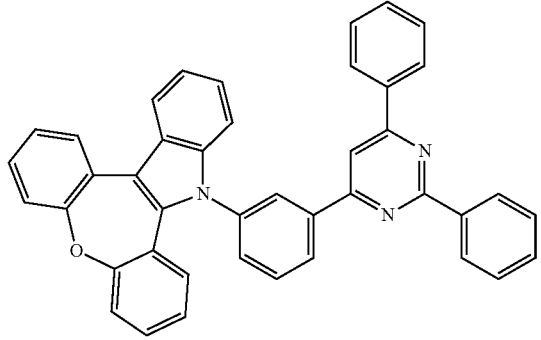
F-15
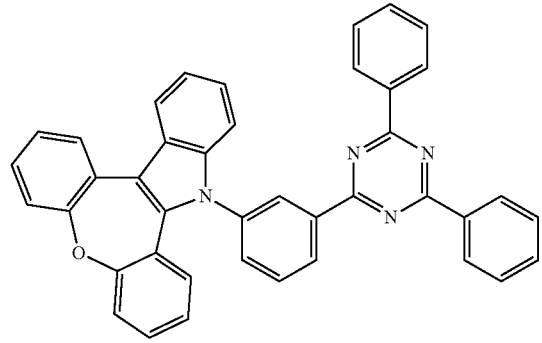
F-16
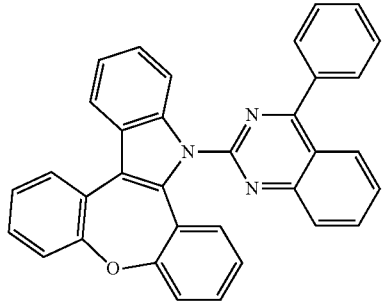

-continued
F-17
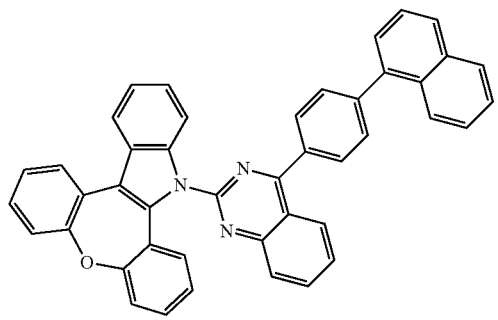
F-18
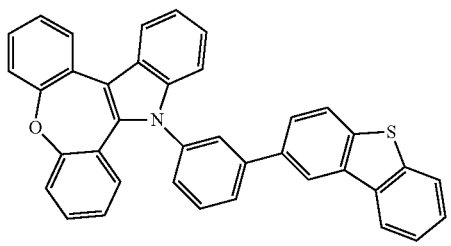
F-19
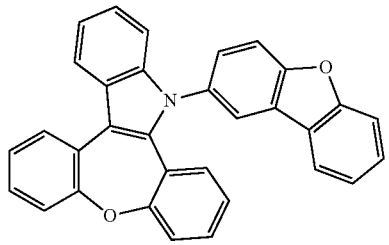
F-20
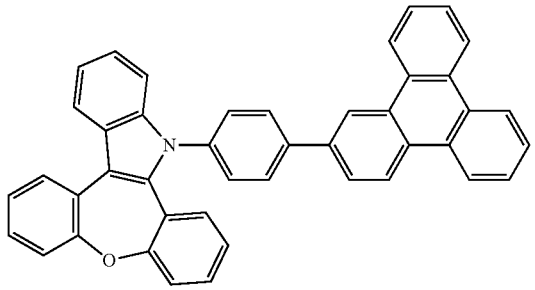
F-21
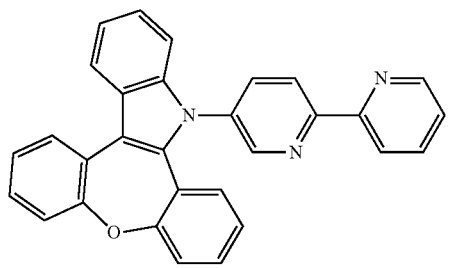
F-22
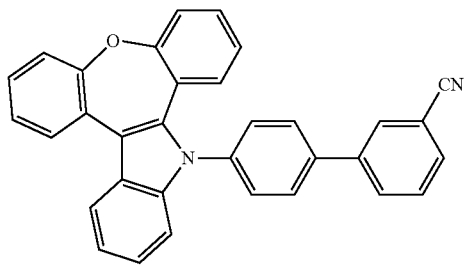
F-23
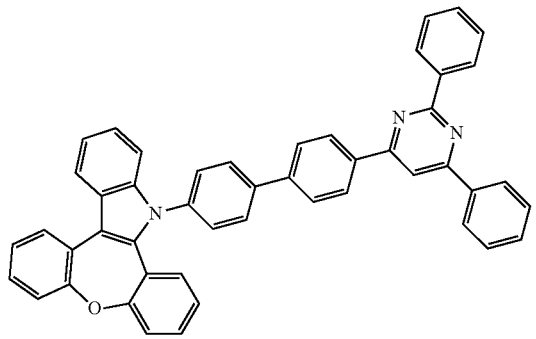
G-1
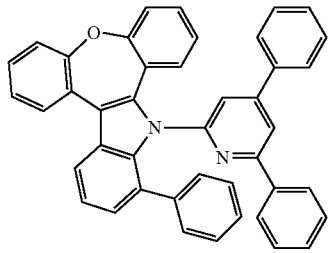
G-2
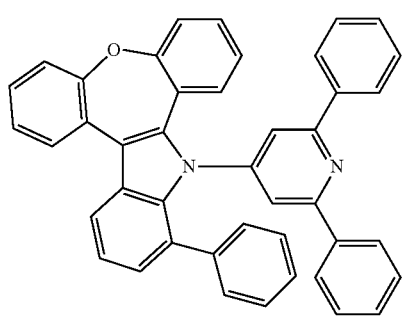
G-3
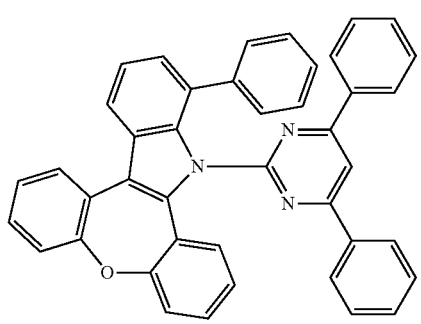

-continued
G-4
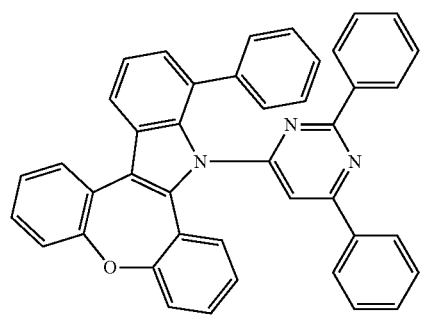
G-5
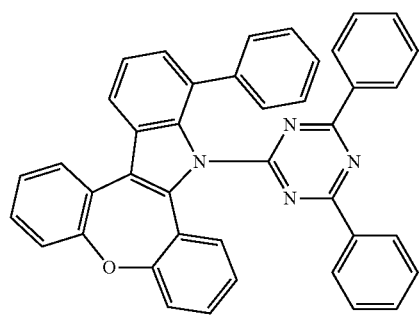
G-6
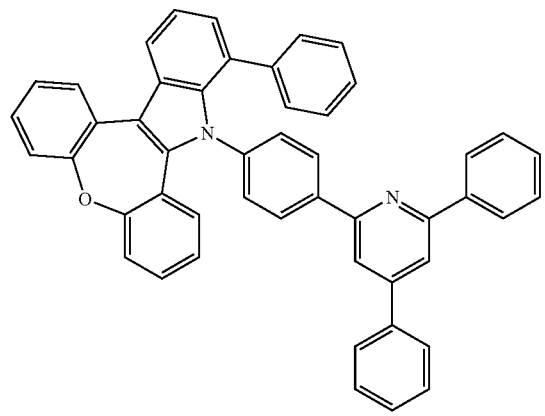
G-7
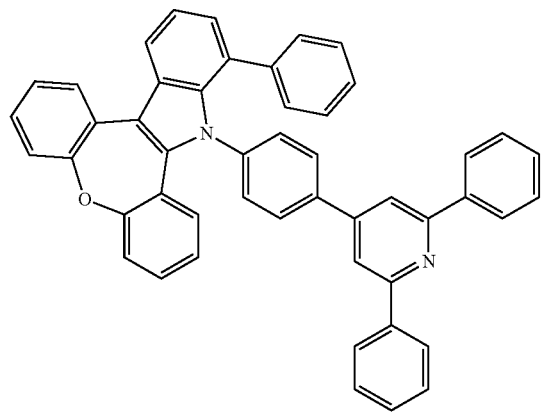
G-8
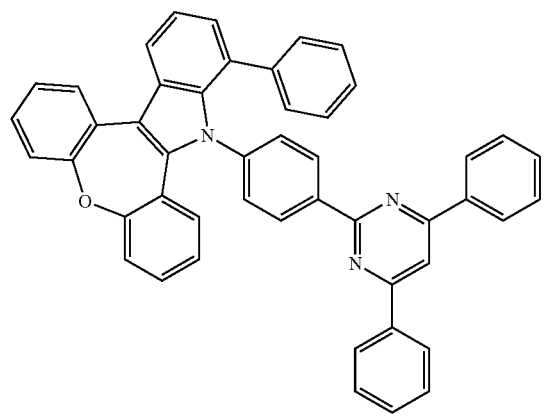
G-9
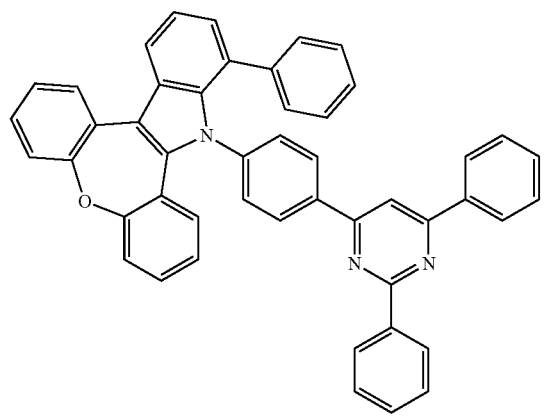
G-10
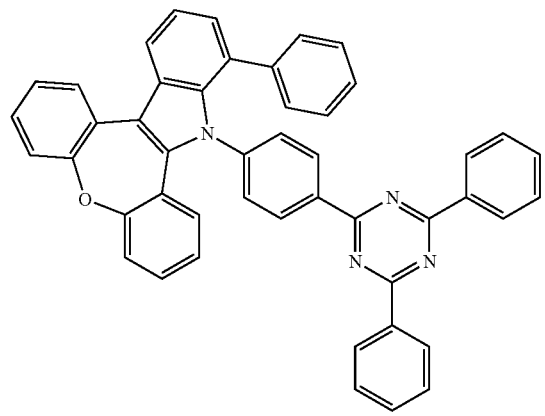
G-11
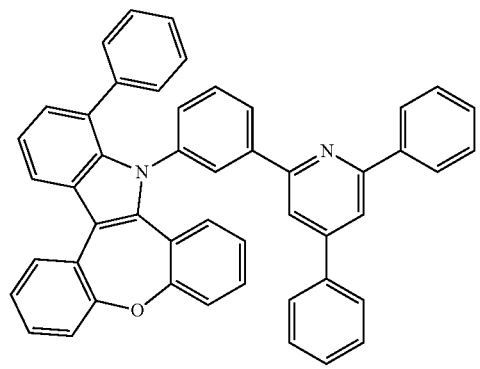

-continued
G-12
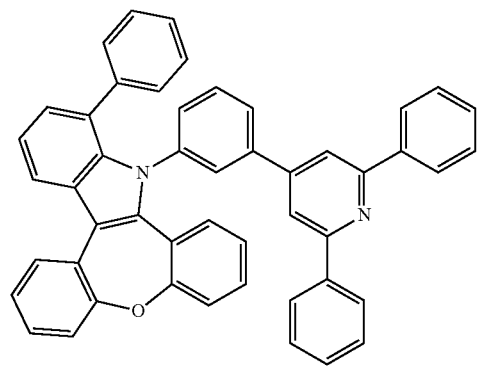
G-13
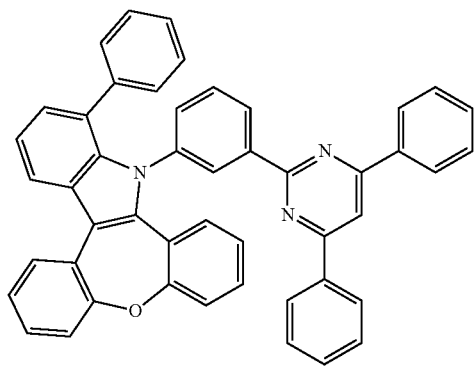
G-14
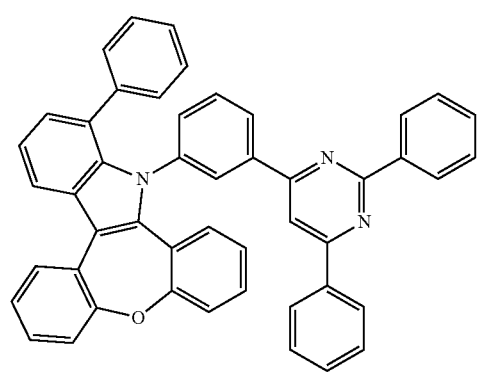
G-15
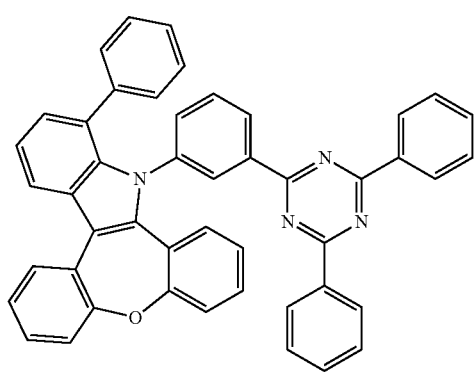
G-16
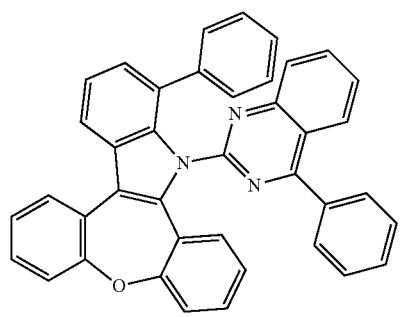
G-17
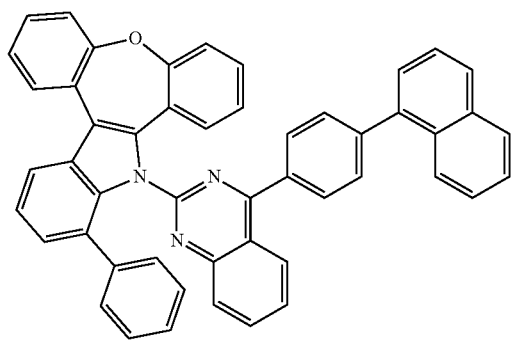
G-18
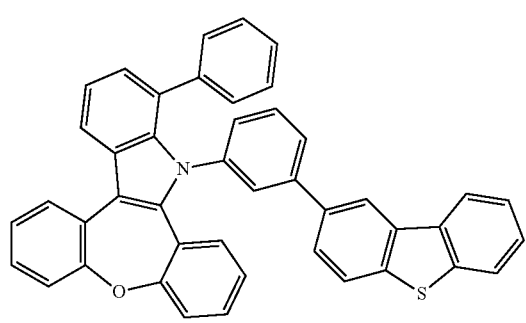
G-19
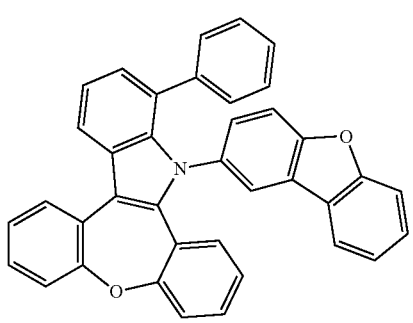

-continued
G-20
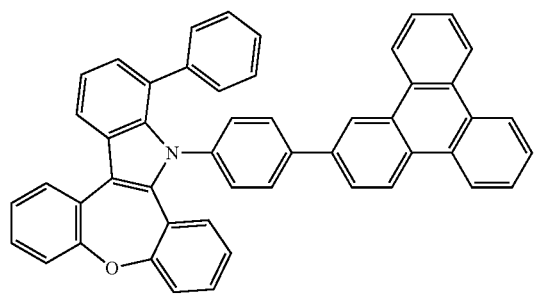
G-21
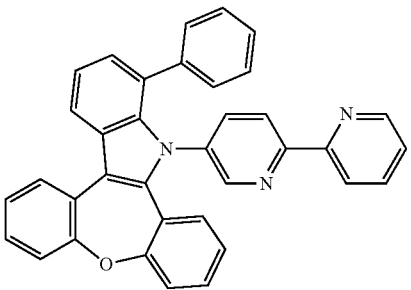
G-22
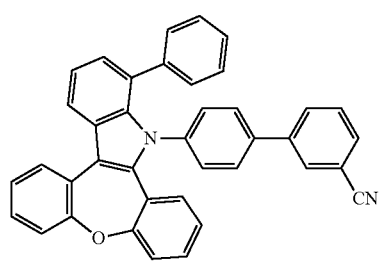
G-23
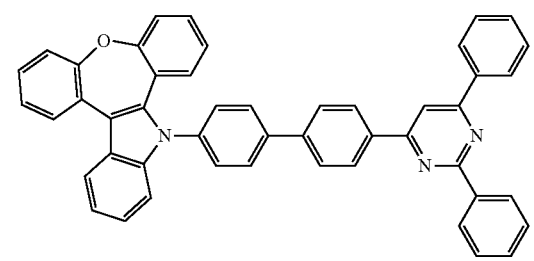
H-1
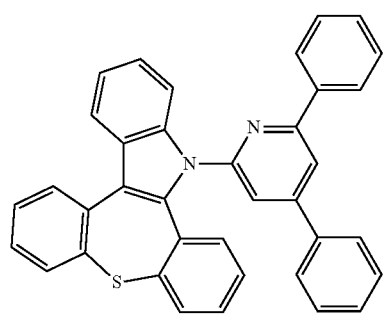
H-2
H-3
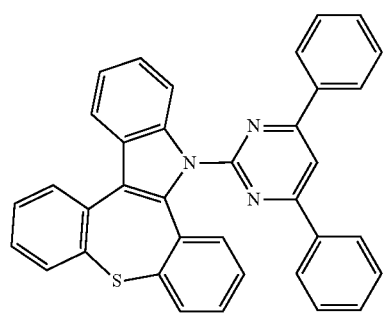
H-4
H-5
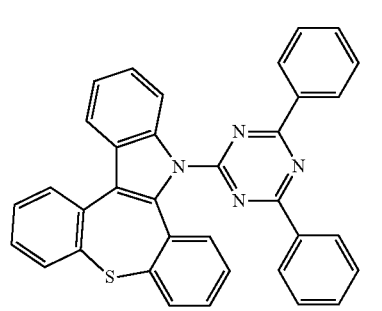
H-6
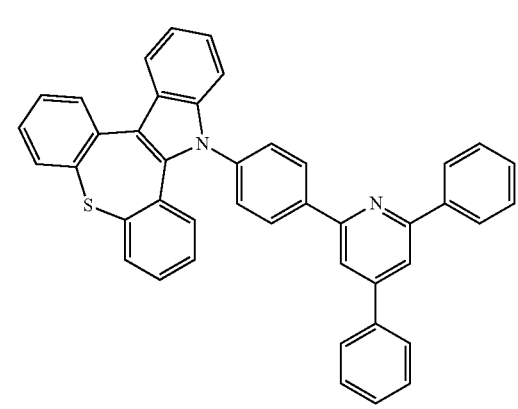

-continued
H-7
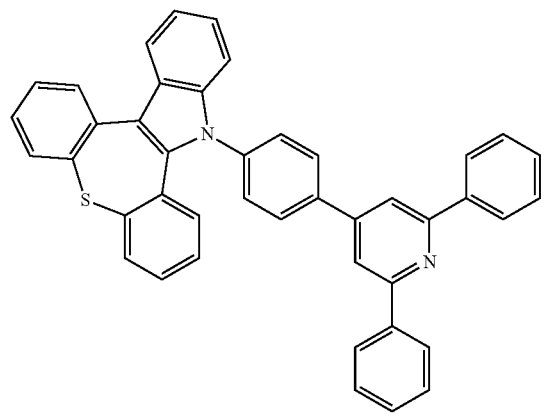
H-8
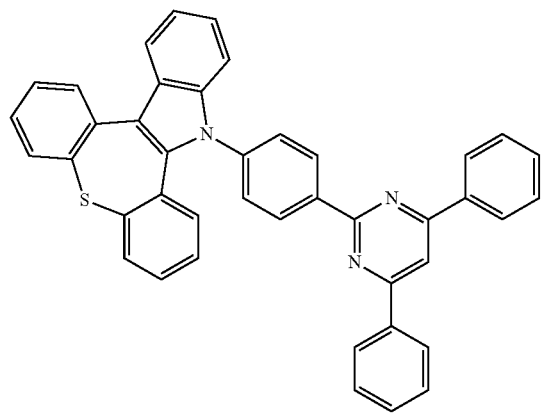
H-9
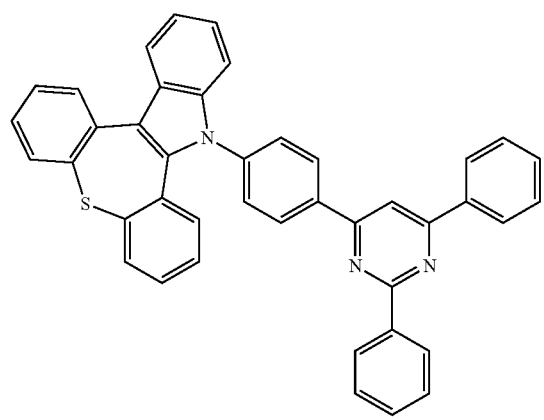
H-10
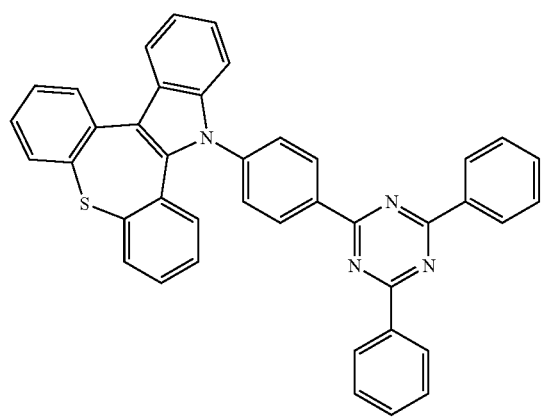
H-11
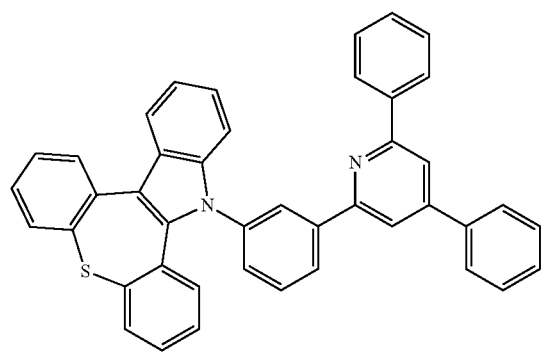
H-12
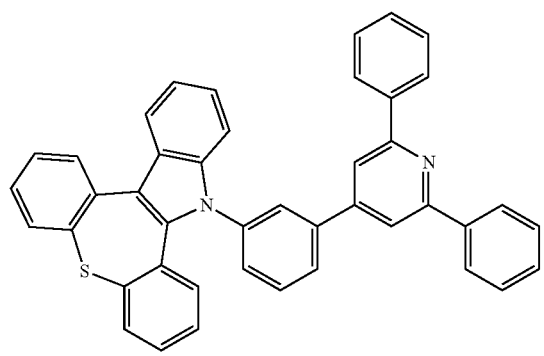
H-13
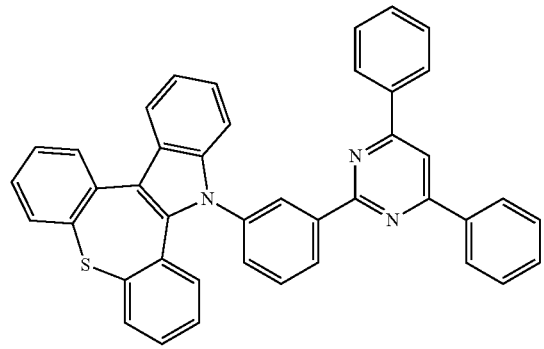
H-14
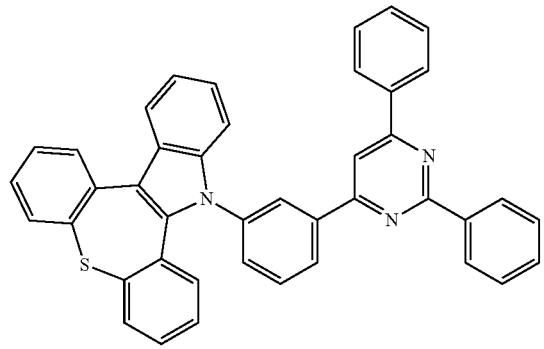

-continued
H-15
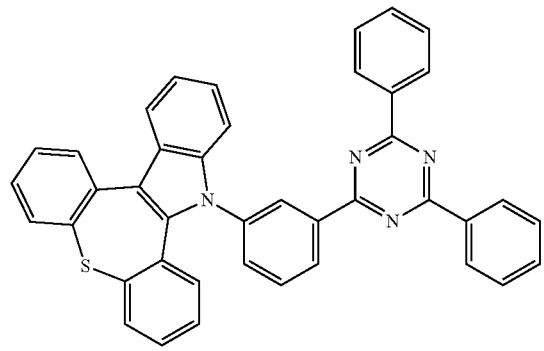
H-16
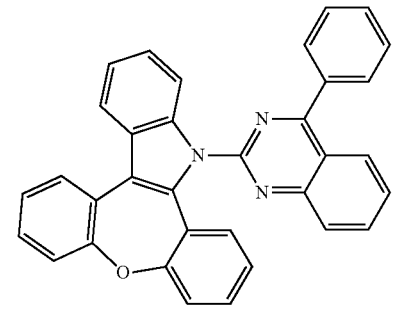
H-17
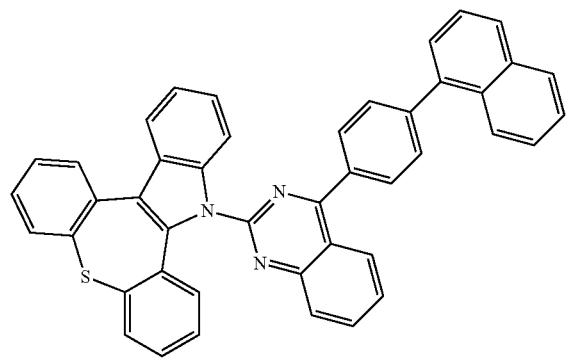
H-18
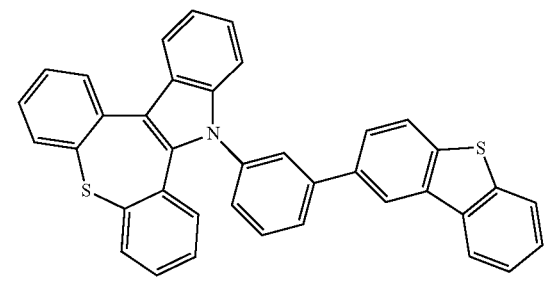
H-19
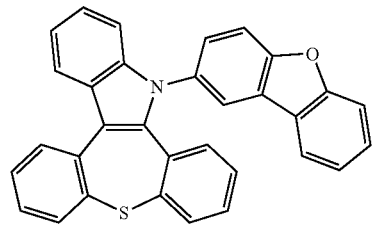
H-20
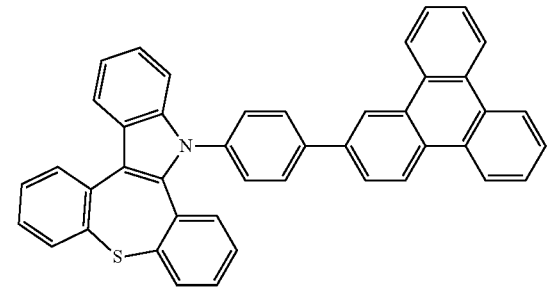
H-21
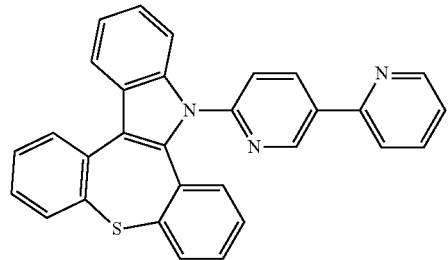
H-22
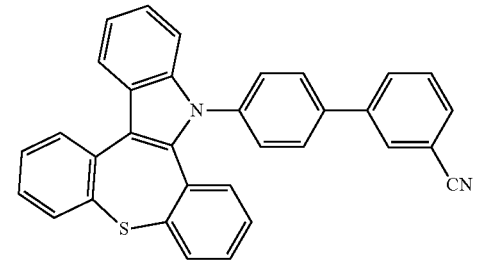
H-23
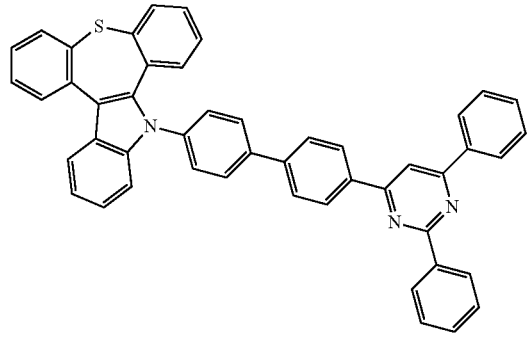
I-1
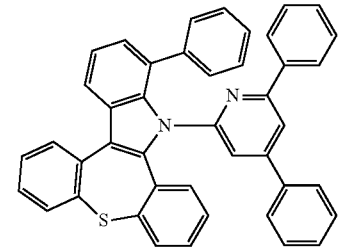

-continued
I-2
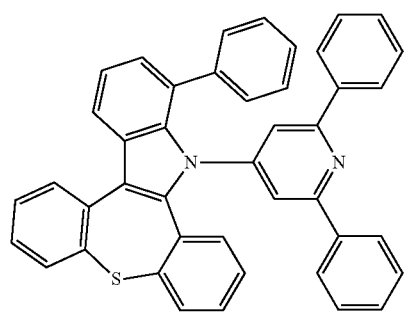
I-3
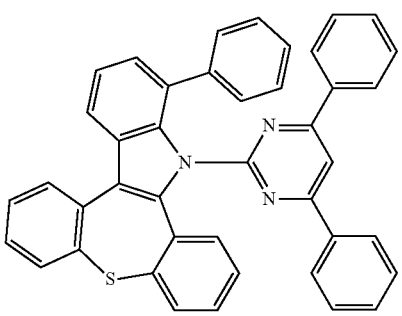
I-4
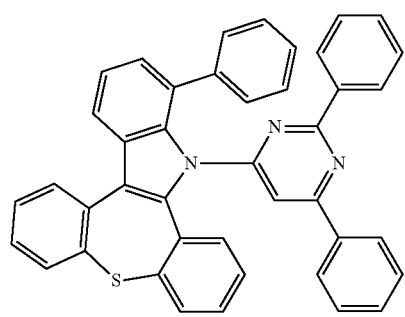
I-5
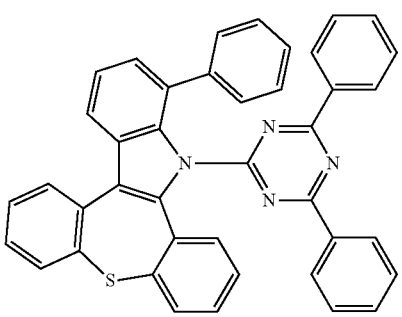
I-6
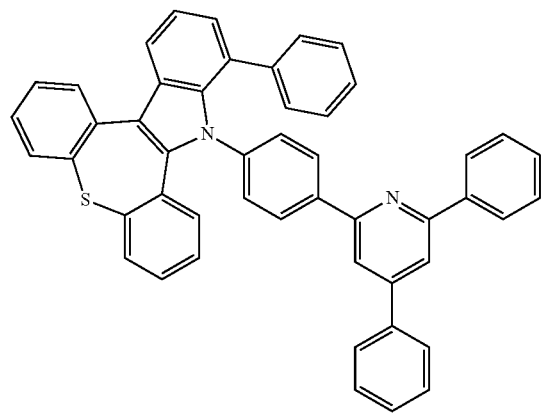
I-7
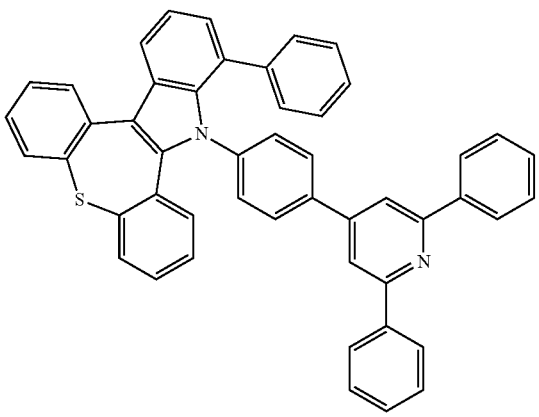
I-8
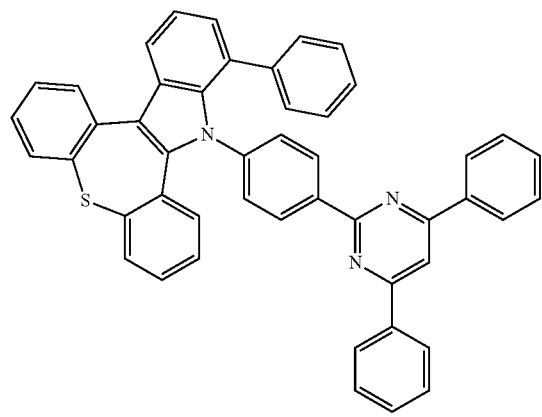
I-9
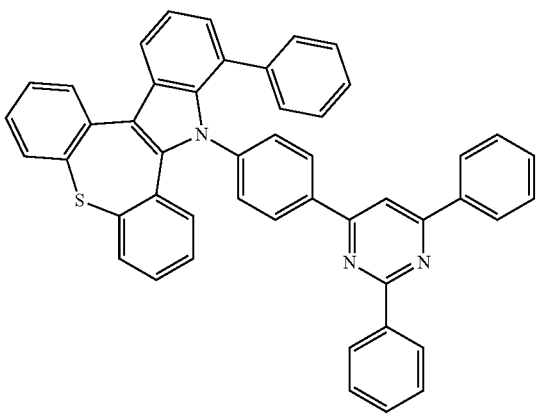

-continued
I-10
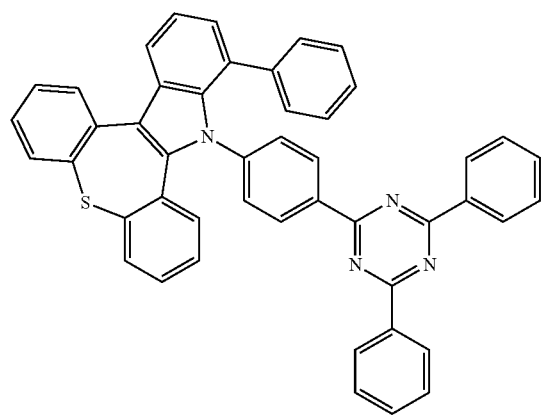
I-11
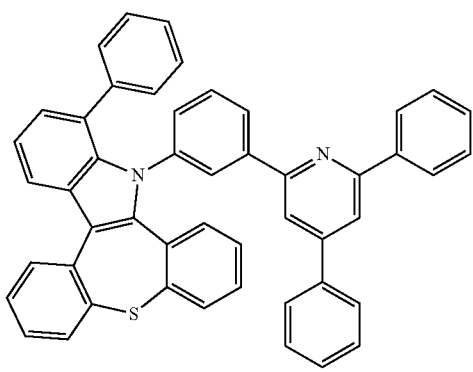
I-12
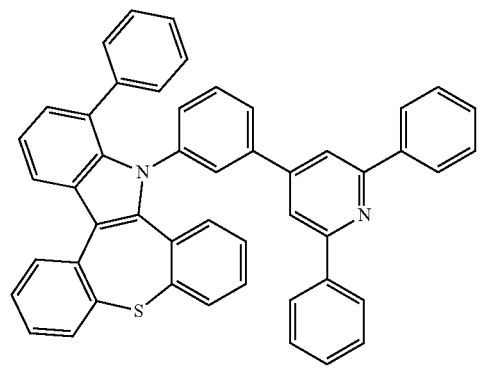
I-13
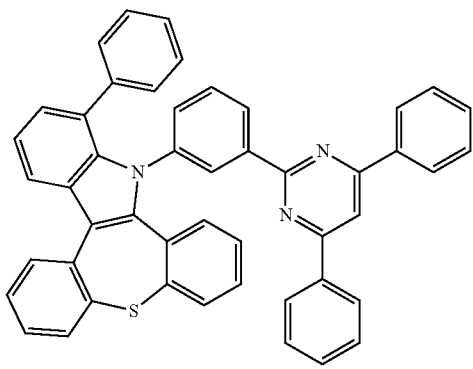
I-14
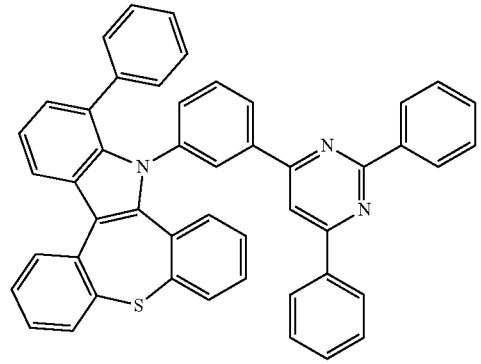
I-15
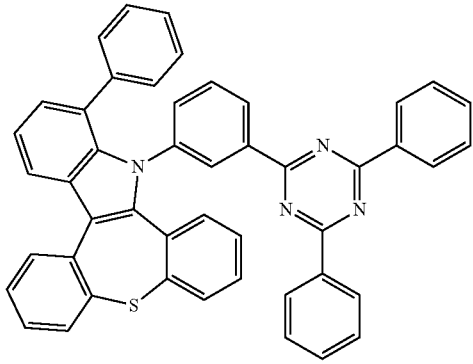
I-16
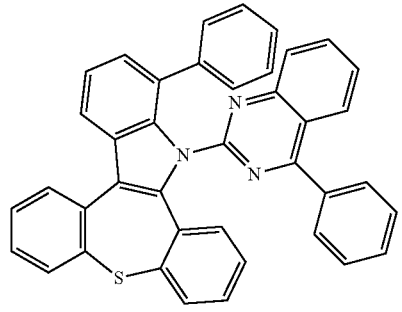
I-17
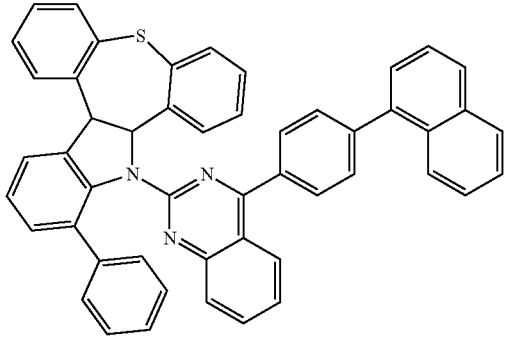

-continued
I-18
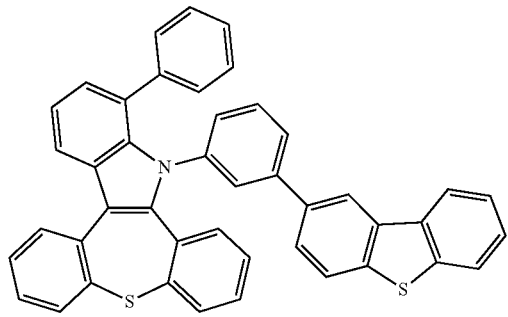
I-19
I-20
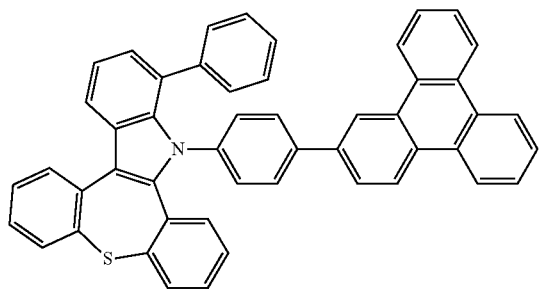
I-21
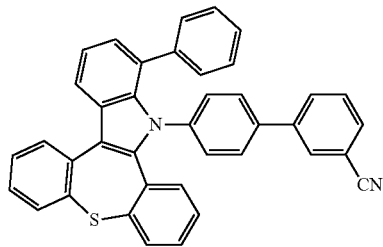
I-22
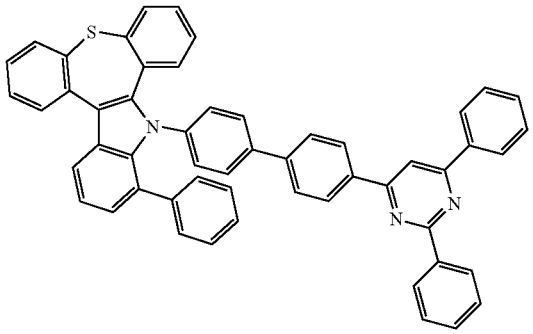
I-23
J-1
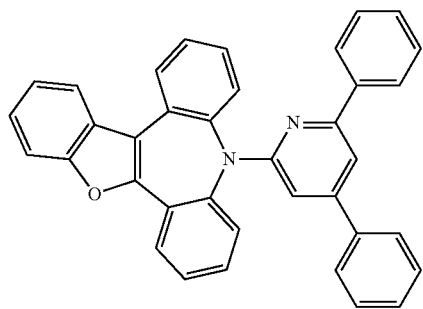
J-2
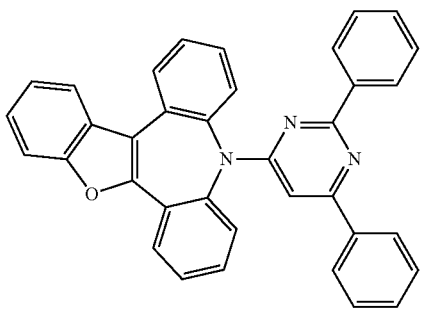
J-3
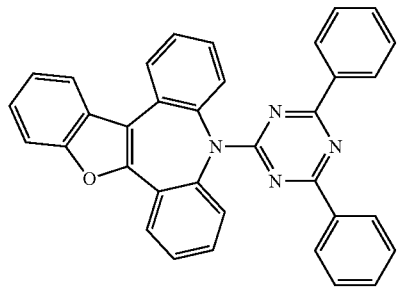
J-4
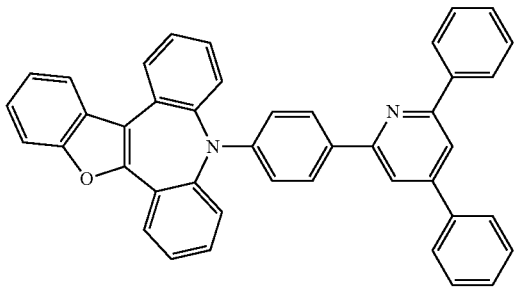

-continued
J-5
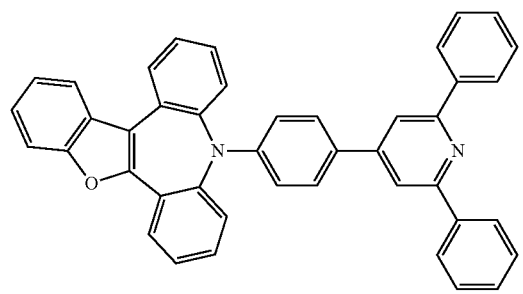
J-6
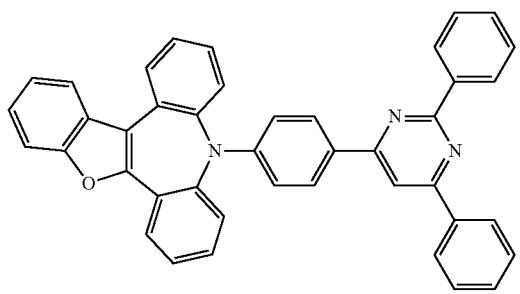
J-7
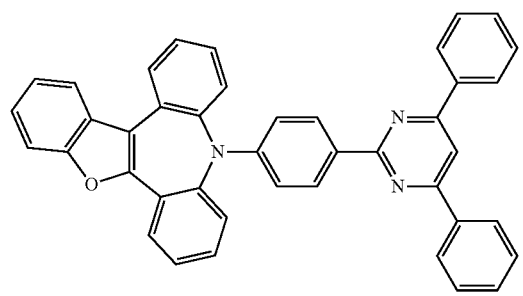
J-8
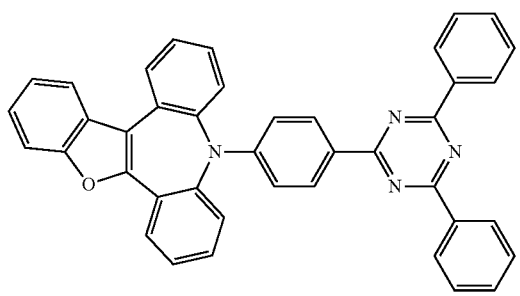
J-9
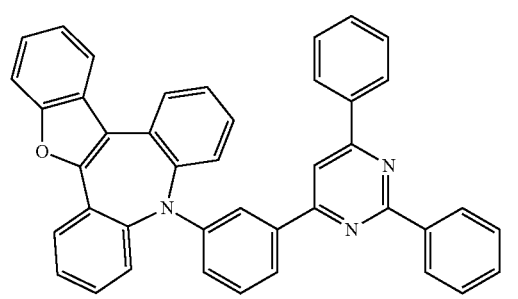
J-10
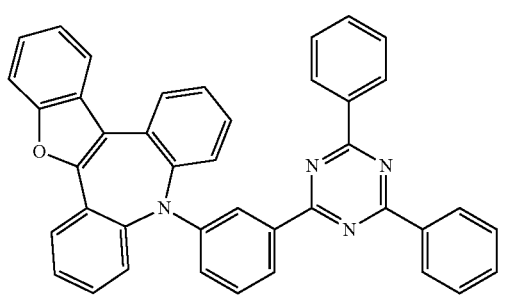
K-1
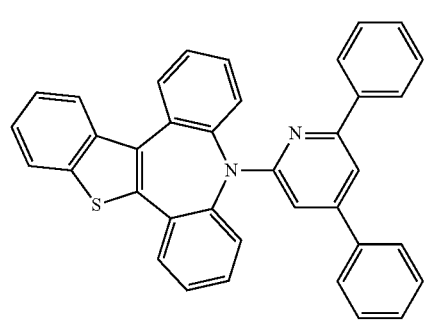
K-2
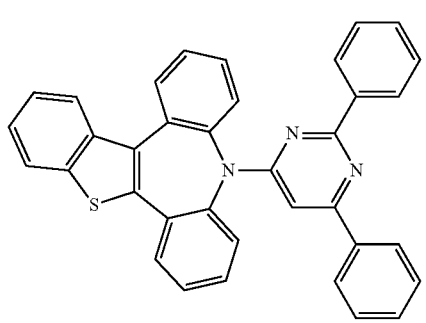
K-3
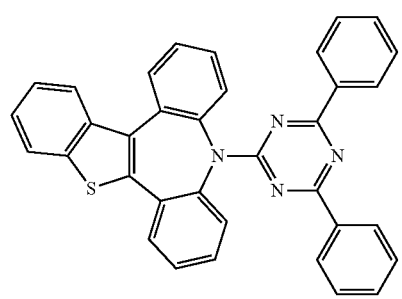
K-4
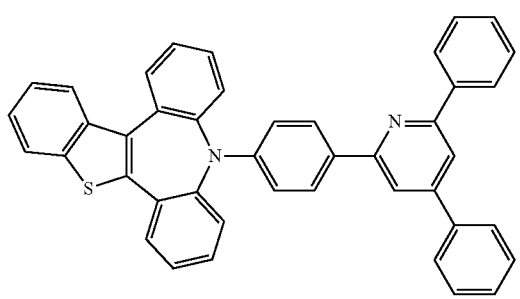

-continued
K-5
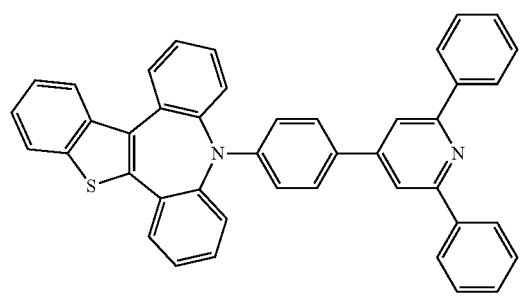
K-6
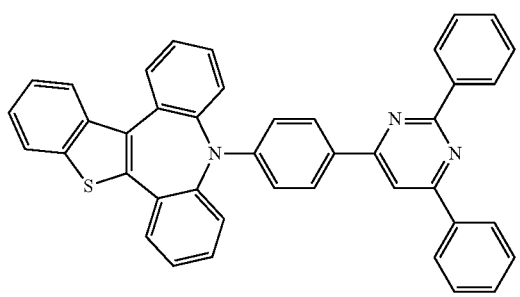
K-7
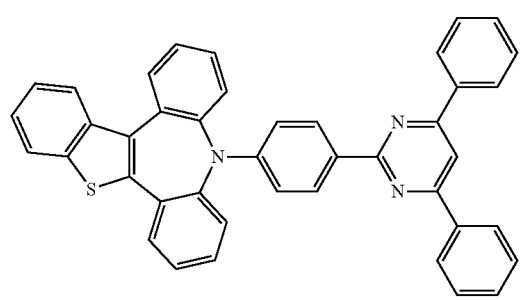
K-8
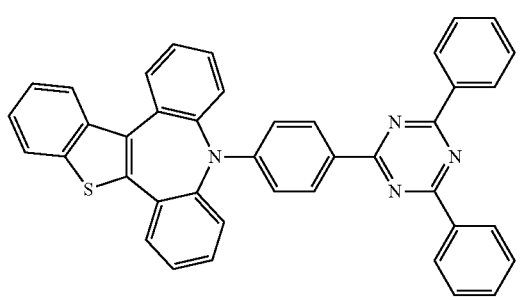
K-9
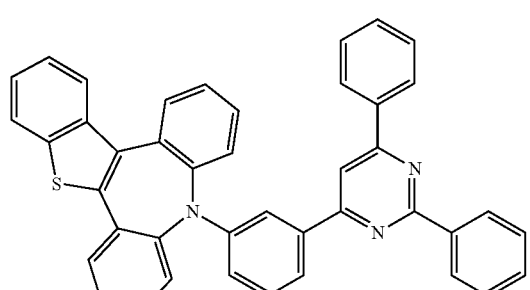
K-10
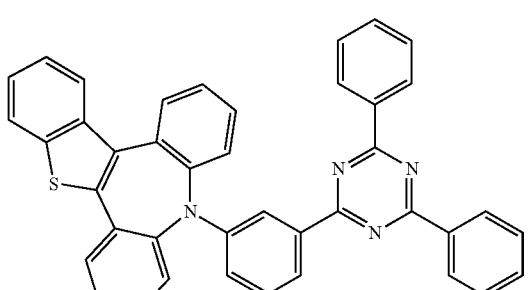
L-1
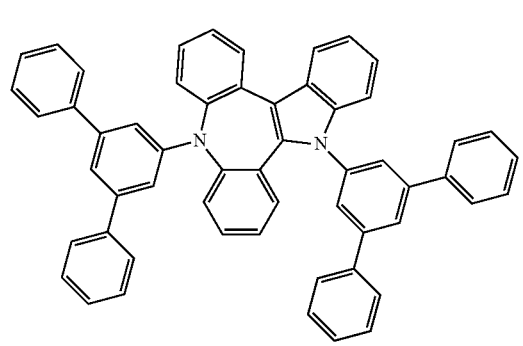
L-2
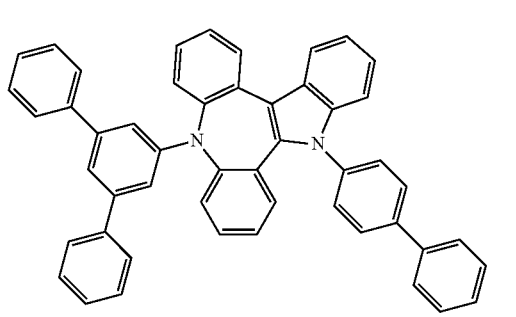
L-3
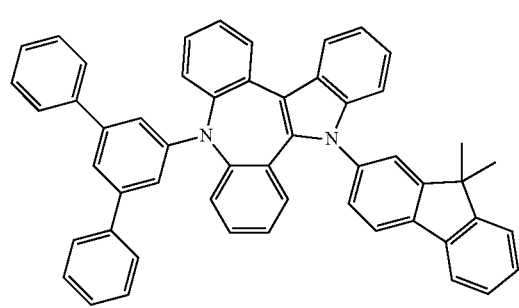
M-1
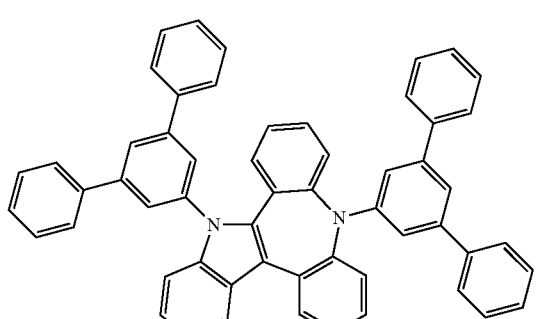

-continued
M-2
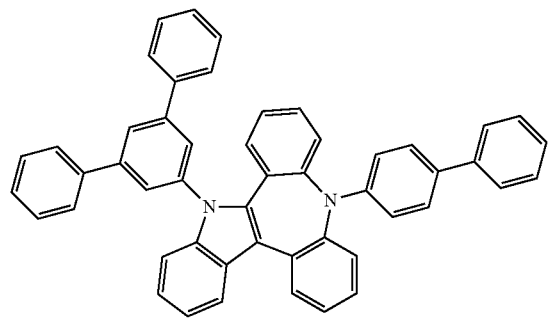
M-3
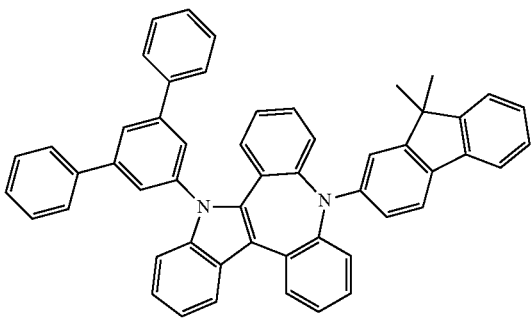
N-1
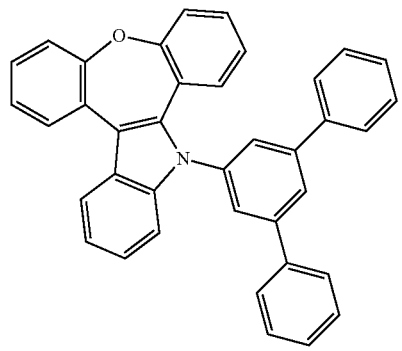
N-2
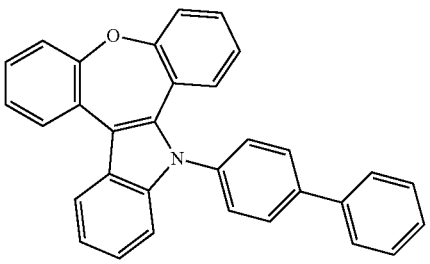
N-3
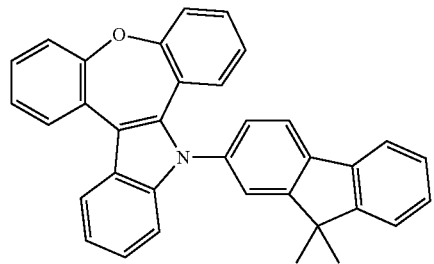
O-1
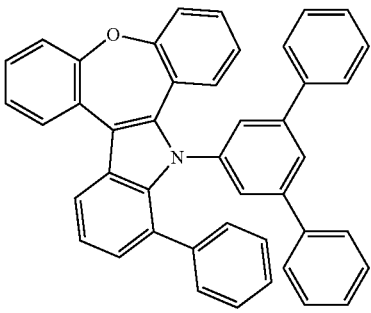
O-2
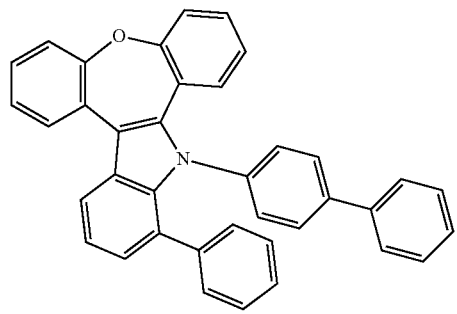
O-3
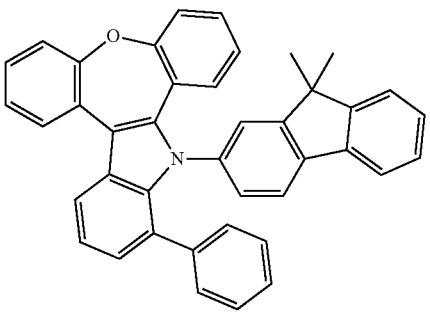
P-1
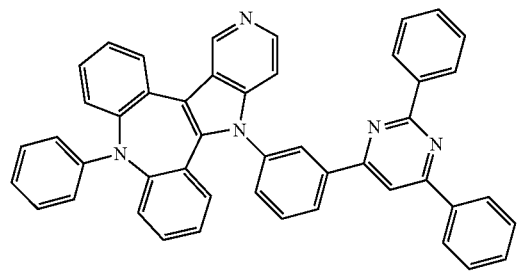
P-2
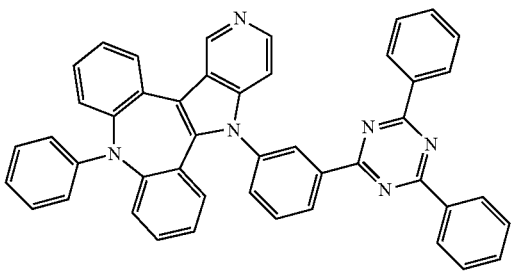

P-3
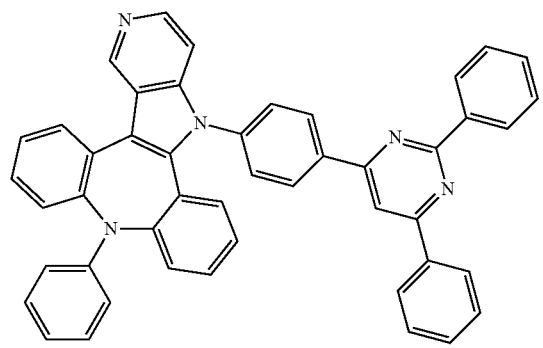
P-4
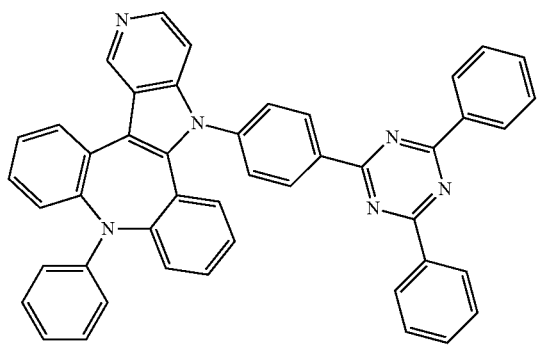
P-5
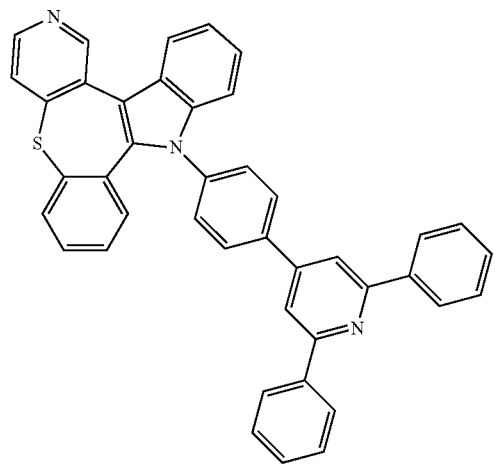
P-6
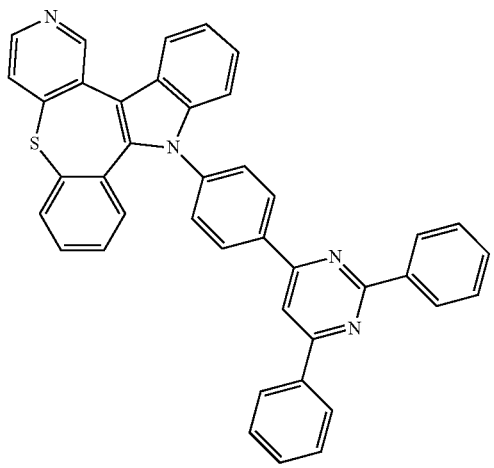
P-7
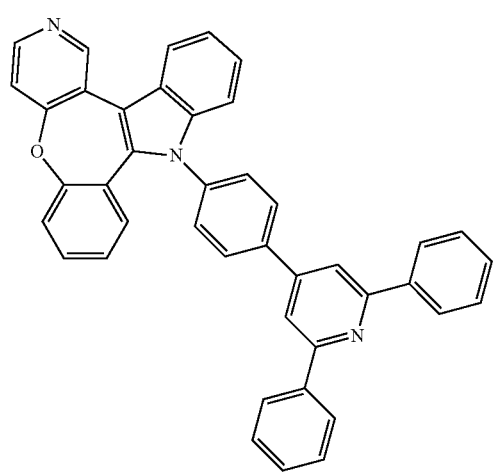
P-8
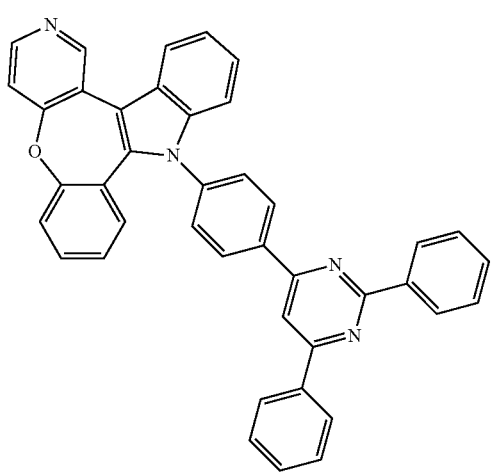
P-9
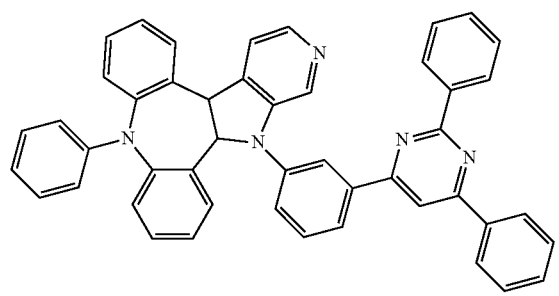
P-10
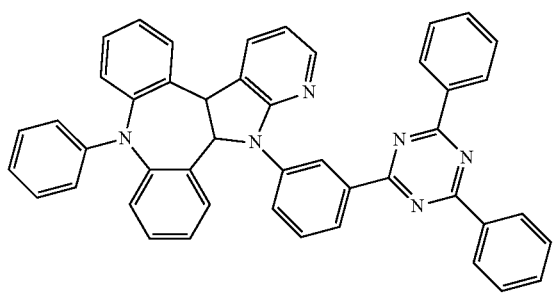

-continued
P-11
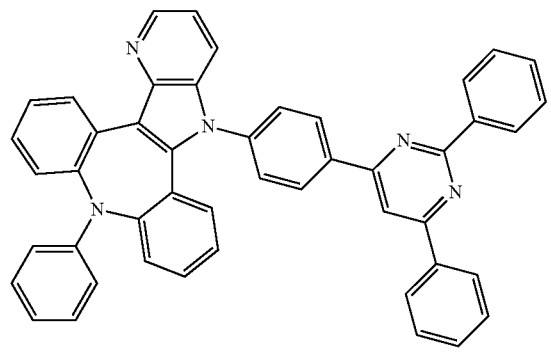
P-12
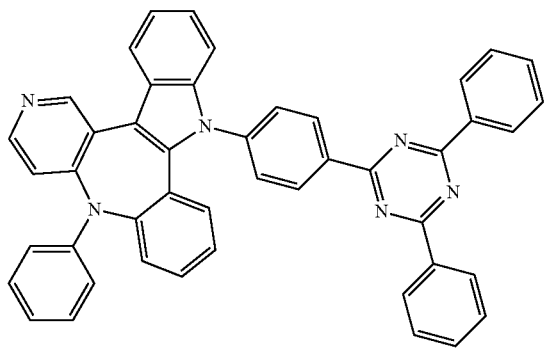
P-13
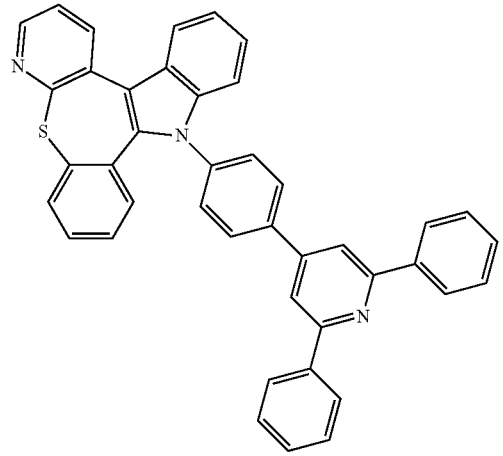
P-14
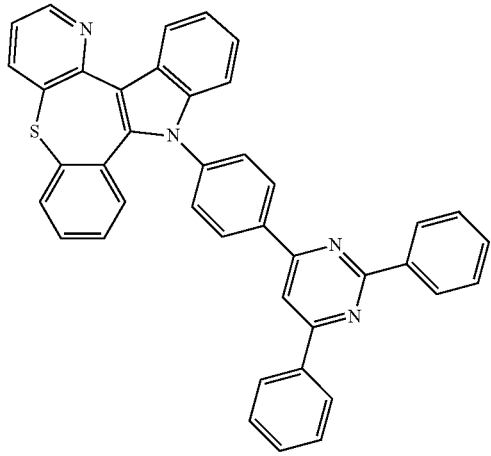
P-15
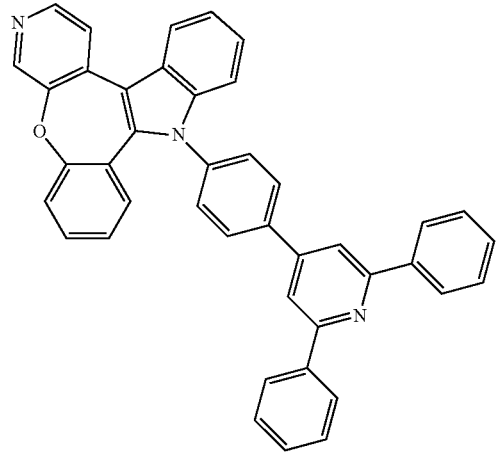
P-16
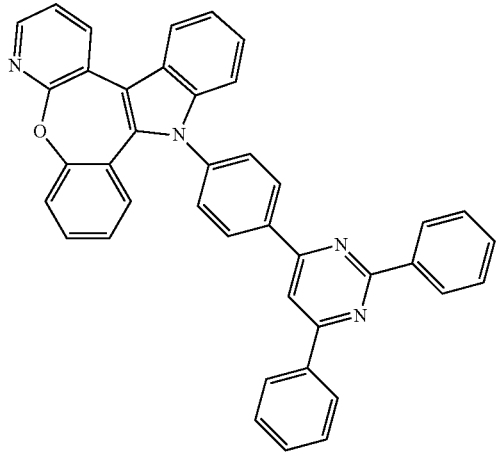
Q-1
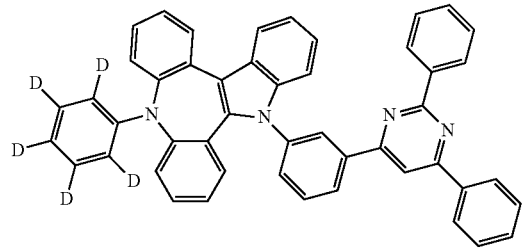
Q-2
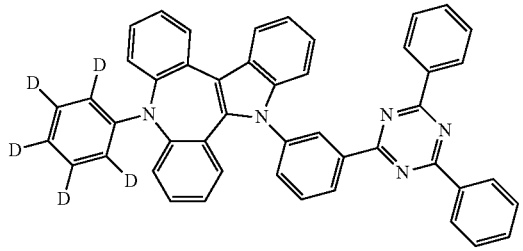

-continued
Q-3
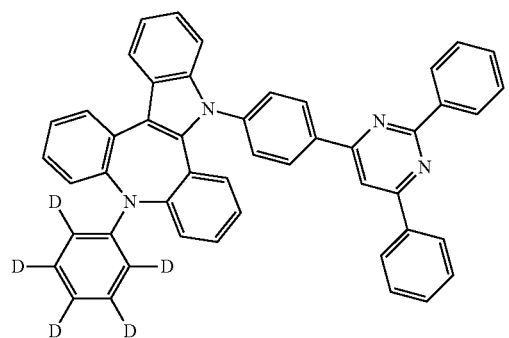
Q-4
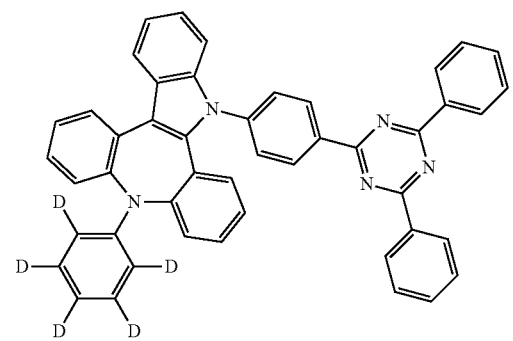
Q-5
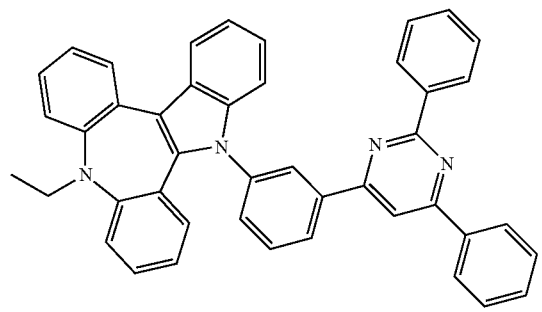
Q-6
Q-7
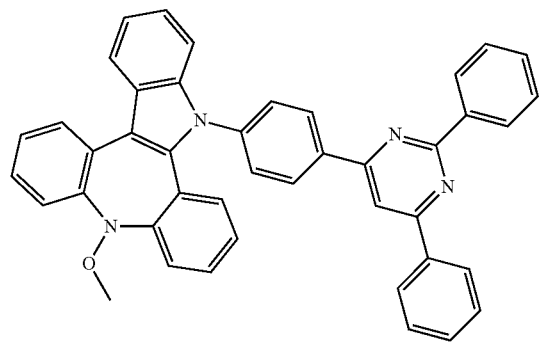
Q-8
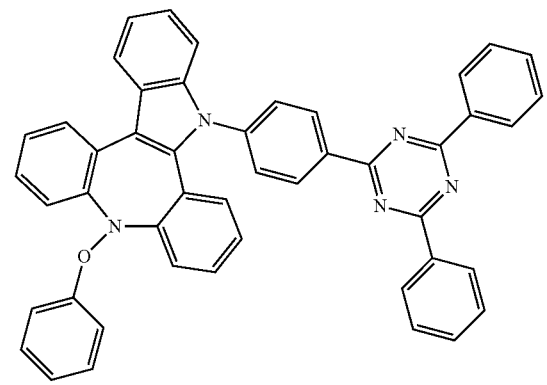
Q-9
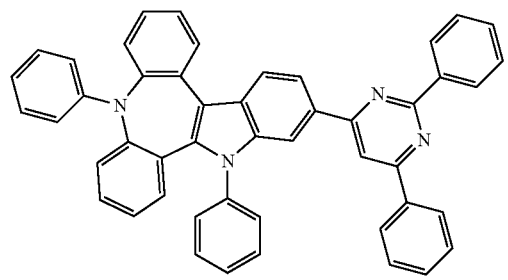
Q-10
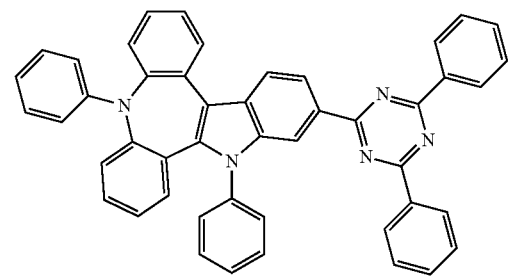

Q-11
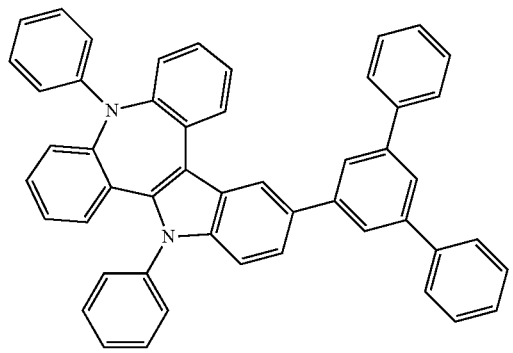
Q-12
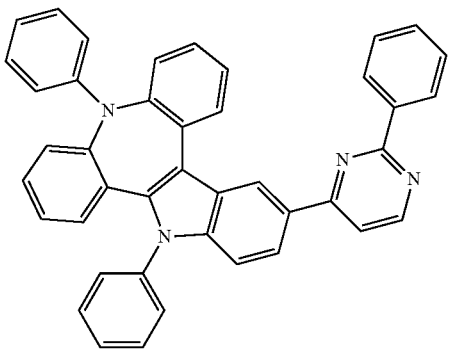
Q-13
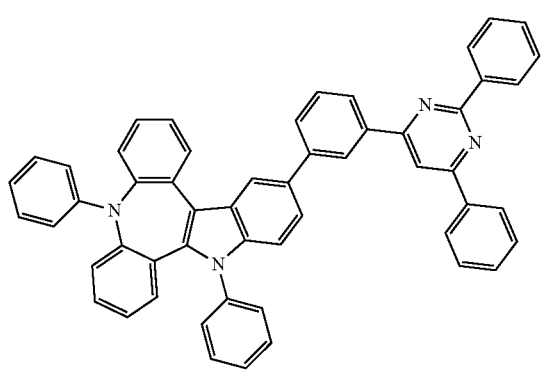
Q-14
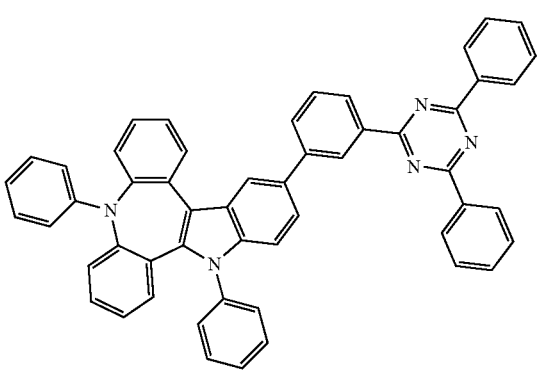
Q-15
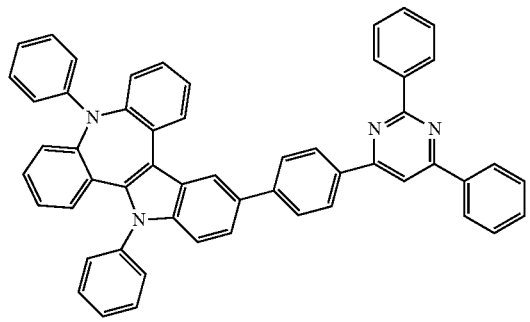
Q-16
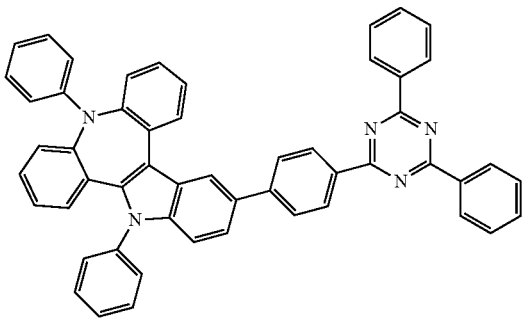
Q-17
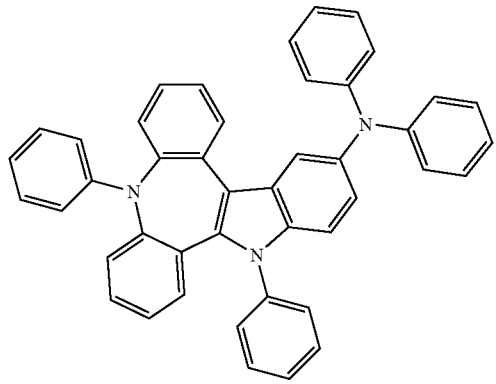
Q-18
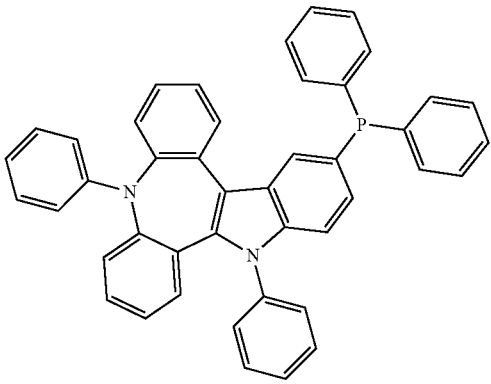

-continued
Q-19
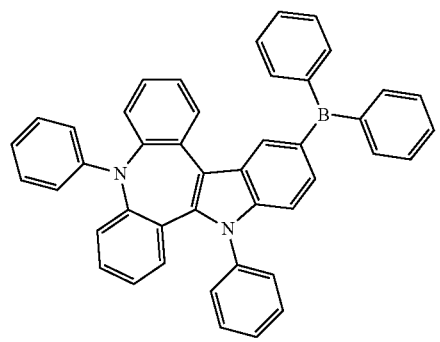
Q-20
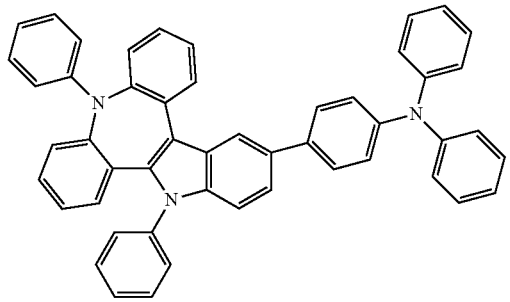
Q-21
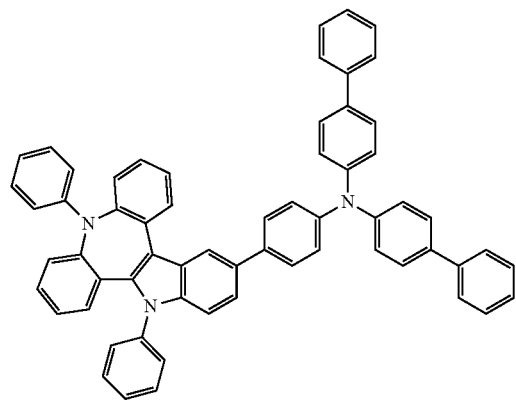
Q-22
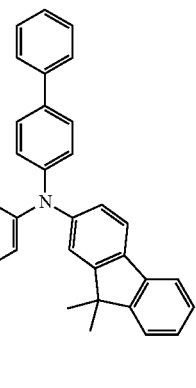
Q-23
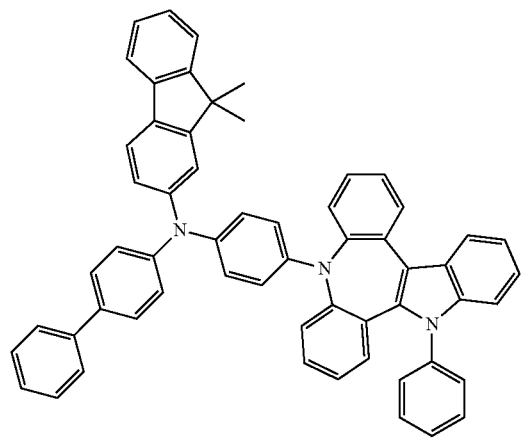
Q-24
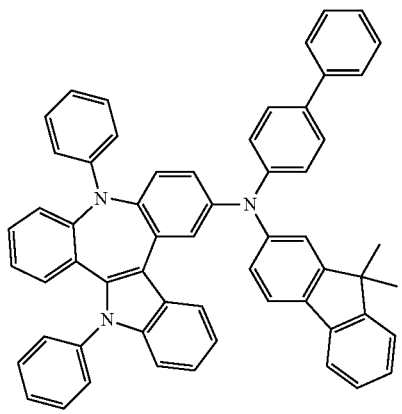
Q-25
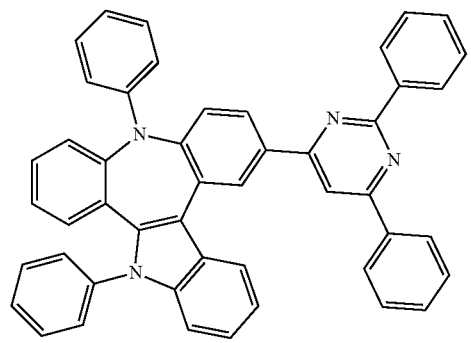
Q-26
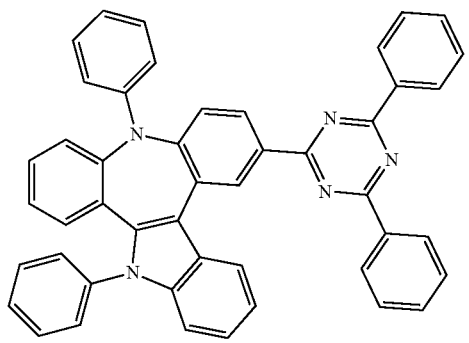

-continued
Q-27
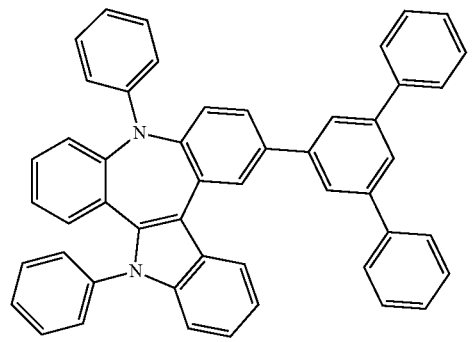
Q-28
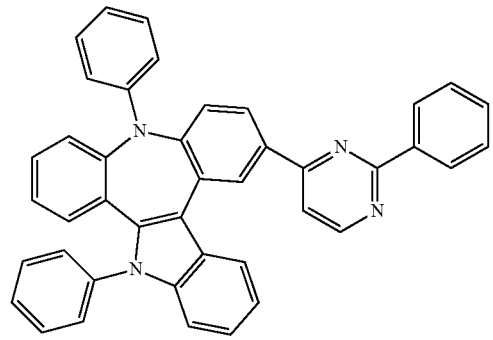
Q-29
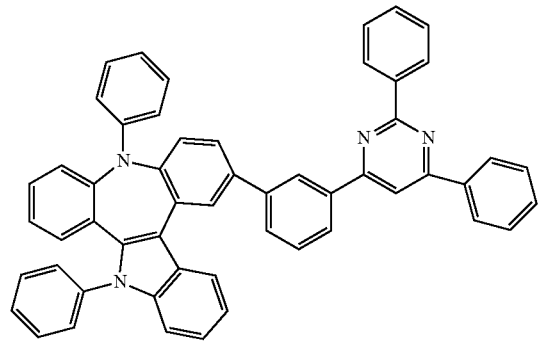
Q-30
Q-31
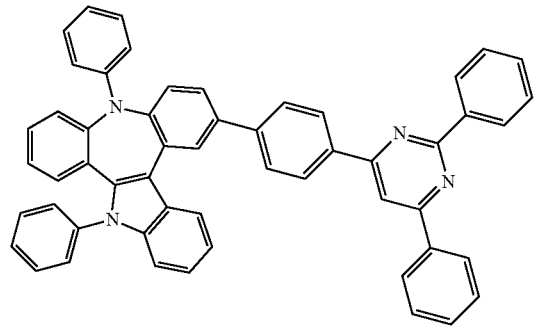
Q-32
Q-33
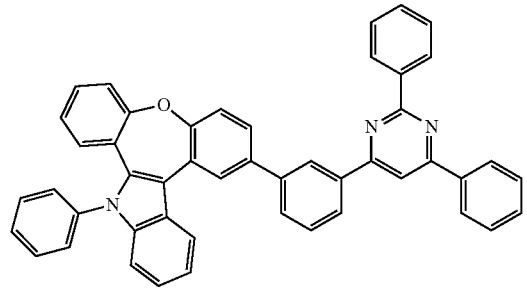
Q-34
Q-35
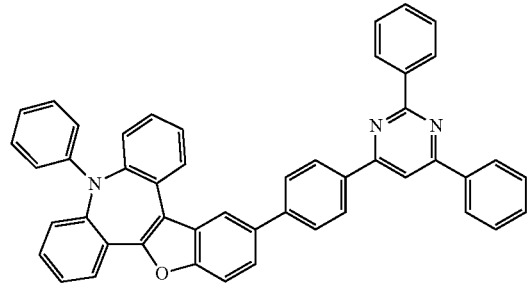
Q-36
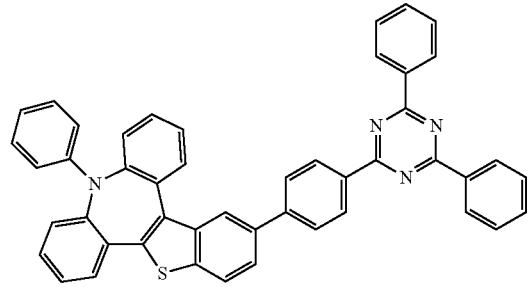

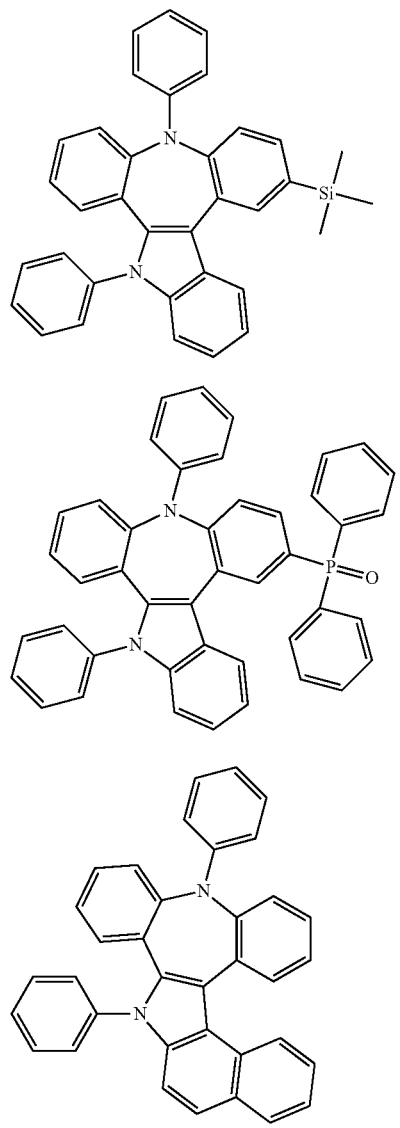

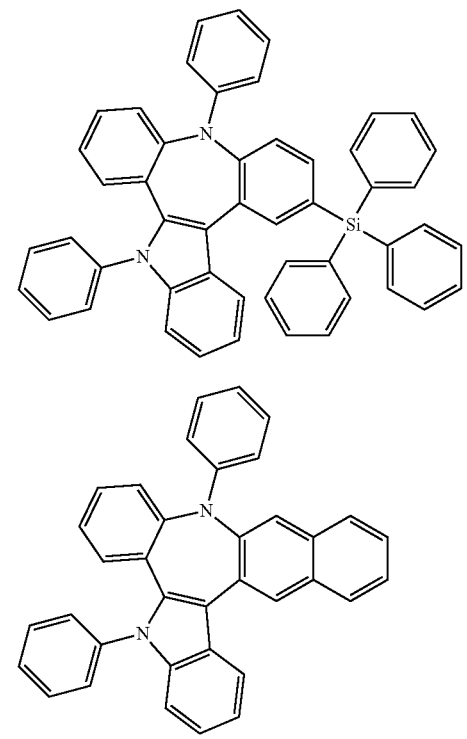

The "unsubstituted alkyl" used in the present disclosure means a monovalent functional group obtained by removing a hydrogen atom from a linear or branched, saturated hydrocarbon having 1 to 40 carbon atoms. Non-limiting examples of the alkyl include methyl, ethyl, propyl, isobutyl, sec-butyl, pentyl, iso-amyl, hexyl, and the like.

The "unsubstituted cycloalkyl" used in the present disclosure means a monovalent functional group obtained by removing a hydrogen atom from a monocyclic or polycyclic non-aromatic hydrocarbon (saturated cyclic hydrocarbon) having 3 to 40 carbon atoms. Non-limiting examples of the cycloalkyl include cyclopropyl, cyclopentyl, cyclohexyl, norbornyl, adamantine, and the like.

The "unsubstituted heterocycloalkyl" used in the present disclosure means a monovalent functional group obtained by removing a hydrogen atom from a non-aromatic hydrocarbon (saturated cyclic hydrocarbon) having 3 to 40 nuclear atoms. In this case, in the heterocycloalkyl, one or more carbons, preferably 1 to 3 carbons in the ring are substituted with a heteroatom such as N, O, or S. Non-limiting examples of the heterocycloalkyl include morpholine, piperazine, and the like.

The "unsubstituted aryl" used in the present disclosure means a monovalent functional group obtained by removing a hydrogen atom from an aromatic hydrocarbon having 6 to 60 carbon atoms, in which a single ring or two or more rings are combined. In this case, in the aryl, two or more rings may be simply pendant to each other, or pendant to each other in a fused form. Non-limiting examples of the aryl include phenyl, biphenyl, terphenyl, naphthyl, phenanthryl, anthryl, and the like.

The "unsubstituted heteroaryl" used in the present disclosure means a monovalent functional group obtained by removing a hydrogen atom from a monoheterocyclic or polyheterocyclic aromatic hydrocarbon having 5 to 60 nuclear atoms. In this case, in the heteroaryl, one or more carbons, preferably 1 to 3 carbons in the ring are substituted with a heteroatom such as nitrogen (N), oxygen (O), sulfur (S) or selenium (Se). Further, in the heteroaryl, two or more rings may be simply pendant to each other, or pendant to each other in a fused form, and furthermore, may also include a fused form with an aryl group. Non-limiting examples of the heteroaryl include: a 6-membered monocyclic ring, such as pyridyl, pyrazinyl, pyrimidinyl, pyridazinyl, and triazinyl; a polycyclic ring, such as phenoxathienyl, indolizinyl, indolyl, purinyl, quinolyl, benzothiazole, and carbazolyl; and 2-furanyl, N-imidazolyl, 2-isoxazolyl, 2-pyridinyl, 2-pyrimidinyl, and the like.

The "unsubstituted alkyloxy" used in the present disclosure means a monovalent functional group represented by RO—. In this case, R may include a linear, branched, or cyclic structure as an alkyl having 1 to 40 carbon atoms. Non-limiting examples of the alkyloxy include methoxy, ethoxy, n-propoxy, 1-propoxy, t-butoxy, n-butoxy, pentoxy, and the like.

The "unsubstituted aryloxy" used in the present disclosure means a monovalent functional group represented by R'O—. In this case, R' is an aryl having 6 to 60 carbon atoms. Non-limiting examples of the aryloxy include phenyloxy, naphthyloxy, diphenyloxy, and the like.

The "unsubstituted alkylsilyl" used in the present disclosure means a silyl which is substituted with an alkyl having 1 to 40 carbon atoms, the "unsubstituted arylsilyl" means a silyl which is substituted with an aryl having 6 to 60 carbon atoms, the "unsubstituted alkylboron group" means a boron group which is substituted with an alkyl having 1 to 40 carbon atoms, the "unsubstituted arylboron group" means a boron group which is substituted with an aryl having 6 to 60 carbon atoms, the "unsubstituted arylphosphine group" means a phosphine group which is substituted with an aryl having 1 to 60 carbon atoms, and the "unsubstituted arylamine" means an amine which is substituted with an aryl having 6 to 60 carbon atoms.

The "fused ring" used in the present disclosure means a fused aliphatic ring, a fused aromatic ring, a fused heteroaliphatic ring, a fused heteroaromatic ring, or a combined form thereof.

The compound of Chemical Formula 1 of the present disclosure may be synthesized by a general synthesis method (see *Chem. Rev.*, 60:313 (1960); *J. Chem. SOC.* 4482 (1955); *Chem. Rev.* 95: 2457 (1995), and the like). The detailed synthesis process of the compound of the present disclosure will be described in detail in the Synthesis Examples to be described below.

2. Organic Electroluminescent Element

Meanwhile, the present disclosure provides an organic electroluminescent element including the above-described compound represented by Chemical Formula 1.

Specifically, the present disclosure provides an organic electroluminescent element including an anode, a cathode, and one or more organic material layers interposed between the anode and the cathode, in which at least one of the organic material layers includes the compound represented by Chemical Formula 1. In this case, the compounds represented by Chemical Formula 1 may be used either alone or in mixture of two or more thereof.

According to an exemplary embodiment of the present disclosure, the one or more organic material layers include a hole injection layer, a hole transporting layer, a light emitting layer, an electron transporting layer, and an electron injection layer, and among them, at least one organic material layer may include the compound represented by Chemical Formula 1. Preferably, the organic material layer including the compound of Chemical Formula 1 may be a light emitting layer or an electron transporting layer. Optionally, a hole blocking layer may be interposed between the light emitting layer and the electron transporting layer.

For example, when the light emitting layer of the organic electroluminescent element includes a host material, in this case, the light emitting layer may include the compound represented by Chemical Formula 1 as the host material. As described above, when the compound represented by Chemical Formula 1 is included as a light emitting layer material, preferably a green or red phosphorescent host of the organic electroluminescent element, the efficiency (light emitting efficiency and power efficiency), lifetime, brightness, driving voltage, and the like of the organic electroluminescent element may be improved because the binding force of holes and electrons is increased in the light emitting layer.

According to another exemplary embodiment of the present disclosure, the one or more organic material layers may include a hole injection layer, a hole transporting layer, a light emitting auxiliary layer, a light emitting layer, an electron transporting layer, and an electron injection layer, and in this case, at least one of the organic material layers, preferably a light emitting auxiliary layer may include the compound of Chemical Formula 1. Optionally, a hole blocking layer may be interposed between the light emitting layer and the electron transporting layer.

Further, according to still another exemplary embodiment of the present disclosure, the one or more organic material layers may include a hole injection layer, a hole transporting layer, a light emitting layer, a lifetime enhancement layer, an electron transporting layer, and an electron injection layer, and in this case, at least one of the organic material layers, preferably a lifetime enhancement layer may include the compound of Chemical Formula 1. When the compound of Chemical Formula 1 is used as a material for the lifetime enhancement layer, the compound has a higher triplet energy than that of BCP in the related art, and thus may improve the lifetime of the organic electroluminescent element.

The structure of the above-described organic electroluminescent element according to the present disclosure is not particularly limited, and may be, for example, a structure in which an anode, one or more organic material layers, and a cathode are sequentially laminated on a substrate, and an insulation layer or an adhesion layer is inserted into the interface between the electrode and the organic material layer.

Specifically, the structure of the organic electroluminescent element may be a structure in which an anode, a hole injection layer, a hole transporting layer, a light emitting layer, an electron transporting layer, an electron injection layer, and a cathode are sequentially laminated on a substrate. Optionally, a light emitting auxiliary layer may be interposed between the hole transporting layer and the light emitting layer. Further, a lifetime enhancement layer may be interposed between the light emitting layer and the electron transporting layer. In this case, one or more of the hole injection layer, the hole transporting layer, the light emitting layer, the electron transporting layer, the electron injection layer, the light emitting auxiliary layer, and the lifetime enhancement layer may include the compound represented by Chemical Formula 1, and preferably, one or more of the phosphorescent light emitting layer, the electron transporting layer, the lifetime enhancement layer, and the light emitting auxiliary layer may include the compound represented by Chemical Formula 1.

The organic electroluminescent element of the present disclosure may be manufactured by forming other organic material layers and electrodes using materials and methods known in the art, except that at least one of the the organic material layers (for example, one or more of the light emitting layer, the electron transporting layer, the light emitting auxiliary layer, and the lifetime enhancement layer) are formed so as to include the compound represented by Chemical Formula 1.

The organic material layers may be formed by a vacuum deposition method or a solution application method. Examples of the solution application method include spin coating, dip coating, doctor blading, inkjet printing, or a thermal transferring method, and the like, but are not limited thereto.

A substrate which may be used in the present disclosure is not particularly limited, and a silicon wafer, quartz, a glass plate, a metal plate, a plastic film and sheet or the like may be used.

Further, examples of an anode material include: a metal, such as vanadium, chromium, copper, zinc, and gold, or alloys thereof; a metal oxide, such as zinc oxide, indium oxide, indium tin oxide (ITO), and indium zinc oxide (IZO); a combination of metal and oxide, such as ZnO:Al or SnO$_2$:Sb; an electrically conductive polymer, such as polythiophene, poly(3-methylthiophene), poly[3,4-(ethylene-1,2-dioxy)thiophene] (PEDT), polypyrrole, and polyaniline; carbon black, and the like, but are not limited thereto.

Further, examples of a cathode material include: a metal, such as magnesium, calcium, sodium, potassium, titanium, indium, yttrium, lithium, gadolinium, aluminum, silver, tin or lead, or alloys thereof; and a multi-layered structural material, such as LiF/Al or LiO$_2$/Al, and the like, but are not limited thereto.

Hereinafter, the present disclosure will be described in detail through the Examples. However, the following Examples only exemplify the present disclosure, and the present disclosure is not limited by the following Examples.

[Preparation Example 1] Synthesis of Compound IAz-1

<Step 1> Synthesis of 1-(5H-dibenzo[b,f]azepin-5-yl)ethanone

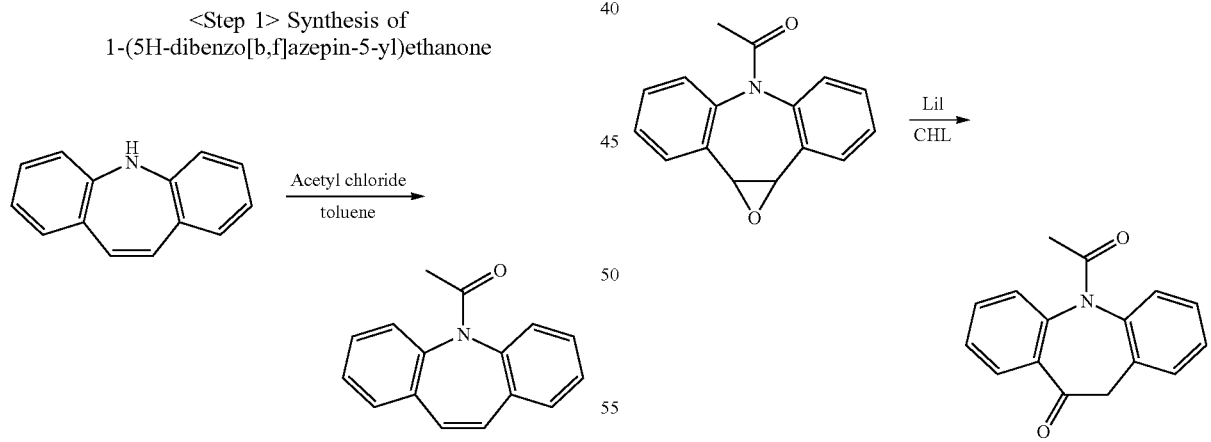

5H-dibenzo[b,f]azepine (100.0 g, 517.5 mmol), acetyl chloride (44.3 ml, 621.0 mmol), and toluene (1,000 ml) were mixed under nitrogen flow, and the resulting mixture was stirred at 80° C. for 2 hours.

After the reaction was terminated, the organic layer was extracted with ethyl acetate, and then concentrated and recrystallized with ethanol to obtain 1-(5H-dibenzo[b,f]azepin-5-yl)ethanone (113.2 g, yield 93%).

$^1$H-NMR: δ 1.86 (s, 3H), 6.92 (d, 1H), 6.98 (d, 1H), 7.26-7.45 (m, 8H)

<Step 2> Synthesis of 1-(1aH-dibenzo[b,f]oxireno[2,3-d]azepin-6(10bH)-yl)ethanone

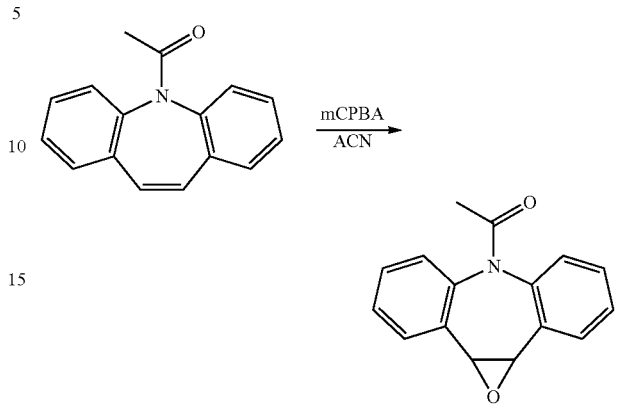

1-(5H-dibenzo[b,f]azepin-5-yl)ethanone (113.2 g, 481.3 mmol) obtained in <Step 1> of Preparation Example 1, meta-chloroperoxybenzoic acid (99.7 g, 577.5 mmol), silica (226.5 g), NaOCl (226.5 g), and acetonitrile (1,100 ml) were mixed under nitrogen flow, and the resulting mixture was stirred at 80° C. for 2 hours.

After the reaction was terminated, the organic layer was extracted with methylene chloride, MgSO$_4$ was added thereto, and the resulting product was filtered. The solvent was removed from the obtained organic layer, and then recrystallized with ethanol to obtain 1-(1aH-dibenzo[b,f]oxireno[2,3-d]azepin-6(10bH)-yl)ethanone (87.1 g, yield 72%).

$^1$H-NMR: δ 1.95 (s, 3H), 4.28 (s, 2H), 7.26-7.53 (m, 8H)

<Step 3> Synthesis of 5-acetyl-5H-dibenzo[b,f]azepin-10(11H)-one

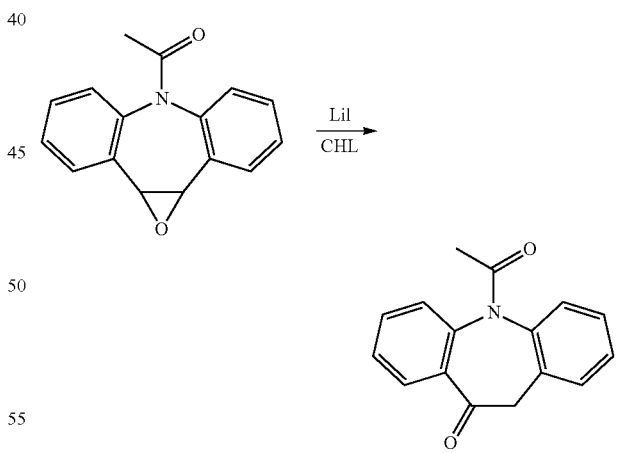

1-(1aH-dibenzo[b,f]oxireno[2,3-d]azepin-6(10bH)-yl)ethanone (87.1 g, 346.5 mmol) obtained in <Step 2> of Preparation Example 1, lithium iodide (55.7 g, 415.8 mmol), and chloroform (870 ml) were mixed under nitrogen flow, and the resulting mixture was stirred at 60° C. for 1 hour.

After the reaction was terminated, the organic layer was extracted with ethyl acetate, and then moisture was removed using MgSO$_4$, and recrystallization was performed in ethanol to obtain 5-acetyl-5H-dibenzo[b,f]azepin-10(11H)-one (70.5 g, yield 81%).

¹H-NMR: δ 2.10 (s, 3H), 3.85 (d, 1H), 4.33 (d, 1H), 7.30-7.40 (m, 5H), 7.51-7.59 (m, 2H), 8.10 (d, 1H)

<Step 4> Synthesis of 5H-dibenzo[b,f]azepin-10(11H)-one

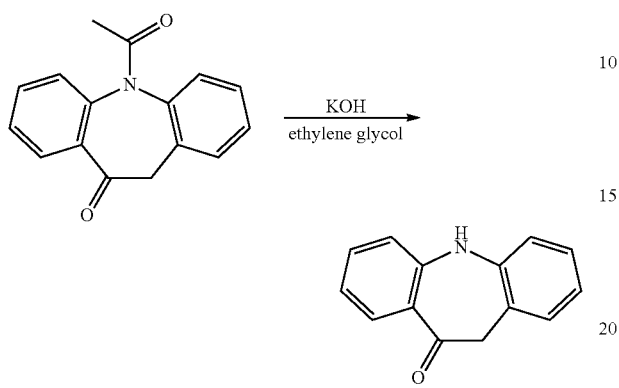

5-acetyl-5H-dibenzo[b,f]azepin-10(11H)-one (70.5 g, 280.7 mmol) obtained in <Step 3> of Preparation Example 1, potassium hydroxide (17.3 g, 308.7 mmol), and ethylene glycol (700 ml) were mixed under nitrogen flow, and the resulting mixture was stirred at 200° C. for 6 hours.

After the reaction was terminated, the organic layer was extracted with ethyl acetate, and then moisture was removed using MgSO₄, and purification was performed by column chromatography (hexane:EA=6:1 (v/v)) to obtain 5H-dibenzo[b,f]azepin-10(11H)-one.

¹H-NMR: δ 3.80 (d, 1H), 4.25 (d, 1H), 7.20-7.35 (m, 5H), 7.45-7.51 (m, 2H), 7.61 (b, 1H), 8.07 (d, 1H)

<Step 5> Synthesis of Compound IAz-1

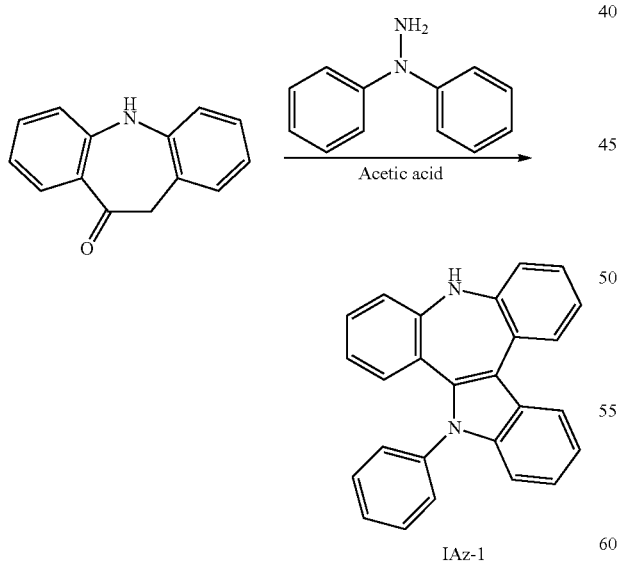

5H-dibenzo[b,f]azepin-10(11H)-one (52.9 g, 252.6 mmol) obtained in <Step 4> of Preparation Example 1, N,N-diphenylhydrazine (51.2 g, 277.9 mmol), and acetic acid (500 ml) were mixed under nitrogen flow, and then the resulting mixture was stirred at 120° C. for 12 hours.

After the reaction was terminated, the organic layer was extracted with dichloromethane, MgSO₄ was added thereto, and the resulting product was filtered. Compound IAz-1 (66.1 g, yield 73%) was obtained by removing the solvent from the obtained organic layer, and then purifying the residue with column chromatography (hexane:MC=4:1 (v:v)).

¹H-NMR of IAz-1: δ 6.68-6.70 (m, 2H), 6.91-6.99 (m, 2H), 7.09 (t, 1H), 7.19-7.25 (m, 7H), 7.34-7.39 (m, 3H), 7.60 (b, 1H), 7.88 (d, 1H), 8.02 (d, 1H)

[Preparation Example 2] Synthesis of Compound IAz-2

<Step 1> Synthesis of 5-phenyl-5H-dibenzo[b,f]azepine

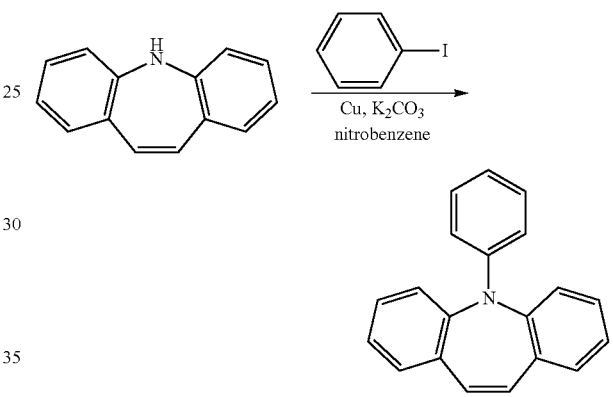

5-H-dibenzo[b,f]azepine (100 g, 517.5 mmol), iodobenzene (126.7 g, 621.0 mmol), Cu (16.4 g, 258.7 mmol), K₂CO₃ (143.0 g, 1,035.0 mmol), and nitrobenzene (1,000 ml) were mixed under nitrogen flow, and the resulting mixture was stirred at 210° C. for 12 hours.

After the reaction was terminated, the organic layer was extracted with ethyl acetate, and then concentrated and recrystallized with ethanol to obtain 5-phenyl-5H-dibenzo[b,f]azepine (100.4 g, yield 72%).

¹H-NMR: δ 6.63-6.81 (m, 3H), 6.92 (d, 1H), 6.98 (d, 1H), 7.20 (d, 2H), 7.26-7.45 (m, 8H)

<Step 2> Synthesis of 6-phenyl-6,10b-dihydro-1aH-dibenzo[b,f]oxireno[2,3-d]azepine

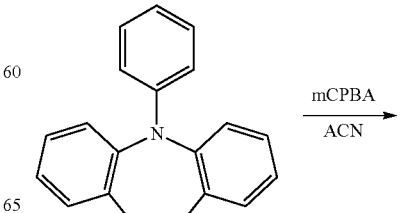

-continued

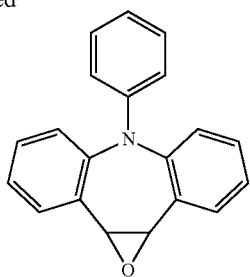

5-phenyl-5H-dibenzo[b,f]azepine (100.4 g, 372.6 mmol) obtained in <Step 1> of Preparation Example 2, meta-chloroperoxybenzoic acid (77.2 g, 447.1 mmol), silica (200.7 g), NaOCl (200.7 g), and acetonitrile (1,000 ml) were mixed under nitrogen flow, and the resulting mixture was stirred at 80° C. for 2 hours.

After the reaction was terminated, the organic layer was extracted with methylene chloride, MgSO$_4$ was added thereto, and the resulting product was filtered. The solvent was removed from the obtained organic layer, and then recrystallization was performed with ethanol to obtain 6-phenyl-6,10b-dihydro-1aH-dibenzo[b,f]oxireno[2,3-d]azepine (84.0 g, yield 79%).

$^1$H-NMR: δ 4.31 (s, 2H), 6.63-6.81 (m, 3H), 7.24-7.53 (m, 10H)

<Step 3> Synthesis of 5-phenyl-5H-dibenzo[b,f]azepin-10(11H)-one

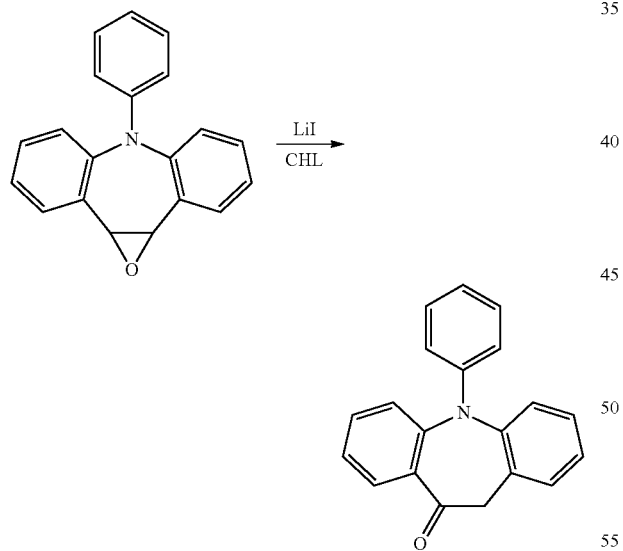

6-phenyl-6,10b-dihydro-1aH-dibenzo[b,f]oxireno[2,3-d]azepine (84.0 g, 294.3 mmol) obtained in <Step 2> of Preparation Example 2, lithium iodide (47.3 g, 353.2 mmol), and chloroform (840 ml) were mixed under nitrogen flow, and the resulting mixture was stirred at 60° C. for 1 hour.

After the reaction was terminated, the organic layer was extracted with ethyl acetate, and then moisture was removed using MgSO$_4$, and recrystallization was performed in ethanol to obtain 5-phenyl-5H-dibenzo[b,f]azepin-10(11H)-one (68.0 g, yield 81%).

$^1$H-NMR: 3.42 (d, 1H), 4.21 (d, 1H), 6.62-6.74 (m, 3H), 7.25-7.40 (m, 7H), 7.51-7.59 (m, 2H), 8.10 (d, 1H)

<Step 4> Synthesis of Compound IAz-2

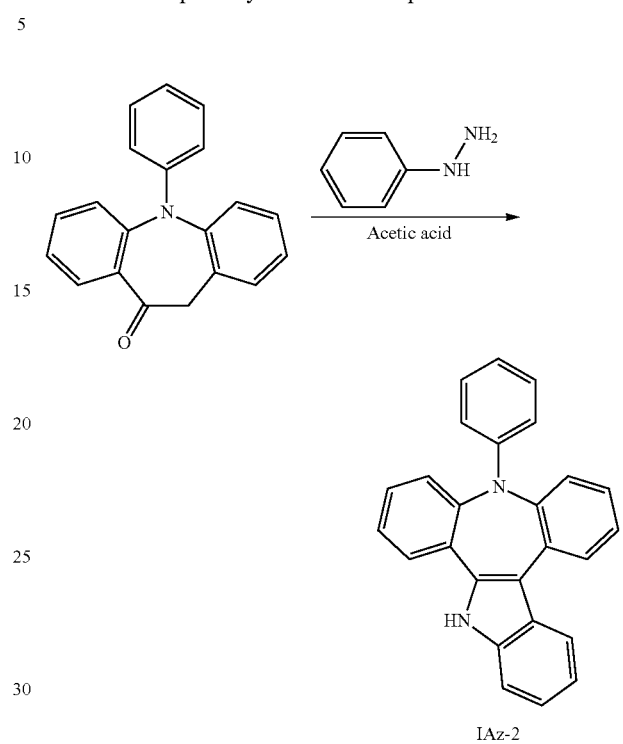

IAz-2

5-phenyl-5H-dibenzo[b,f]azepin-10(11H)-one (68.0 g, 238.4 mmol) obtained in <Step 3> of Preparation Example 2, phenylhydrazine (28.4 g, 262.3 mmol), and acetic acid (700 ml) were mixed under nitrogen flow, and then the resulting mixture was stirred at 120° C. for 12 hours.

After the reaction was terminated, the organic layer was extracted with dichloromethane, MgSO$_4$ was added thereto, and the resulting product was filtered. Compound IAz-2 (60.7 g, yield 71%) was obtained by removing the solvent from the obtained organic layer, and then purifying the residue with column chromatography (hexane:MC=3:1 (v:v)).

$^1$H-NMR of IAz-2: δ 6.63-6.69 (m, 4H), 6.81-6.87 (m, 3H), 7.08-7.20 (m, 6H), 7.44-7.56 (m, 3H), 8.83 (d, 1H), 11.36 (b, 1H)

[Preparation Example 3] Synthesis of Compound IAz-3

<Step 1> Synthesis of 5-(1-bromo-3,5-diphenylbenzene)-5H-dibenzo[b,f]azepine

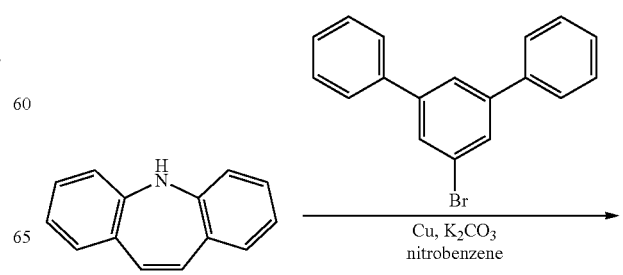

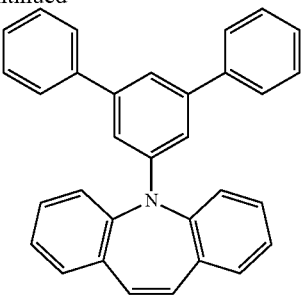

5-H-dibenzo[b,f]azepine (100 g, 517.5 mmol), 1-bromo-3,5-diphenylbenzene (192.0 g, 621.0 mmol), Cu (16.4 g, 258.7 mmol), K$_2$CO$_3$ (143.0 g, 1,035.0 mmol), and nitrobenzene (1,000 ml) were mixed under nitrogen flow, and the resulting mixture was stirred at 210° C. for 12 hours.

After the reaction was terminated, the organic layer was extracted with ethyl acetate, and then concentrated and recrystallized with ethanol to obtain 5-(1-bromo-3,5-diphenylbenzene)-5H-dibenzo[b,f]azepine (146.2 g, yield 67%).

$^1$H-NMR: δ 6.63 (d, 2H), 6.81-6.85 (m, 4H), 6.99-7.06 (m, 5H), 7.25 (d, 2H), 7.41-7.52 (m, 10H)

<Step 2> Synthesis of 6-(1-bromo-3,5-diphenylbenzene)-6,10b-dihydro-1aH-dibenzo[b,f]oxireno[2,3-d]azepin

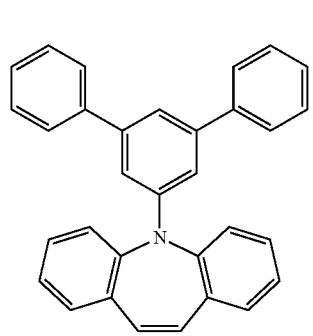

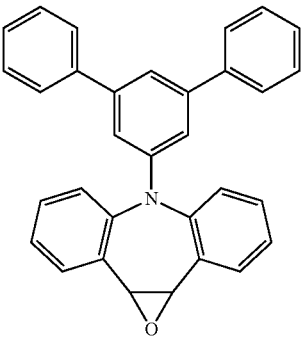

5-(1-bromo-3,5-diphenylbenzene)-5H-dibenzo[b,f]azepine (146.2 g, 346.7 mmol) obtained in <Step 1> of Preparation Example 3, meta-chloroperoxybenzoic acid (71.8 g, 416.1 mmol), silica (292.3 g), NaOCl (292.3 g), and acetonitrile (1,500 ml) were mixed under nitrogen flow, and the resulting mixture was stirred at 80° C. for 2 hours.

After the reaction was terminated, the organic layer was extracted with methylene chloride, MgSO$_4$ was added thereto, and the resulting product was filtered. The solvent was removed from the obtained organic layer, and then recrystallization was performed with ethanol to obtain 6-(1-bromo-3,5-diphenylbenzene)-6,10b-dihydro-1aH-dibenzo[b,f]oxireno[2,3-d]azepine (113.8 g, yield 75%).

$^1$H-NMR: δ 4.20 (s, 2H), 6.56 (d, 2H), 6.74 (t, 2H), 6.85 (s, 2H), 7.06-7.13 (m, 5H), 7.41-7.52 (m, 10H)

<Step 3> Synthesis of 5-(1-bromo-3,5-diphenylbenzene)-5H-dibenzo[b,f]azepin-10(11H)-one

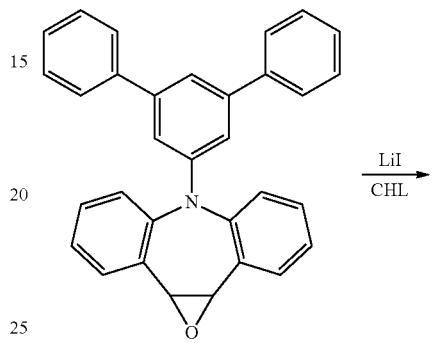

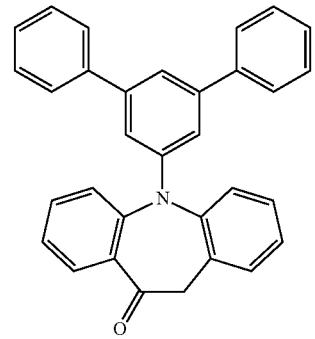

6-(1-bromo-3,5-diphenylbenzene)-6,10b-dihydro-1aH-dibenzo[b,f]oxireno[2,3-d]azepine (113.8 g, 260.0 mmol) obtained in <Step 2> of Preparation Example 3, lithium iodide (41.8 g, 312.0 mmol), and chloroform (1,100 ml) were mixed under nitrogen flow, and the resulting mixture was stirred at 60° C. for 1 hour.

After the reaction was terminated, the organic layer was extracted with ethyl acetate, and then moisture was removed using MgSO$_4$, and recrystallization was performed in ethanol to obtain 5-(1-bromo-3,5-diphenylbenzene)-5H-dibenzo[b,f]azepin-10(11H)-one (89.9 g, yield 79%).

$^1$H-NMR: δ 3.41 (d, 1H), 4.20 (d, 1H), 6.51 (d, 1H), 6.69-6.74 (m, 2H), 6.85 (s, 2H), 6.92-7.06 (m, 4H), 7.39-7.54 (m, 12H)

<Step 4> Synthesis of Compound IAz-3

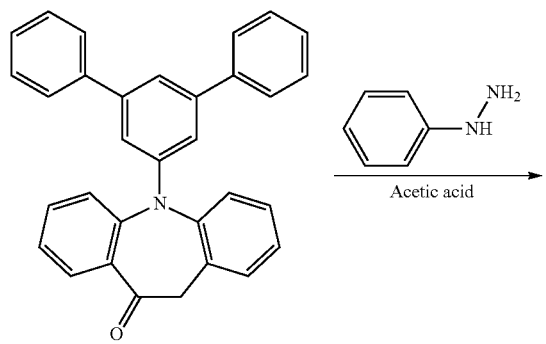

5-(1-bromo-3,5-diphenylbenzene)-5H-dibenzo[b,f]azepin-10(11H)-one (89.9 g, 205.4 mmol) obtained in <Step 3> of Preparation Example 3, phenylhydrazine (24.4 g, 226.0 mmol), and acetic acid (900 ml) were mixed under nitrogen flow, and then the resulting mixture was stirred at 120° C. for 12 hours.

After the reaction was terminated, the organic layer was extracted with dichloromethane, MgSO₄ was added thereto, and the resulting product was filtered. Compound IAz-3 (69.2 g, yield 66%) was obtained by removing the solvent from the obtained organic layer, and then purifying the residue with column chromatography (hexane:MC=2:1 (v:v)).

¹H-NMR of IAz-3: δ 6.69-6.70 (m, 2H), 6.85-6.87 (m, 4H), 7.08-7.16 (m, 5H), 7.41-7.54 (m, 13H), 8.83 (d, 1H), 11.36 (b, 1H)

[Preparation Example 4] Synthesis of Compound IAz-4

<Step 1> Synthesis of 5-acetyl-10,11-(1H-indolo)-5H-dibenzo[b,f]azepin

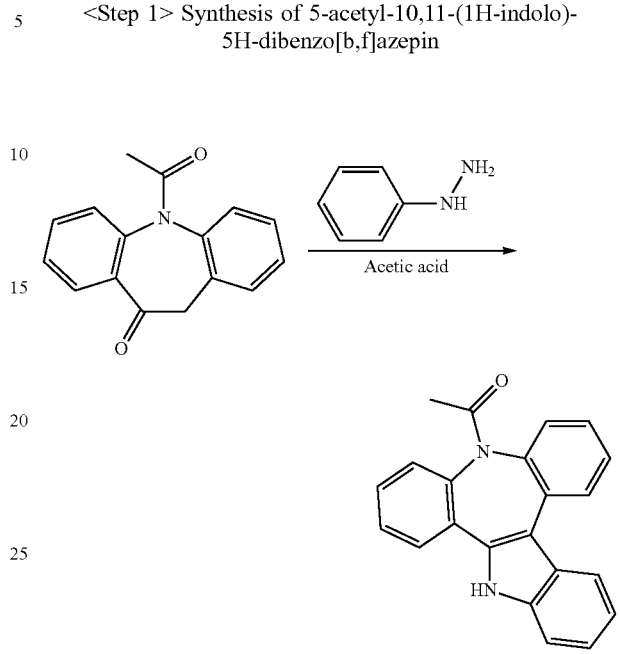

5-acetyl-5H-dibenzo[b,f]azepin-10(11H)-one (70.5 g, 280.7 mmol) obtained in <Step 3> of Preparation Example 1, phenylhydrazine (33.4 g, 308.7 mmol), and acetic acid (700 ml) were mixed under nitrogen flow, and then the resulting mixture was stirred at 120° C. for 12 hours.

After the reaction was terminated, the organic layer was extracted with ethyl acetate, and then moisture was removed using MgSO₄, and recrystallization was performed in ethanol to obtain 5-acetyl-10,11-(1H-indolo)-5H-dibenzo[b,f]azepin (59.2 g, yield 65%).

¹H-NMR: δ 2.04 (s, 3H), 7.08-7.10 (m, 2H), 7.25-7.27 (m, 2H), 7.39-7.44 (m, 3H), 7.56 (d, 1H), 7.77-7.87 (m, 3H), 9.06 (d, 1H), 11.36 (b, 1H)

<Step 2> Synthesis of 5-acetyl-10,11-[1-(1-bromo-3,5-diphenylbenzene)-1H-indolo]-5H-dibenzo[b,f]azepin

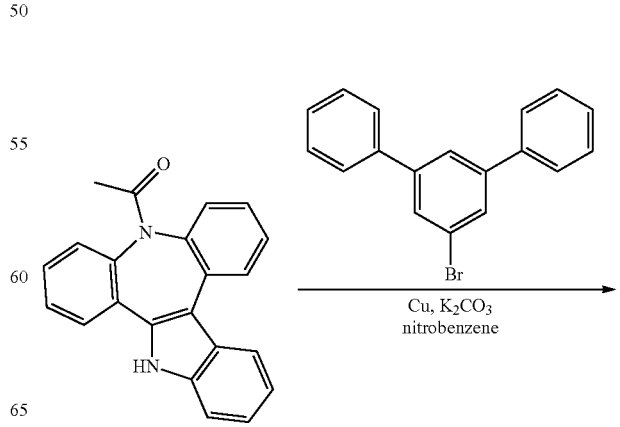

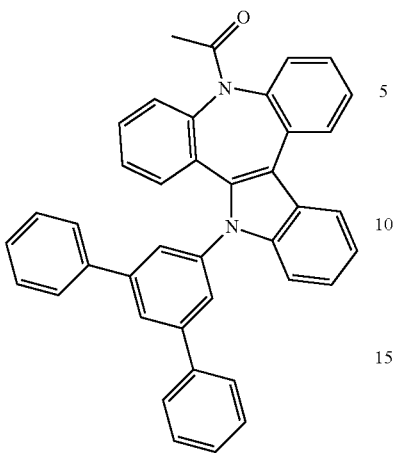

5-acetyl-10,11-(1H-indolo)-5H-dibenzo[b,f]azepin (59.2 g, 182.4 mmol) obtained in <Step 1> of Preparation Example 4, 1-bromo-3,5-diphenylbenzene (67.7 g, 218.9 mmol), Cu (5.8 g, 91.2 mmol), $K_2CO_3$ (50.4 g, 364.9 mmol), and nitrobenzene (600 ml) were mixed under nitrogen flow, and the resulting mixture was stirred at 210° C. for 12 hours.

After the reaction was terminated, the organic layer was extracted with ethyl acetate, and then moisture was removed using $MgSO_4$, and recrystallization was performed in ethanol to obtain 5-acetyl-10,11-[1-(1-bromo-3,5-diphenylbenzene)-1H-indolo]-5H-dibenzo[b,f]azepin (67.6 g, yield 67%).

$^1$H-NMR: δ 2.04 (s, 3H), 7.25-7.26 (m, 2H), 7.39-7.52 (m, 14H), 7.71-7.77 (m, 2H), 7.87-7.88 (m, 3H), 8.05-8.06 (m, 2H), 8.17 (d, 1H), 9.06 (d, 1H)

<Step 3> Synthesis of Compound IAz-4

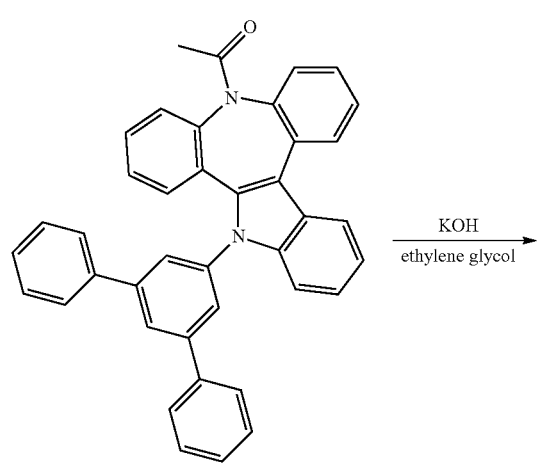

5-acetyl-10,11-[1-(1-bromo-3,5-diphenylbenzene)-1H-indolo]-5H-dibenzo[b,f]azepin (67.6 g, 122.2 mmol) obtained in <Step 2> of Preparation Example 4, potassium hydroxide (7.5 g, 134.4 mmol), and ethylene glycol (700 ml) were mixed under nitrogen flow, and the resulting mixture was stirred at 200° C. for 6 hours.

After the reaction was terminated, the organic layer was extracted with ethyl acetate, and then moisture was removed using $MgSO_4$, and purification was performed by column chromatography (hexane:EA=4:1 (v/v)) to obtain Compound IAz-4 (53.1 g, yield 85%).

$^1$H-NMR of IAz-4: δ 6.68-6.69 (m, 2H), 6.87-6.88 (m, 2H), 7.16-7.17 (m, 2H), 7.42-7.54 (m, 13H), 7.60 (b, 1H), 7.71 (d, 1H), 7.88 (s, 1H), 8.05-8.06 (m, 2H), 8.17 (d, 1H), 8.83 (d, 1H)

[Preparation Example 5] Synthesis of Compound IAz-5

<Step 1> Synthesis of 5-acetyl-10,11-(7-phenyl-1H-indolo)-5H-dibenzo[b,f]azepin

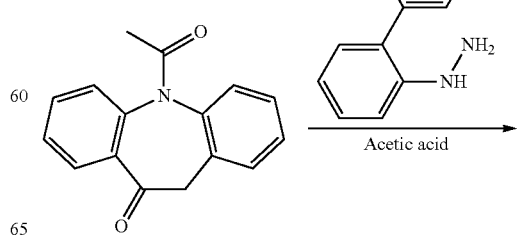

-continued

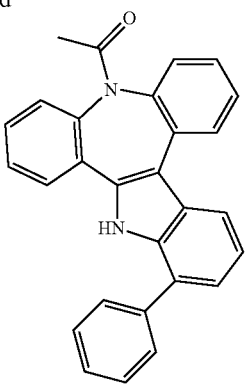

5-acetyl-5H-dibenzo[b,f]azepin-10(11H)-one (70.5 g, 280.7 mmol) obtained in <Step 3> of Preparation Example 1, biphenyl-2-ylhydrazine (56.9 g, 308.7 mmol), and acetic acid (700 ml) were mixed under nitrogen flow, and then the resulting mixture was stirred at 120° C. for 12 hours.

After the reaction was terminated, the organic layer was extracted with ethyl acetate, and then moisture was removed using MgSO$_4$, and recrystallization was performed in ethanol to obtain 5-acetyl-10,11-(7-phenyl-1H-indolo)-5H-dibenzo[b,f]azepin (66.3 g, yield 59%).

$^1$H-NMR: δ 2.03 (s, 3H), 7.14-7.25 (m, 5H), 7.39-7.52 (m, 6H), 7.77-7.87 (m, 4H), 9.06 (d, 1H), 11.36 (b, 1H)

<Step 2> Synthesis of 5-acetyl-10,11-(1,7-diphenyl-1H-indolo)-5H-dibenzo[b,f]azepin

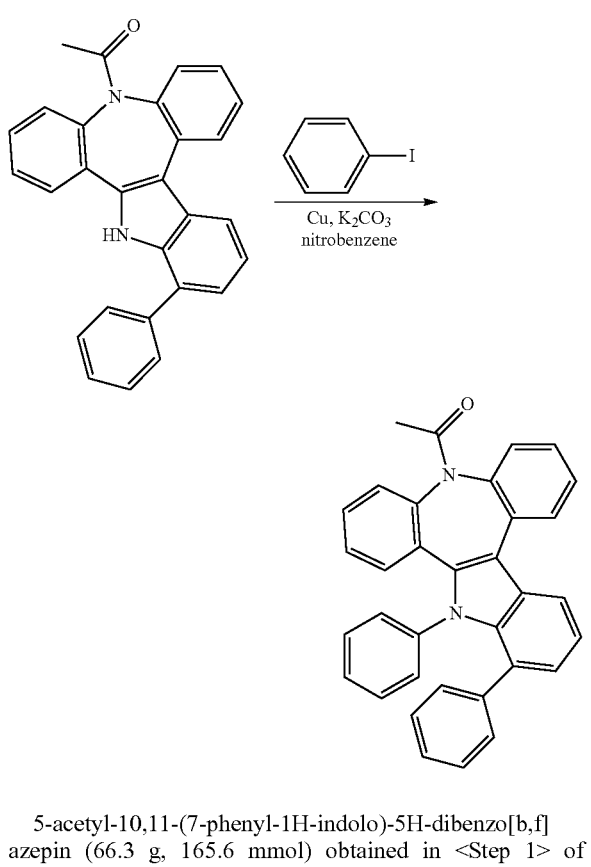

5-acetyl-10,11-(7-phenyl-1H-indolo)-5H-dibenzo[b,f]azepin (66.3 g, 165.6 mmol) obtained in <Step 1> of Preparation Example 4, iodobenzene (40.5 g, 198.7 mmol), Cu (5.3 g, 82.8 mmol), K$_2$CO$_3$ (45.8 g, 331.2 mmol), and nitrobenzene (650 ml) were mixed under nitrogen flow, and the resulting mixture was stirred at 210° C. for 12 hours.

After the reaction was terminated, the organic layer was extracted with ethyl acetate, and then moisture was removed using MgSO$_4$, and recrystallization was performed in ethanol to obtain 5-acetyl-10,11-(1,7-diphenyl-1H-indolo)-5H-dibenzo[b,f]azepin (56.0 g, yield 71%).

$^1$H-NMR: δ 2.03 (s, 3H), 7.19-7.25 (m, 4H), 7.39-7.58 (m, 11H), 7.77 (d, 1H), 7.87-7.88 (m, 2H), 8.13 (d, 1H), 8.39 (d, 1H), 9.06 (d, 1H)

<Step 3> Synthesis of Compound IAz-5

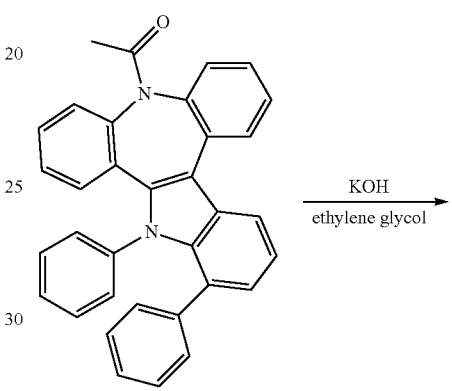

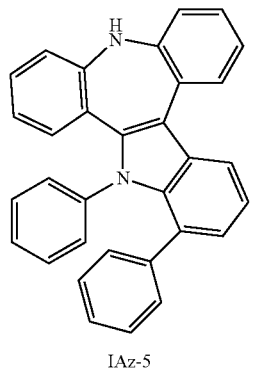

IAz-5

5-acetyl-10,11-(1,7-diphenyl-1H-indolo)-5H-dibenzo[b,f]azepin (56.0 g, 117.6 mmol) obtained in <Step 2> of Preparation Example 4, potassium hydroxide (7.3 g, 129.3 mmol), and ethylene glycol (550 ml) were mixed under nitrogen flow, and the resulting mixture was stirred at 200° C. for 6 hours.

After the reaction was terminated, the organic layer was extracted with ethyl acetate, and then moisture was removed using MgSO$_4$, and purification was performed by column chromatography (hexane:EA=3:1 (v/v)) to obtain Compound IAz-5 (45.0 g, yield 88%).

$^1$H-NMR of IAz-5: δ 6.69-6.70 (m, 2H), 6.86-6.87 (m, 2H), 7.16-7.19 (m, 4H), 7.41-7.58 (m, 10H), 7.60 (b, 1H), 8.13 (d, 1H), 8.39 (d, 1H), 8.83 (d, 1H)

[Preparation Example 6] Synthesis of Compound IAz-6

<Step 1> Synthesis of 1a,10b-dihydrodibenzo[b,f]oxireno[2,3-d]oxepine

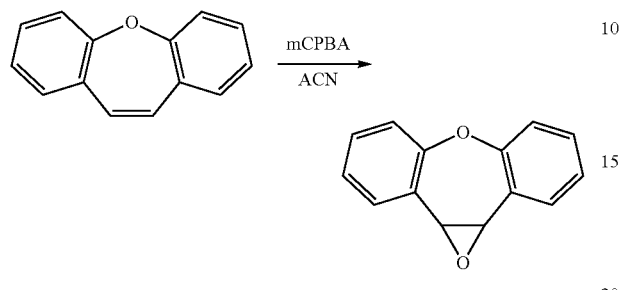

Dibenzo[b,f]oxepine (100.0 g, 514.9 mmol), meta-chloroperoxybenzoic acid (106.6 g, 617.8 mmol), silica (200.0 g), NaOCl (200.0 g), and acetonitrile (1,000 ml) were mixed under nitrogen flow, and the resulting mixture was stirred at 80° C. for 2 hours.

After the reaction was terminated, the organic layer was extracted with methylene chloride, MgSO$_4$ was added thereto, and the resulting product was filtered. The solvent was removed from the obtained organic layer, and then recrystallization was performed with ethanol to obtain 1a,10b-dihydrodibenzo[b,f]oxireno[2,3-d]oxepine (87.7 g, yield 81%).

$^1$H-NMR: δ 4.30 (s, 2H), 7.10 (d, 2H), 7.26-7.34 (m, 6H)

<Step 2> Synthesis of dibenzo[b,f]oxepin-10(11H)-one

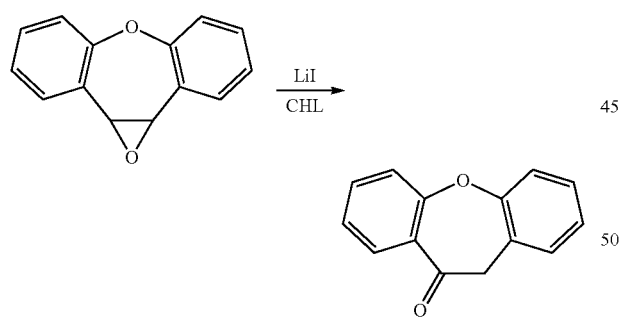

1a,10b-dihydrodibenzo[b,f]oxireno[2,3-b]oxepine (87.7 g, 417.0 mmol) obtained in <Step 1> of Preparation Example 6, lithium iodide (67.0 g, 500.4 mmol), and chloroform (900 ml) were mixed under nitrogen flow, and the resulting mixture was stirred at 60° C. for 1 hour.

After the reaction was terminated, the organic layer was extracted with ethyl acetate, and then moisture was removed using MgSO$_4$, and recrystallization was performed in ethanol to obtain dibenzo[b,f]oxepin-10(11H)-one (69.3 g, yield 79%).

$^1$H-NMR: δ 3.51 (d, 1H), 4.42 (d, 1H), 7.05 (t, 1H), 7.19-7.28 (m, 4H), 7.43-7.44 (m, 2H), 7.60 (t, 1H)

<Step 3> Synthesis of Compound IAz-6

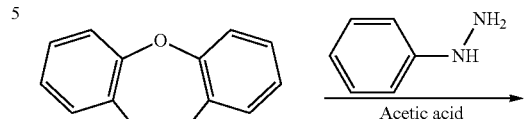

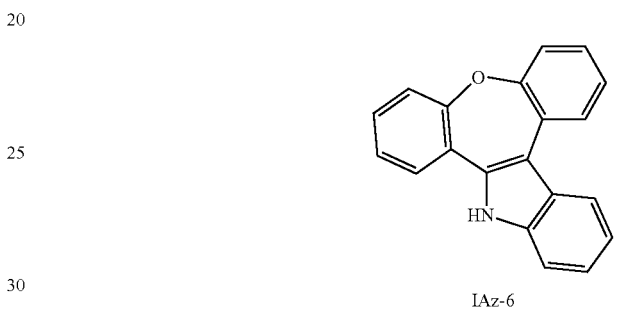

IAz-6

Dibenzo[b,f]oxepin-10(11H)-one (69.3 g, 329.5 mmol) obtained in <Step 2> of Preparation Example 6, phenylhydrazine (39.2 g, 362.4 mmol), and acetic acid (700 ml) were mixed under nitrogen flow, and then the resulting mixture was stirred at 120° C. for 12 hours.

After the reaction was terminated, the organic layer was extracted with dichloromethane, MgSO$_4$ was added thereto, and the resulting product was filtered. Compound IAz-6 (60.7 g, yield 65%) was obtained by removing the solvent from the obtained organic layer, and then purifying the residue with column chromatography (hexane:MC=3:1 (v:v)).

$^1$H-NMR of IAz-6: δ 7.08-7.09 (m, 2H), 7.20-7.23 (m, 4H), 7.37-7.44 (m, 3H), 7.56 (d, 1H), 7.75 (d, 1H), 8.39 (d, 1H), 11.36 (b, 1H)

[Preparation Example 7] Synthesis of Compound IAz-7

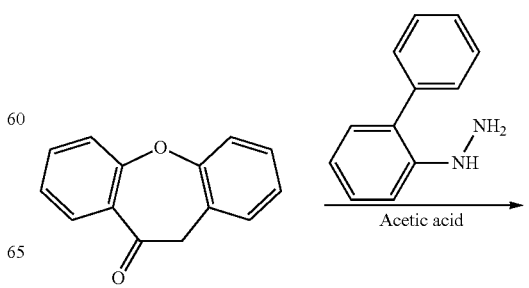

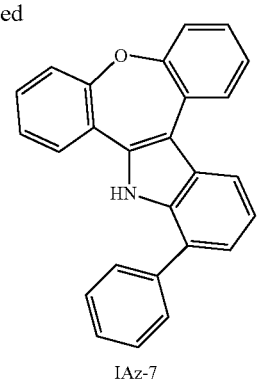

IAz-7

Dibenzo[b,f]oxepin-10(11H)-one (69.3 g, 329.5 mmol) obtained in <Step 2> of Preparation Example 6, biphenyl-2-ylhydrazine (66.8 g, 362.4 mmol), and acetic acid (700 ml) were mixed under nitrogen flow, and then the resulting mixture was stirred at 120° C. for 12 hours.

After the reaction was terminated, the organic layer was extracted with dichloromethane, MgSO$_4$ was added thereto, and the resulting product was filtered. Compound IAz-7 (55.1 g, yield 59%) was obtained by removing the solvent from the obtained organic layer, and then purifying the residue with column chromatography (hexane:MC=2:1 (v:v)).

$^1$H-NMR of IAz-7: δ 7.14-7.23 (m, 7H), 7.37-7.52 (m, 6H), 7.75-7.78 (m, 2H), 8.39 (d, 1H), 11.36 (b, 1H)

[Preparation Example 8] Synthesis of Compound IAz-8

<Step 1> Synthesis of 1a,10b-dihydrodibenzo[b,f]oxireno[2,3-d]thiepine

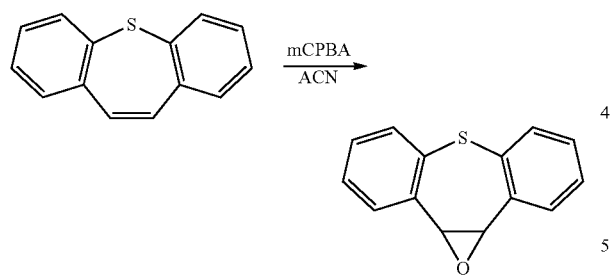

Dibenzo[b,f]oxepine (100.0 g, 475.5 mmol), meta-chloroperoxybenzoic acid (98.5 g, 570.6 mmol), silica (200.0 g), NaOCl (200.0 g), and acetonitrile (1,000 ml) were mixed under nitrogen flow, and the resulting mixture was stirred at 80° C. for 2 hours.

After the reaction was terminated, the organic layer was extracted with methylene chloride, MgSO$_4$ was added thereto, and the resulting product was filtered. The solvent was removed from the obtained organic layer, and then recrystallization was performed with ethanol to obtain 1a,10b-dihydrodibenzo[b,f]oxireno[2,3-d]thiepine (80.7 g, yield 75%).

$^1$H-NMR: δ 4.40 (s, 2H), 7.12-7.16 (m, 4H), 7.45 (t, 2H), 7.70 (d, 2H)

<Step 2> Synthesis of dibenzo[b,f]thiepin-10(11H)-one

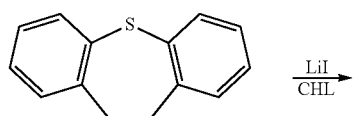

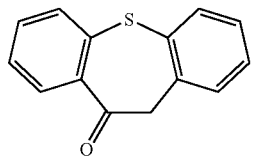

1a,10b-dihydrodibenzo[b,f]oxireno[2,3-d]thiepine (80.7 g, 356.7 mmol) obtained in <Step 1> of Preparation Example 8, lithium iodide (57.3.0 g, 428.0 mmol), and chloroform (800 ml) were mixed under nitrogen flow, and the resulting mixture was stirred at 60° C. for 1 hour.

After the reaction was terminated, the organic layer was extracted with ethyl acetate, and then moisture was removed using MgSO$_4$, and recrystallization was performed in ethanol to obtain dibenzo[b,f]thiepin-10(11H)-one (59.7 g, yield 74%).

$^1$H-NMR: δ 3.61 (d, 1H), 4.47 (d, 1H), 7.03-7.07 (m, 2H), 7.30-7.33 (m, 2H), 7.44-7.52 (m, 2H), 7.65 (d, 1H), 7.74 (d, 1H)

<Step 3> Synthesis of Compound IAz-8

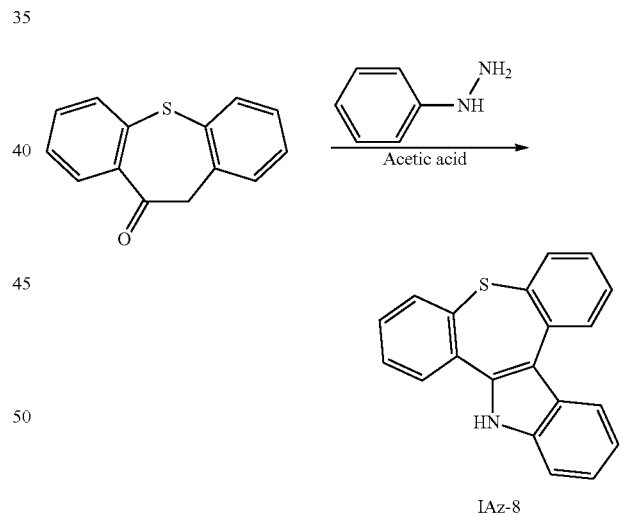

IAz-8

Dibenzo[b,f]thiepin-10(11H)-one (59.7 g, 263.9 mmol) obtained in <Step 2> of Preparation Example 8, phenylhydrazine (31.4 g, 290.3 mmol), and acetic acid (600 ml) were mixed under nitrogen flow, and then the resulting mixture was stirred at 120° C. for 12 hours.

After the reaction was terminated, the organic layer was extracted with dichloromethane, MgSO$_4$ was added thereto, and the resulting product was filtered. Compound IAz-8 (42.7 g, yield 54%) was obtained by removing the solvent from the obtained organic layer, and then purifying the residue with column chromatography (hexane:MC=3:1 (v:v)).

¹H-NMR of IAz-8: δ 7.09-7.10 (m, 2H), 7.21-7.25 (m, 4H), 7.44-7.59 (m, 6H), 11.36 (b, 1H)

[Preparation Example 9] Synthesis of Compound IAz-9

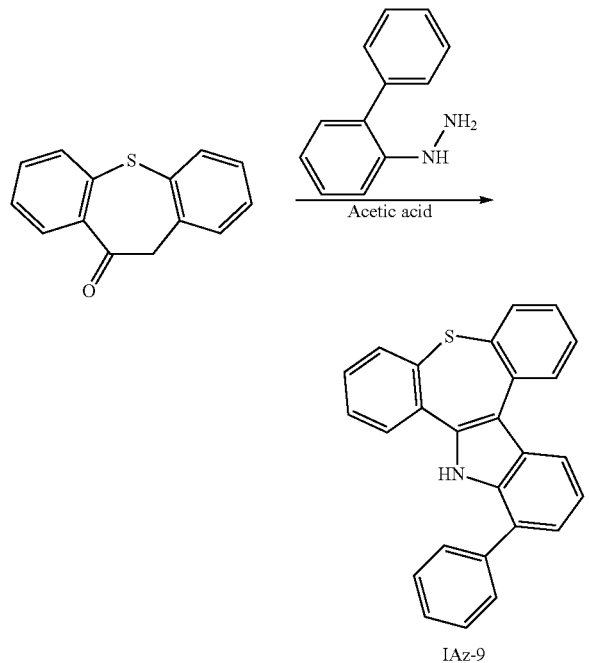

IAz-9

Dibenzo[b,f]thiepin-10(11H)-one (59.7 g, 263.9 mmol) obtained in <Step 2> of Preparation Example 8, biphenyl-2-ylhydrazine (53.5 g, 290.3 mmol), and acetic acid (600 ml) were mixed under nitrogen flow, and then the resulting mixture was stirred at 120° C. for 12 hours.

After the reaction was terminated, the organic layer was extracted with dichloromethane, MgSO₄ was added thereto, and the resulting product was filtered. Compound IAz-9 (50.5 g, yield 51%) was obtained by removing the solvent from the obtained organic layer, and then purifying the residue with column chromatography (hexane:MC=2:1 (v:v)).

¹H-NMR of IAz-9: δ 7.14-7.25 (m, 7H), 7.41-7.59 (m, 8H), 7.78 (d, 1H), 11.36 (b, 1H)

[Synthesis Example 1] Synthesis of Compound A-1

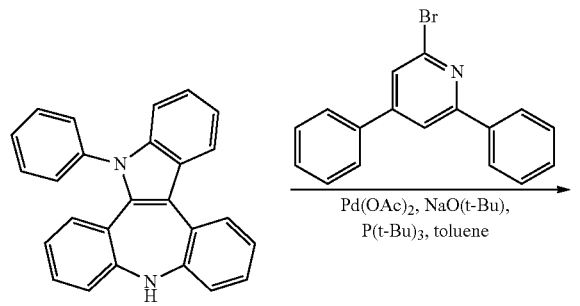

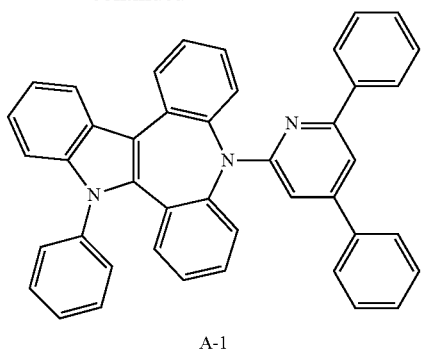

A-1

IAz-1 (2.4 g, 6.7 mmol) synthesized in Preparation Example 1, 2-bromo-4,6-diphenylpyridine (2.5 g, 8.0 mmol), Pd(OAc)₂ (0.08 g, 0.34 mmol), P(t-Bu)₃ (0.16 ml, 0.67 mmol), NaO(t-Bu) (1.29 g, 13.4 mmol), and toluene (70 ml) were mixed under nitrogen flow, and the resulting mixture was stirred at 110° C. for 5 hours. After the reaction was terminated, toluene was concentrated, a solid salt was filtered, and then, purified with recrystallization to obtain Compound A-1 (2.5 g, yield 64%).

Mass (theoretical value: 587.24, measured value: 587 g/mol)

[Synthesis Example 2] Synthesis of Compound A-2

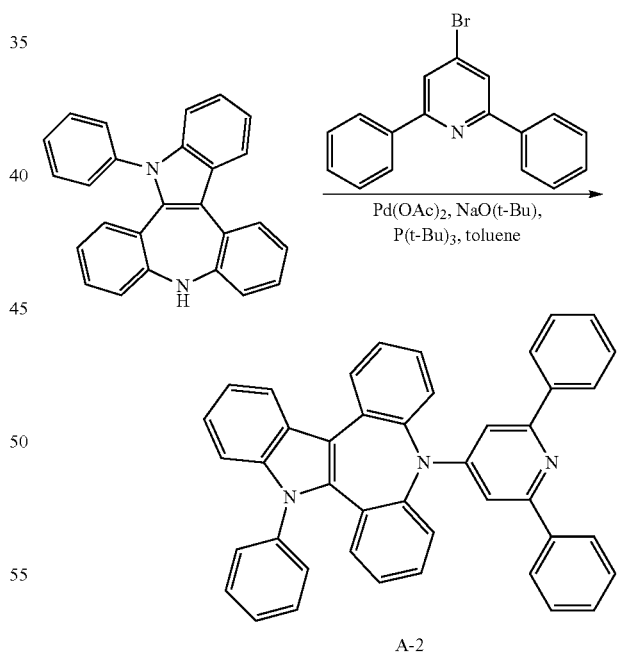

A-2

Compound A-2 (2.4 g, yield 61%) was obtained by performing the same process as in Synthesis Example 1, except that 4-bromo-2,6-diphenylpyridine (2.5 g, 8.0 mmol) was used instead of 2-bromo-4,6-diphenylpyridine used in Synthesis Example 1.

Mass (theoretical value: 587.24, measured value: 587 g/mol)

[Synthesis Example 3] Synthesis of Compound A-3

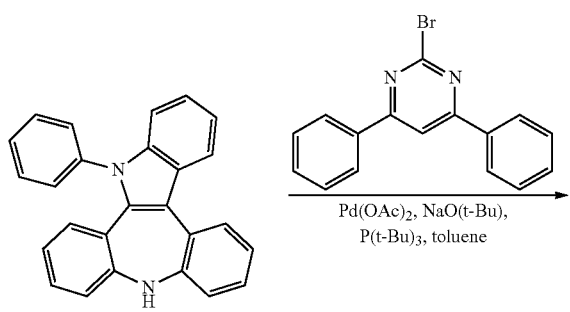

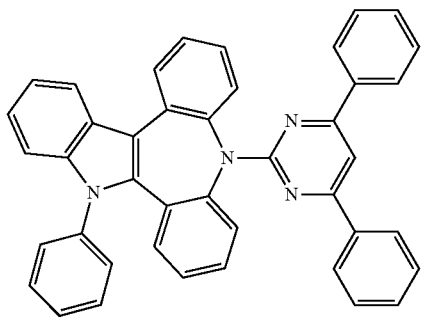

A-3

Compound A-3 (2.7 g, yield 69%) was obtained by performing the same process as in Synthesis Example 1, except that 2-bromo-4,6-diphenylpyrimidine (2.5 g, 8.0 mmol) was used instead of 2-bromo-4,6-diphenylpyridine used in Synthesis Example 1.

Mass (theoretical value: 588.23, measured value: 588 g/mol)

[Synthesis Example 4] Synthesis of Compound A-4

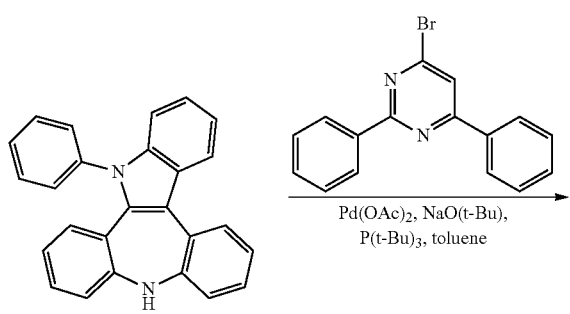

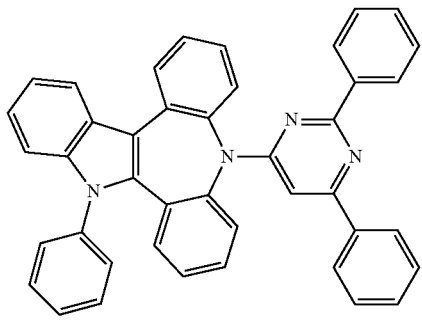

A-4

Compound A-4 (2.5 g, yield 73%) was obtained by performing the same process as in Synthesis Example 1, except that 4-bromo-2,6-diphenylpyrimidine (2.5 g, 8.0 mmol) was used instead of 2-bromo-4,6-diphenylpyridine used in Synthesis Example 1.

Mass (theoretical value: 588.23, measured value: 588 g/mol)

[Synthesis Example 5] Synthesis of Compound A-5

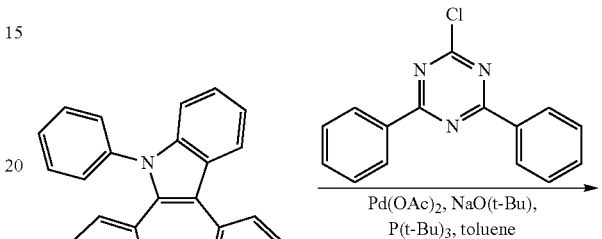

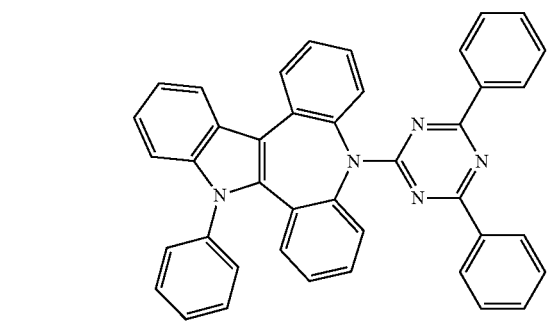

A-5

Compound A-5 (2.8 g, yield 70%) was obtained by performing the same process as in Synthesis Example 1, except that 2-chloro-4,6-diphenyl-1,3,5-triazine (2.1 g, 8.0 mmol) was used instead of 2-bromo-4,6-diphenylpyridine used in Synthesis Example 1.

Mass (theoretical value: 589.23, measured value: 589 g/mol)

[Synthesis Example 6] Synthesis of Compound A-6

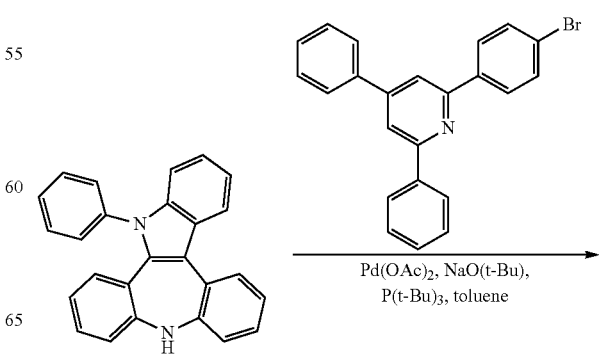

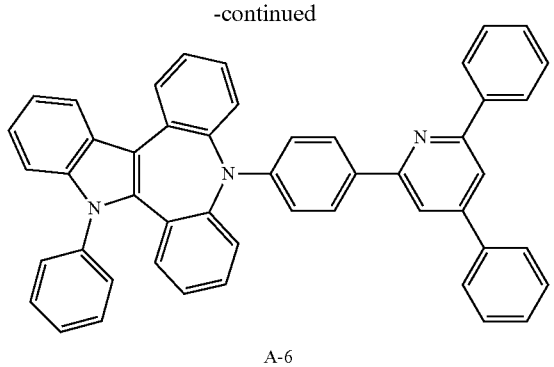

A-6

Compound A-6 (3.0 g, yield 68%) was obtained by performing the same process as in Synthesis Example 1, except that 2-(4-bromophenyl)-4,6-diphenylpyridine (3.1 g, 8.0 mmol) was used instead of 2-bromo-4,6-diphenylpyridine used in Synthesis Example 1.

Mass (theoretical value: 663.27, measured value: 663 g/mol)

[Synthesis Example 7] Synthesis of Compound A-7

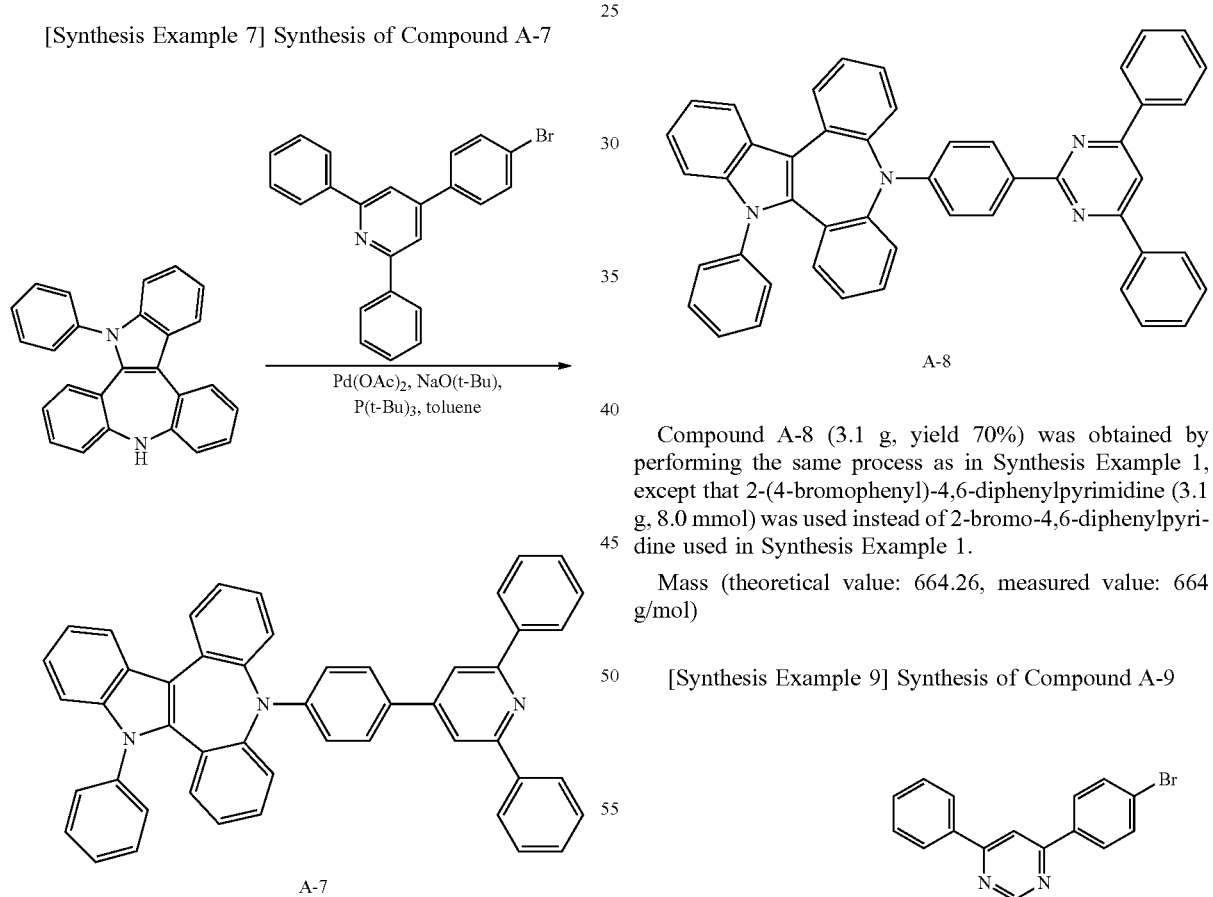

A-7

Compound A-7 (2.7 g, yield 61%) was obtained by performing the same process as in Synthesis Example 1, except that 4-(4-bromophenyl)-2,6-diphenylpyridine (3.1 g, 8.0 mmol) was used instead of 2-bromo-4,6-diphenylpyridine used in Synthesis Example 1.

Mass (theoretical value: 663.27, measured value: 663 g/mol)

[Synthesis Example 8] Synthesis of Compound A-8

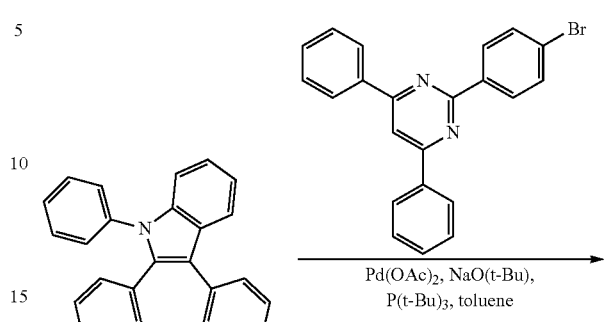

A-8

Compound A-8 (3.1 g, yield 70%) was obtained by performing the same process as in Synthesis Example 1, except that 2-(4-bromophenyl)-4,6-diphenylpyrimidine (3.1 g, 8.0 mmol) was used instead of 2-bromo-4,6-diphenylpyridine used in Synthesis Example 1.

Mass (theoretical value: 664.26, measured value: 664 g/mol)

[Synthesis Example 9] Synthesis of Compound A-9

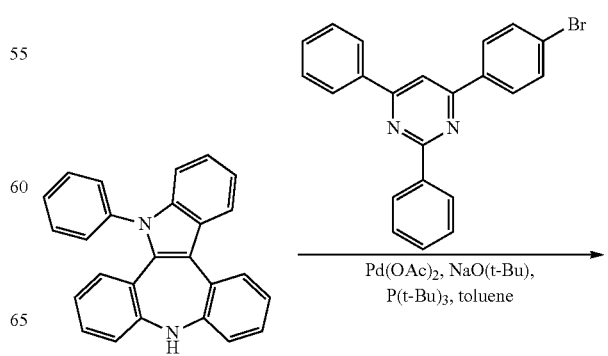

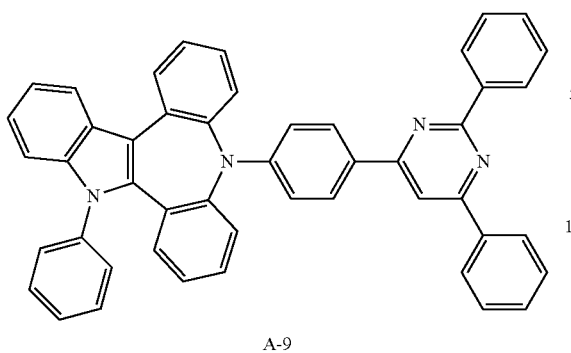

A-9

Compound A-9 (3.3 g, yield 74%) was obtained by performing the same process as in Synthesis Example 1, except that 4-(4-bromophenyl)-2,6-diphenylpyrimidine (3.1 g, 8.0 mmol) was used instead of 2-bromo-4,6-diphenylpyridine used in Synthesis Example 1.

Mass (theoretical value: 664.26, measured value: 664 g/mol)

[Synthesis Example 10] Synthesis of Compound A-10

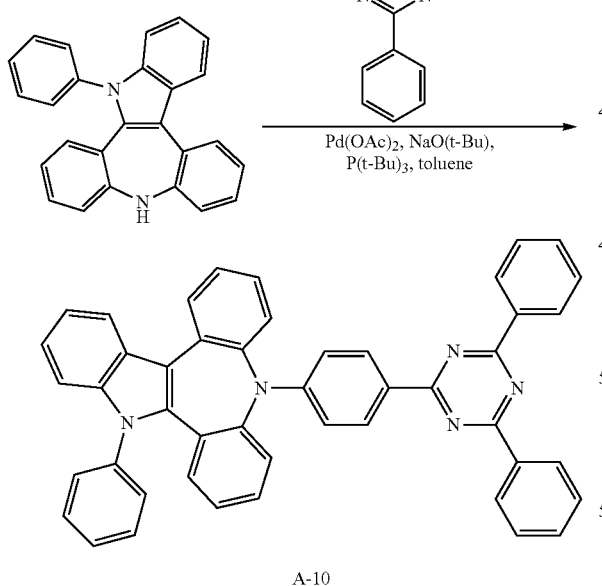

A-10

Compound A-10 (2.9 g, yield 65%) was obtained by performing the same process as in Synthesis Example 1, except that 2-(4-bromophenyl)-4,6-diphenyl-1,3,5-triazine (3.1 g, 8.0 mmol) was used instead of 2-bromo-4,6-diphenylpyridine used in Synthesis Example 1.

Mass (theoretical value: 665.26, measured value: 665 g/mol)

[Synthesis Example 11] Synthesis of Compound A-11

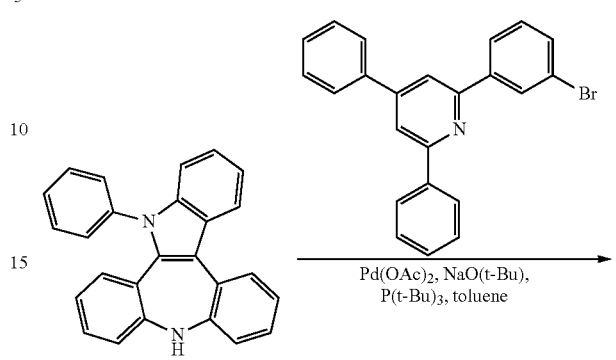

A-11

Compound A-11 (2.8 g, yield 62%) was obtained by performing the same process as in Synthesis Example 1, except that 2-(3-bromophenyl)-4,6-diphenylpyridine (3.1 g, 8.0 mmol) was used instead of 2-bromo-4,6-diphenylpyridine used in Synthesis Example 1.

Mass (theoretical value: 663.27, measured value: 663 g/mol)

[Synthesis Example 12] Synthesis of Compound A-12

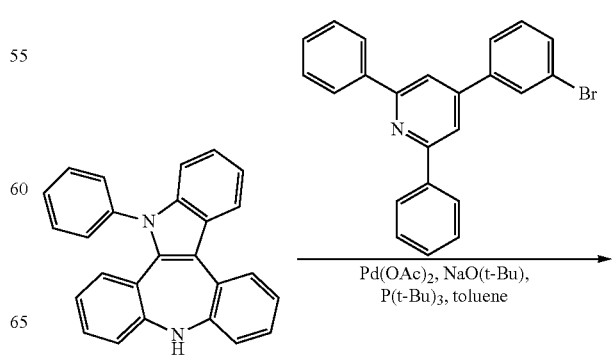

-continued

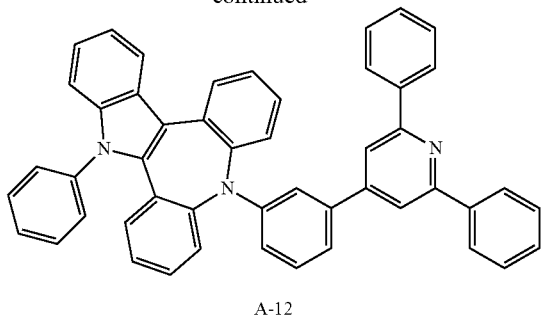

A-12

Compound A-12 (3.0 g, yield 68%) was obtained by performing the same process as in Synthesis Example 1, except that 4-(3-bromophenyl)-2,6-diphenylpyridine (3.1 g, 8.0 mmol) was used instead of 2-bromo-4,6-diphenylpyridine used in Synthesis Example 1.

Mass (theoretical value: 663.27, measured value: 663 g/mol)

[Synthesis Example 13] Synthesis of Compound A-13

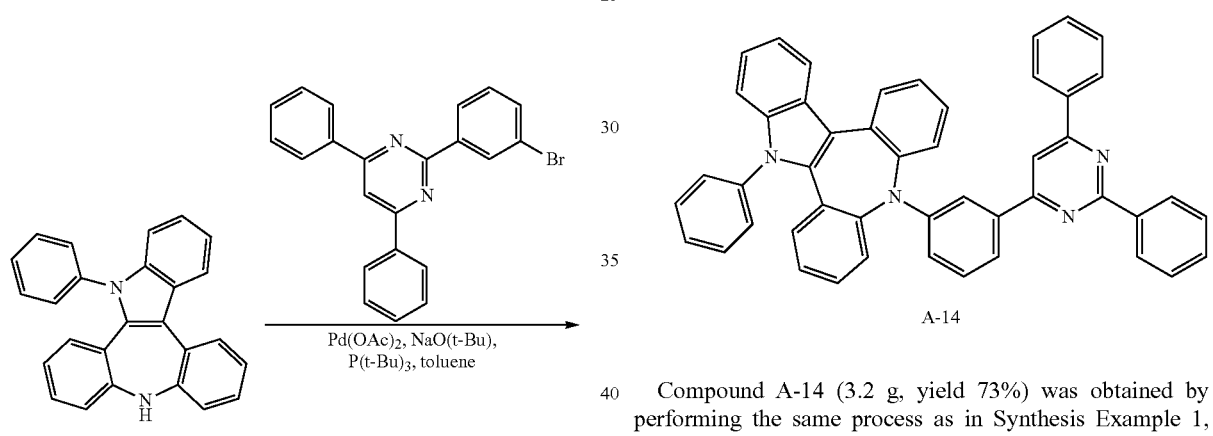

A-13

Compound A-13 (2.9 g, yield 66%) was obtained by performing the same process as in Synthesis Example 1, except that 2-(3-bromophenyl)-4,6-diphenylpyrimidine (3.1 g, 8.0 mmol) was used instead of 2-bromo-4,6-diphenylpyridine used in Synthesis Example 1.

Mass (theoretical value: 664.26, measured value: 664 g/mol)

[Synthesis Example 14] Synthesis of Compound A-14

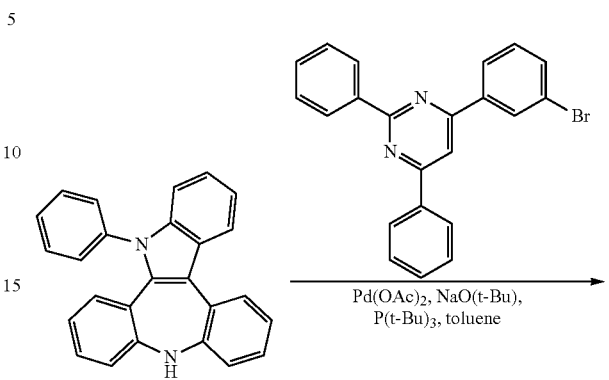

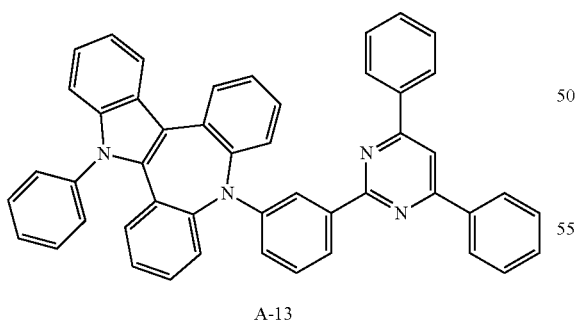

A-14

Compound A-14 (3.2 g, yield 73%) was obtained by performing the same process as in Synthesis Example 1, except that 4-(3-bromophenyl)-2,6-diphenylpyrimidine (3.1 g, 8.0 mmol) was used instead of 2-bromo-4,6-diphenylpyridine used in Synthesis Example 1.

Mass (theoretical value: 664.26, measured value: 664 g/mol)

[Synthesis Example 15] Synthesis of Compound A-15

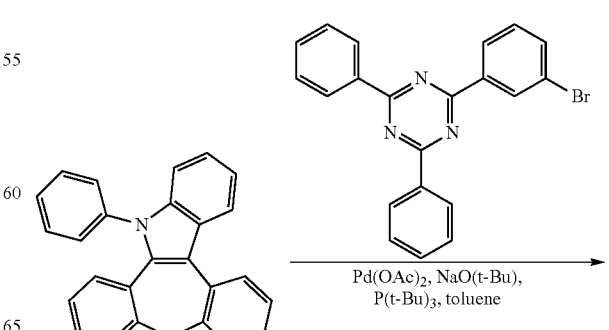

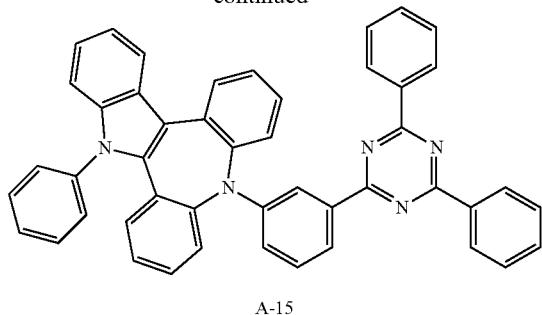

A-15

Compound A-15 (3.2 g, yield 71%) was obtained by performing the same process as in Synthesis Example 1, except that 2-(3-bromophenyl)-4,6-diphenyl-1,3,5-triazine (3.1 g, 8.0 mmol) was used instead of 2-bromo-4,6-diphenylpyridine used in Synthesis Example 1.

Mass (theoretical value: 665.26, measured value: 665 g/mol)

[Synthesis Example 16] Synthesis of Compound A-16

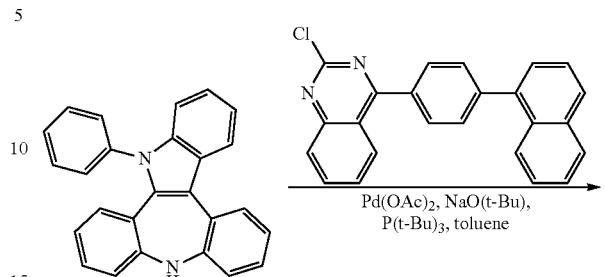

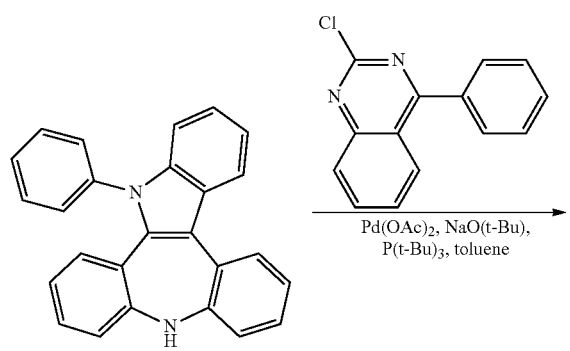

A-16

Compound A-16 (2.6 g, yield 68%) was obtained by performing the same process as in Synthesis Example 1, except that 2-chloro-4-phenylquinazoline (1.9 g, 8.0 mmol) was used instead of 2-bromo-4,6-diphenylpyridine used in Synthesis Example 1.

Mass (theoretical value: 562.22, measured value: 562 g/mol)

[Synthesis Example 17] Synthesis of Compound A-17

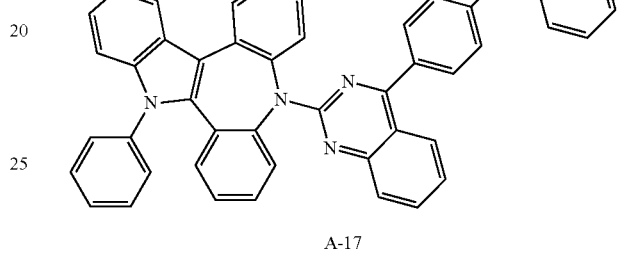

A-17

Compound A-17 (3.1 g, yield 67%) was obtained by performing the same process as in Synthesis Example 1, except that 2-chloro-4-(4-(naphthalen-1-yl)phenyl)quinazoline (2.9 g, 8.0 mmol) was used instead of 2-bromo-4,6-diphenylpyridine used in Synthesis Example 1.

Mass (theoretical value: 688.26, measured value: 688 g/mol)

[Synthesis Example 18] Synthesis of Compound A-18

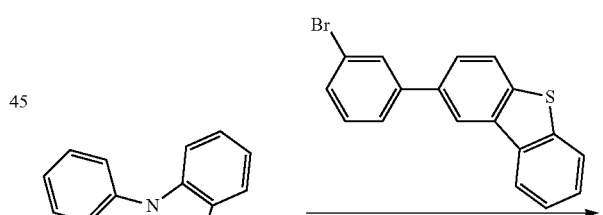

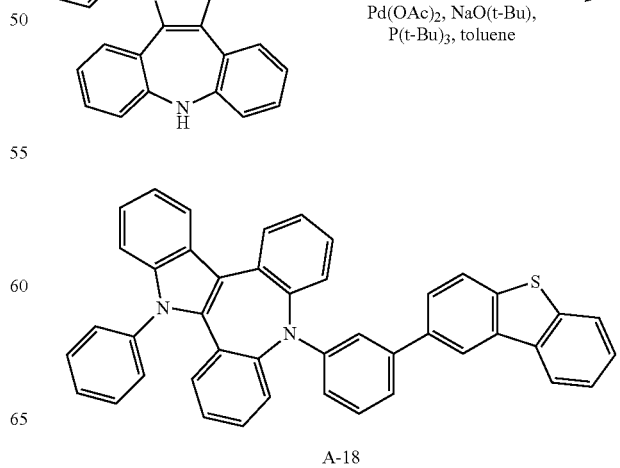

A-18

Compound A-18 (3.2 g, yield 78%) was obtained by performing the same process as in Synthesis Example 1, except that 2-(3-bromophenyl)dibenzo[b,d]thiophene (2.7 g, 8.0 mmol) was used instead of 2-bromo-4,6-diphenylpyridine used in Synthesis Example 1.

Mass (theoretical value: 616.20, measured value: 616 g/mol)

[Synthesis Example 19] Synthesis of Compound A-19

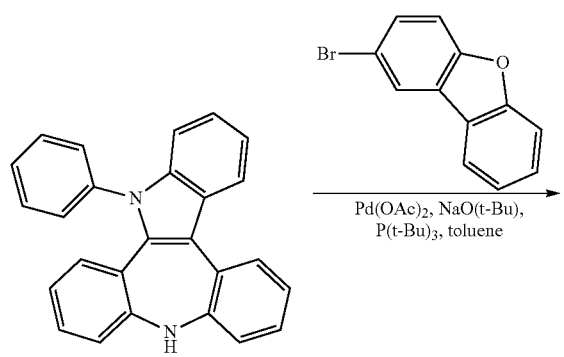

A-19

Compound A-19 (2.5 g, yield 71%) was obtained by performing the same process as in Synthesis Example 1, except that 2-bromodibenzo[b,d]furan (2.0 g, 8.0 mmol) was used instead of 2-bromo-4,6-diphenylpyridine used in Synthesis Example 1.

Mass (theoretical value: 524.19, measured value: 524 g/mol)

[Synthesis Example 20] Synthesis of Compound A-20

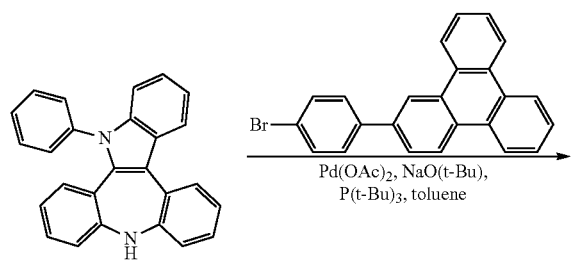

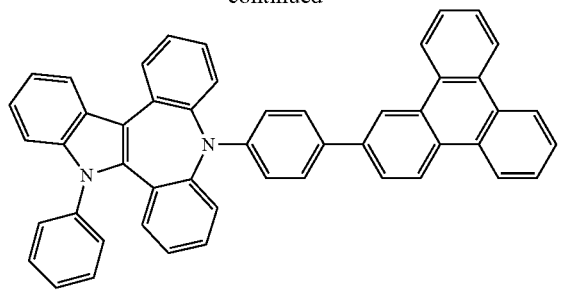

A-20

Compound A-20 (3.3 g, yield 75%) was obtained by performing the same process as in Synthesis Example 1, except that 2-(4-bromophenyl)triphenylene (3.1 g, 8.0 mmol) was used instead of 2-bromo-4,6-diphenylpyridine used in Synthesis Example 1.

Mass (theoretical value: 660.26, measured value: 660 g/mol)

[Synthesis Example 21] Synthesis of Compound A-21

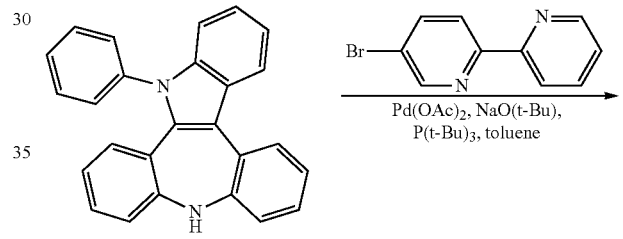

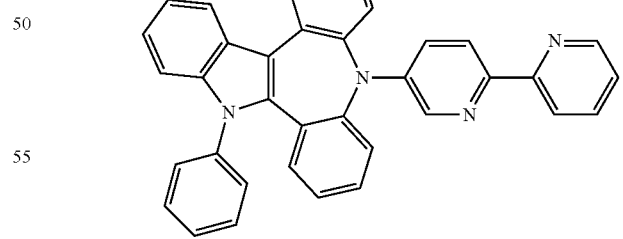

A-21

Compound A-21 (2.2 g, yield 64%) was obtained by performing the same process as in Synthesis Example 1, except that 5-bromo-2,2'-bipyridine (1.9 g, 8.0 mmol) was used instead of 2-bromo-4,6-diphenylpyridine used in Synthesis Example 1. Mass (theoretical value: 512.20, measured value: 512 g/mol)

[Synthesis Example 22] Synthesis of Compound A-22
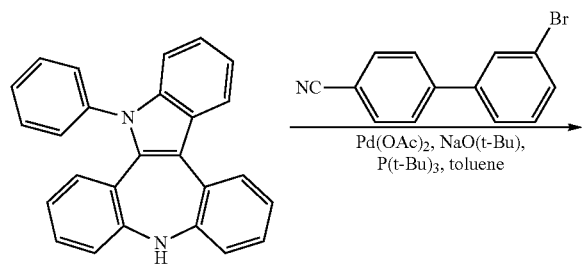
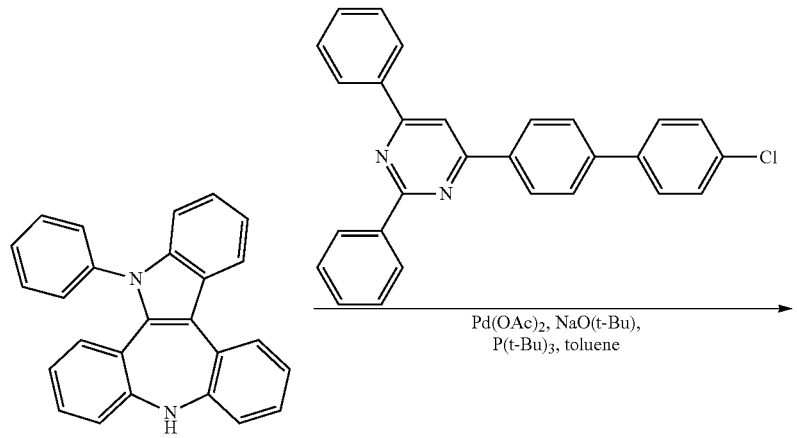
Compound A-22 (2.4 g, yield 68%) was obtained by performing the same process as in Synthesis Example 1, except that 3'-bromobiphenyl-4-carbonitrile (2.1 g, 8.0 mmol) was used instead of 2-bromo-4,6-diphenylpyridine used in Synthesis Example 1.
Mass (theoretical value: 535.21, measured value: 535 g/mol)
[Synthesis Example 23] Synthesis of Compound A-23
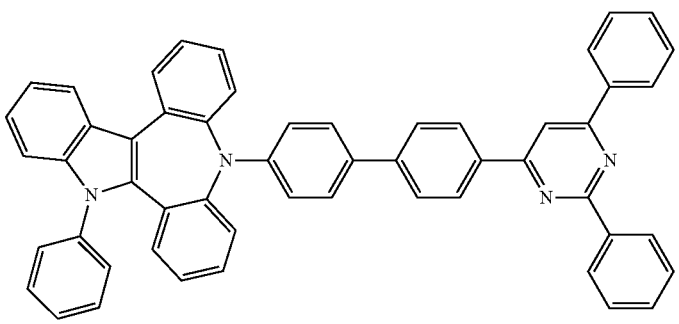

Compound A-23 (3.1 g, yield 62%) was obtained by performing the same process as in Synthesis Example 1, except that 4-(4'-chlorobiphenyl-4-yl)-2,6-diphenylpyrimidine (3.4 g, 8.0 mmol) was used instead of 2-bromo-4,6-diphenylpyridine used in Synthesis Example 1.

Mass (theoretical value: 740.29, measured value: 740 g/mol)

[Synthesis Example 24] Synthesis of Compound B-1

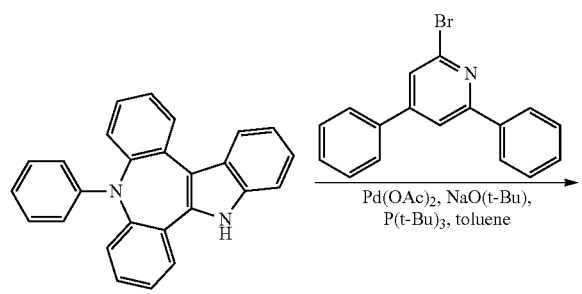

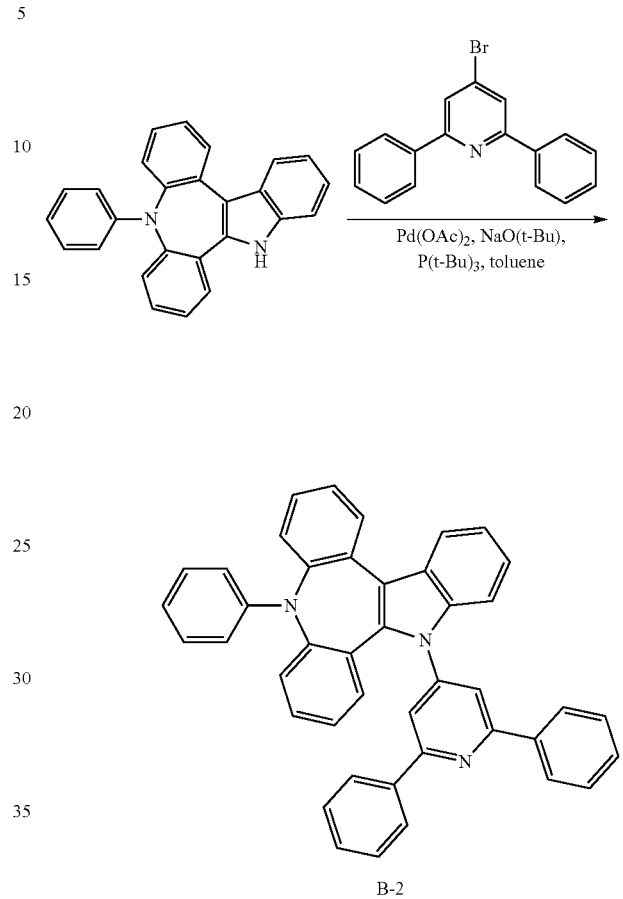

B-1

Compound IAz-2 (2.4 g, 6.7 mmol) synthesized in Preparation Example 2, 2-bromo-4,6-diphenylpyridine (2.5 g, 8.0 mmol), Pd(OAc)$_2$ (0.08 g, 0.34 mmol), P(t-Bu)$_3$ (0.16 ml, 0.67 mmol), NaO(t-Bu) (1.29 g, 13.4 mmol), and toluene (70 ml) were mixed under nitrogen flow, and the resulting mixture was stirred at 110° C. for 5 hours. After the reaction was terminated, toluene was concentrated, and a solid salt was filtered and then purified with recrystallization to obtain Compound B-1 (2.6 g, yield 66%).

Mass (theoretical value: 587.24, measured value: 587 g/mol)

[Synthesis Example 25] Synthesis of Compound B-2

Compound B-2 (2.7 g, yield 69%) was obtained by performing the same process as in Synthesis Example 24, except that 4-bromo-2,6-diphenylpyridine (2.5 g, 8.0 mmol) was used instead of 2-bromo-4,6-diphenylpyridine used in Synthesis Example 24.

Mass (theoretical value: 587.24, measured value: 587 g/mol)

[Synthesis Example 26] Synthesis of Compound B-3

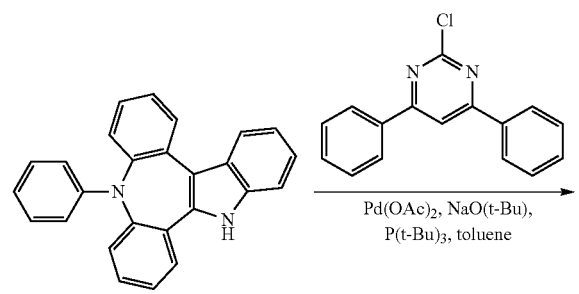

-continued

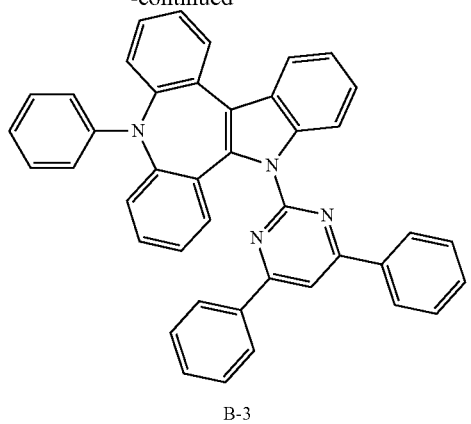

B-3

Compound B-3 (2.4 g, yield 62%) was obtained by performing the same process as in Synthesis Example 24, except that 2-chloro-4,6-diphenylpyrimidine (2.5 g, 8.0 mmol) was used instead of 2-bromo-4,6-diphenylpyridine used in Synthesis Example 24.

Mass (theoretical value: 588.23, measured value: 588 g/mol)

[Synthesis Example 27] Synthesis of Compound B-4

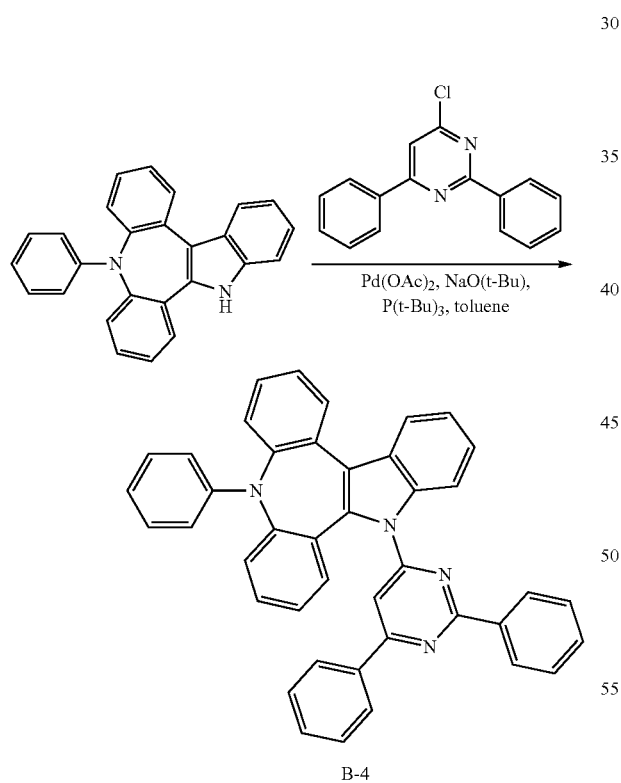

B-4

Compound B-4 (2.8 g, yield 72%) was obtained by performing the same process as in Synthesis Example 24, except that 4-chloro-2,6-diphenylpyrimidine (2.5 g, 8.0 mmol) was used instead of 2-bromo-4,6-diphenylpyridine used in Synthesis Example 24.

Mass (theoretical value: 588.23, measured value: 588 g/mol)

[Synthesis Example 28] Synthesis of Compound B-5

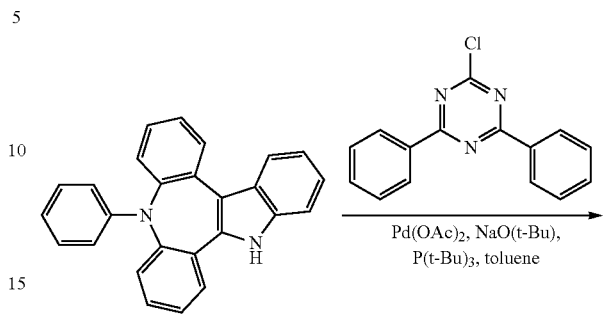

B-5

Compound B-5 (2.4 g, yield 61%) was obtained by performing the same process as in Synthesis Example 24, except that 2-chloro-4,6-diphenyl-1,3,5-triazine (2.1 g, 8.0 mmol) was used instead of 2-bromo-4,6-diphenylpyridine used in Synthesis Example 24.

Mass (theoretical value: 589.23, measured value: 589 g/mol)

[Synthesis Example 29] Synthesis of Compound B-6

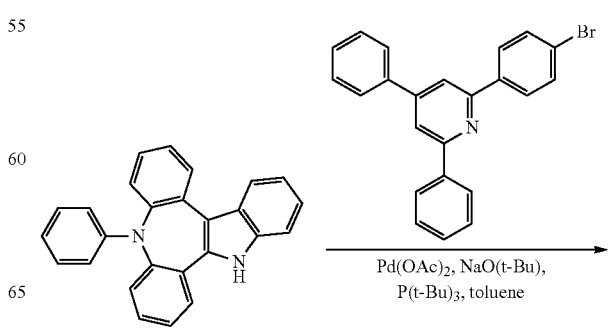

-continued

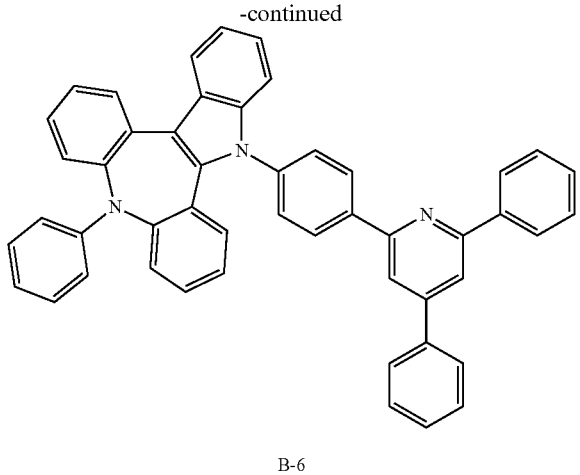

B-6

Compound B-6 (2.9 g, yield 65%) was obtained by performing the same process as in Synthesis Example 24, except that 2-(4-bromophenyl)-4,6-diphenylpyridine (3.1 g, 8.0 mmol) was used instead of 2-bromo-4,6-diphenylpyridine used in Synthesis Example 24.

Mass (theoretical value: 663.27, measured value: 663 g/mol)

[Synthesis Example 30] Synthesis of Compound B-7

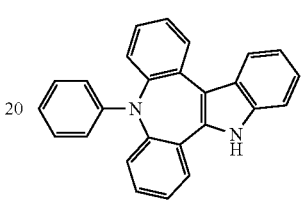

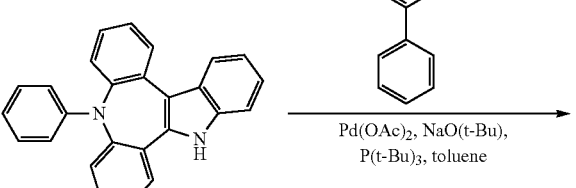

B-7

Compound B-7 (3.3 g, yield 74%) was obtained by performing the same process as in Synthesis Example 24, except that 4-(4-bromophenyl)-2,6-diphenylpyridine (3.1 g, 8.0 mmol) was used instead of 2-bromo-4,6-diphenylpyridine used in Synthesis Example 24.

Mass (theoretical value: 663.27, measured value: 663 g/mol)

[Synthesis Example 31] Synthesis of Compound B-8

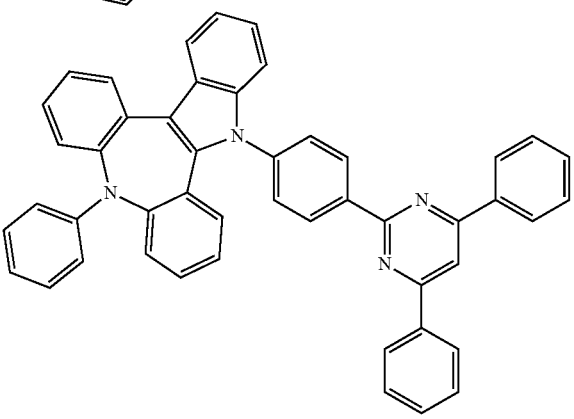

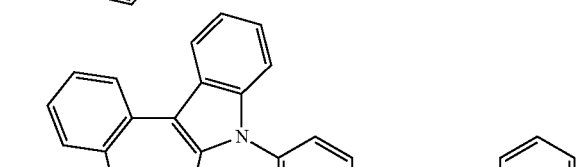

B-8

Compound B-8 (3.5 g, yield 78%) was obtained by performing the same process as in Synthesis Example 24, except that 2-(4-bromophenyl)-4,6-diphenylpyrimidine (3.1 g, 8.0 mmol) was used instead of 2-bromo-4,6-diphenylpyridine used in Synthesis Example 24.

Mass (theoretical value: 664.26, measured value: 664 g/mol)

[Synthesis Example 32] Synthesis of Compound B-9

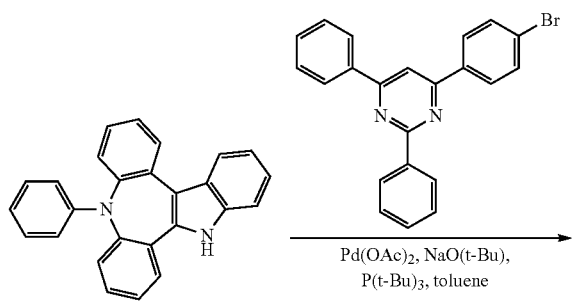

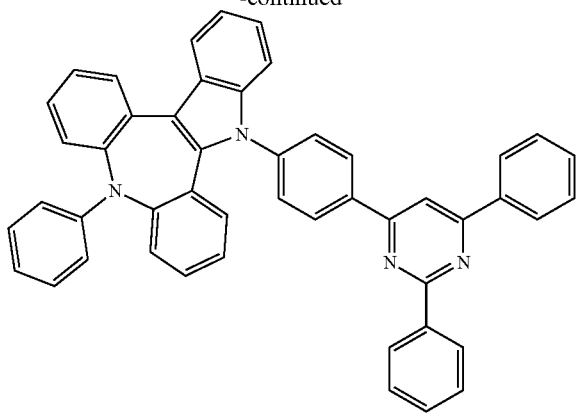

B-9

Compound B-9 (3.1 g, yield 70%) was obtained by performing the same process as in Synthesis Example 24, except that 4-(4-bromophenyl)-2,6-diphenylpyrimidine (3.1 g, 8.0 mmol) was used instead of 2-bromo-4,6-diphenylpyridine used in Synthesis Example 24.

Mass (theoretical value: 664.26, measured value: 664 g/mol)

[Synthesis Example 33] Synthesis of Compound B-10

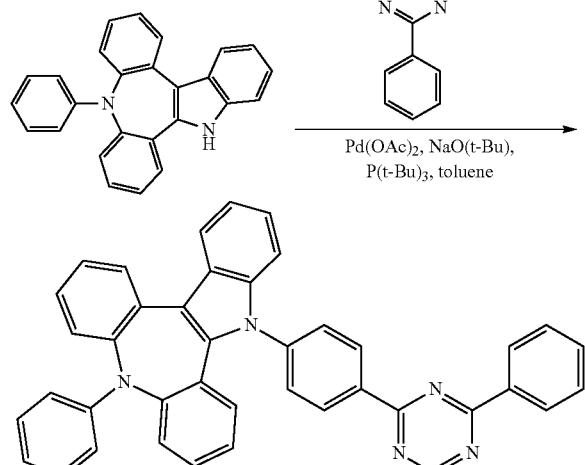

B-10

Compound B-10 (2.7 g, yield 61%) was obtained by performing the same process as in Synthesis Example 24, except that 2-(4-bromophenyl)-4,6-diphenyl-1,3,5-triazine (3.1 g, 8.0 mmol) was used instead of 2-bromo-4,6-diphenylpyridine used in Synthesis Example 24.

Mass (theoretical value: 665.26, measured value: 665 g/mol)

[Synthesis Example 34] Synthesis of Compound B-11

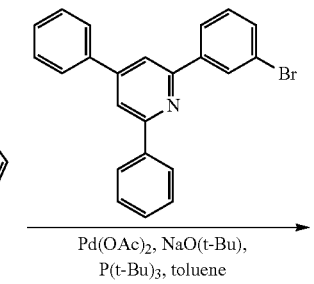

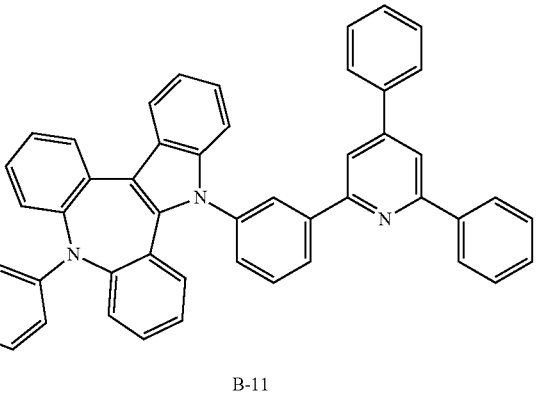

B-11

Compound B-11 (3.0 g, yield 61%) was obtained by performing the same process as in Synthesis Example 24, except that 2-(3-bromophenyl)-4,6-diphenylpyridine (3.1 g, 8.0 mmol) was used instead of 2-bromo-4,6-diphenylpyridine used in Synthesis Example 24.

Mass (theoretical value: 663.27, measured value: 663 g/mol)

[Synthesis Example 35] Synthesis of Compound B-12

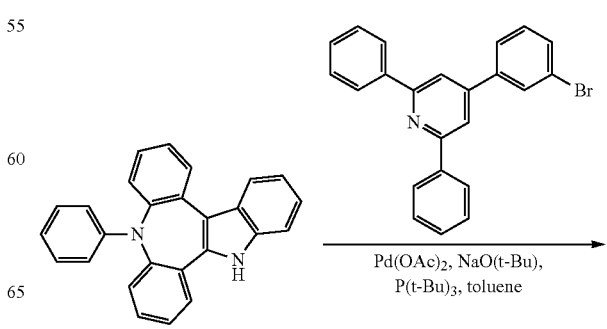

161
-continued

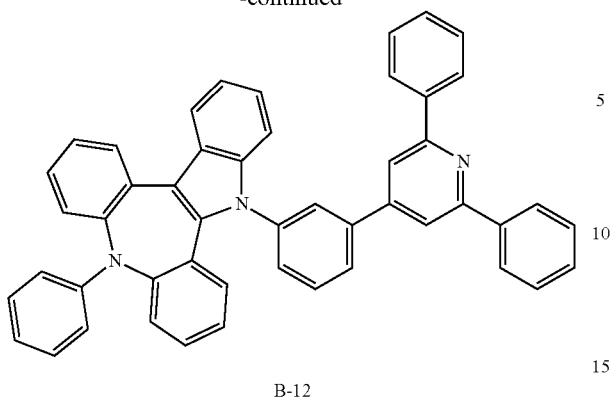

B-12

Compound B-12 (2.8 g, yield 64%) was obtained by performing the same process as in Synthesis Example 24, except that 4-(3-bromophenyl)-2,6-diphenylpyridine (3.1 g, 8.0 mmol) was used instead of 2-bromo-4,6-diphenylpyridine used in Synthesis Example 24.

Mass (theoretical value: 663.27, measured value: 663 g/mol)

[Synthesis Example 36] Synthesis of Compound B-13

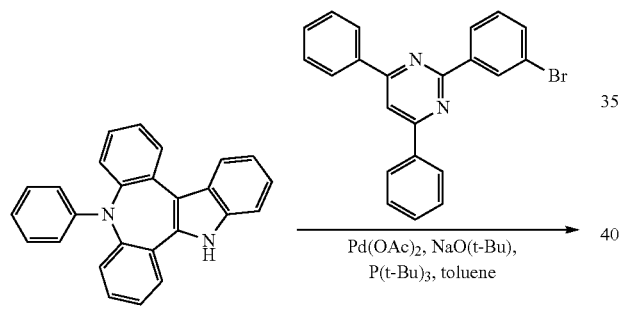

B-13

162

Compound B-13 (3.1 g, yield 65%) was obtained by performing the same process as in Synthesis Example 24, except that 2-(3-bromophenyl)-4,6-diphenylpyrimidine (3.1 g, 8.0 mmol) was used instead of 2-bromo-4,6-diphenylpyridine used in Synthesis Example 24.

Mass (theoretical value: 664.26, measured value: 664 g/mol)

[Synthesis Example 37] Synthesis of Compound B-14

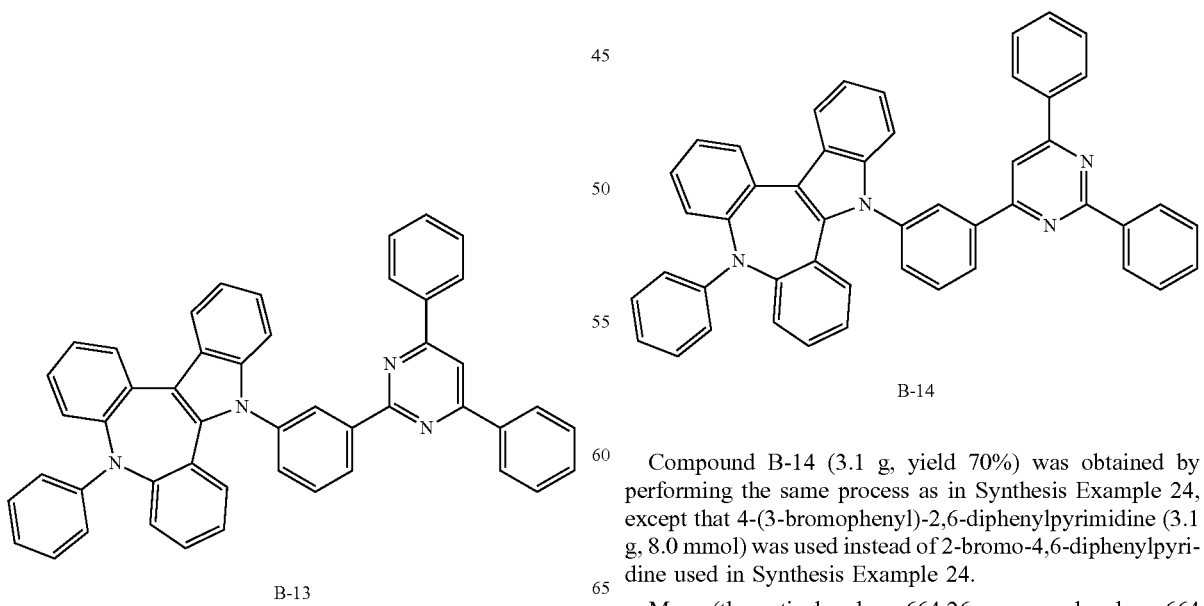

B-14

Compound B-14 (3.1 g, yield 70%) was obtained by performing the same process as in Synthesis Example 24, except that 4-(3-bromophenyl)-2,6-diphenylpyrimidine (3.1 g, 8.0 mmol) was used instead of 2-bromo-4,6-diphenylpyridine used in Synthesis Example 24.

Mass (theoretical value: 664.26, measured value: 664 g/mol)

[Synthesis Example 38] Synthesis of Compound B-15

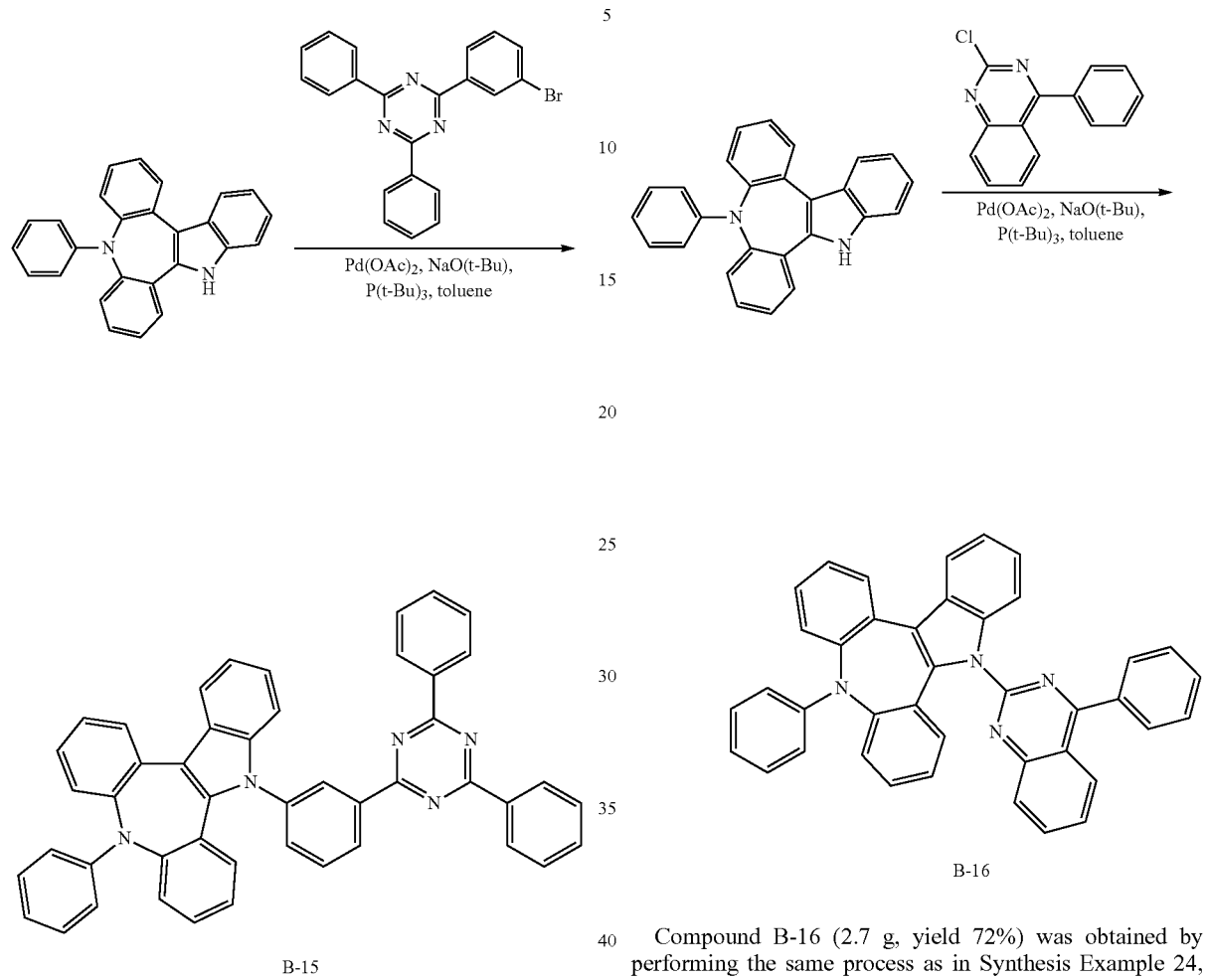

B-15

Compound B-15 (3.3 g, yield 73%) was obtained by performing the same process as in Synthesis Example 24, except that 2-(3-bromophenyl)-4,6-diphenyl-1,3,5-triazine (3.1 g, 8.0 mmol) was used instead of 2-bromo-4,6-diphenylpyridine used in Synthesis Example 24.

Mass (theoretical value: 665.26, measured value: 665 g/mol)

[Synthesis Example 39] Synthesis of Compound B-16

B-16

Compound B-16 (2.7 g, yield 72%) was obtained by performing the same process as in Synthesis Example 24, except that 2-chloro-4-phenylquinazoline (1.9 g, 8.0 mmol) was used instead of 2-bromo-4,6-diphenylpyridine used in Synthesis Example 24.

Mass (theoretical value: 562.22, measured value: 562 g/mol)

[Synthesis Example 40] Synthesis of Compound B-17

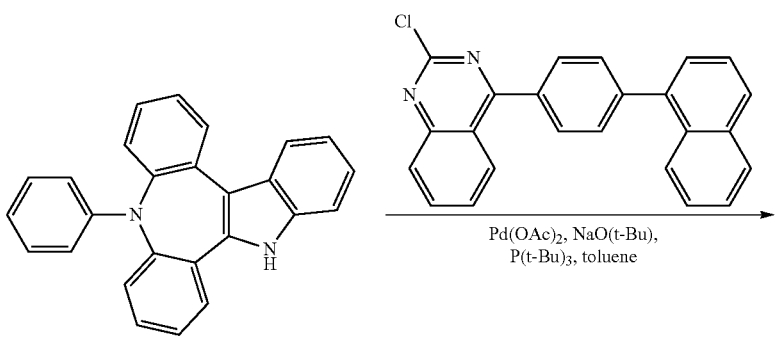

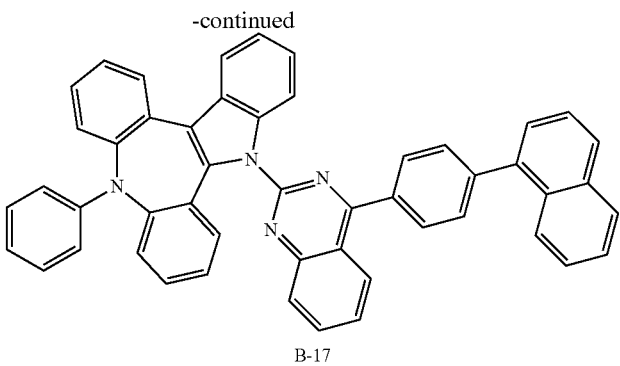

B-17

Compound B-17 (3.6 g, yield 77%) was obtained by performing the same process as in Synthesis Example 24, except that 2-chloro-4-(4-(naphthalen-1-yl)phenyl)quinazoline (2.9 g, 8.0 mmol) was used instead of 2-bromo-4,6-diphenylpyridine used in Synthesis Example 24.

Mass (theoretical value: 688.26, measured value: 688 g/mol)

[Synthesis Example 41] Synthesis of Compound B-18

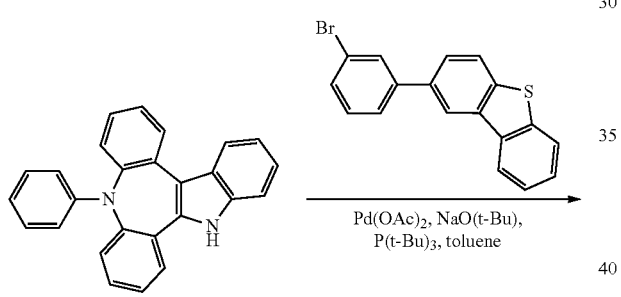

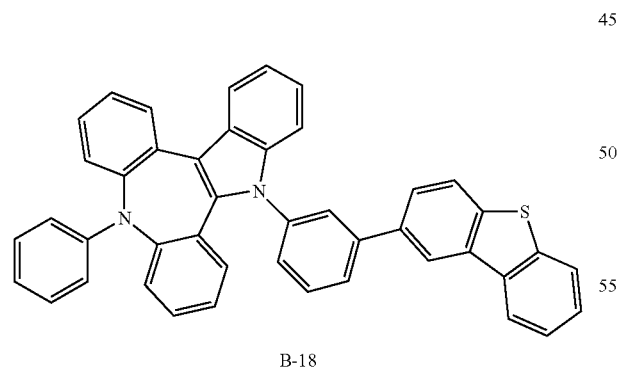

B-18

Compound B-18 (2.7 g, yield 66%) was obtained by performing the same process as in Synthesis Example 24, except that 2-(3-bromophenyl)dibenzo[b,d]thiophene (2.7 g, 8.0 mmol) was used instead of 2-bromo-4,6-diphenylpyridine used in Synthesis Example 24.

Mass (theoretical value: 616.20, measured value: 616 g/mol)

[Synthesis Example 42] Synthesis of Compound B-19

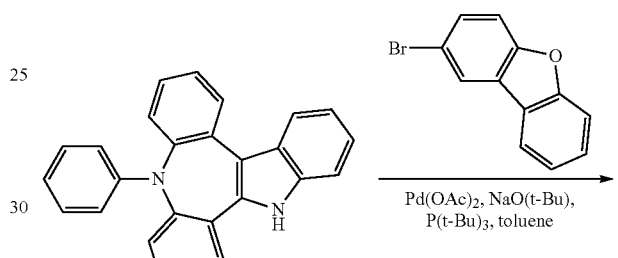

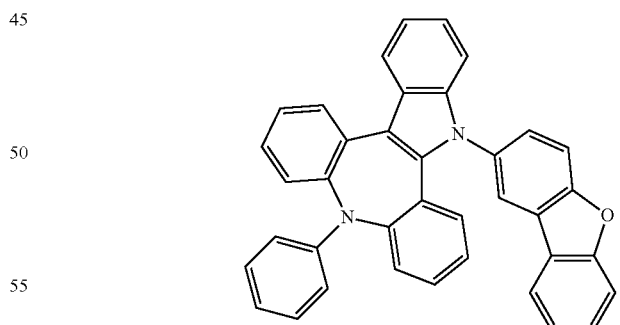

B-19

Compound B-19 (2.3 g, yield 65%) was obtained by performing the same process as in Synthesis Example 24, except that 2-bromodibenzo[b,d]furan (2.0 g, 8.0 mmol) was used instead of 2-bromo-4,6-diphenylpyridine used in Synthesis Example 24.

Mass (theoretical value: 524.19, measured value: 524 g/mol)

[Synthesis Example 43] Synthesis of Compound B-20

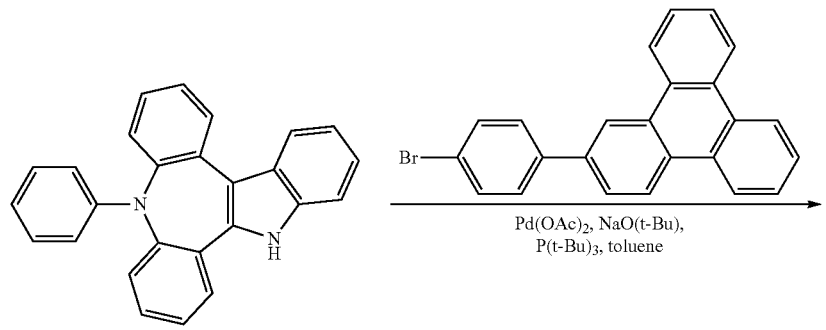

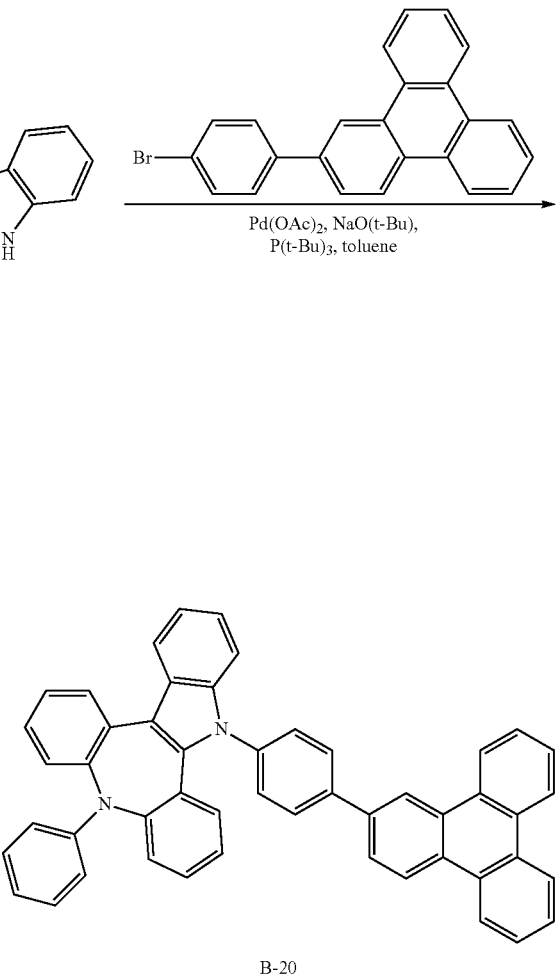

B-20

Compound B-20 (3.1 g, yield 69%) was obtained by performing the same process as in Synthesis Example 24, except that 2-(4-bromophenyl)triphenylene (3.1 g, 8.0 mmol) was used instead of 2-bromo-4,6-diphenylpyridine used in Synthesis Example 24.

Mass (theoretical value: 660.26, measured value: 660 g/mol)

[Synthesis Example 44] Synthesis of Compound B-21

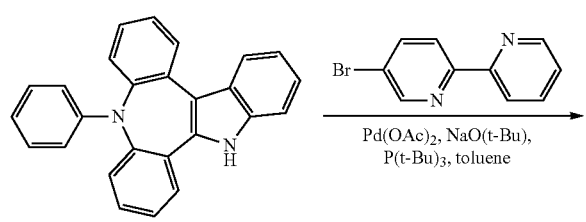

-continued

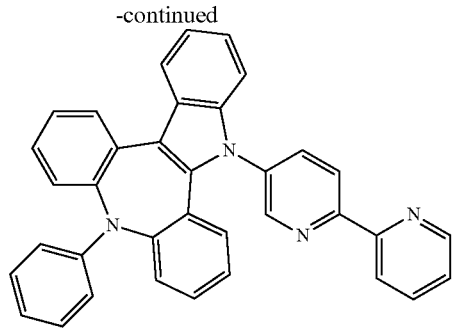

B-21

Compound B-21 (2.1 g, yield 61%) was obtained by performing the same process as in Synthesis Example 24, except that 5-bromo-2,2'-bipyridine (1.9 g, 8.0 mmol) was used instead of 2-bromo-4,6-diphenylpyridine used in Synthesis Example 24.

Mass (theoretical value: 512.20, measured value: 512 g/mol)

[Synthesis Example 45] Synthesis of Compound B-22
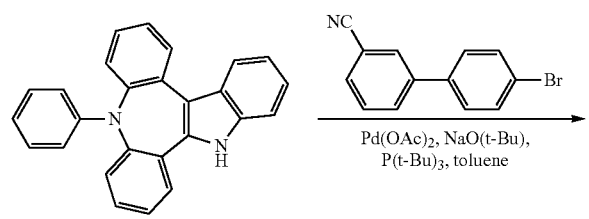
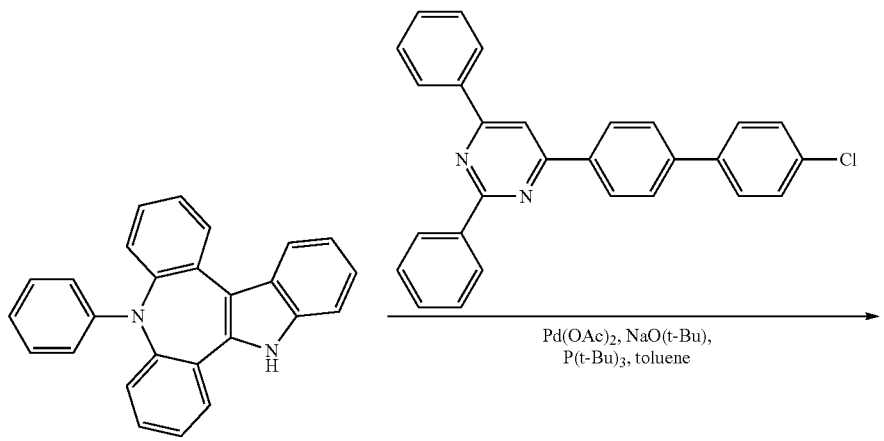
B-22
Compound B-22 (2.2 g, yield 60%) was obtained by performing the same process as in Synthesis Example 24, except that 4'-bromobiphenyl-3-carbonitrile (2.1 g, 8.0 mmol) was used instead of 2-bromo-4,6-diphenylpyridine used in Synthesis Example 24.
Mass (theoretical value: 535.21, measured value: 535 g/mol)
[Synthesis Example 46] Synthesis of Compound B-23
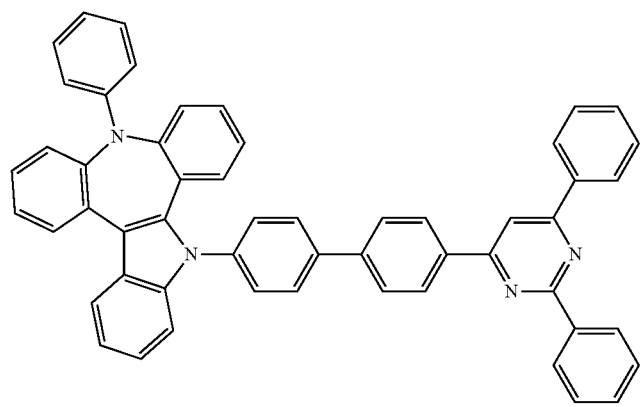
B-23

Compound B-23 (3.5 g, yield 70%) was obtained by performing the same process as in Synthesis Example 24, except that 4-(4'-chlorobiphenyl-4-yl)-2,6-diphenylpyrimidine (3.4 g, 8.0 mmol) was used instead of 2-bromo-4,6-diphenylpyridine used in Synthesis Example 24.

Mass (theoretical value: 740.29, measured value: 740 g/mol)

[Synthesis Example 47] Synthesis of Compound C-1

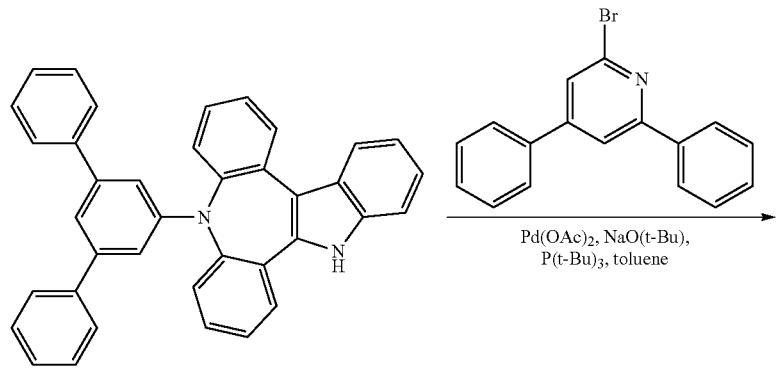

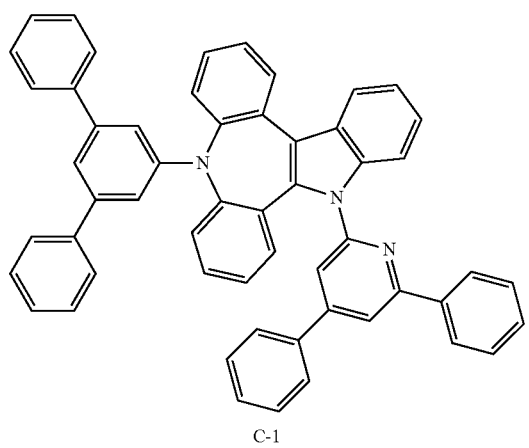

C-1

Compound IAz-3 (3.4 g, 6.7 mmol) synthesized in Preparation Example 3, 2-bromo-4,6-diphenylpyridine (2.5 g, 8.0 mmol), Pd(OAc)$_2$ (0.08 g, 0.34 mmol), P(t-Bu)$_3$ (0.16 ml, 0.67 mmol), NaO(t-Bu) (1.29 g, 13.4 mmol), and toluene (70 ml) were mixed under nitrogen flow, and the resulting mixture was stirred at 110° C. for 5 hours. After the reaction was terminated, toluene was concentrated, and a solid salt was filtered and then purified with recrystallization to obtain Compound C-1 (3.0 g, yield 61%).

Mass (theoretical value: 739.30, measured value: 739 g/mol)

[Synthesis Example 48] Synthesis of Compound C-2
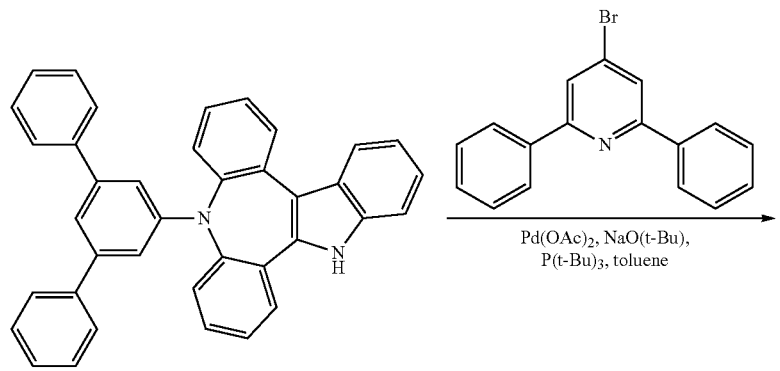
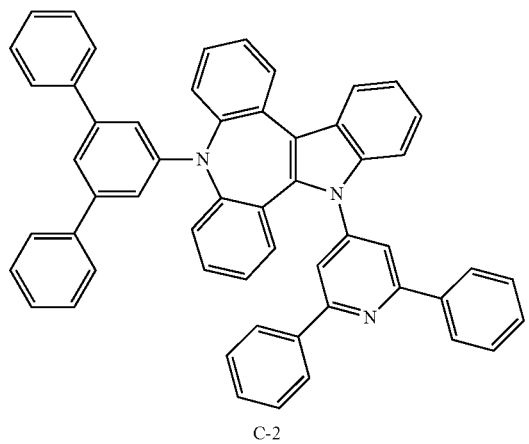
C-2
Compound C-2 (3.6 g, yield 73%) was obtained by performing the same process as in Synthesis Example 47, except that 4-bromo-2,6-diphenylpyridine (2.5 g, 8.0 mmol) was used instead of 2-bromo-4,6-diphenylpyridine used in Synthesis Example 47.
Mass (theoretical value: 739.30, measured value: 739 g/mol)
[Synthesis Example 49] Synthesis of Compound C-3
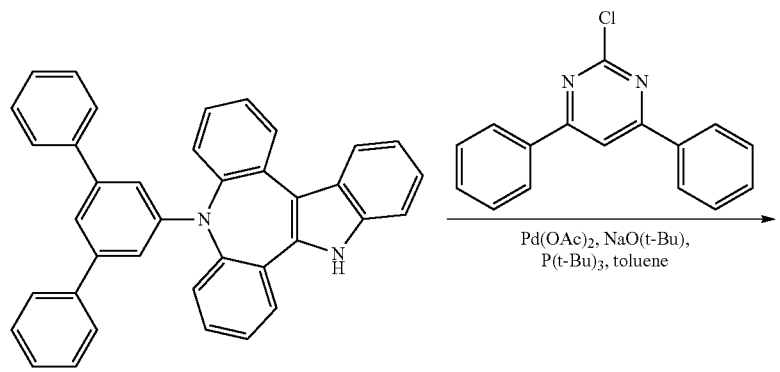

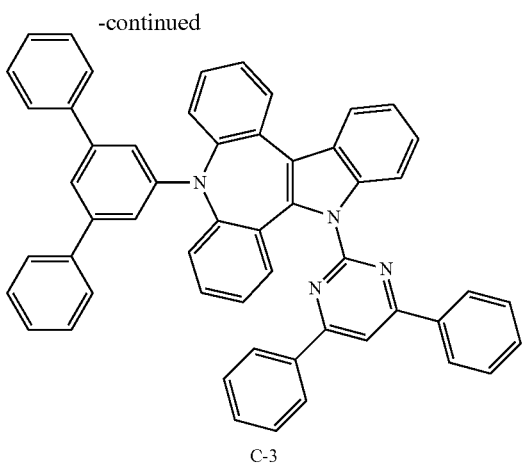
C-3
Compound C-3 (3.7 g, yield 75%) was obtained by performing the same process as in Synthesis Example 47, except that 2-chloro-4,6-diphenylpyrimidine (2.5 g, 8.0 mmol) was used instead of 2-bromo-4,6-diphenylpyridine used in Synthesis Example 47.
Mass (theoretical value: 740.29, measured value: 740 g/mol)
[Synthesis Example 50] Synthesis of Compound C-4
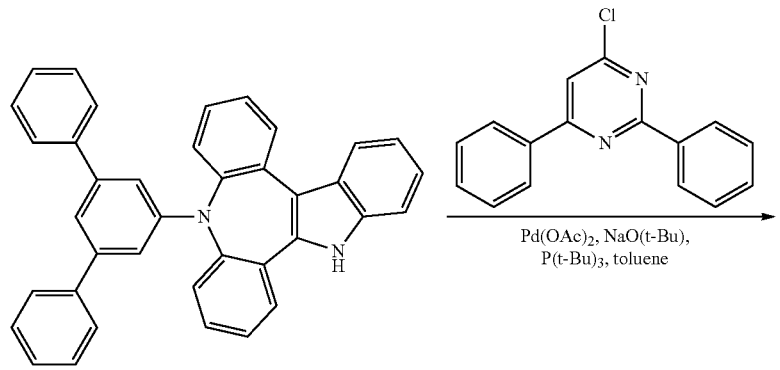
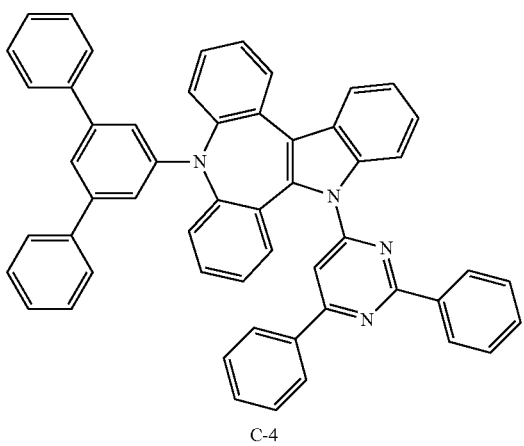
C-4

Compound C-4 (3.2 g, yield 65%) was obtained by performing the same process as in Synthesis Example 47, except that 4-chloro-2,6-diphenylpyrimidine (2.5 g, 8.0 mmol) was used instead of 2-bromo-4,6-diphenylpyridine used in Synthesis Example 47.

Mass (theoretical value: 740.29, measured value: 740 g/mol)

[Synthesis Example 51] Synthesis of Compound C-5

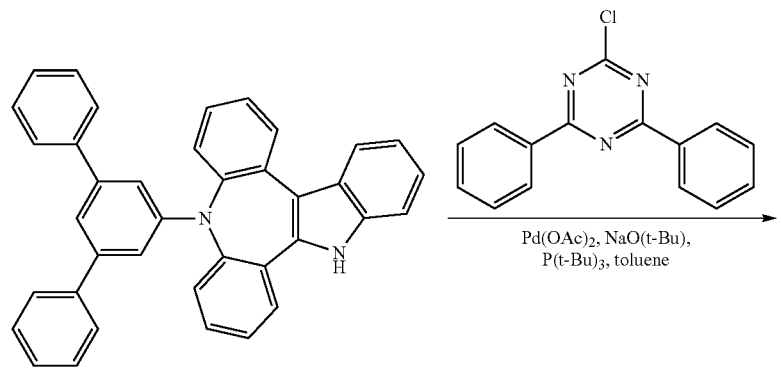

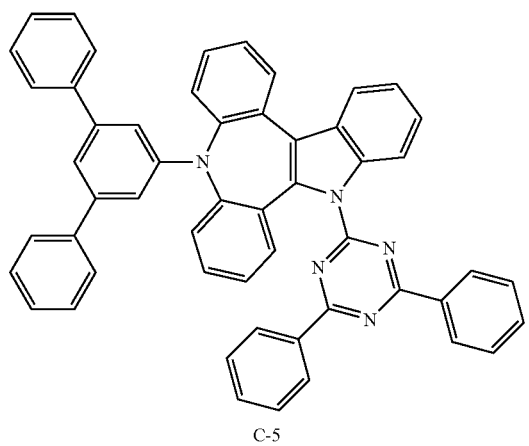

C-5

Compound C-5 (3.3 g, yield 66%) was obtained by performing the same process as in Synthesis Example 47, except that 2-chloro-4,6-diphenyl-1,3,5-triazine (2.1 g, 8.0 mmol) was used instead of 2-bromo-4,6-diphenylpyridine used in Synthesis Example 47.

Mass (theoretical value: 741.29, measured value: 741 g/mol)

[Synthesis Example 52] Synthesis of Compound C-6
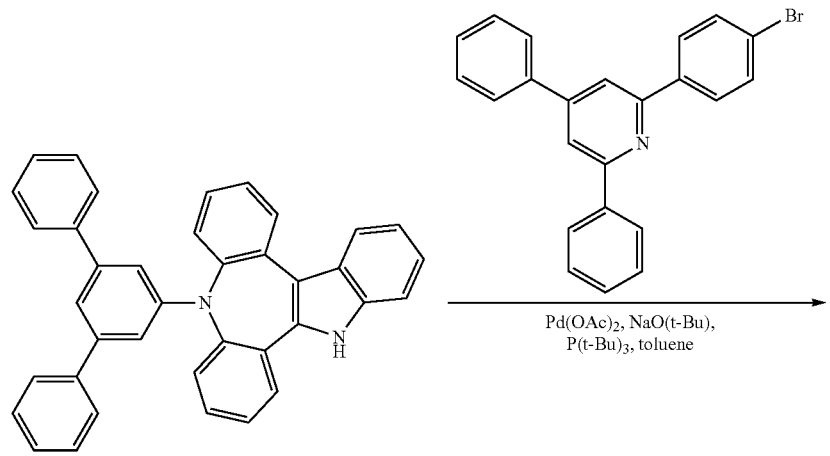
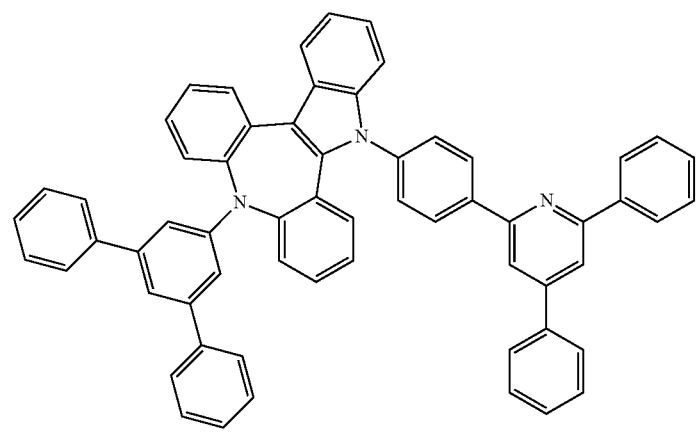
C-6
Compound C-6 (4.3 g, yield 78%) was obtained by performing the same process as in Synthesis Example 47, except that 2-(4-bromophenyl)-4,6-diphenylpyridine (3.1 g, 8.0 mmol) was used instead of 2-bromo-4,6-diphenylpyridine used in Synthesis Example 47.
Mass (theoretical value: 815.33, measured value: 815 g/mol)

[Synthesis Example 53] Synthesis of Compound C-7
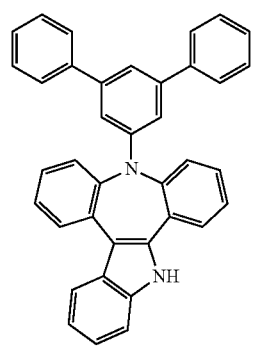
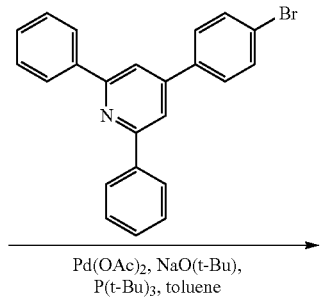
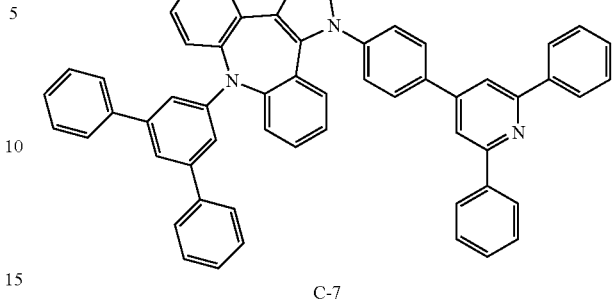
Compound C-7 (3.9 g, yield 71%) was obtained by performing the same process as in Synthesis Example 47, except that 4-(4-bromophenyl)-2,6-diphenylpyridine (3.1 g, 8.0 mmol) was used instead of 2-bromo-4,6-diphenylpyridine used in Synthesis Example 47.
Mass (theoretical value: 815.33, measured value: 815 g/mol)
[Synthesis Example 54] Synthesis of Compound C-8
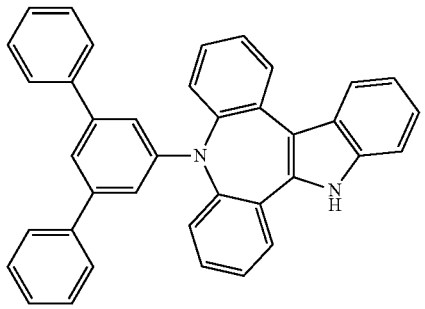
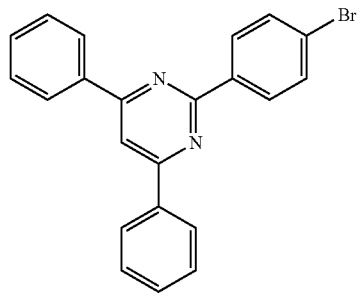
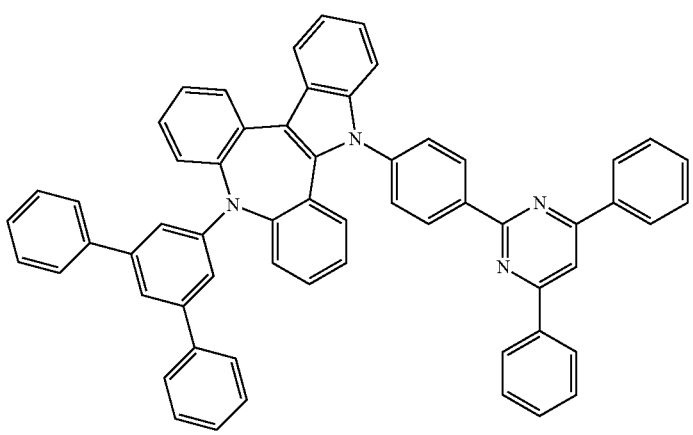

Compound C-8 (3.8 g, yield 70%) was obtained by performing the same process as in Synthesis Example 47, except that 2-(4-bromophenyl)-4,6-diphenylpyrimidine (3.1 g, 8.0 mmol) was used instead of 2-bromo-4,6-diphenylpyridine used in Synthesis Example 47.

Mass (theoretical value: 816.32, measured value: 816 g/mol)

[Synthesis Example 55] Synthesis of Compound C-9

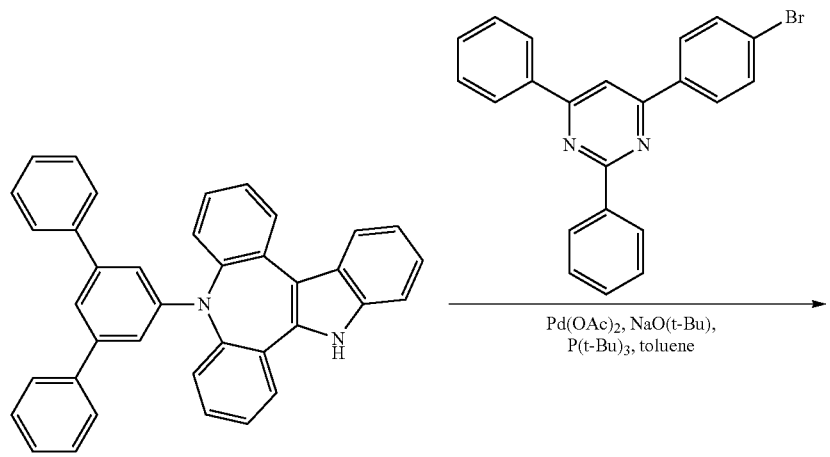

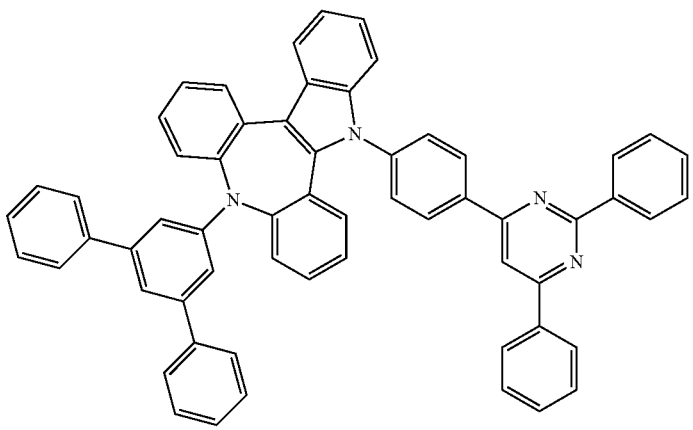

C-9

Compound C-9 (3.7 g, yield 68%) was obtained by performing the same process as in Synthesis Example 47, except that 4-(4-bromophenyl)-2,6-diphenylpyrimidine (3.1 g, 8.0 mmol) was used instead of 2-bromo-4,6-diphenylpyridine used in Synthesis Example 47.

Mass (theoretical value: 816.32, measured value: 816 g/mol)

[Synthesis Example 56] Synthesis of Compound C-10
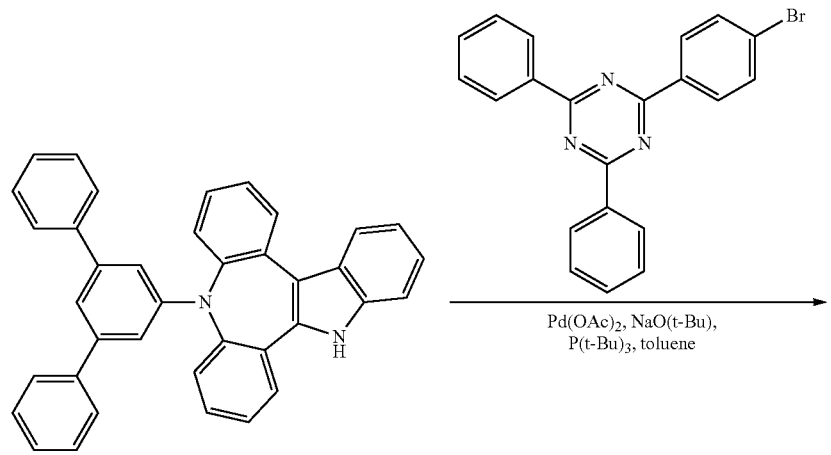
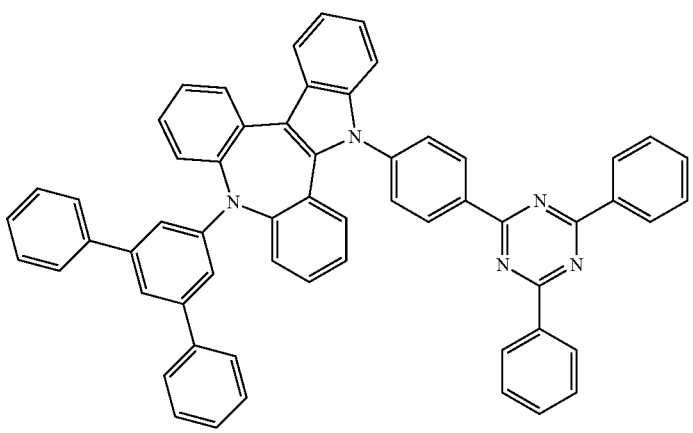
C-10
Compound C-10 (3.7 g, yield 67%) was obtained by performing the same process as in Synthesis Example 47, except that 2-(4-bromophenyl)-4,6-diphenyl-1,3,5-triazine (3.1 g, 8.0 mmol) was used instead of 2-bromo-4,6-diphenylpyridine used in Synthesis Example 47.
Mass (theoretical value: 817.32, measured value: 817 g/mol)

[Synthesis Example 57] Synthesis of Compound C-11
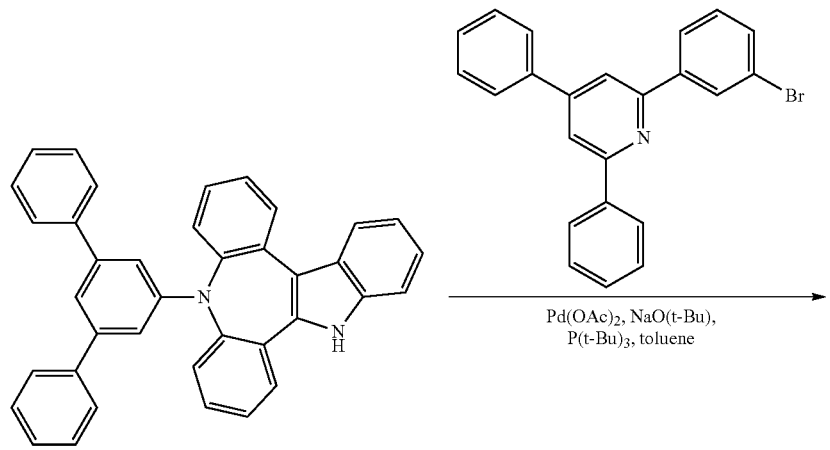
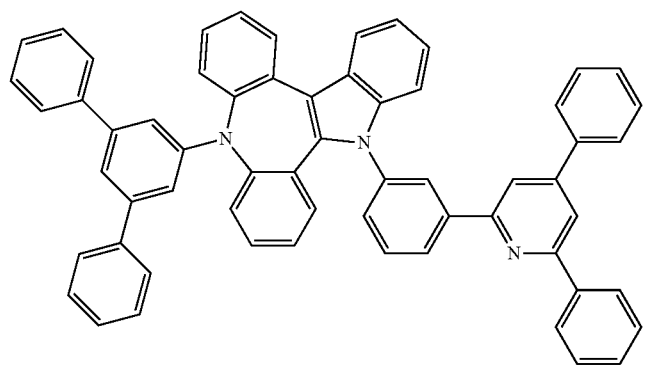
C-11
Compound C-11 (3.3 g, yield 60%) was obtained by performing the same process as in Synthesis Example 47, except that 2-(3-bromophenyl)-4,6-diphenylpyridine (3.1 g, 8.0 mmol) was used instead of 2-bromo-4,6-diphenylpyridine used in Synthesis Example 47.
Mass (theoretical value: 815.33, measured value: 815 g/mol)

[Synthesis Example 58] Synthesis of Compound C-12
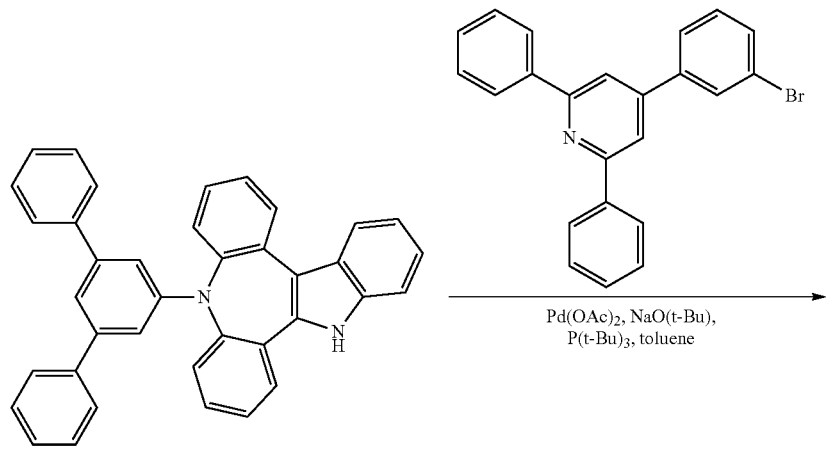
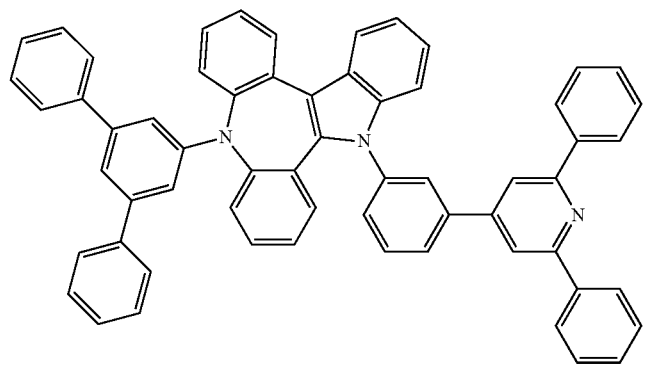
C-12
Compound C-12 (3.3 g, yield 61%) was obtained by performing the same process as in Synthesis Example 47, except that 4-(3-bromophenyl)-2,6-diphenylpyridine (3.1 g, 8.0 mmol) was used instead of 2-bromo-4,6-diphenylpyridine used in Synthesis Example 47.
Mass (theoretical value: 815.33, measured value: 815 g/mol)

[Synthesis Example 59] Synthesis of Compound C-13
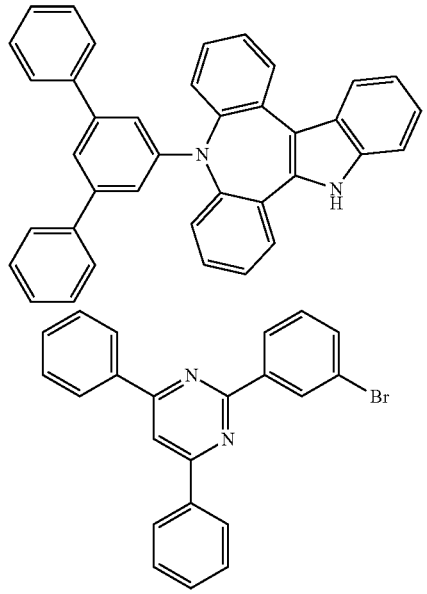
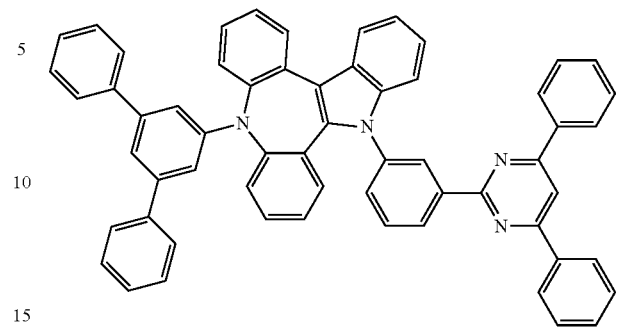
Compound C-13 (3.6 g, yield 65%) was obtained by performing the same process as in Synthesis Example 47, except that 2-(3-bromophenyl)-4,6-diphenylpyrimidine (3.1 g, 8.0 mmol) was used instead of 2-bromo-4,6-diphenylpyridine used in Synthesis Example 47.
Mass (theoretical value: 816.32, measured value: 816 g/mol)
[Synthesis Example 60] Synthesis of Compound C-14
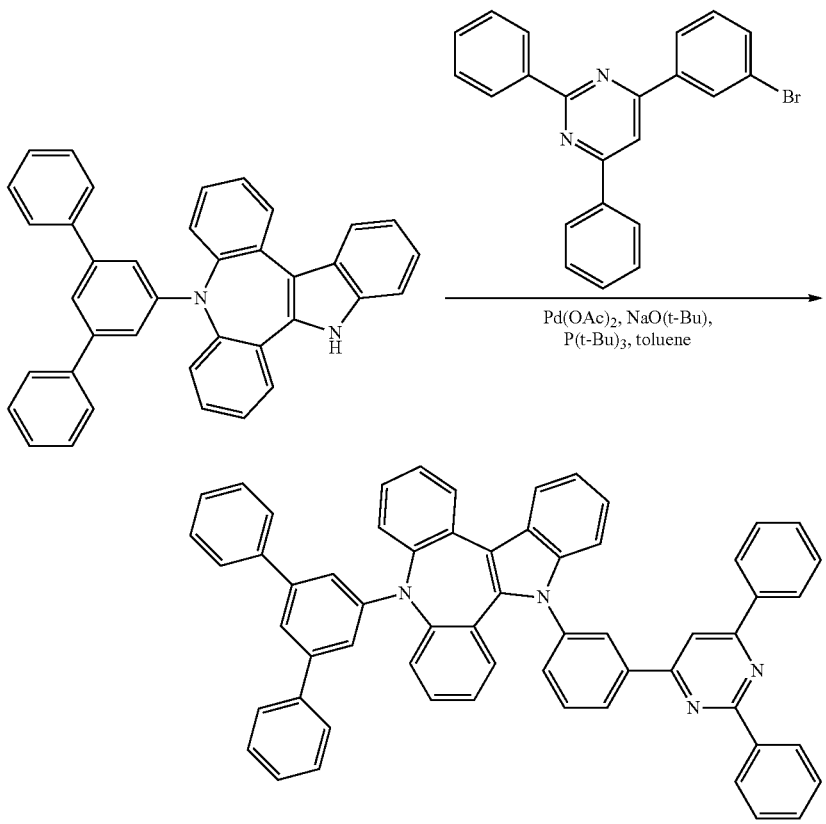

Compound C-14 (3.9 g, yield 72%) was obtained by performing the same process as in Synthesis Example 47, except that 4-(3-bromophenyl)-2,6-diphenylpyrimidine (3.1 g, 8.0 mmol) was used instead of 2-bromo-4,6-diphenylpyridine used in Synthesis Example 47.

Mass (theoretical value: 816.32, measured value: 816 g/mol)

[Synthesis Example 61] Synthesis of Compound C-15

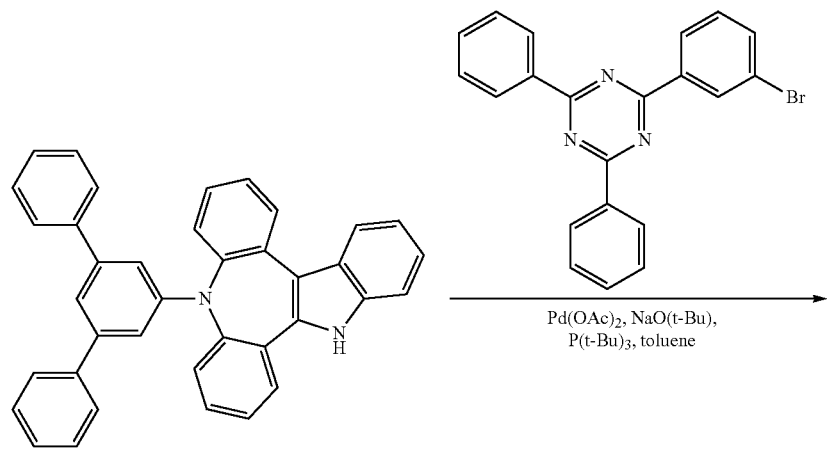

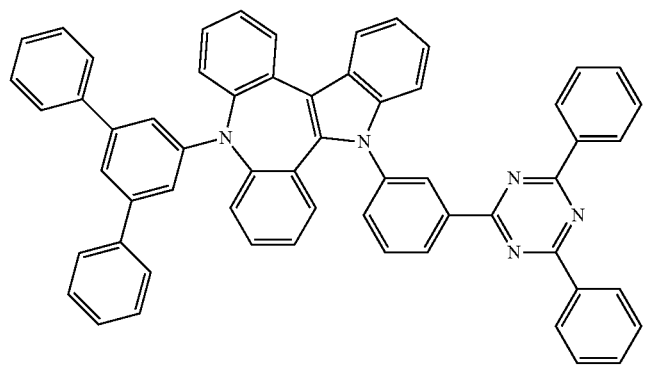

C-15

Compound C-15 (4.2 g, yield 77%) was obtained by performing the same process as in Synthesis Example 47, except that 2-(3-bromophenyl)-4,6-diphenyl-1,3,5-triazine (3.1 g, 8.0 mmol) was used instead of 2-bromo-4,6-diphenylpyridine used in Synthesis Example 47.

Mass (theoretical value: 817.32, measured value: 817 g/mol)

[Synthesis Example 62] Synthesis of Compound C-16

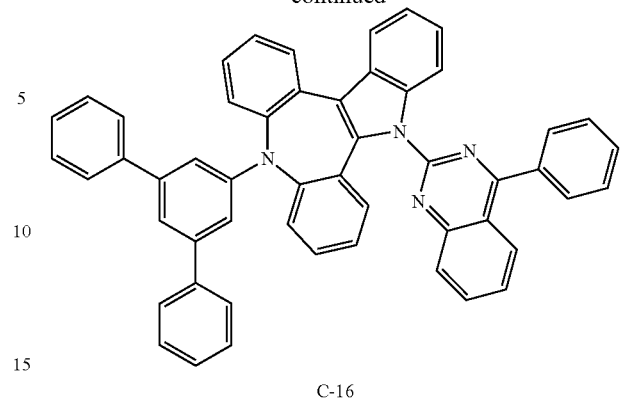
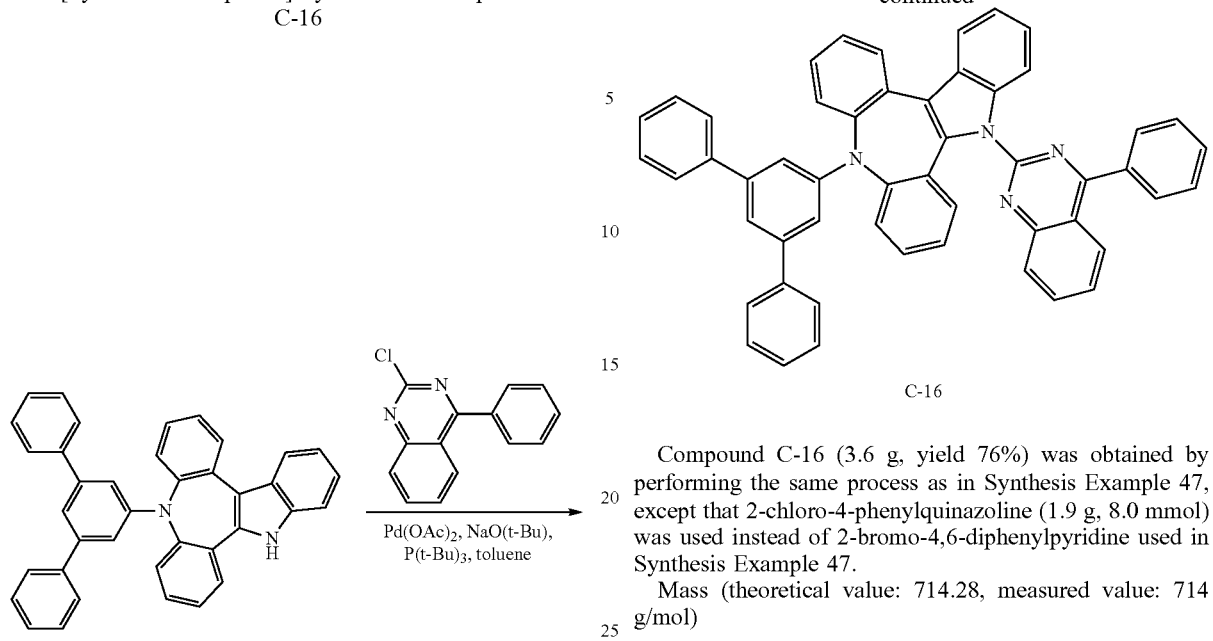

C-16

Compound C-16 (3.6 g, yield 76%) was obtained by performing the same process as in Synthesis Example 47, except that 2-chloro-4-phenylquinazoline (1.9 g, 8.0 mmol) was used instead of 2-bromo-4,6-diphenylpyridine used in Synthesis Example 47.

Mass (theoretical value: 714.28, measured value: 714 g/mol)

[Synthesis Example 63] Synthesis of Compound C-17

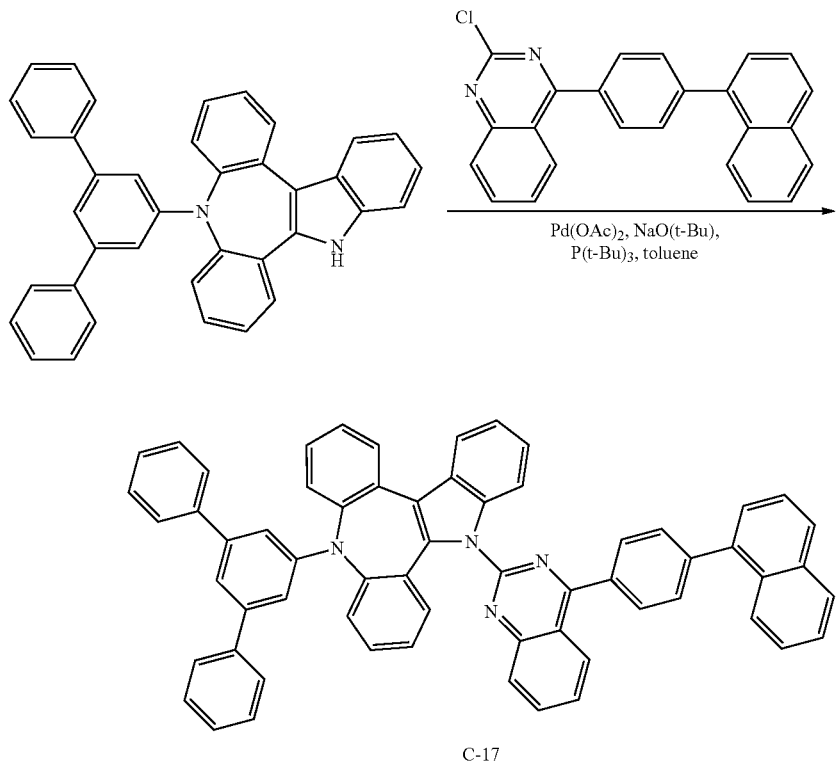

C-17

Compound C-17 (3.6 g, yield 64%) was obtained by performing the same process as in Synthesis Example 47, except that 2-chloro-4-(4-(naphthalen-1-yl)phenyl)quinazoline (2.9 g, 8.0 mmol) was used instead of 2-bromo-4,6-diphenylpyridine used in Synthesis Example 47.

Mass (theoretical value: 840.32, measured value: 840 g/mol)

[Synthesis Example 64] Synthesis of Compound C-18

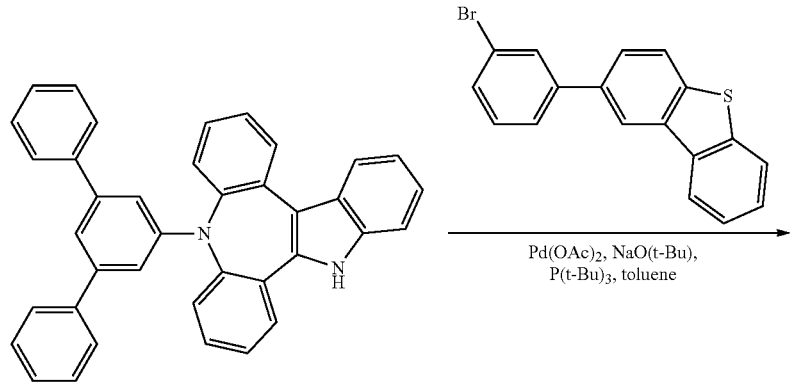

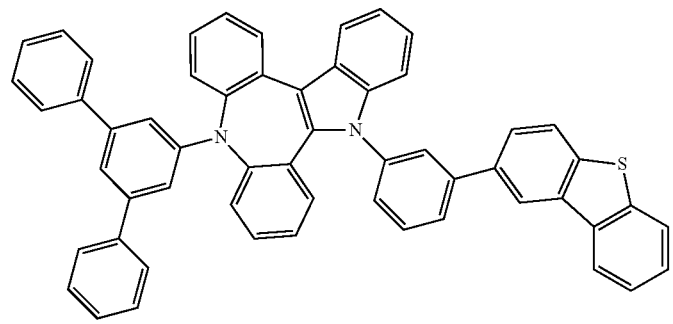

C-18

Compound C-18 (3.2 g, yield 62%) was obtained by performing the same process as in Synthesis Example 47, except that 2-(3-bromophenyl)dibenzo[b,d]thiophene (2.7 g, 8.0 mmol) was used instead of 2-bromo-4,6-diphenylpyridine used in Synthesis Example 47.

Mass (theoretical value: 768.26, measured value: 768 g/mol)

[Synthesis Example 65] Synthesis of Compound C-19

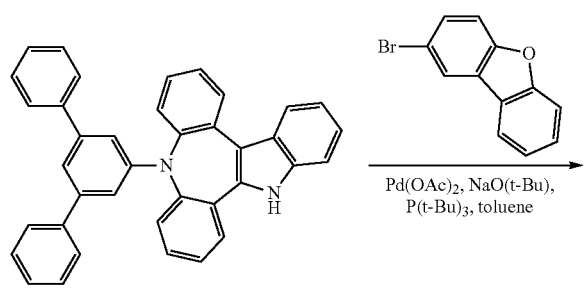

-continued

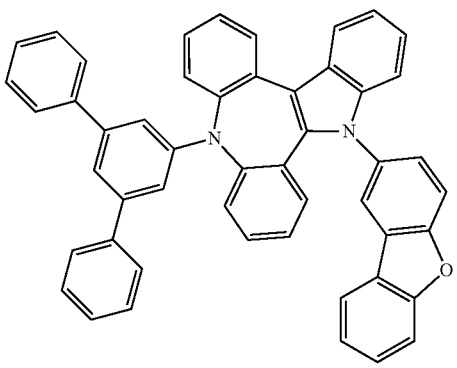

C-19

Compound C-19 (3.1 g, yield 68%) was obtained by performing the same process as in Synthesis Example 47, except that 2-bromodibenzo[b,d]furan (2.0 g, 8.0 mmol) was used instead of 2-bromo-4,6-diphenylpyridine used in Synthesis Example 47.

Mass (theoretical value: 676.25, measured value: 676 g/mol)

[Synthesis Example 66] Synthesis of Compound C-20

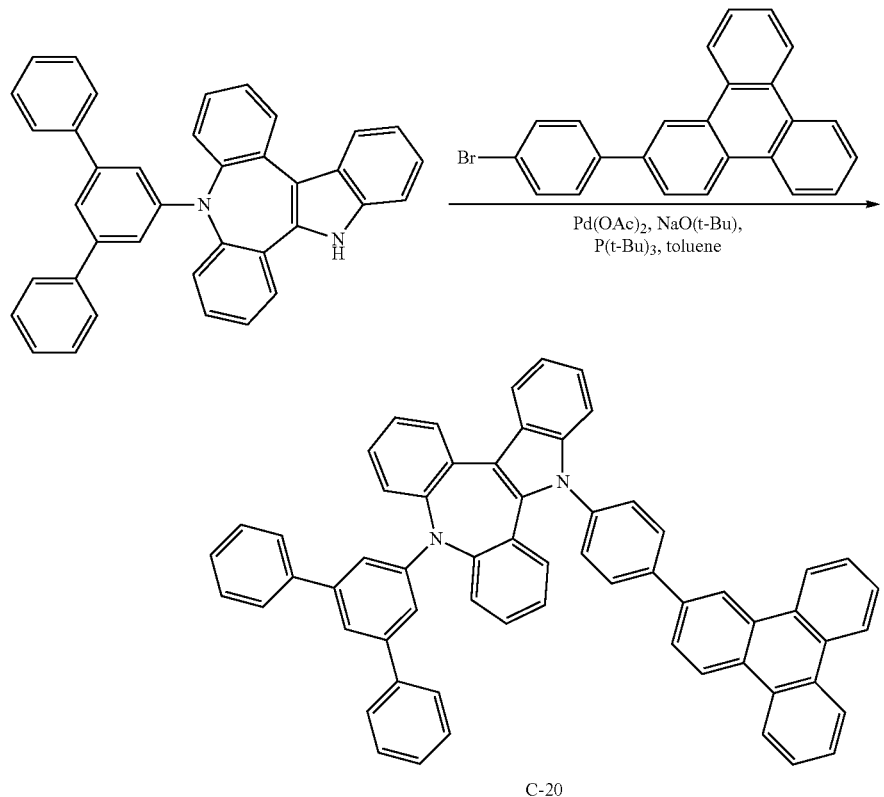

Compound C-20 (3.9 g, yield 72%) was obtained by performing the same process as in Synthesis Example 47, except that 2-(4-bromophenyl)triphenylene (3.1 g, 8.0 mmol) was used instead of 2-bromo-4,6-diphenylpyridine used in Synthesis Example 47.

Mass (theoretical value: 812.32, measured value: 812 g/mol)

[Synthesis Example 67] Synthesis of Compound C-21

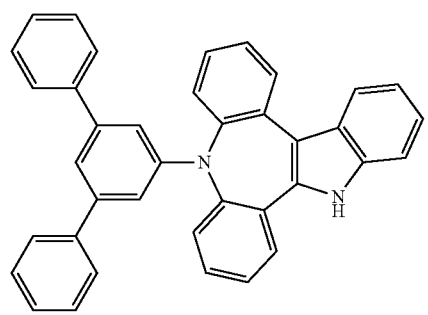

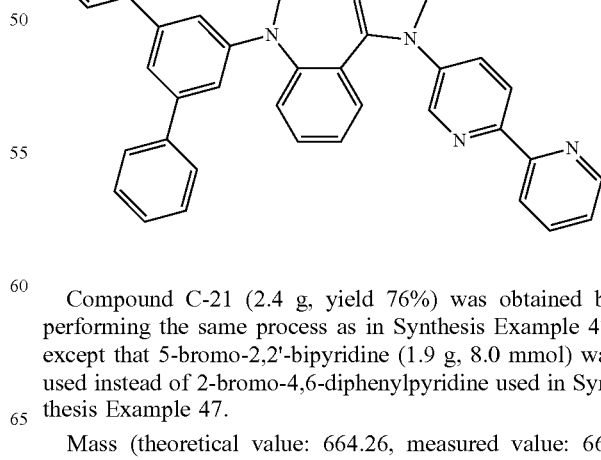

Compound C-21 (2.4 g, yield 76%) was obtained by performing the same process as in Synthesis Example 47, except that 5-bromo-2,2'-bipyridine (1.9 g, 8.0 mmol) was used instead of 2-bromo-4,6-diphenylpyridine used in Synthesis Example 47.

Mass (theoretical value: 664.26, measured value: 664 g/mol)

[Synthesis Example 68] Synthesis of Compound C-22
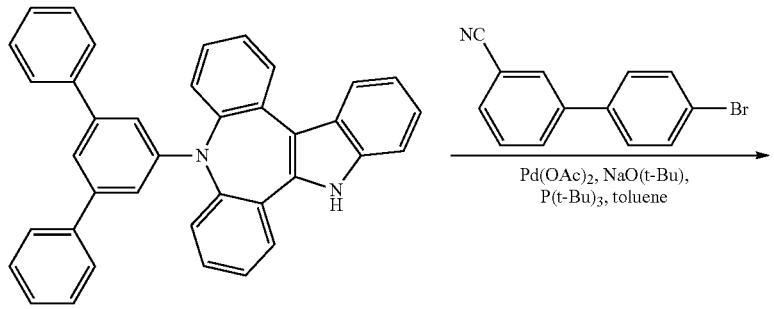
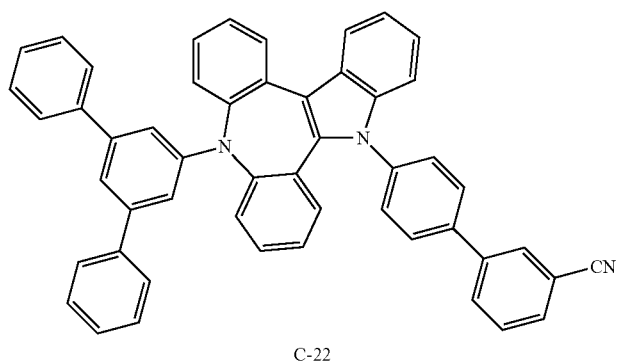
C-22
Compound C-22 (3.5 g, yield 75%) was obtained by performing the same process as in Synthesis Example 47, except that 4'-bromobiphenyl-3-carbonitrile (2.1 g, 8.0 mmol) was used instead of 2-bromo-4,6-diphenylpyridine used in Synthesis Example 47.
Mass (theoretical value: 687.27, measured value: 687 g/mol)
[Synthesis Example 69] Synthesis of Compound C-23
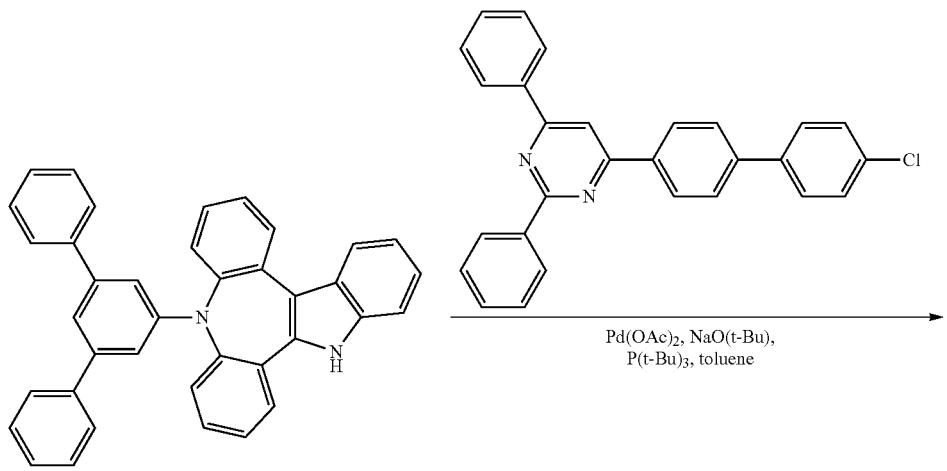

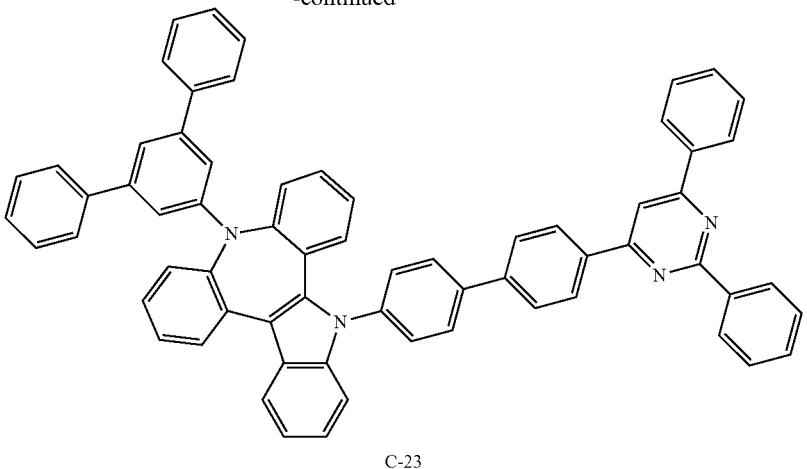

C-23

Compound C-23 (3.9 g, yield 65%) was obtained by performing the same process as in Synthesis Example 47, except that 4-(4'-chlorobiphenyl-4-yl)-2,6-diphenylpyrimidine (3.4 g, 8.0 mmol) was used instead of 2-bromo-4,6-diphenylpyridine used in Synthesis Example 47.

Mass (theoretical value: 892.35, measured value: 892 g/mol)

[Synthesis Example 70] Synthesis of Compound D-1

(70 ml) were mixed under nitrogen flow, and the resulting mixture was stirred at 110° C. for 5 hours. After the reaction was terminated, toluene was concentrated, and a solid salt was filtered and then purified with recrystallization to obtain Compound D-1 (3.1 g, yield 63%).

Mass (theoretical value: 739.30, measured value: 739 g/mol)

[Synthesis Example 71] Synthesis of Compound D-2

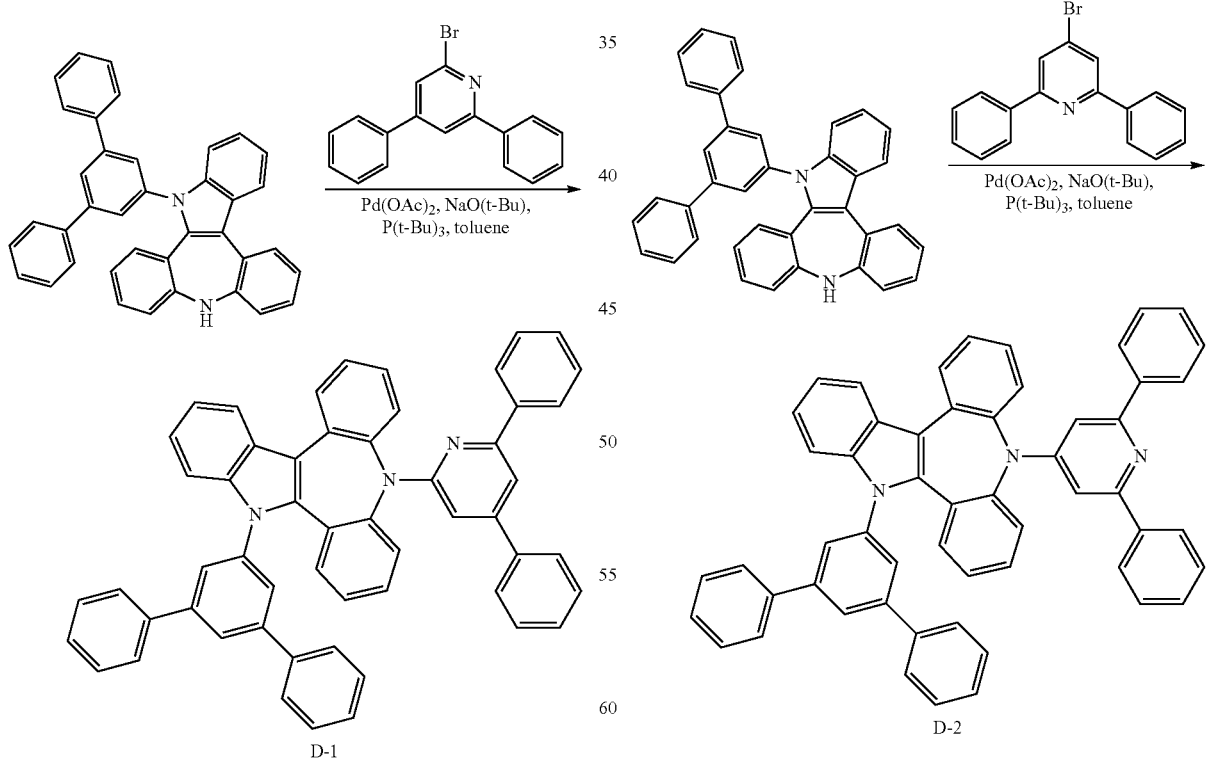

D-1

D-2

Compound IAz-4 (3.4 g, 6.7 mmol) synthesized in Preparation Example 4, 2-bromo-4,6-diphenylpyridine (2.5 g, 8.0 mmol), Pd(OAc)$_2$ (0.08 g, 0.34 mmol), P(t-Bu)$_3$ (0.16 ml, 0.67 mmol), NaO(t-Bu) (1.29 g, 13.4 mmol), and toluene Compound D-2 (3.3 g, yield 66%) was obtained by performing the same process as in Synthesis Example 70, except that 4-bromo-2,6-diphenylpyridine (2.5 g, 8.0 mmol) was used instead of 2-bromo-4,6-diphenylpyridine used in Synthesis Example 70.

Mass (theoretical value: 739.30, measured value: 739 g/mol)

[Synthesis Example 72] Synthesis of Compound D-3

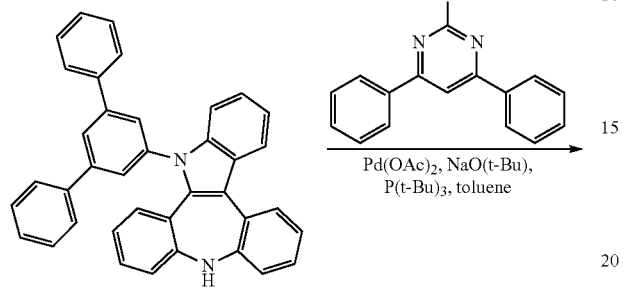

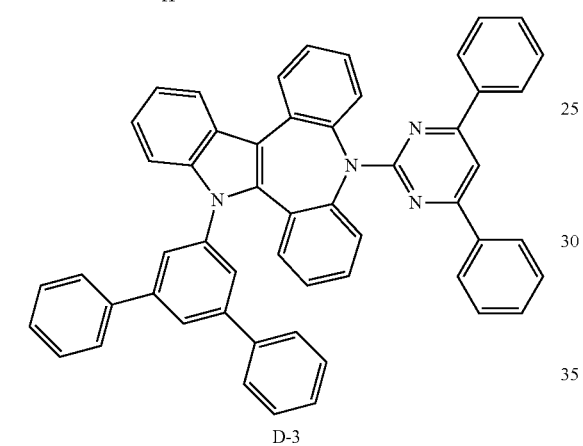

D-3

Compound D-3 (3.4 g, yield 68%) was obtained by performing the same process as in Synthesis Example 70, except that 2-chloro-4,6-diphenylpyrimidine (2.5 g, 8.0 mmol) was used instead of 2-bromo-4,6-diphenylpyridine used in Synthesis Example 70.

Mass (theoretical value: 740.29, measured value: 740 g/mol)

[Synthesis Example 73] Synthesis of Compound D-4

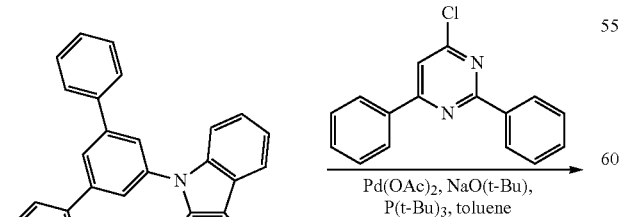

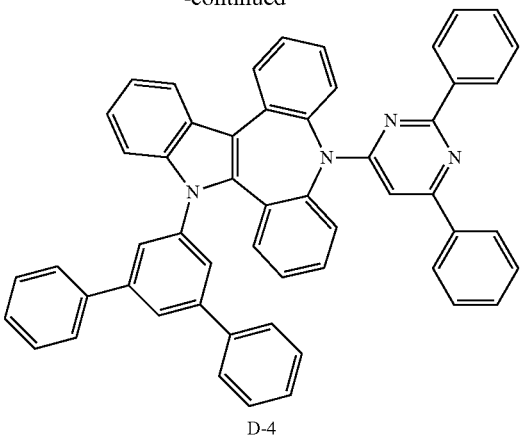

D-4

Compound D-4 (3.1 g, yield 62%) was obtained by performing the same process as in Synthesis Example 70, except that 4-chloro-2,6-diphenylpyrimidine (2.5 g, 8.0 mmol) was used instead of 2-bromo-4,6-diphenylpyridine used in Synthesis Example 70.

Mass (theoretical value: 740.29, measured value: 740 g/mol)

[Synthesis Example 74] Synthesis of Compound D-5

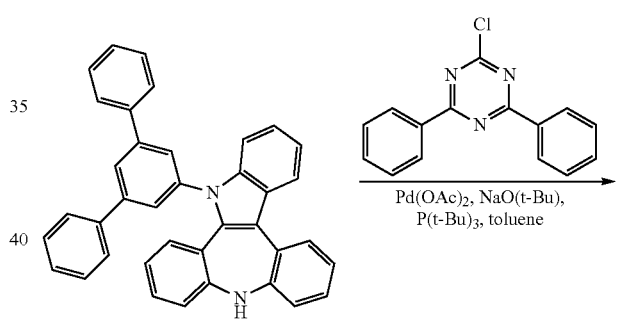

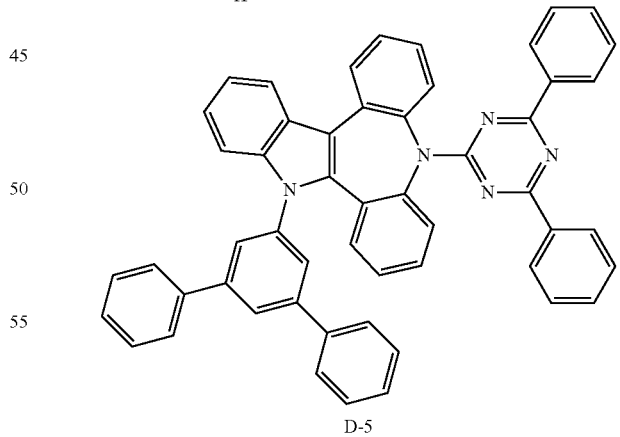

D-5

Compound D-5 (3.4 g, yield 69%) was obtained by performing the same process as in Synthesis Example 70, except that 2-chloro-4,6-diphenyl-1,3,5-triazine (2.1 g, 8.0 mmol) was used instead of 2-bromo-4,6-diphenylpyridine used in Synthesis Example 70.

Mass (theoretical value: 741.29, measured value: 741 g/mol)

[Synthesis Example 75] Synthesis of Compound D-6
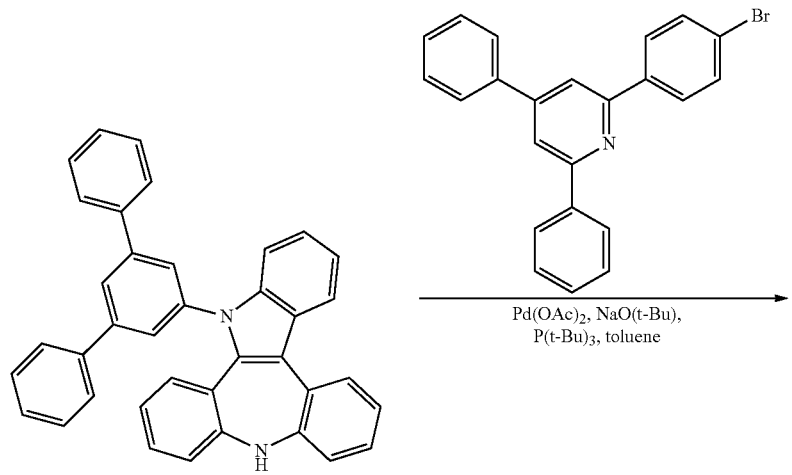
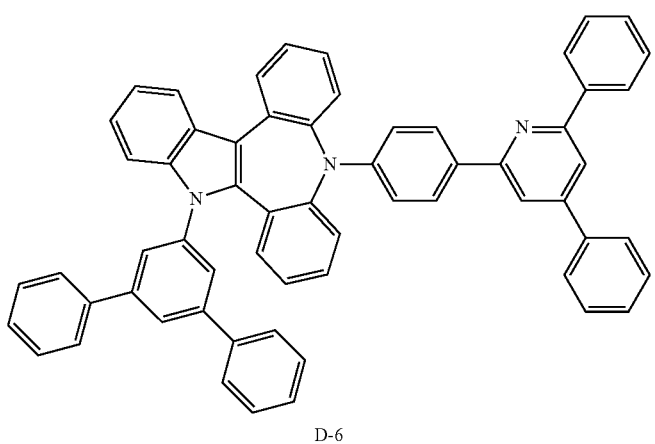
Compound D-6 (3.9 g, yield 71%) was obtained by performing the same process as in Synthesis Example 70, except that 2-(4-bromophenyl)-4,6-diphenylpyridine (3.1 g, 8.0 mmol) was used instead of 2-bromo-4,6-diphenylpyridine used in Synthesis Example 70.
Mass (theoretical value: 815.33, measured value: 815 g/mol)

[Synthesis Example 76] Synthesis of Compound D-7
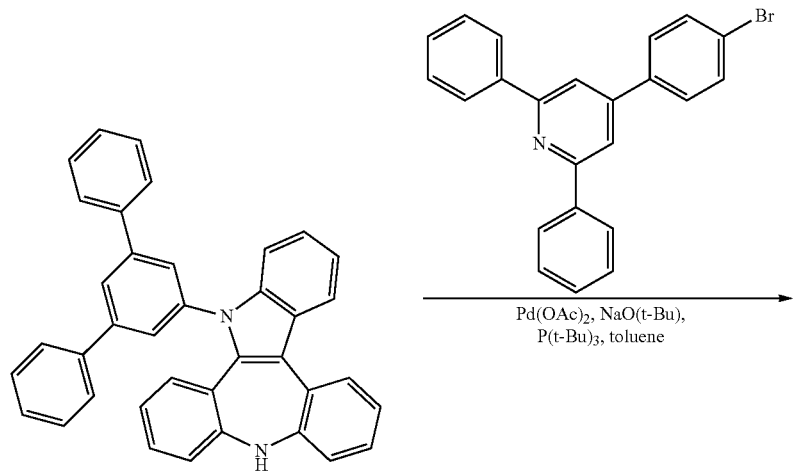
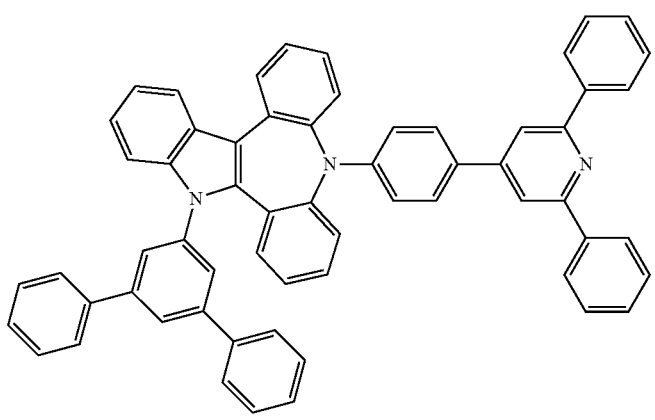
D-7
Compound D-7 (3.6 g, yield 65%) was obtained by performing the same process as in Synthesis Example 70, except that 4-(4-bromophenyl)-2,6-diphenylpyridine (3.1 g, 8.0 mmol) was used instead of 2-bromo-4,6-diphenylpyridine used in Synthesis Example 70.
Mass (theoretical value: 815.33, measured value: 815 g/mol)

[Synthesis Example 77] Synthesis of Compound D-8
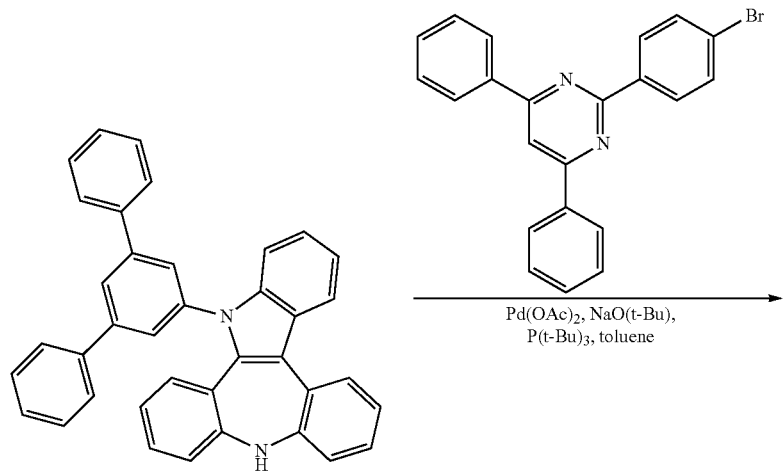
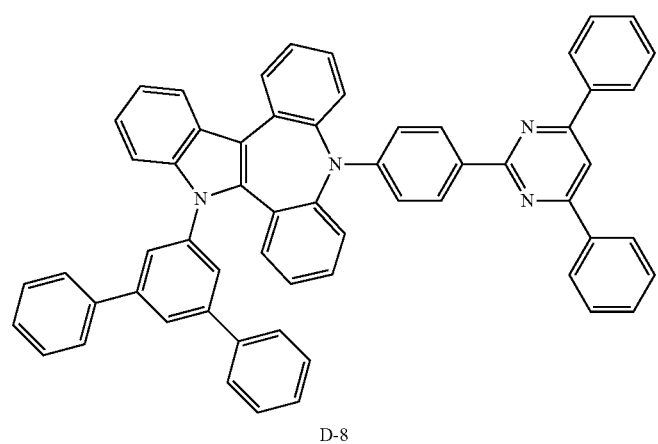
D-8
Compound D-8 (3.4 g, yield 63%) was obtained by performing the same process as in Synthesis Example 70, except that 2-(4-bromophenyl)-4,6-diphenylpyrimidine (3.1 g, 8.0 mmol) was used instead of 2-bromo-4,6-diphenylpyridine used in Synthesis Example 70.
Mass (theoretical value: 816.32, measured value: 816 g/mol)

[Synthesis Example 78] Synthesis of Compound D-9
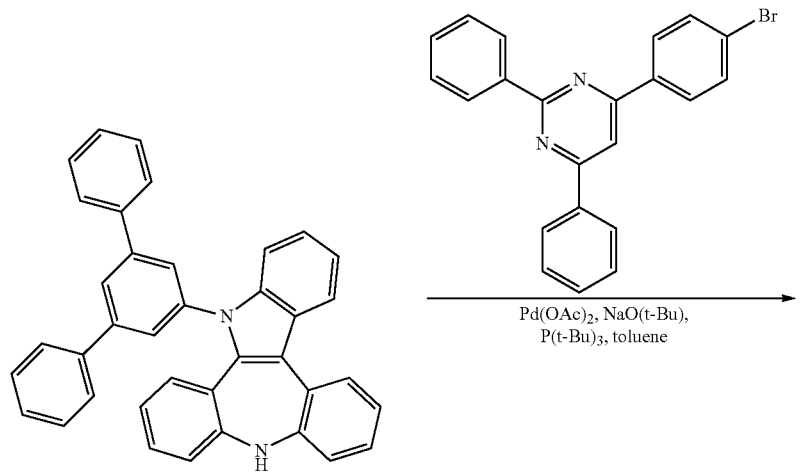
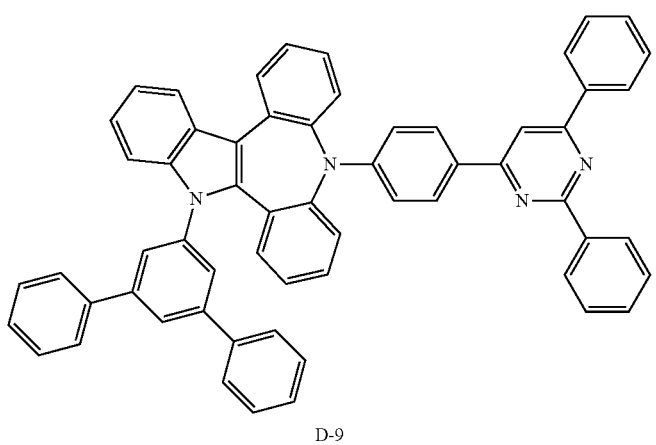
D-9
Compound D-9 (3.7 g, yield 67%) was obtained by performing the same process as in Synthesis Example 70, except that 4-(4-bromophenyl)-2,6-diphenylpyrimidine (3.1 g, 8.0 mmol) was used instead of 2-bromo-4,6-diphenylpyridine used in Synthesis Example 70.
Mass (theoretical value: 816.32, measured value: 816 g/mol)

[Synthesis Example 79] Synthesis of Compound D-10
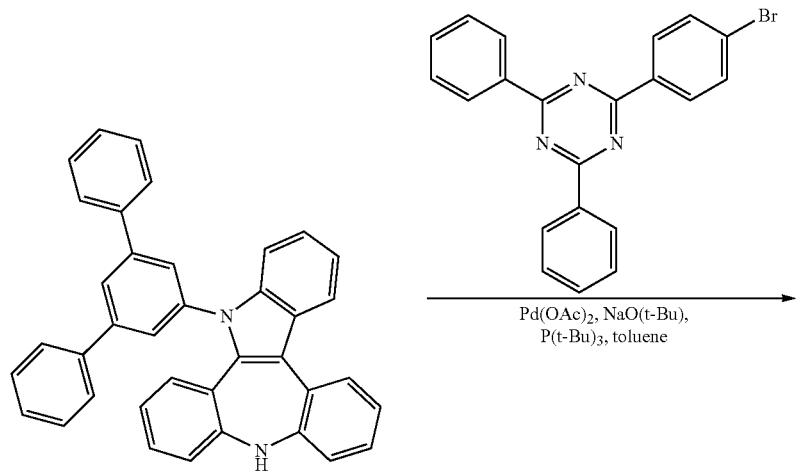
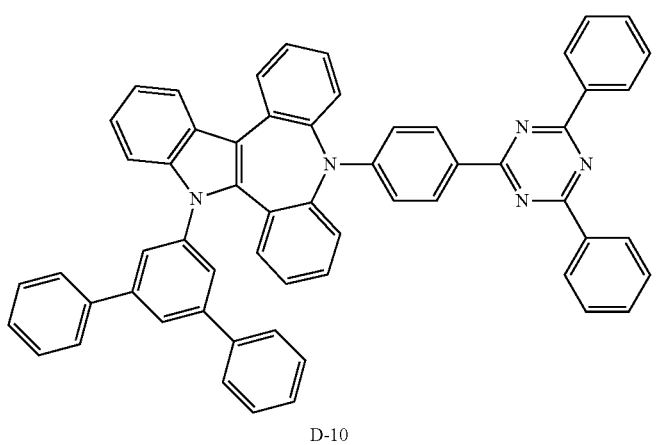
D-10
Compound D-10 (3.5 g, yield 64%) was obtained by performing the same process as in Synthesis Example 70, except that 2-(4-bromophenyl)-4,6-diphenyl-1,3,5-triazine (3.1 g, 8.0 mmol) was used instead of 2-bromo-4,6-diphenylpyridine used in Synthesis Example 70.
Mass (theoretical value: 817.32, measured value: 817 g/mol)

[Synthesis Example 80] Synthesis of Compound D-11
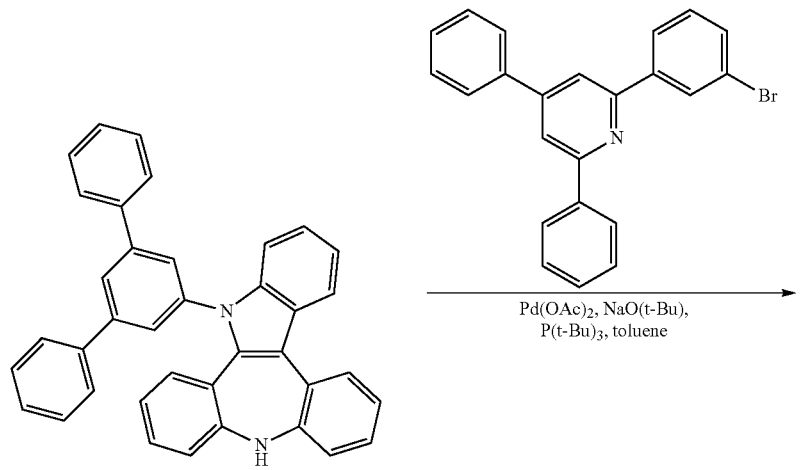
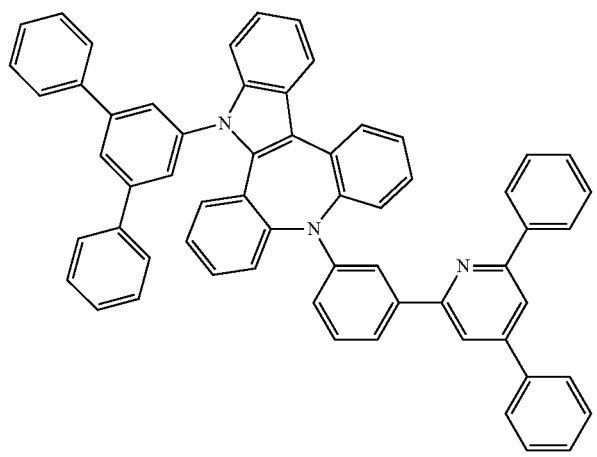
D-11
Compound D-11 (3.6 g, yield 66%) was obtained by performing the same process as in Synthesis Example 70, except that 2-(3-bromophenyl)-4,6-diphenylpyridine (3.1 g, 8.0 mmol) was used instead of 2-bromo-4,6-diphenylpyridine used in Synthesis Example 70.
Mass (theoretical value: 815.33, measured value: 815 g/mol)

[Synthesis Example 81] Synthesis of Compound D-12
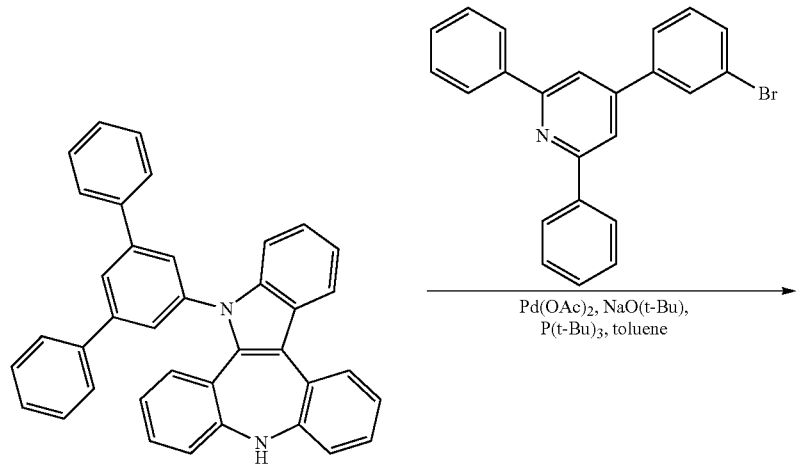
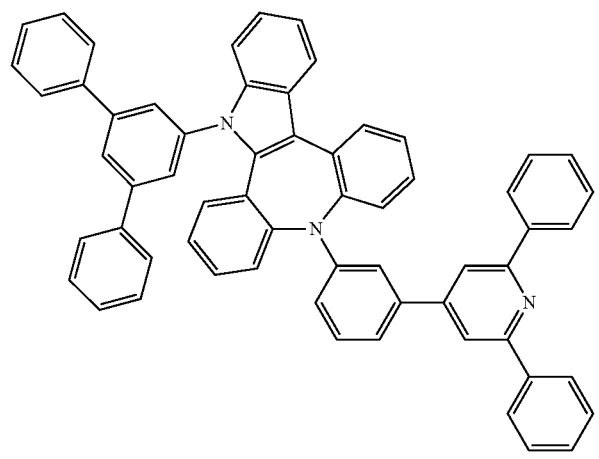
D-12
Compound D-12 (3.3 g, yield 60%) was obtained by performing the same process as in Synthesis Example 70, except that 4-(3-bromophenyl)-2,6-diphenylpyridine (3.1 g, 8.0 mmol) was used instead of 2-bromo-4,6-diphenylpyridine used in Synthesis Example 70.
Mass (theoretical value: 815.33, measured value: 815 g/mol)

[Synthesis Example 82] Synthesis of Compound D-13
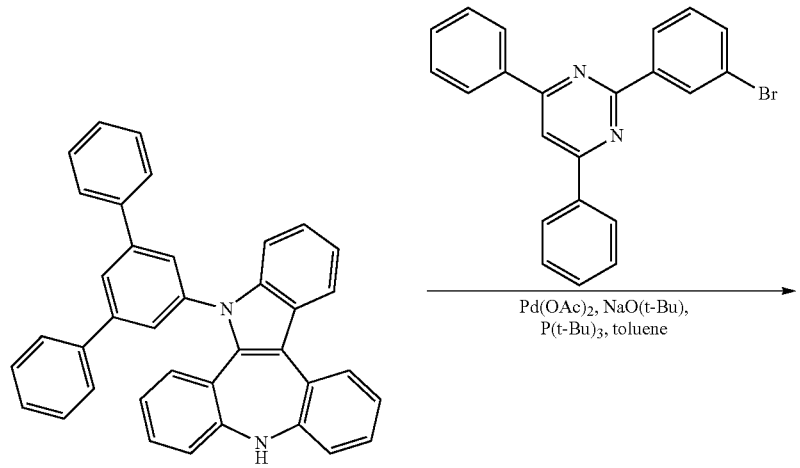
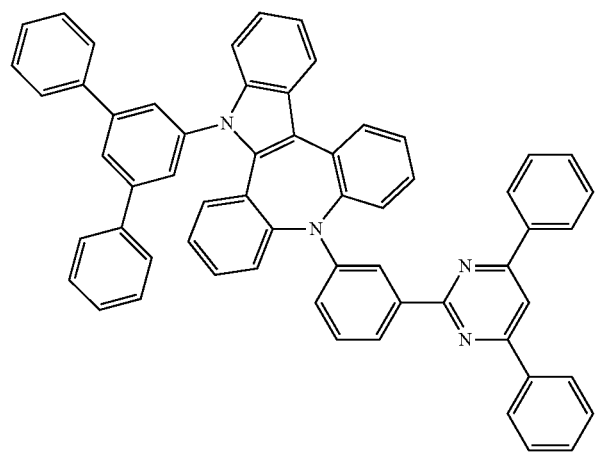
D-13
Compound D-13 (3.4 g, yield 62%) was obtained by performing the same process as in Synthesis Example 70, except that 2-(3-bromophenyl)-4,6-diphenylpyrimidine (3.1 g, 8.0 mmol) was used instead of 2-bromo-4,6-diphenylpyridine used in Synthesis Example 70.
Mass (theoretical value: 816.32, measured value: 816 g/mol)

[Synthesis Example 83] Synthesis of Compound D-14
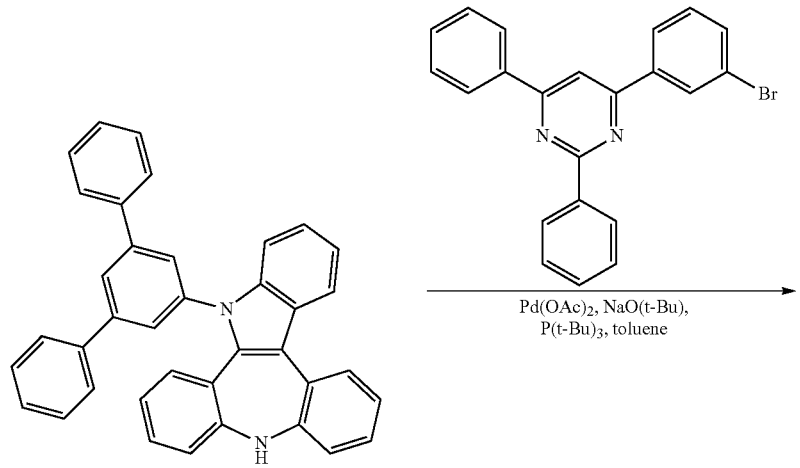
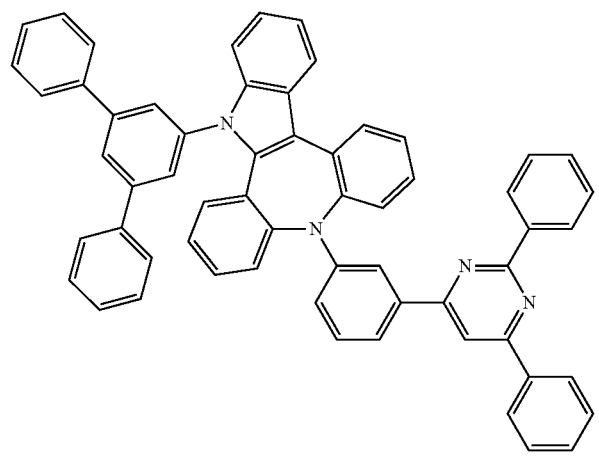
D-14
Compound D-14 (3.7 g, yield 68%) was obtained by performing the same process as in Synthesis Example 70, except that 4-(3-bromophenyl)-2,6-diphenylpyrimidine (3.1 g, 8.0 mmol) was used instead of 2-bromo-4,6-diphenylpyridine used in Synthesis Example 70.
Mass (theoretical value: 816.32, measured value: 816 g/mol)

[Synthesis Example 84] Synthesis of Compound D-15

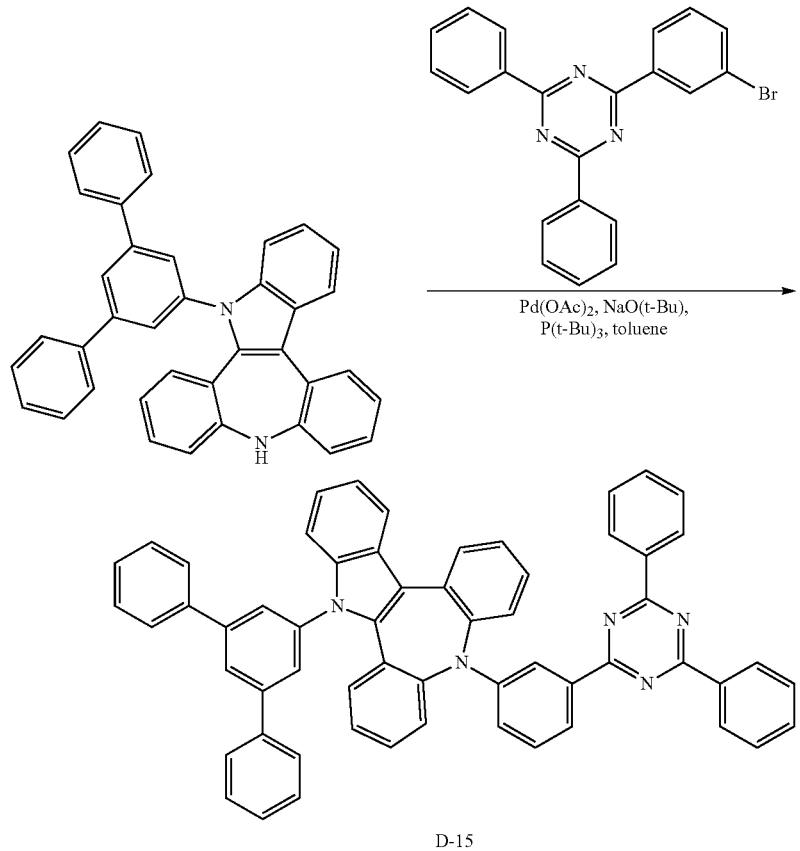

D-15

Compound D-15 (3.8 g, yield 70%) was obtained by performing the same process as in Synthesis Example 70, except that 2-(3-bromophenyl)-4,6-diphenyl-1,3,5-triazine (3.1 g, 8.0 mmol) was used instead of 2-bromo-4,6-diphenylpyridine used in Synthesis Example 70.

Mass (theoretical value: 817.32, measured value: 817 g/mol)

[Synthesis Example 85] Synthesis of Compound D-16

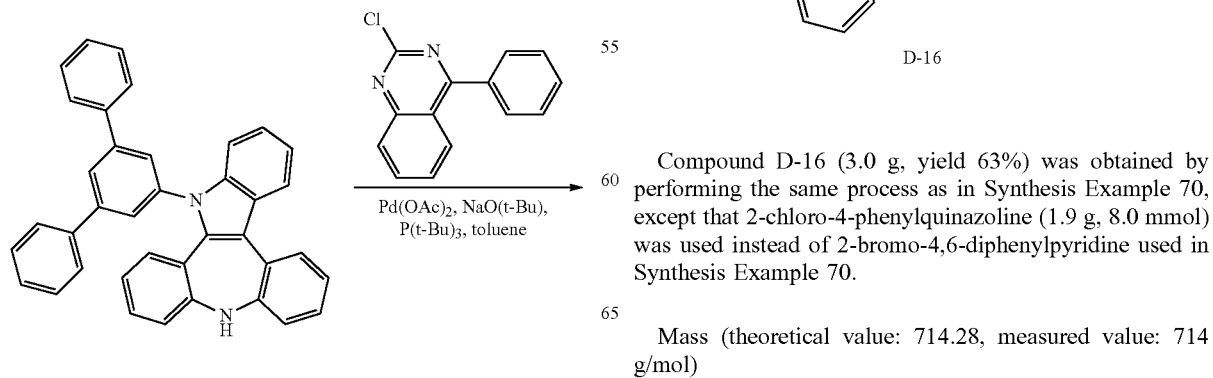

D-16

Compound D-16 (3.0 g, yield 63%) was obtained by performing the same process as in Synthesis Example 70, except that 2-chloro-4-phenylquinazoline (1.9 g, 8.0 mmol) was used instead of 2-bromo-4,6-diphenylpyridine used in Synthesis Example 70.

Mass (theoretical value: 714.28, measured value: 714 g/mol)

[Synthesis Example 86] Synthesis of Compound D-17

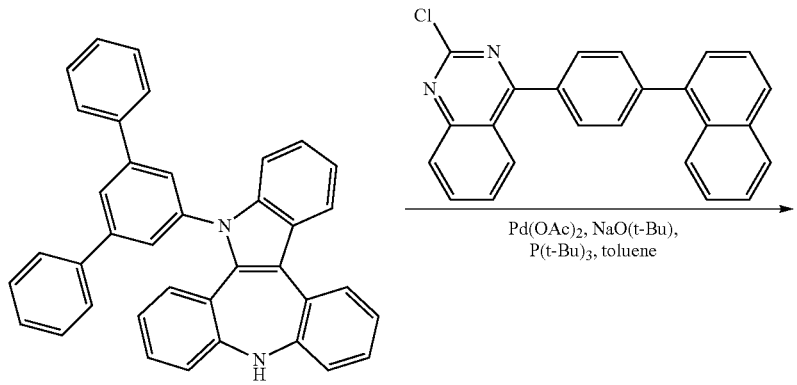

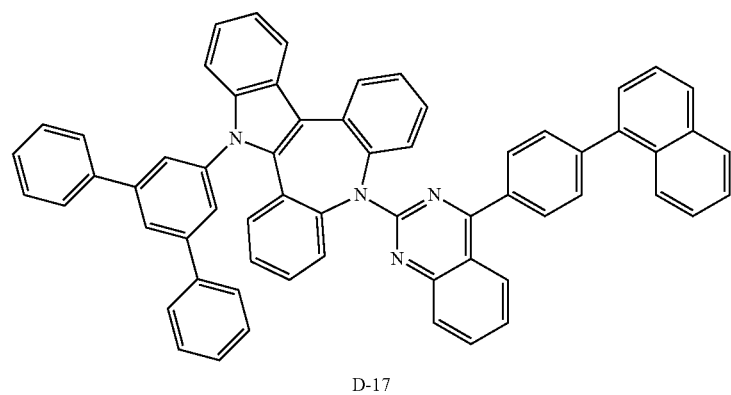

D-17

Compound D-17 (4.0 g, yield 71%) was obtained by performing the same process as in Synthesis Example 70, except that 2-chloro-4-(4-(naphthalen-1-yl)phenyl)quinazoline (2.9 g, 8.0 mmol) was used instead of 2-bromo-4,6-diphenylpyridine used in Synthesis Example 70.

Mass (theoretical value: 840.32, measured value: 840 g/mol)

[Synthesis Example 87] Synthesis of Compound D-18

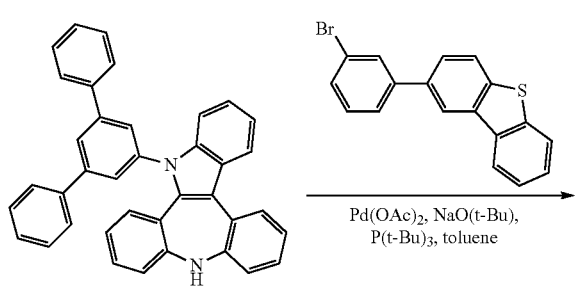

-continued

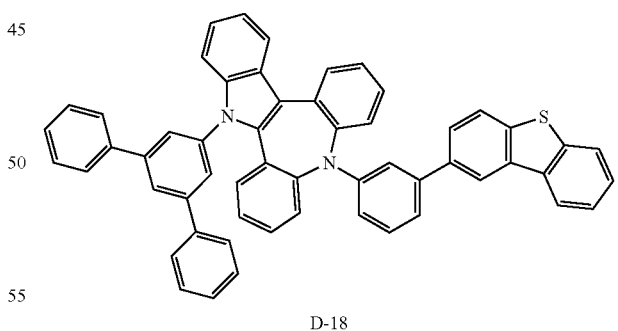

D-18

Compound D-18 (3.8 g, yield 74%) was obtained by performing the same process as in Synthesis Example 70, except that 2-(3-bromophenyl)dibenzo[b,d]thiophene (2.7 g, 8.0 mmol) was used instead of 2-bromo-4,6-diphenylpyridine used in Synthesis Example 70.

Mass (theoretical value: 768.26, measured value: 768 g/mol)

[Synthesis Example 88] Synthesis of Compound D-19
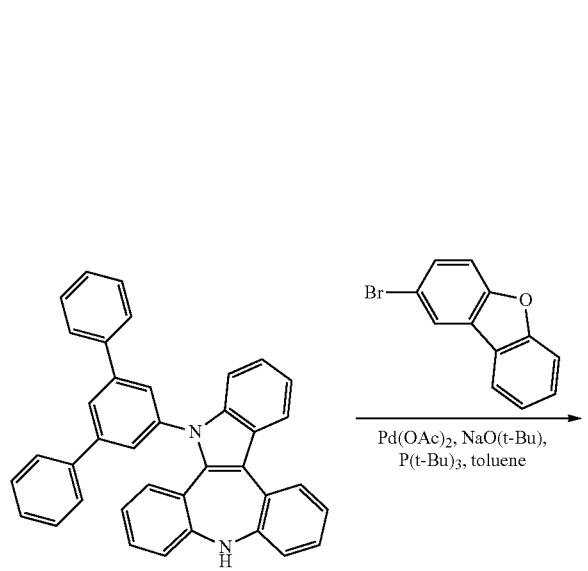
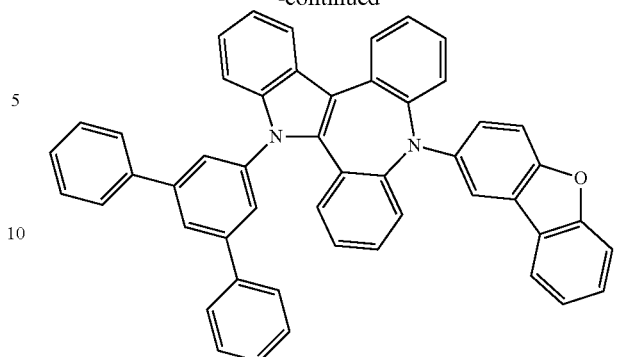
D-19
Compound D-19 (3.3 g, yield 72%) was obtained by performing the same process as in Synthesis Example 70, except that 2-bromodibenzo[b,d]furan (2.0 g, 8.0 mmol) was used instead of 2-bromo-4,6-diphenylpyridine used in Synthesis Example 70.
Mass (theoretical value: 676.25, measured value: 676 g/mol)
[Synthesis Example 89] Synthesis of Compound D-20
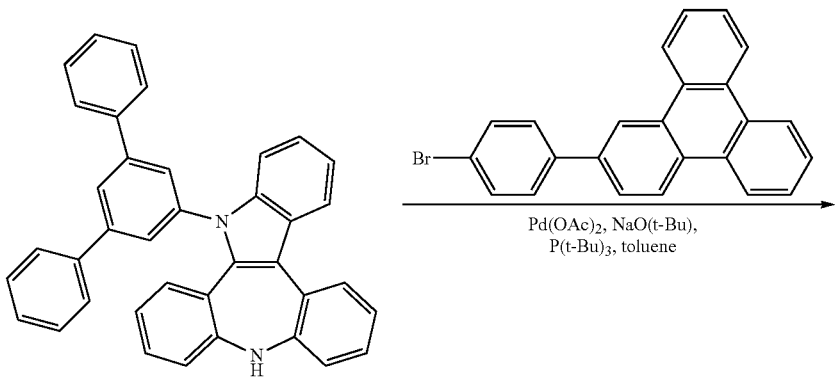
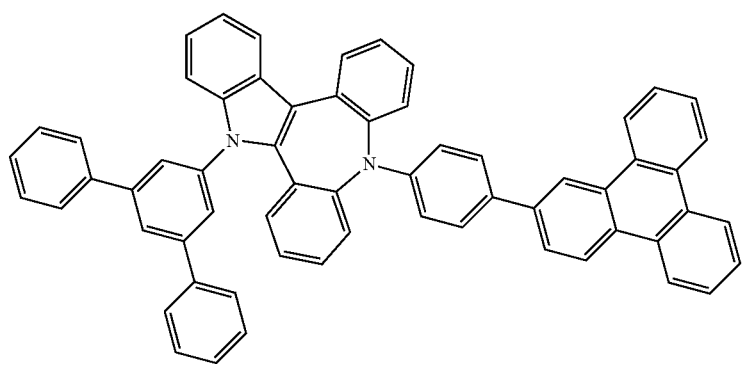
D-20

Compound D-20 (3.8 g, yield 70%) was obtained by performing the same process as in Synthesis Example 70, except that 2-(4-bromophenyl)triphenylene (3.1 g, 8.0 mmol) was used instead of 2-bromo-4,6-diphenylpyridine used in Synthesis Example 70.

Mass (theoretical value: 812.32, measured value: 812 g/mol)

[Synthesis Example 90] Synthesis of Compound D-21

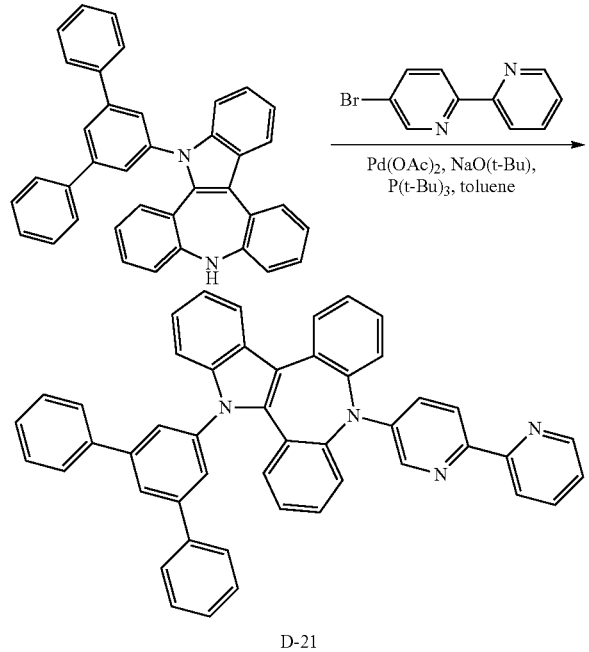

D-21

Compound D-21 (2.9 g, yield 65%) was obtained by performing the same process as in Synthesis Example 70, except that 5-bromo-2,2'-bipyridine (1.9 g, 8.0 mmol) was used instead of 2-bromo-4,6-diphenylpyridine used in Synthesis Example 70.

Mass (theoretical value: 664.26, measured value: 664 g/mol)

[Synthesis Example 91] Synthesis of Compound D-22

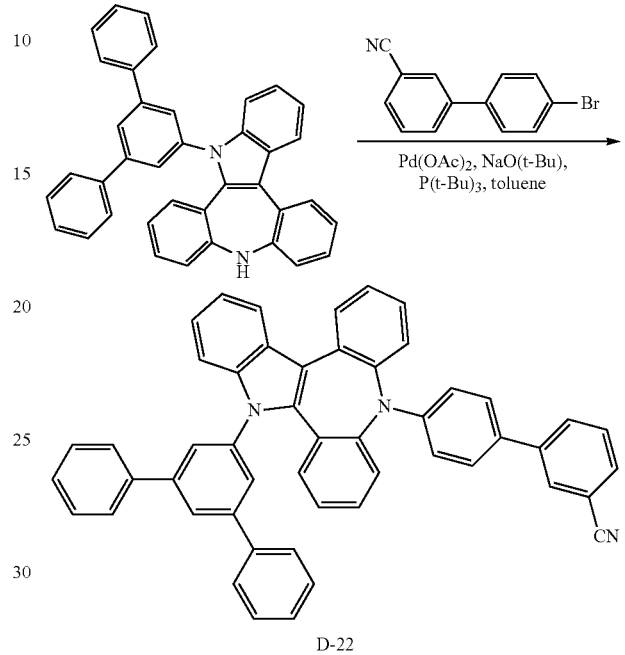

D-22

Compound D-22 (2.8 g, yield 61%) was obtained by performing the same process as in Synthesis Example 70, except that 4'-bromobiphenyl-3-carbonitrile (2.1 g, 8.0 mmol) was used instead of 2-bromo-4,6-diphenylpyridine used in Synthesis Example 70.

Mass (theoretical value: 687.27, measured value: 687 g/mol)

[Synthesis Example 92] Synthesis of Compound D-23

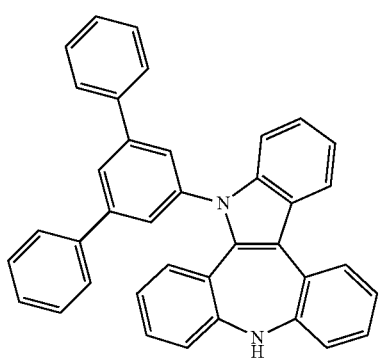

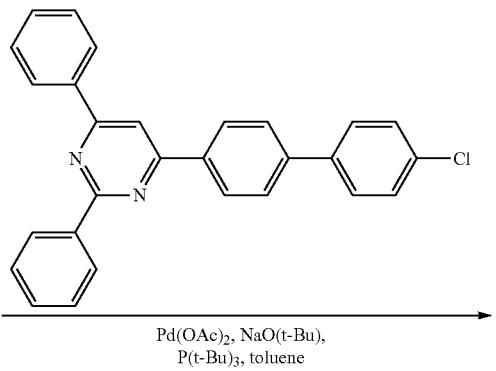

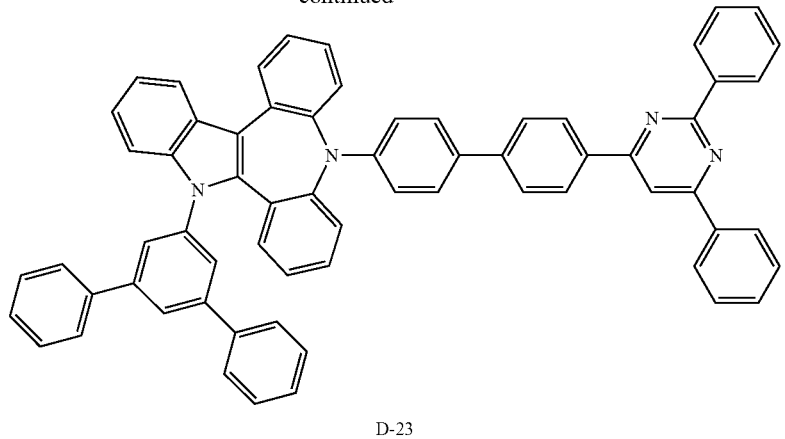

D-23

Compound D-23 (3.9 g, yield 66%) was obtained by performing the same process as in Synthesis Example 70, except that 4-(4'-chlorobiphenyl-4-yl)-2,6-diphenylpyrimidine (3.4 g, 8.0 mmol) was used instead of 2-bromo-4,6-diphenylpyridine used in Synthesis Example 70.

Mass (theoretical value: 892.35, measured value: 892 g/mol)

[Synthesis Example 93] Synthesis of Compound E-1

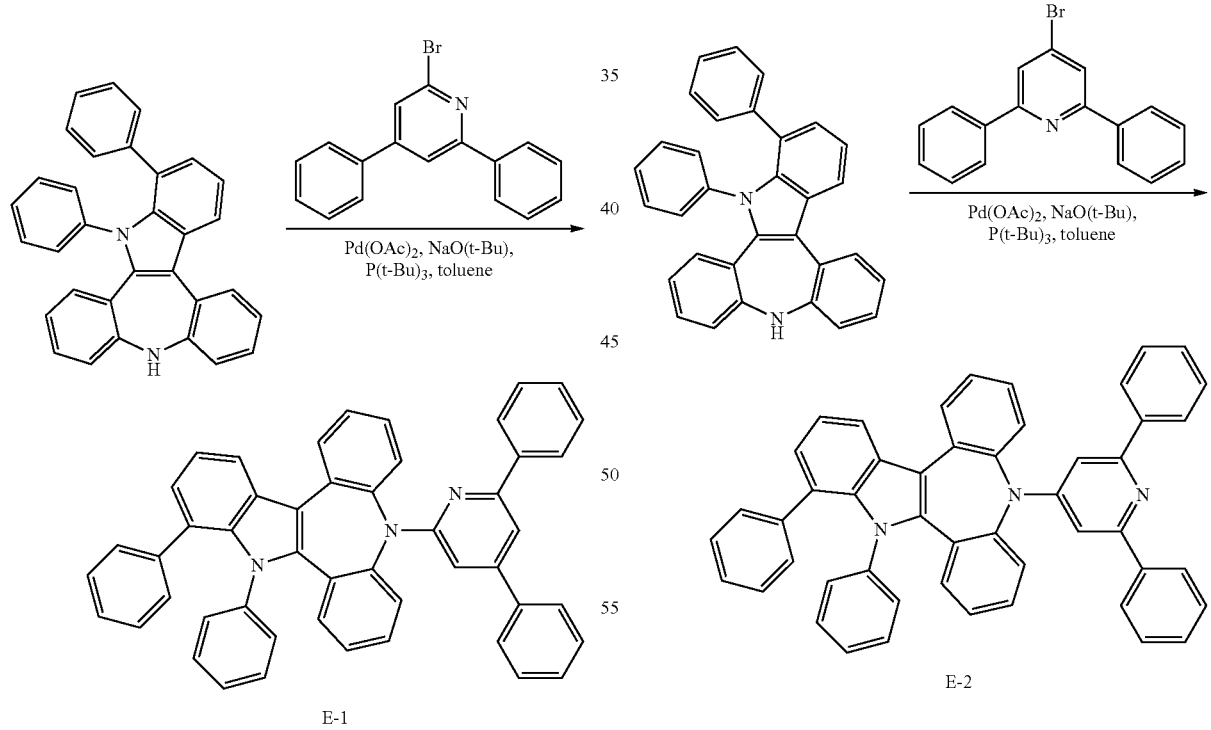

E-1

E-2

Compound IAz-5 (2.9 g, 6.7 mmol) synthesized in Preparation Example 5, 2-bromo-4,6-diphenylpyridine (2.5 g, 8.0 mmol), Pd(OAc)$_2$ (0.08 g, 0.34 mmol), P(t-Bu)$_3$ (0.16 ml, 0.67 mmol), NaO(t-Bu) (1.29 g, 13.4 mmol), and toluene (70 ml) were mixed under nitrogen flow, and the resulting mixture was stirred at 110° C. for 5 hours. After the reaction was terminated, toluene was concentrated, and a solid salt was filtered and then purified with recrystallization to obtain Compound E-1 (2.9 g, yield 65%).

Mass (theoretical value: 663.27, measured value: 663 g/mol)

[Synthesis Example 94] Synthesis of Compound E-2

Compound E-2 (3.2 g, yield 71%) was obtained by performing the same process as in Synthesis Example 93, except that 4-bromo-2,6-diphenylpyridine (2.5 g, 8.0 mmol) was used instead of 2-bromo-4,6-diphenylpyridine used in Synthesis Example 93.

Mass (theoretical value: 663.27, measured value: 663 g/mol)

[Synthesis Example 95] Synthesis of Compound E-3

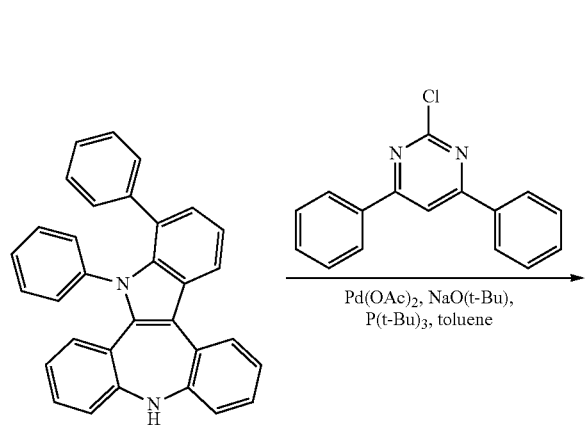

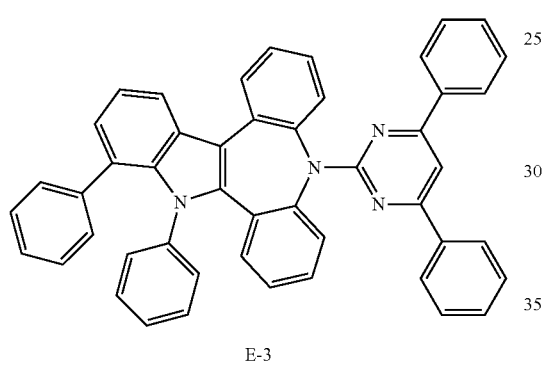

E-3

Compound E-3 (2.9 g, yield 66%) was obtained by performing the same process as in Synthesis Example 93, except that 2-chloro-4,6-diphenylpyrimidine (2.5 g, 8.0 mmol) was used instead of 2-bromo-4,6-diphenylpyridine used in Synthesis Example 93.

Mass (theoretical value: 664.26, measured value: 664 g/mol)

[Synthesis Example 96] Synthesis of Compound E-4

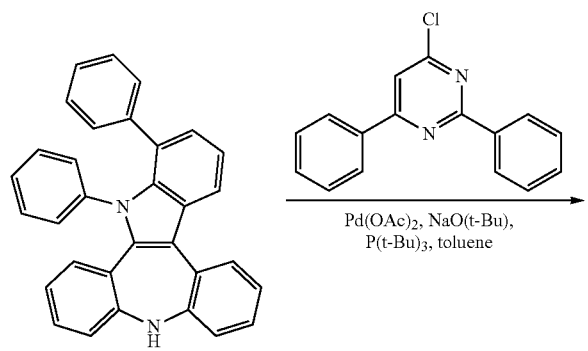

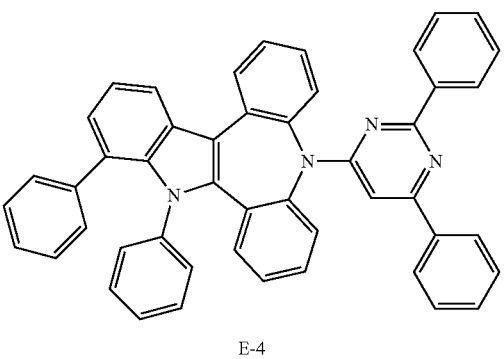

E-4

Compound E-4 (3.0 g, yield 67%) was obtained by performing the same process as in Synthesis Example 93, except that 4-chloro-2,6-diphenylpyrimidine (2.5 g, 8.0 mmol) was used instead of 2-bromo-4,6-diphenylpyridine used in Synthesis Example 93.

Mass (theoretical value: 664.26, measured value: 664 g/mol)

[Synthesis Example 97] Synthesis of Compound E-5

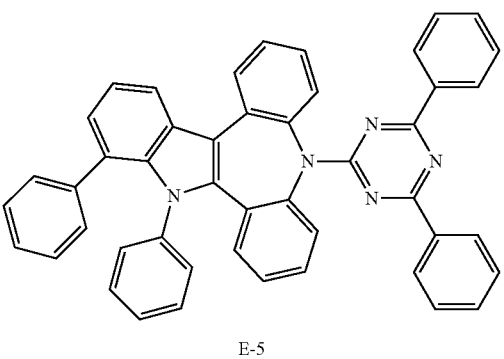

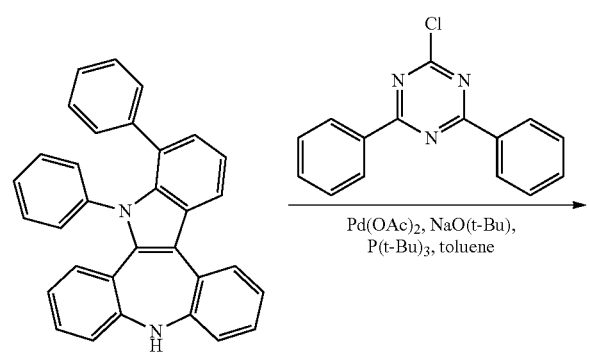

E-5

Compound E-5 (2.7 g, yield 61%) was obtained by performing the same process as in Synthesis Example 93, except that 2-chloro-4,6-diphenyl-1,3,5-triazine (2.1 g, 8.0 mmol) was used instead of 2-bromo-4,6-diphenylpyridine used in Synthesis Example 93.

Mass (theoretical value: 665.26, measured value: 665 g/mol)

[Synthesis Example 98] Synthesis of Compound E-6

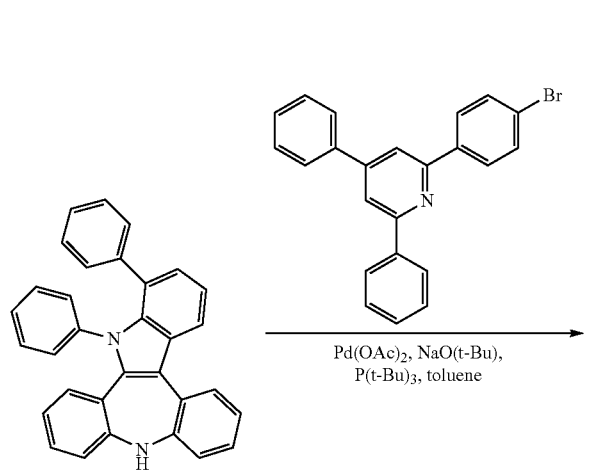

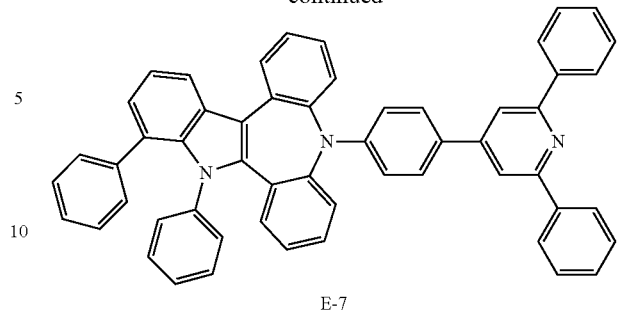

E-7

Compound E-7 (3.4 g, yield 69%) was obtained by performing the same process as in Synthesis Example 93, except that 4-(4-bromophenyl)-2,6-diphenylpyridine (3.1 g, 8.0 mmol) was used instead of 2-bromo-4,6-diphenylpyridine used in Synthesis Example 93.

Mass (theoretical value: 739.30, measured value: 739 g/mol)

[Synthesis Example 100] Synthesis of Compound E-8

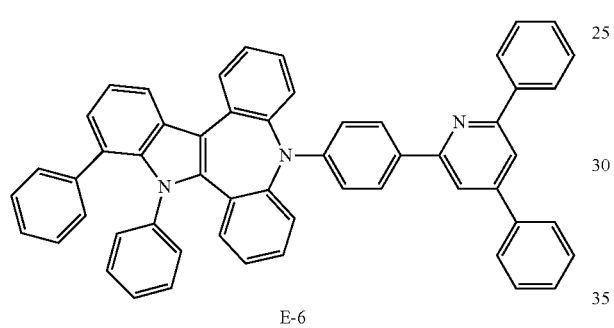

E-6

Compound E-6 (3.8 g, yield 76%) was obtained by performing the same process as in Synthesis Example 93, except that 2-(4-bromophenyl)-4,6-diphenylpyridine (3.1 g, 8.0 mmol) was used instead of 2-bromo-4,6-diphenylpyridine used in Synthesis Example 93.

Mass (theoretical value: 739.30, measured value: 739 g/mol)

[Synthesis Example 99] Synthesis of Compound E-7

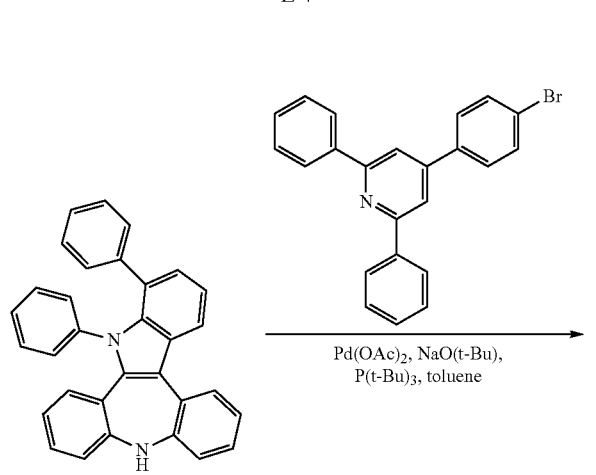

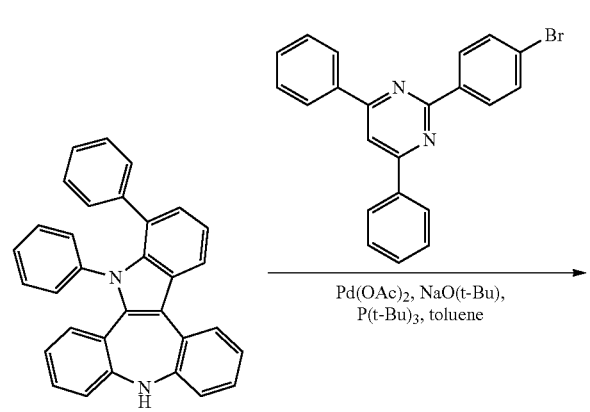

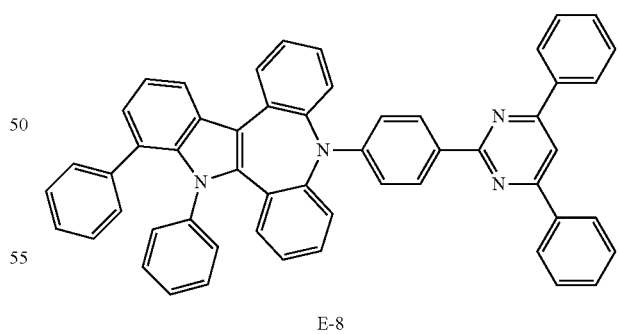

E-8

Compound E-8 (3.2 g, yield 64%) was obtained by performing the same process as in Synthesis Example 93, except that 2-(4-bromophenyl)-4,6-diphenylpyrimidine (3.1 g, 8.0 mmol) was used instead of 2-bromo-4,6-diphenylpyridine used in Synthesis Example 93.

Mass (theoretical value: 740.29, measured value: 740 g/mol)

[Synthesis Example 101] Synthesis of Compound E-9

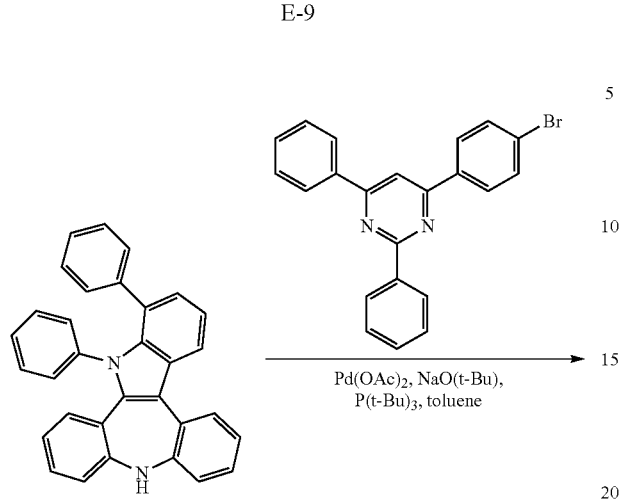

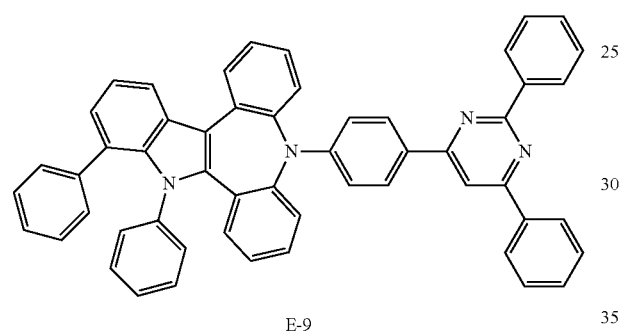

E-9

Compound E-9 (3.1 g, yield 62%) was obtained by performing the same process as in Synthesis Example 93, except that 4-(4-bromophenyl)-2,6-diphenylpyrimidine (3.1 g, 8.0 mmol) was used instead of 2-bromo-4,6-diphenylpyridine used in Synthesis Example 93.

Mass (theoretical value: 740.29, measured value: 740 g/mol)

[Synthesis Example 102] Synthesis of Compound E-10

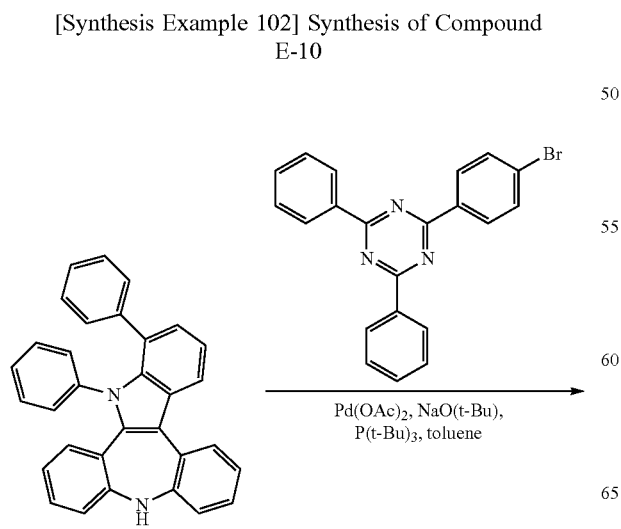

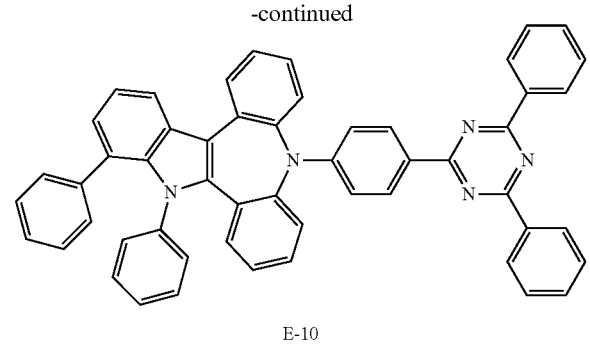

E-10

Compound E-10 (3.6 g, yield 73%) was obtained by performing the same process as in Synthesis Example 93, except that 2-(4-bromophenyl)-4,6-diphenyl-1,3,5-triazine (3.1 g, 8.0 mmol) was used instead of 2-bromo-4,6-diphenylpyridine used in Synthesis Example 93.

Mass (theoretical value: 741.29, measured value: 741 g/mol)

[Synthesis Example 103] Synthesis of Compound E-11

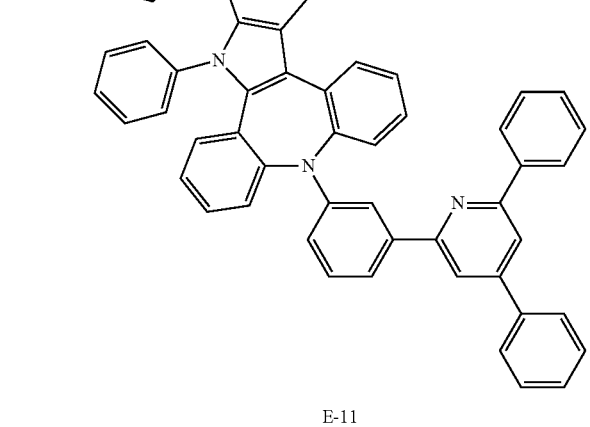

E-11

Compound E-11 (3.5 g, yield 70%) was obtained by performing the same process as in Synthesis Example 93, except that 2-(3-bromophenyl)-4,6-diphenylpyridine (3.1 g, 8.0 mmol) was used instead of 2-bromo-4,6-diphenylpyridine used in Synthesis Example 93.

Mass (theoretical value: 739.30, measured value: 739 g/mol)

[Synthesis Example 104] Synthesis of Compound E-12

[Synthesis Example 105] Synthesis of Compound E-13

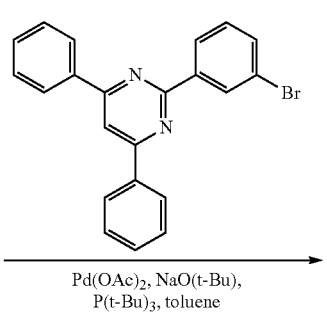

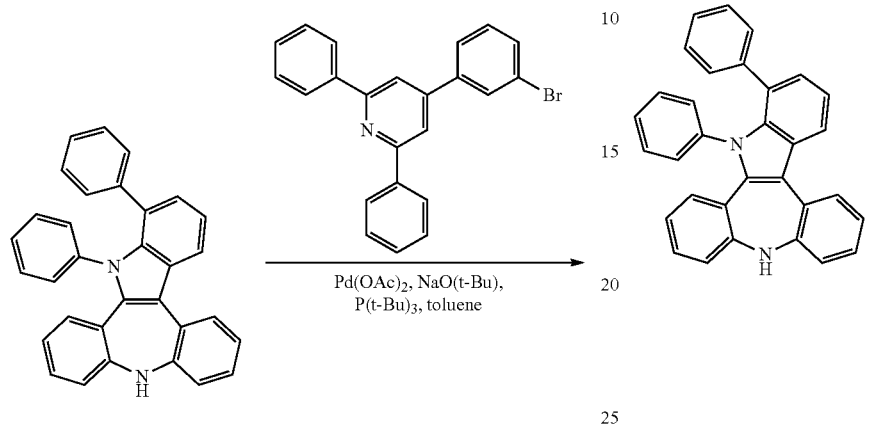

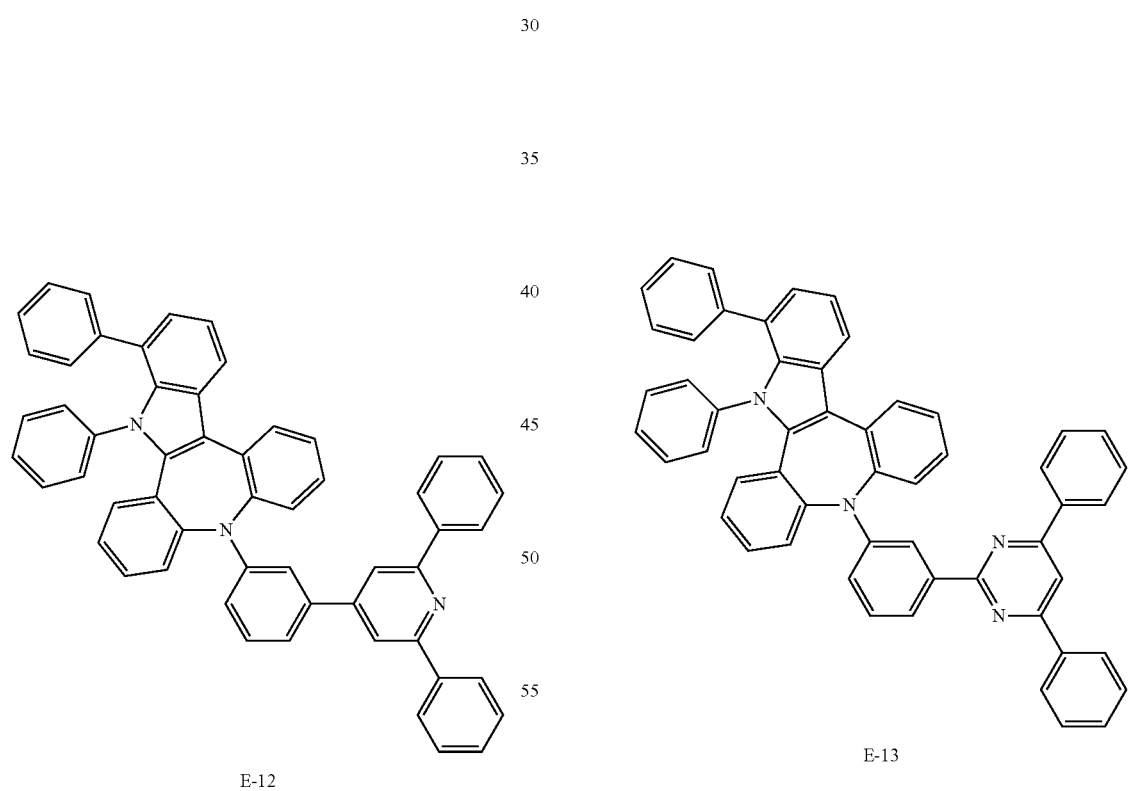

Compound E-12 (3.7 g, yield 75%) was obtained by performing the same process as in Synthesis Example 93, except that 4-(3-bromophenyl)-2,6-diphenylpyridine (3.1 g, 8.0 mmol) was used instead of 2-bromo-4,6-diphenylpyridine used in Synthesis Example 93.

Mass (theoretical value: 739.30, measured value: 739 g/mol)

Compound E-13 (3.6 g, yield 72%) was obtained by performing the same process as in Synthesis Example 93, except that 2-(3-bromophenyl)-4,6-diphenylpyrimidine (3.6 g, 8.0 mmol) was used instead of 2-bromo-4,6-diphenylpyridine used in Synthesis Example 93.

Mass (theoretical value: 740.29, measured value: 740 g/mol)

[Synthesis Example 106] Synthesis of Compound E-14

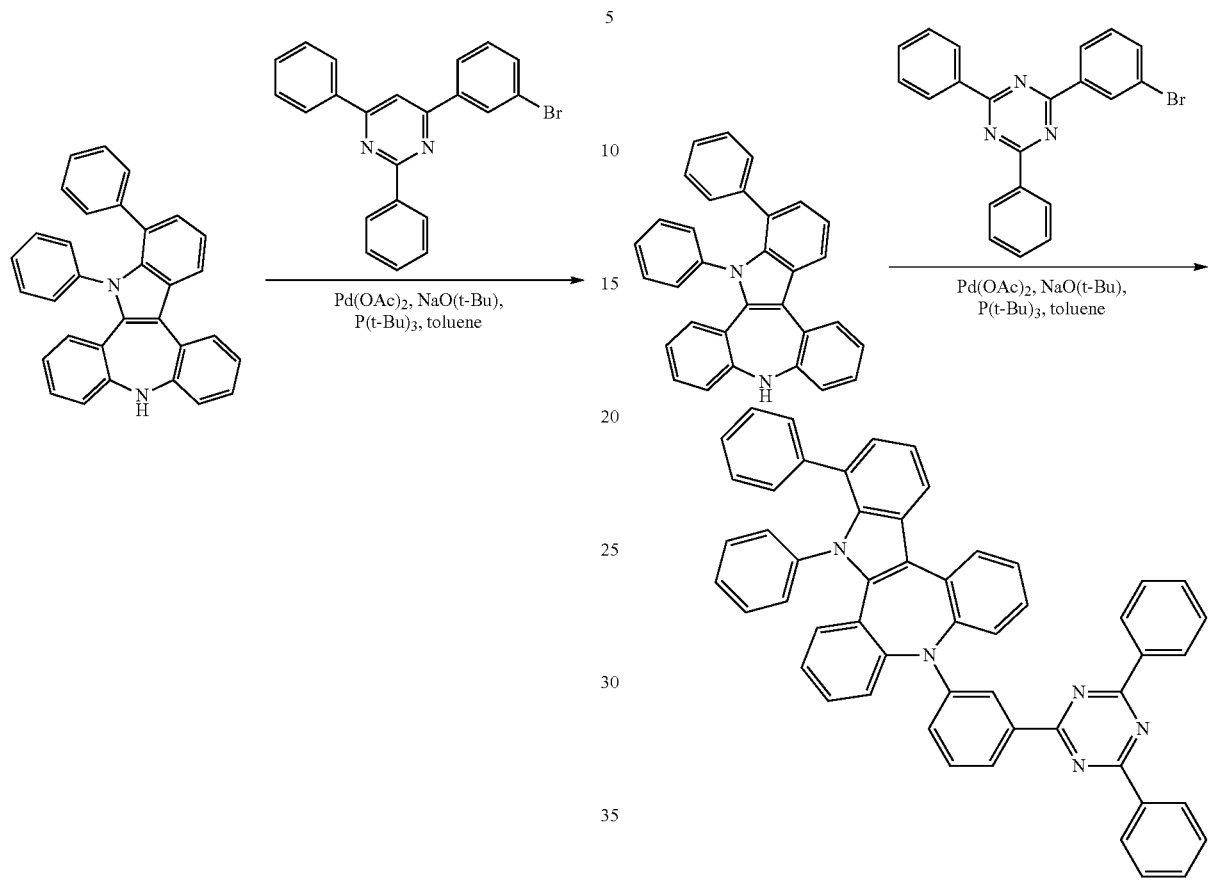

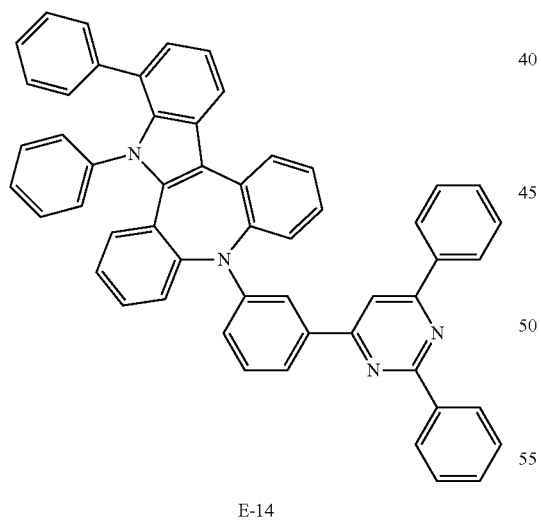

E-14

Compound E-14 (3.5 g, yield 71%) was obtained by performing the same process as in Synthesis Example 93, except that 4-(3-bromophenyl)-2,6-diphenylpyrimidine (3.1 g, 8.0 mmol) was used instead of 2-bromo-4,6-diphenylpyridine used in Synthesis Example 93.

Mass (theoretical value: 740.29, measured value: 740 g/mol)

[Synthesis Example 107] Synthesis of Compound E-15

E-15

Compound E-15 (3.4 g, yield 68%) was obtained by performing the same process as in Synthesis Example 93, except that 2-(3-bromophenyl)-4,6-diphenyl-1,3,5-triazine (3.1 g, 8.0 mmol) was used instead of 2-bromo-4,6-diphenylpyridine used in Synthesis Example 93.

Mass (theoretical value: 741.29, measured value: 741 g/mol)

[Synthesis Example 108] Synthesis of Compound E-16

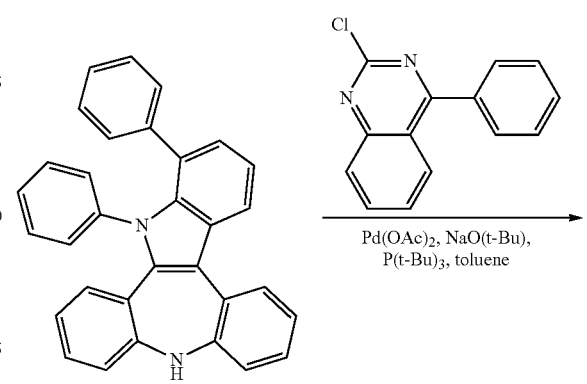

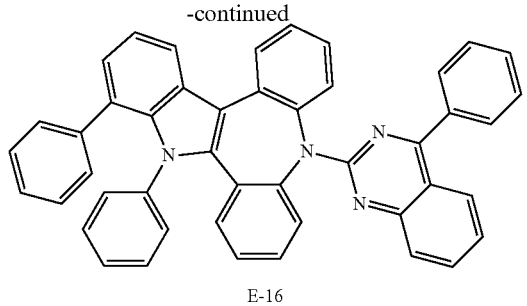

E-16

Compound E-16 (2.8 g, yield 65%) was obtained by performing the same process as in Synthesis Example 93, except that 2-chloro-4-phenylquinazoline (1.9 g, 8.0 mmol) was used instead of 2-bromo-4,6-diphenylpyridine used in Synthesis Example 93.

Mass (theoretical value: 638.25, measured value: 638 g/mol)

[Synthesis Example 109] Synthesis of Compound E-17

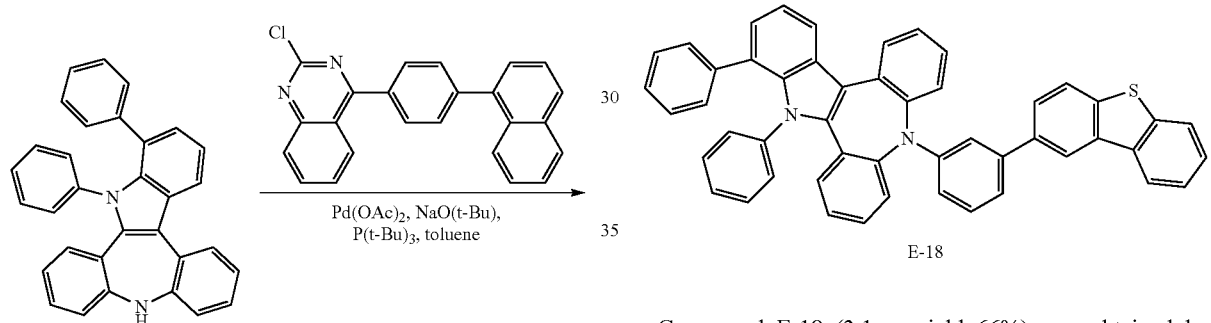

E-17

Compound E-17 (3.3 g, yield 64%) was obtained by performing the same process as in Synthesis Example 93, except that 2-chloro-4-(4-(naphthalen-1-yl)phenyl)quinazoline (2.9 g, 8.0 mmol) was used instead of 2-bromo-4,6-diphenylpyridine used in Synthesis Example 93.

Mass (theoretical value: 764.29, measured value: 764 g/mol)

[Synthesis Example 110] Synthesis of Compound E-18

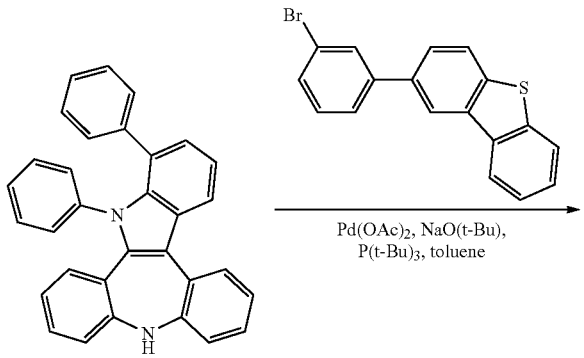

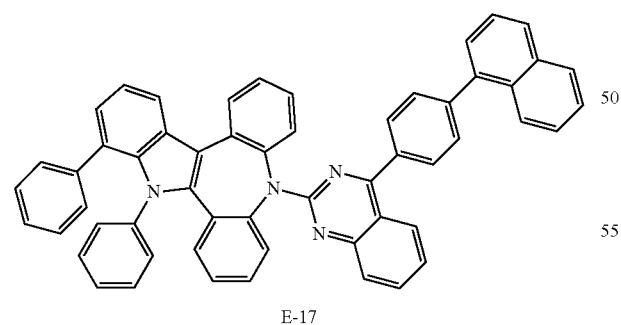

E-18

Compound E-18 (3.1 g, yield 66%) was obtained by performing the same process as in Synthesis Example 93, except that 2-(3-bromophenyl)dibenzo[b,d]thiophene (2.7 g, 8.0 mmol) was used instead of 2-bromo-4,6-diphenylpyridine used in Synthesis Example 93.

Mass (theoretical value: 692.23, measured value: 692 g/mol)

[Synthesis Example 111] Synthesis of Compound E-19

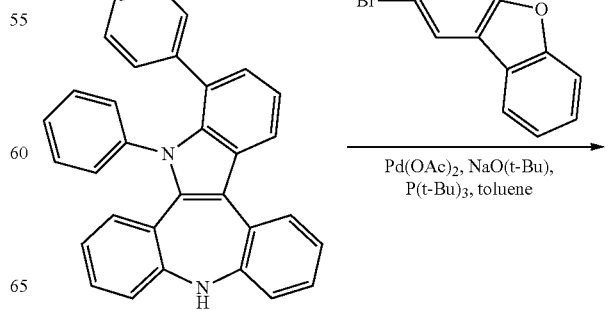

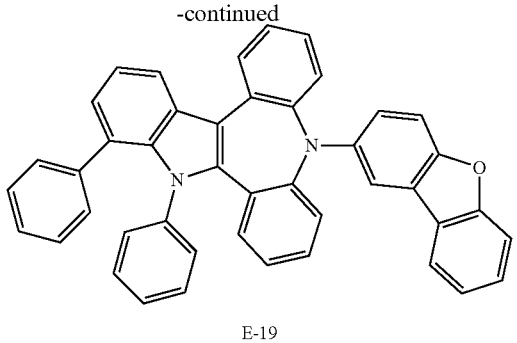

E-19

Compound E-19 (2.7 g, yield 68%) was obtained by performing the same process as in Synthesis Example 93, except that 2-bromodibenzo[b,d]furan (2.0 g, 8.0 mmol) was used instead of 2-bromo-4,6-diphenylpyridine used in Synthesis Example 93.

Mass (theoretical value: 600.22, measured value: 600 g/mol)

[Synthesis Example 112] Synthesis of Compound E-20

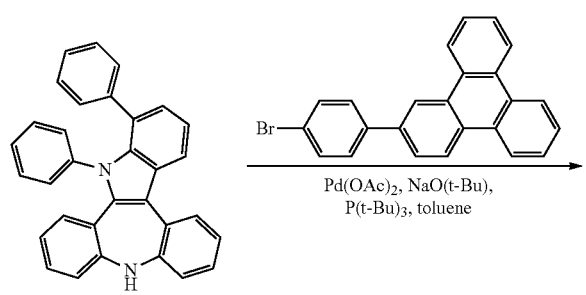

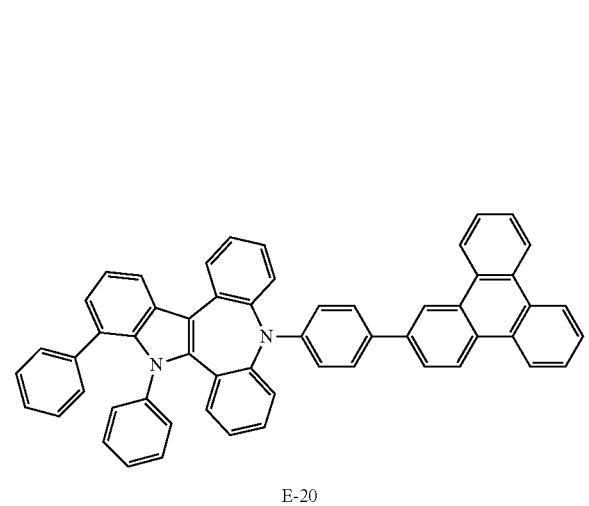

E-20

Compound E-20 (3.1 g, yield 62%) was obtained by performing the same process as in Synthesis Example 93, except that 2-(4-bromophenyl)triphenylene (3.1 g, 8.0 mmol) was used instead of 2-bromo-4,6-diphenylpyridine used in Synthesis Example 93.

Mass (theoretical value: 736.29, measured value: 736 g/mol)

[Synthesis Example 113] Synthesis of Compound E-21

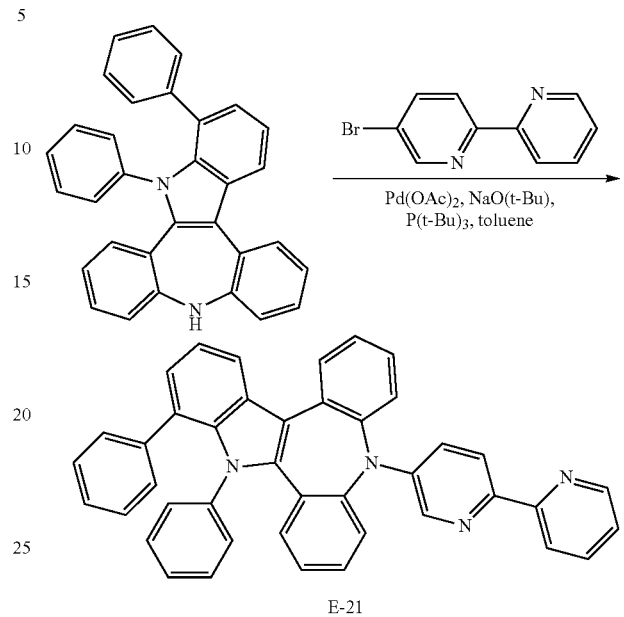

E-21

Compound E-21 (2.5 g, yield 63%) was obtained by performing the same process as in Synthesis Example 93, except that 5-bromo-2,2'-bipyridine (1.9 g, 8.0 mmol) was used instead of 2-bromo-4,6-diphenylpyridine used in Synthesis Example 93.

Mass (theoretical value: 588.23, measured value: 588 g/mol)

[Synthesis Example 114] Synthesis of Compound E-22

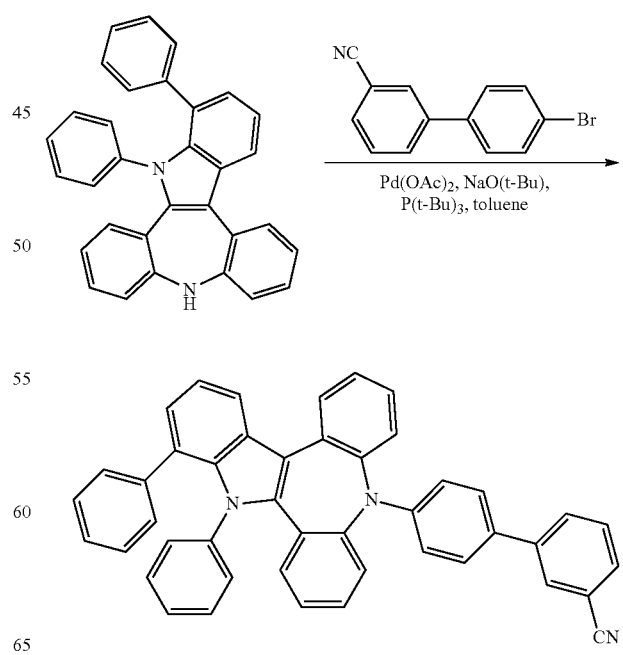

E-22

Compound E-22 (2.8 g, yield 68%) was obtained by performing the same process as in Synthesis Example 93, except that 4'-bromobiphenyl-3-carbonitrile (2.1 g, 8.0 mmol) was used instead of 2-bromo-4,6-diphenylpyridine used in Synthesis Example 93.

Mass (theoretical value: 611.24, measured value: 611 g/mol)

[Synthesis Example 115] Synthesis of Compound E-23

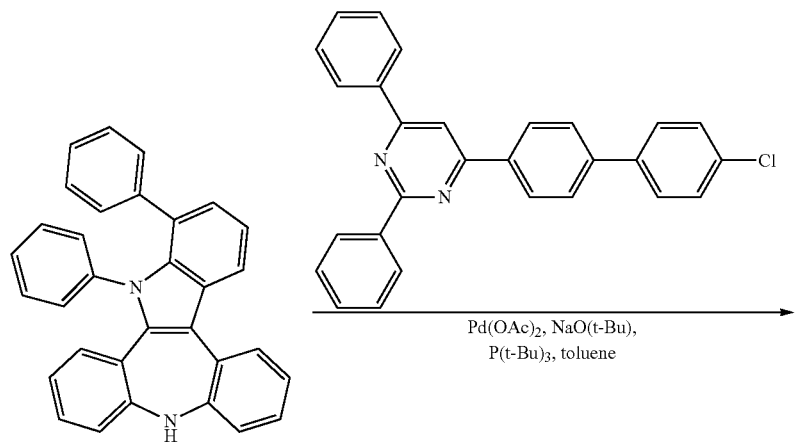

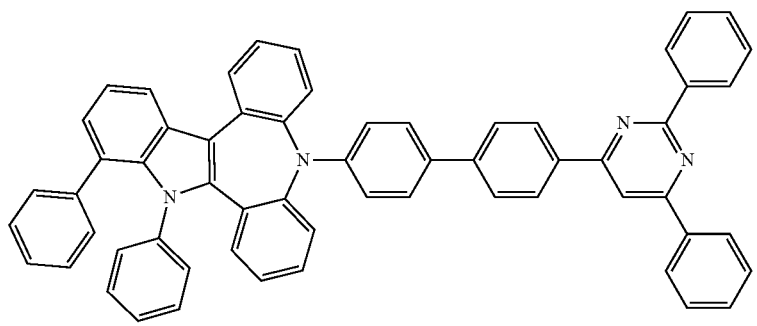

E-23

Compound E-23 (4.0 g, yield 73%) was obtained by performing the same process as in Synthesis Example 93, except that 4-(4'-chlorobiphenyl-4-yl)-2,6-diphenylpyrimidine (3.4 g, 8.0 mmol) was used instead of 2-bromo-4,6-diphenylpyridine used in Synthesis Example 93.

Mass (theoretical value: 816.32, measured value: 816 g/mol)

[Synthesis Example 116] Synthesis of Compound F-1

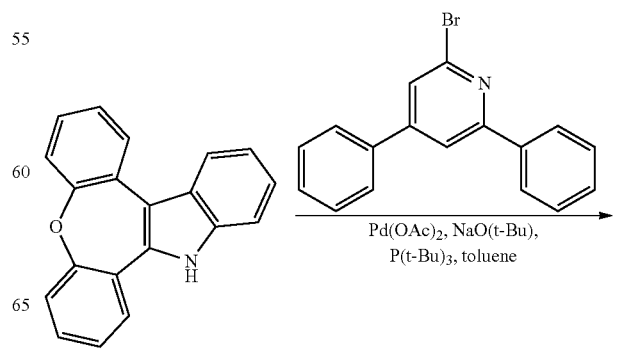

-continued

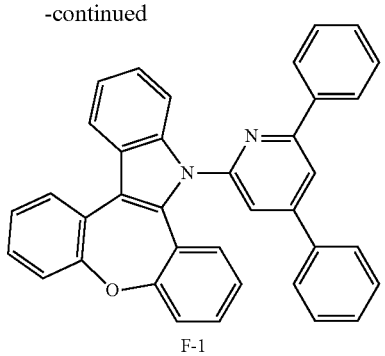

F-1

Compound IAz-6 (1.9 g, 6.7 mmol) synthesized in Preparation Example 6, 2-bromo-4,6-diphenylpyridine (2.5 g, 8.0 mmol), Pd(OAc)$_2$ (0.08 g, 0.34 mmol), P(t-Bu)$_3$ (0.16 ml, 0.67 mmol), NaO(t-Bu) (1.29 g, 13.4 mmol), and toluene (70 ml) were mixed under nitrogen flow, and the resulting mixture was stirred at 110° C. for 5 hours. After the reaction was terminated, toluene was concentrated, and a solid salt was filtered and then purified with recrystallization to obtain target compound F-1 (1.9 g, yield 62%).

Mass (theoretical value: 467.19, measured value: 467 g/mol)

[Synthesis Example 117] Synthesis of Compound F-2

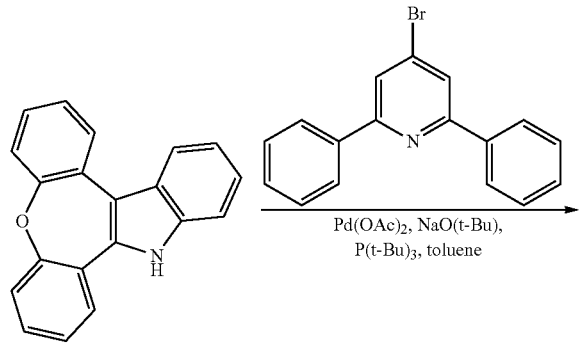

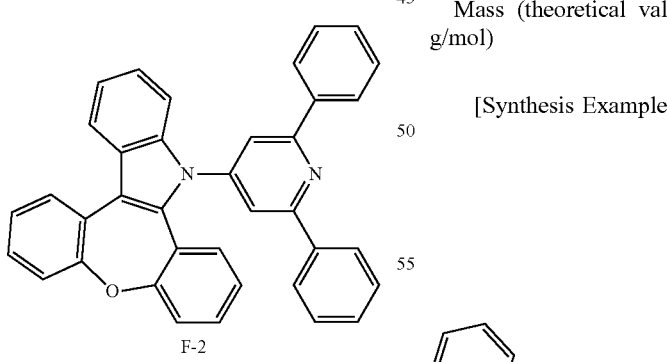

F-2

Compound F-2 (2.1 g, yield 66%) was obtained by performing the same process as in Synthesis Example 116, except that 4-bromo-2,6-diphenylpyridine (2.5 g, 8.0 mmol) was used instead of 2-bromo-4,6-diphenylpyridine used in Synthesis Example 116.

Mass (theoretical value: 467.19, measured value: 467 g/mol)

[Synthesis Example 118] Synthesis of Compound F-3

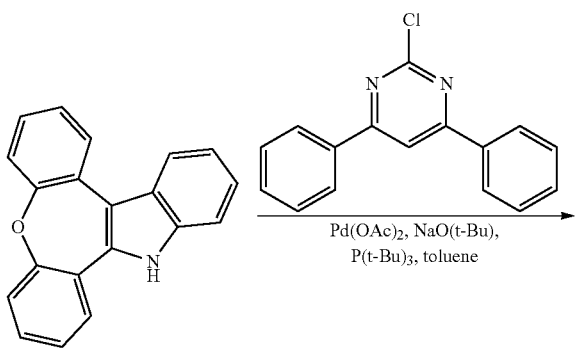

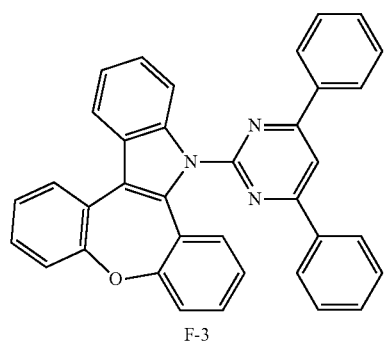

F-3

Compound F-3 (2.3 g, yield 73%) was obtained by performing the same process as in Synthesis Example 116, except that 2-chloro-4,6-diphenylpyrimidine (2.5 g, 8.0 mmol) was used instead of 2-bromo-4,6-diphenylpyridine used in Synthesis Example 116.

Mass (theoretical value: 468.18, measured value: 468 g/mol)

[Synthesis Example 119] Synthesis of Compound F-4

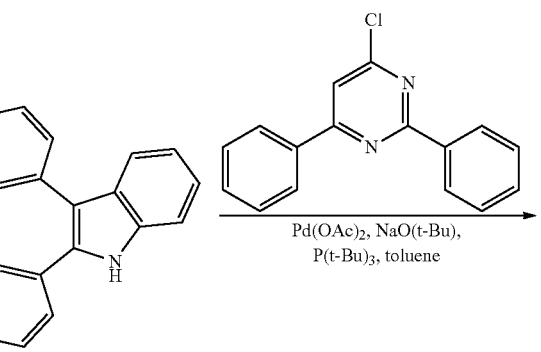

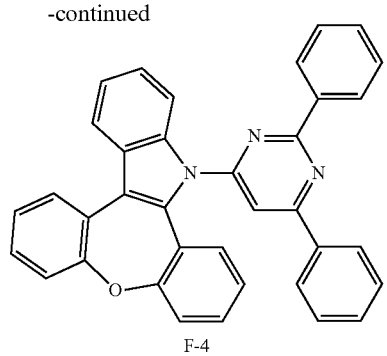

F-4

Compound F-4 (2.1 g, yield 68%) was obtained by performing the same process as in Synthesis Example 116, except that 4-chloro-2,6-diphenylpyrimidine (2.5 g, 8.0 mmol) was used instead of 2-bromo-4,6-diphenylpyridine used in Synthesis Example 116.

Mass (theoretical value: 468.18, measured value: 468 g/mol)

[Synthesis Example 120] Synthesis of Compound F-5

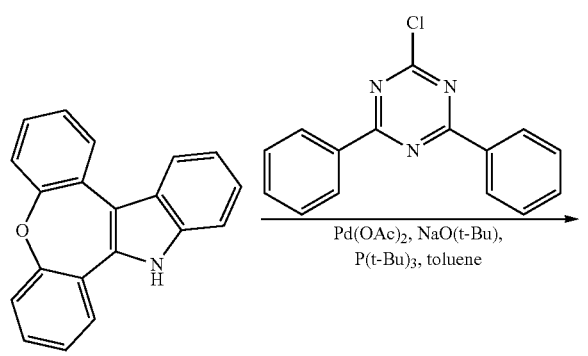

F-5

Compound F-5 (2.0 g, yield 65%) was obtained by performing the same process as in Synthesis Example 116, except that 2-chloro-4,6-diphenyl-1,3,5-triazine (2.1 g, 8.0 mmol) was used instead of 2-bromo-4,6-diphenylpyridine used in Synthesis Example 116.

Mass (theoretical value: 469.18, measured value: 469 g/mol)

[Synthesis Example 121] Synthesis of Compound F-6

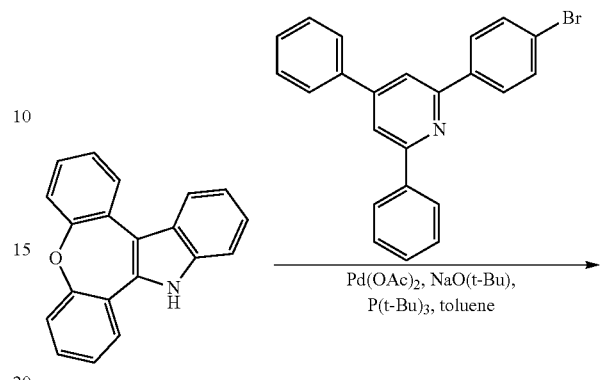

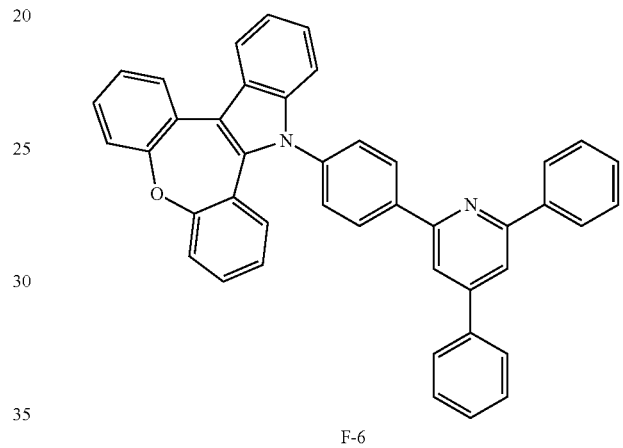

F-6

Compound F-6 (2.2 g, yield 61%) was obtained by performing the same process as in Synthesis Example 116, except that 2-(4-bromophenyl)-4,6-diphenylpyridine (3.1 g, 8.0 mmol) was used instead of 2-bromo-4,6-diphenylpyridine used in Synthesis Example 116.

Mass (theoretical value: 543.22, measured value: 543 g/mol)

[Synthesis Example 122] Synthesis of Compound F-7

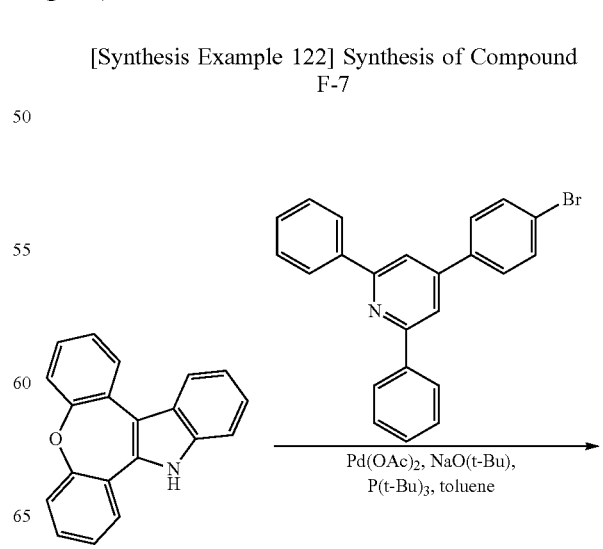

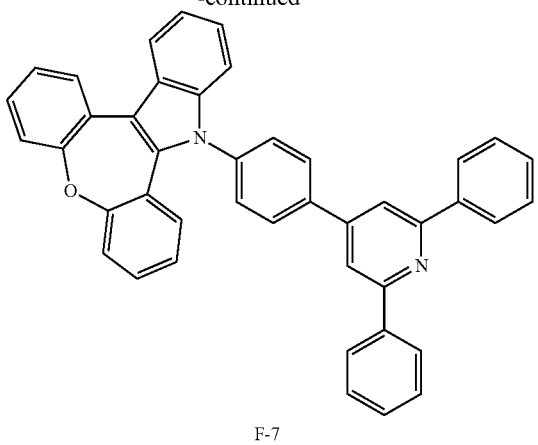

F-7

Compound F-7 (2.6 g, yield 71%) was obtained by performing the same process as in Synthesis Example 116, except that 4-(4-bromophenyl)-2,6-diphenylpyridine (3.1 g, 8.0 mmol) was used instead of 2-bromo-2,6-diphenylpyridine used in Synthesis Example 116.

Mass (theoretical value: 543.22, measured value: 543 g/mol)

[Synthesis Example 123] Synthesis of Compound F-8

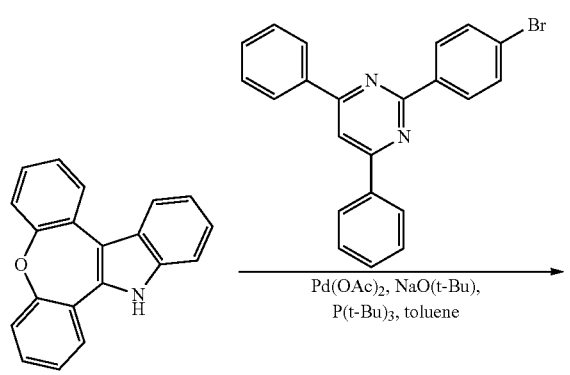

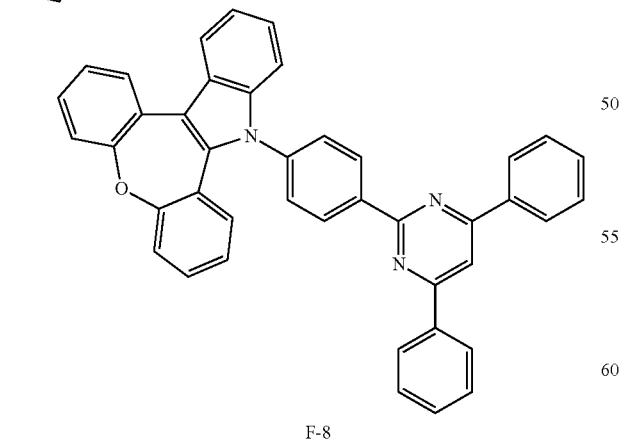

F-8

Compound F-8 (2.7 g, yield 73%) was obtained by performing the same process as in Synthesis Example 116, except that 2-(4-bromophenyl)-4,6-diphenylpyrimidine (3.1 g, 8.0 mmol) was used instead of 2-bromo-4,6-diphenylpyridine used in Synthesis Example 116.

Mass (theoretical value: 544.21, measured value: 544 g/mol)

[Synthesis Example 124] Synthesis of Compound F-9

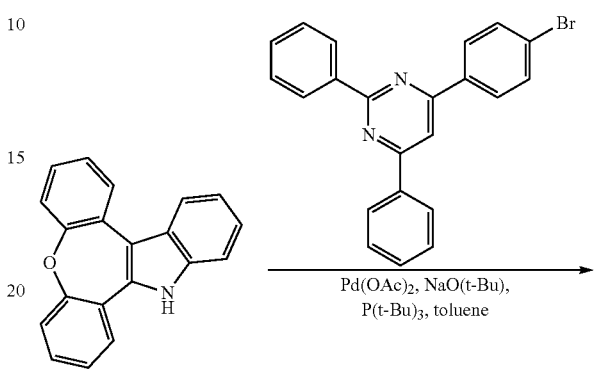

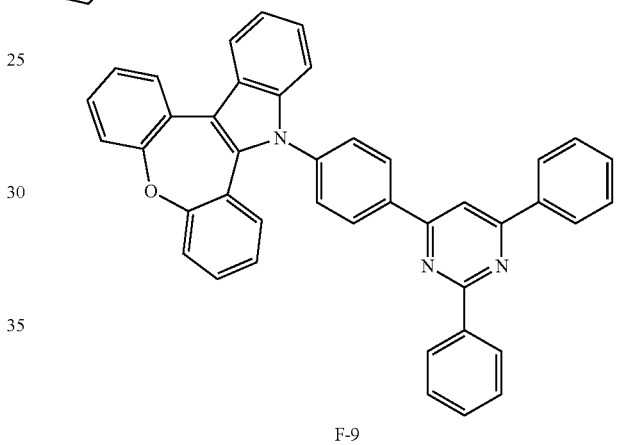

F-9

Compound F-9 (2.4 g, yield 65%) was obtained by performing the same process as in Synthesis Example 116, except that 4-(4-bromophenyl)-2,6-diphenylpyrimidine (3.1 g, 8.0 mmol) was used instead of 2-bromo-4,6-diphenylpyridine used in Synthesis Example 116.

Mass (theoretical value: 544.21, measured value: 544 g/mol)

[Synthesis Example 125] Synthesis of Compound F-10

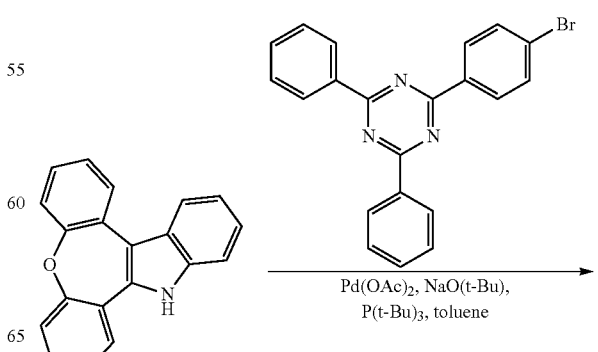

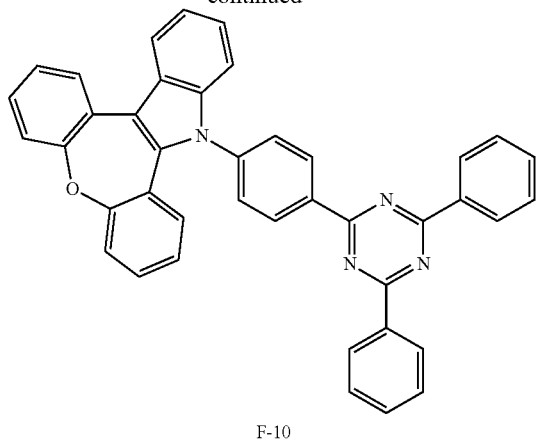

F-10

Compound F-10 (2.5 g, yield 68%) was obtained by performing the same process as in Synthesis Example 116, except that 2-(4-bromophenyl)-4,6-diphenyl-1,3,5-triazine (3.1 g, 8.0 mmol) was used instead of 2-bromo-4,6-diphenylpyridine used in Synthesis Example 116.

Mass (theoretical value: 545.21, measured value: 545 g/mol)

[Synthesis Example 126] Synthesis of Compound F-11

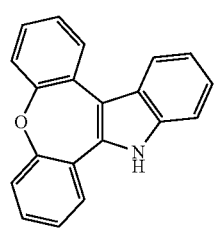

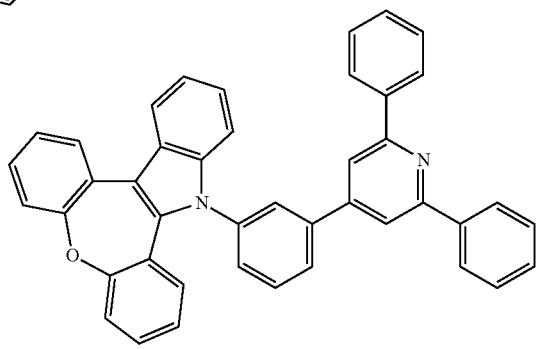

F-11

Compound F-11 (2.4 g, yield 65%) was obtained by performing the same process as in Synthesis Example 116, except that 2-(3-bromophenyl)-4,6-diphenylpyridine (3.1 g, 8.0 mmol) was used instead of 2-bromo-4,6-diphenylpyridine used in Synthesis Example 116.

Mass (theoretical value: 543.22, measured value: 543 g/mol)

[Synthesis Example 127] Synthesis of Compound F-12

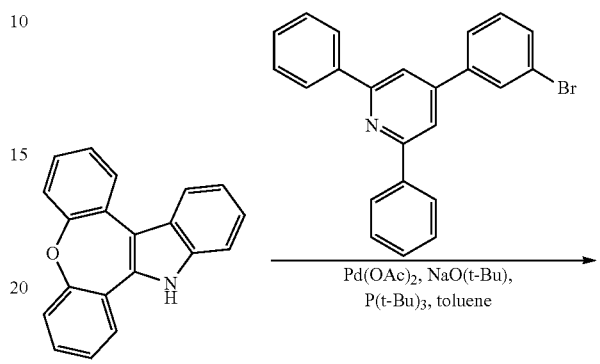

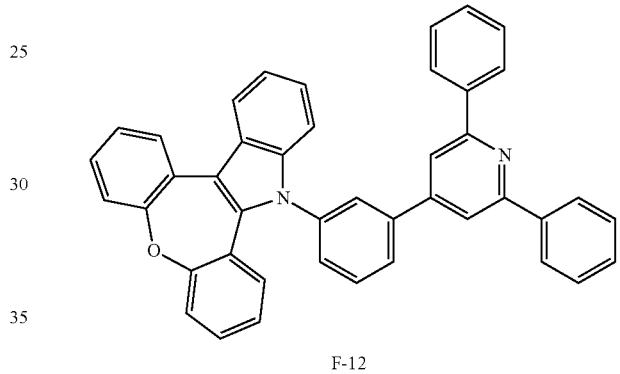

F-12

Compound F-12 (2.3 g, yield 63%) was obtained by performing the same process as in Synthesis Example 116, except that 4-(3-bromophenyl)-2,6-diphenylpyridine (3.1 g, 8.0 mmol) was used instead of 2-bromo-4,6-diphenylpyridine used in Synthesis Example 116.

Mass (theoretical value: 543.22, measured value: 543 g/mol)

[Synthesis Example 128] Synthesis of Compound F-13

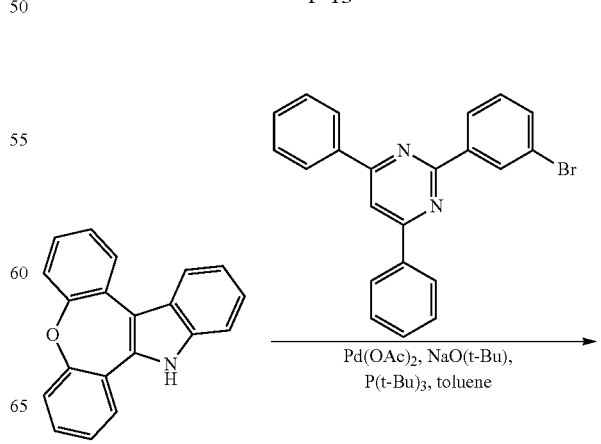

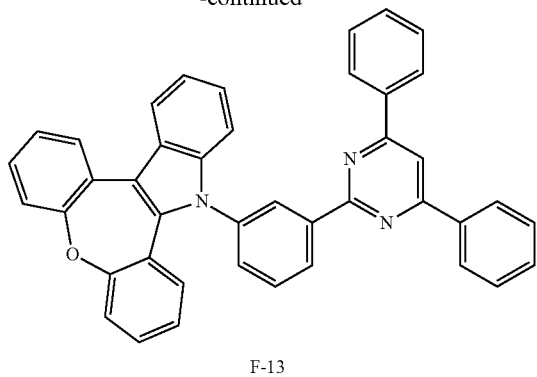

F-13

Compound F-13 (2.5 g, yield 68%) was obtained by performing the same process as in Synthesis Example 116, except that 2-(3-bromophenyl)-4,6-diphenylpyrimidine (3.1 g, 8.0 mmol) was used instead of 2-bromo-4,6-diphenylpyridine used in Synthesis Example 116.

Mass (theoretical value: 544.21, measured value: 544 g/mol)

[Synthesis Example 129] Synthesis of Compound F-14

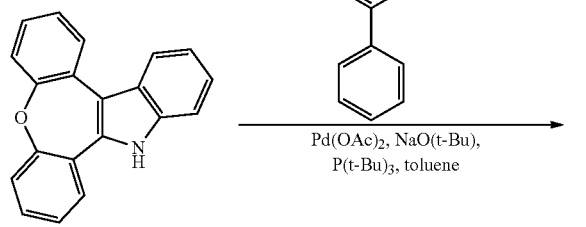

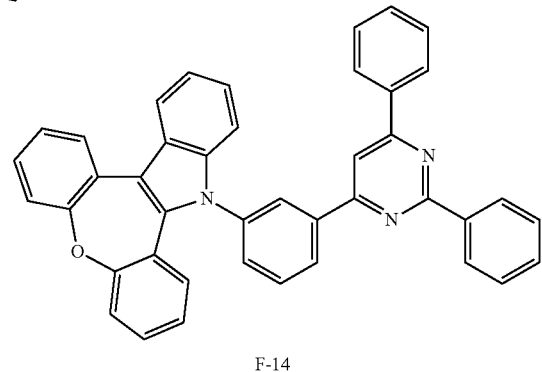

F-14

Compound F-14 (2.3 g, yield 63%) was obtained by performing the same process as in Synthesis Example 116, except that 4-(3-bromophenyl)-2,6-diphenylpyrimidine (3.1 g, 8.0 mmol) was used instead of 2-bromo-4,6-diphenylpyridine used in Synthesis Example 116.

Mass (theoretical value: 544.21, measured value: 544 g/mol)

[Synthesis Example 130] Synthesis of Compound F-15

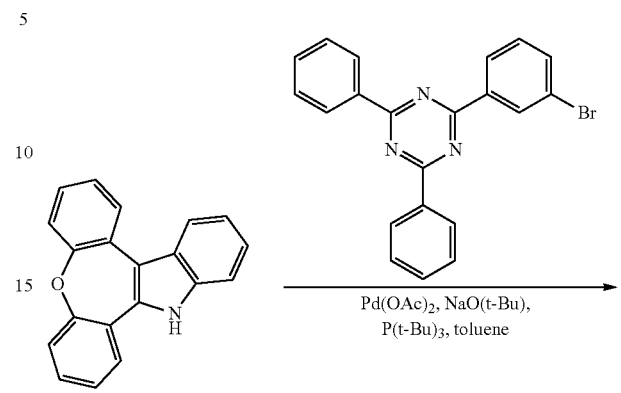

F-15

Compound F-15 (2.4 g, yield 65%) was obtained by performing the same process as in Synthesis Example 116, except that 2-(3-bromophenyl)-4,6-diphenyl-1,3,5-triazine (3.1 g, 8.0 mmol) was used instead of 2-bromo-4,6-diphenylpyridine used in Synthesis Example 116.

Mass (theoretical value: 545.21, measured value: 545 g/mol)

[Synthesis Example 131] Synthesis of Compound F-16

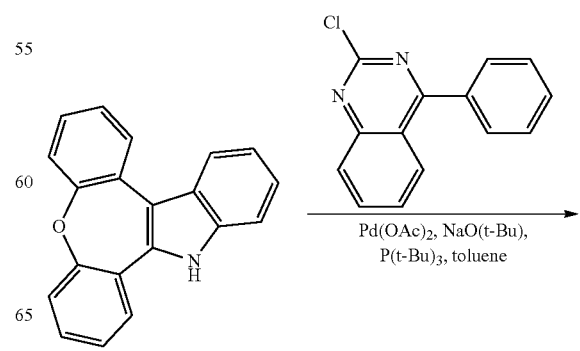

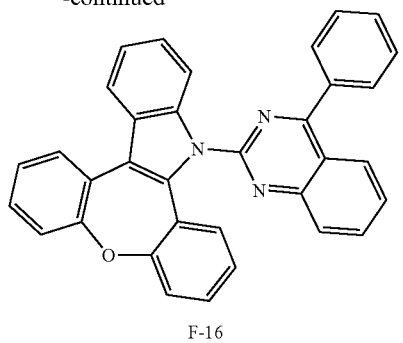

F-16

Compound F-16 (2.1 g, yield 70%) was obtained by performing the same process as in Synthesis Example 116, except that 2-chloro-4-phenylquinazoline (1.9 g, 8.0 mmol) was used instead of 2-bromo-4,6-diphenylpyridine used in Synthesis Example 116.

Mass (theoretical value: 442.17, measured value: 442 g/mol)

[Synthesis Example 132] Synthesis of Compound F-17

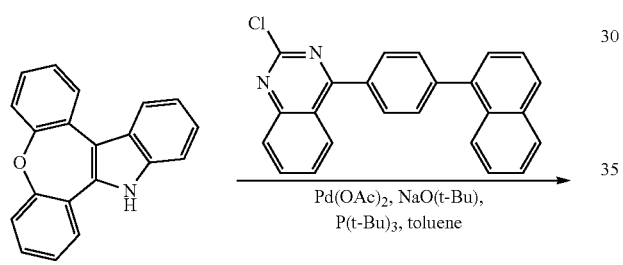

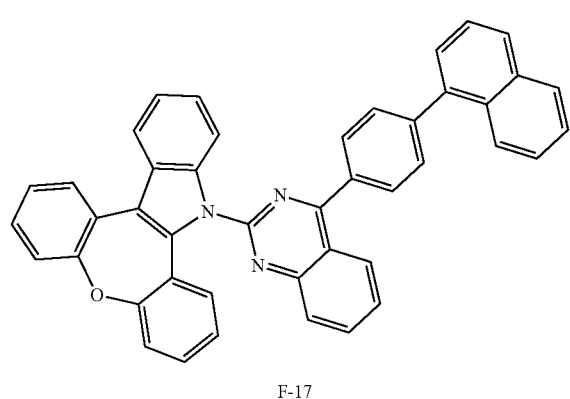

F-17

Compound F-17 (2.3 g, yield 61%) was obtained by performing the same process as in Synthesis Example 116, except that 2-chloro-4-(4-(naphthalen-1-yl)phenyl)quinazoline (2.9 g, 8.0 mmol) was used instead of 2-bromo-4,6-diphenylpyridine used in Synthesis Example 116.

Mass (theoretical value: 568.21, measured value: 568 g/mol)

[Synthesis Example 133] Synthesis of Compound F-18

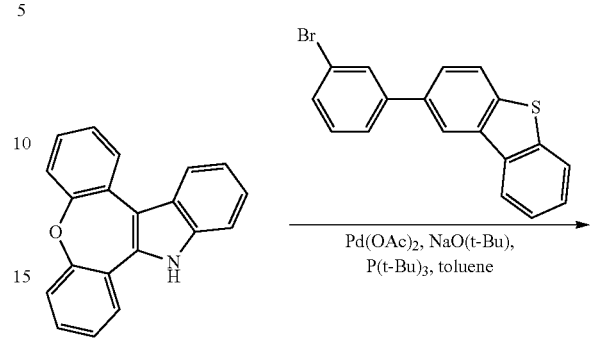

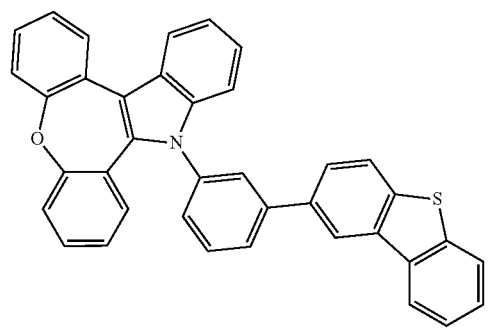

F-18

Compound F-18 (2.1 g, yield 63%) was obtained by performing the same process as in Synthesis Example 116, except that 2-(3-bromophenyl)dibenzo[b,d]thiophene (2.7 g, 8.0 mmol) was used instead of 2-bromo-4,6-diphenylpyridine used in Synthesis Example 116.

Mass (theoretical value: 496.15, measured value: 496 g/mol)

[Synthesis Example 134] Synthesis of Compound F-19

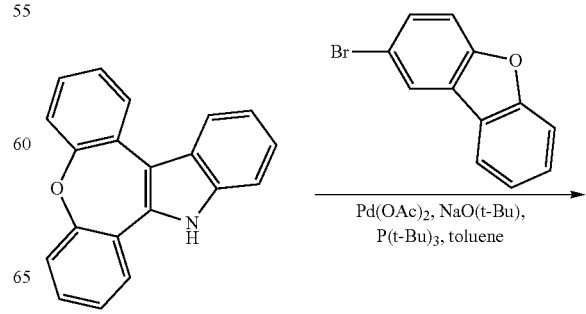

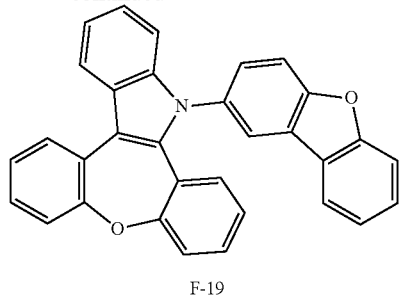

F-19

Compound F-19 (1.9 g, yield 69%) was obtained by performing the same process as in Synthesis Example 116, except that 2-bromodibenzo[b,d]furan (2.0 g, 8.0 mmol) was used instead of 2-bromo-4,6-diphenylpyridine used in Synthesis Example 116.

Mass (theoretical value: 404.14, measured value: 404 g/mol)

[Synthesis Example 135] Synthesis of Compound F-20

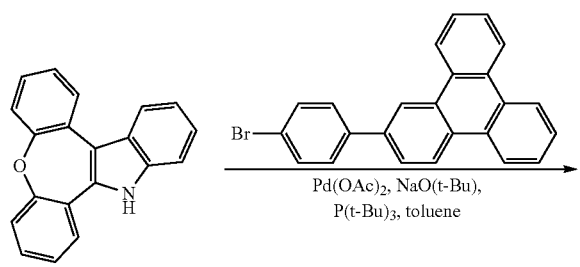

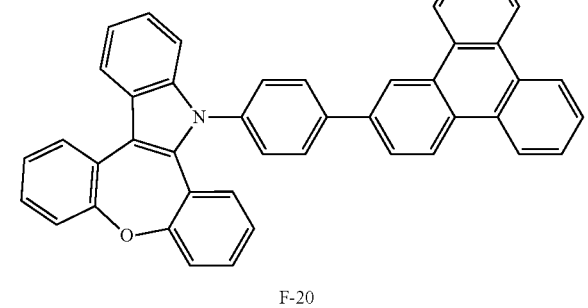

F-20

Compound F-20 (2.6 g, yield 71%) was obtained by performing the same process as in Synthesis Example 116, except that 2-(4-bromophenyl)triphenylene (3.1 g, 8.0 mmol) was used instead of 2-bromo-4,6-diphenylpyridine used in Synthesis Example 116.

Mass (theoretical value: 540.21, measured value: 540 g/mol)

[Synthesis Example 136] Synthesis of Compound F-21

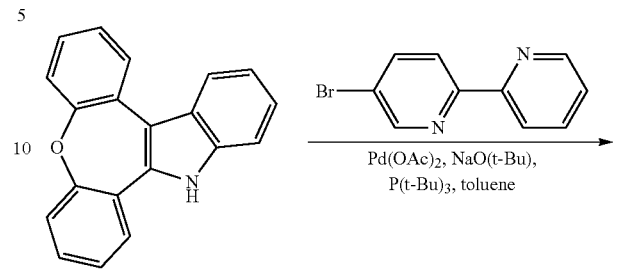

F-21

Compound F-21 (1.9 g, yield 73%) was obtained by performing the same process as in Synthesis Example 116, except that 5-bromo-2,2'-bipyridine (1.9 g, 8.0 mmol) was used instead of 2-bromo-4,6-diphenylpyridine used in Synthesis Example 116.

Mass (theoretical value: 392.15, measured value: 392 g/mol)

[Synthesis Example 137] Synthesis of Compound F-22

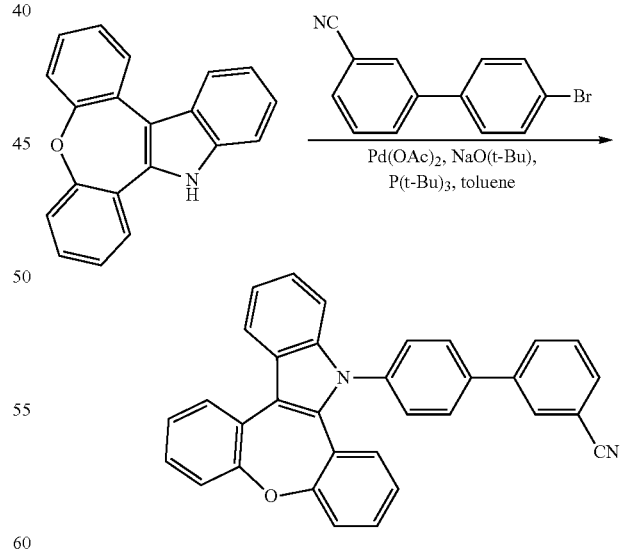

F-22

Compound F-22 (1.9 g, yield 70%) was obtained by performing the same process as in Synthesis Example 116, except that 4'-bromobiphenyl-3-carbonitrile (2.1 g, 8.0 mmol) was used instead of 2-bromo-4,6-diphenylpyridine used in Synthesis Example 116.

Mass (theoretical value: 415.16, measured value: 415 g/mol)

[Synthesis Example 138] Synthesis of Compound F-23

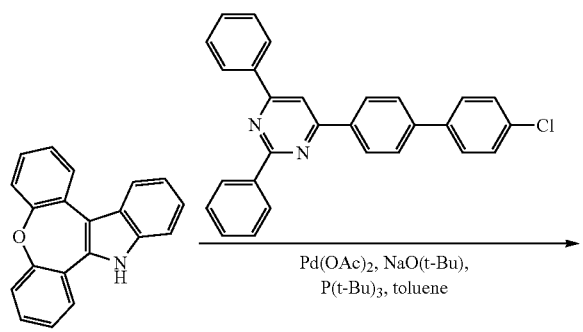

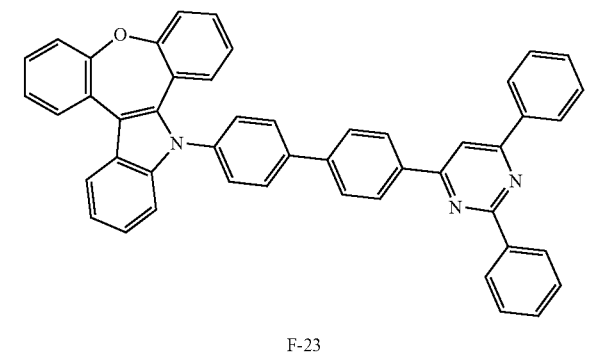

F-23

Compound F-23 (2.7 g, yield 64%) was obtained by performing the same process as in Synthesis Example 116, except that 4-(4'-chlorobiphenyl-4-yl)-2,6-diphenylpyrimidine (3.4 g, 8.0 mmol) was used instead of 2-bromo-4,6-diphenylpyridine used in Synthesis Example 116.

Mass (theoretical value: 620.24, measured value: 620 g/mol)

[Synthesis Example 139] Synthesis of Compound G-1

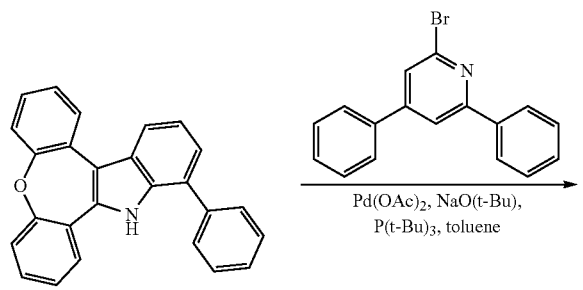

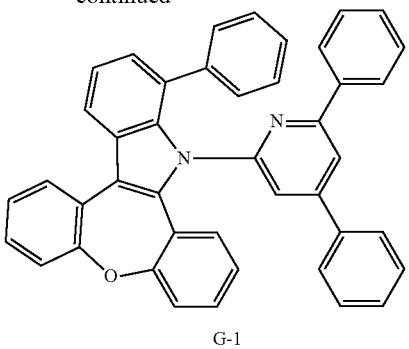

G-1

Compound IAz-7 (2.4 g, 6.7 mmol) synthesized in Preparation Example 7, 2-bromo-4,6-diphenylpyridine (2.5 g, 8.0 mmol), Pd(OAc)$_2$ (0.08 g, 0.34 mmol), P(t-Bu)$_3$ (0.16 ml, 0.67 mmol), NaO(t-Bu) (1.29 g, 13.4 mmol), and toluene (70 ml) were mixed under nitrogen flow, and the resulting mixture was stirred at 110° C. for 5 hours. After the reaction was terminated, toluene was concentrated, and a solid salt was filtered and then purified with recrystallization to obtain Compound G-1 (2.6 g, yield 65%).

Mass (theoretical value: 588.22, measured value: 588 g/mol)

[Synthesis Example 140] Synthesis of Compound G-2

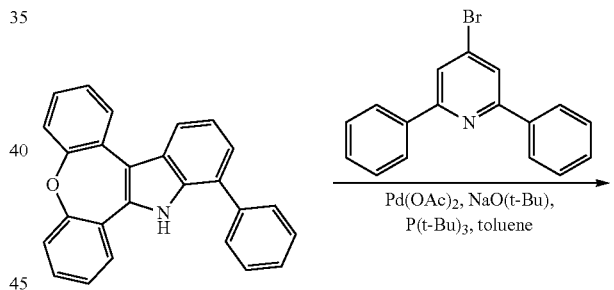

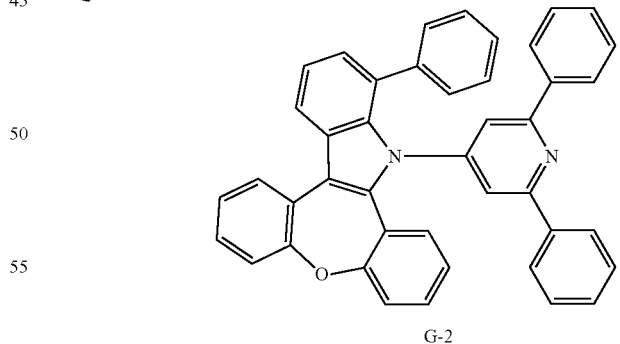

G-2

Compound G-2 (2.4 g, yield 62%) was obtained by performing the same process as in Synthesis Example 139, except that 4-bromo-2,6-diphenylpyridine (2.5 g, 8.0 mmol) was used instead of 2-bromo-4,6-diphenylpyridine used in Synthesis Example 139.

Mass (theoretical value: 588.22, measured value: 588 g/mol)

[Synthesis Example 141] Synthesis of Compound G-3

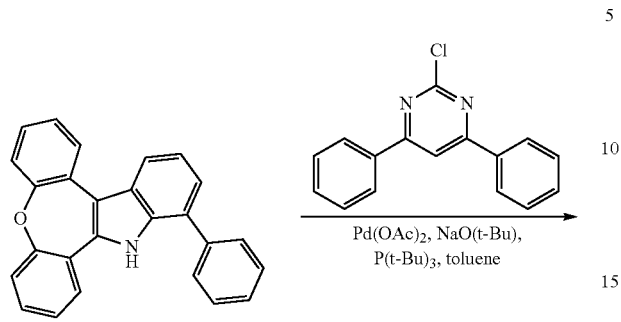

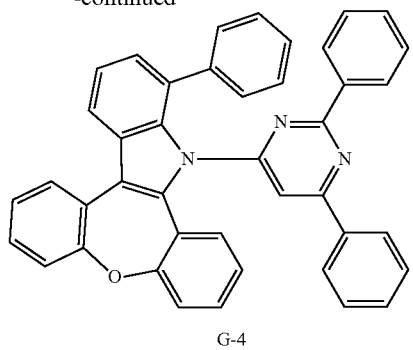

Compound G-4 (2.5 g, yield 64%) was obtained by performing the same process as in Synthesis Example 139, except that 4-chloro-2,6-diphenylpyrimidine (2.5 g, 8.0 mmol) was used instead of 2-bromo-4,6-diphenylpyridine used in Synthesis Example 139.

Mass (theoretical value: 589.21, measured value: 589 g/mol)

[Synthesis Example 143] Synthesis of Compound G-5

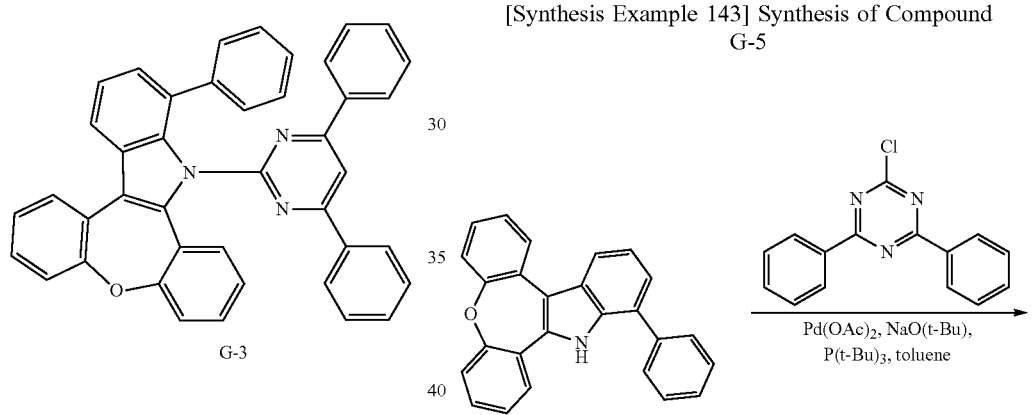

Compound G-3 (2.6 g, yield 67%) was obtained by performing the same process as in Synthesis Example 139, except that 2-chloro-4,6-diphenylpyrimidine (2.5 g, 8.0 mmol) was used instead of 2-bromo-4,6-diphenylpyridine used in Synthesis Example 139.

Mass (theoretical value: 589.21, measured value: 589 g/mol)

[Synthesis Example 142] Synthesis of Compound G-4

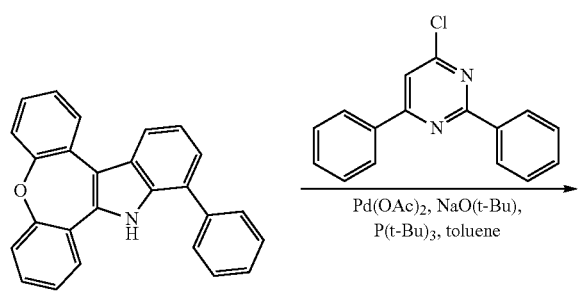

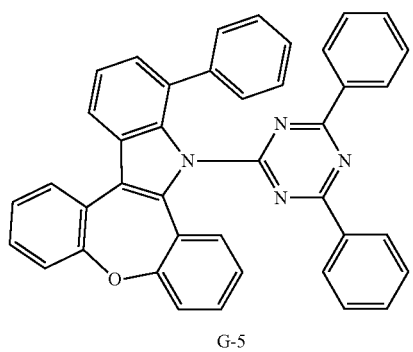

Compound G-5 (2.7 g, yield 68%) was obtained by performing the same process as in Synthesis Example 139, except that 2-chloro-4,6-diphenyl-1,3,5-triazine (2.1 g, 8.0 mmol) was used instead of 2-bromo-4,6-diphenylpyridine used in Synthesis Example 139.

Mass (theoretical value: 590.21, measured value: 590 g/mol)

[Synthesis Example 144] Synthesis of Compound G-6

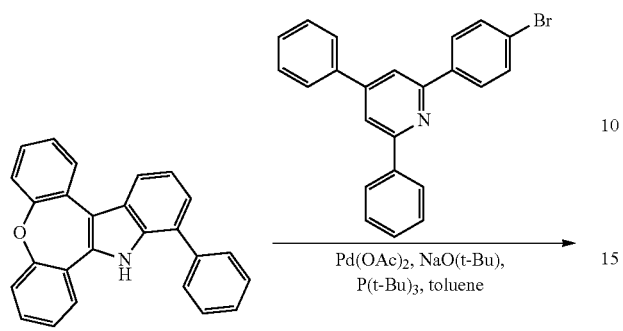

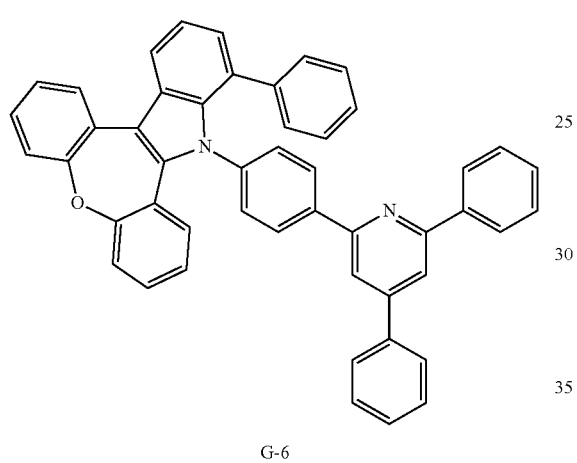

G-6

Compound G-6 (3.1 g, yield 70%) was obtained by performing the same process as in Synthesis Example 139, except that 2-(4-bromophenyl)-4,6-diphenylpyridine (3.1 g, 8.0 mmol) was used instead of 2-bromo-4,6-diphenylpyridine used in Synthesis Example 139.

Mass (theoretical value: 664.25, measured value: 664 g/mol)

[Synthesis Example 145] Synthesis of Compound G-7

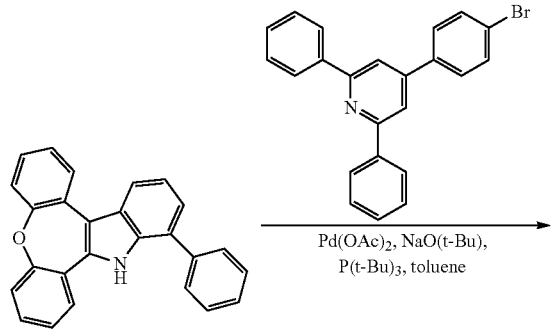

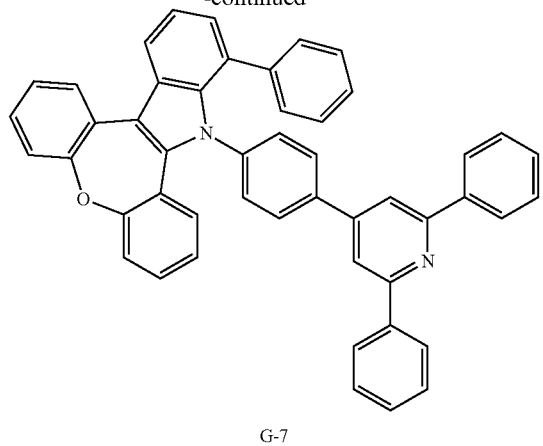

G-7

Compound G-7 (3.2 g, yield 72%) was obtained by performing the same process as in Synthesis Example 139, except that 4-(4-bromophenyl)-2,6-diphenylpyridine (3.1 g, 8.0 mmol) was used instead of 2-bromo-4,6-diphenylpyridine used in Synthesis Example 139.

Mass (theoretical value: 664.25, measured value: 664 g/mol)

[Synthesis Example 146] Synthesis of Compound G-8

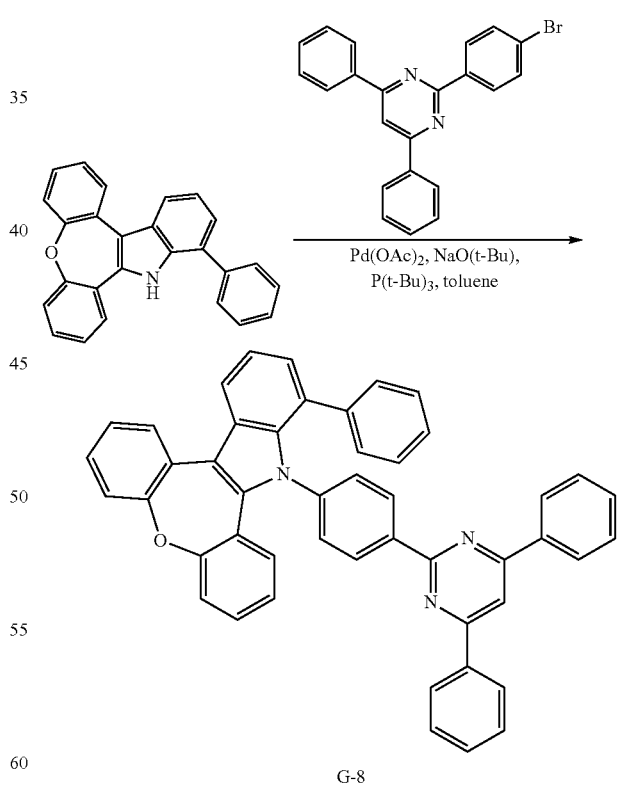

G-8

Compound G-8 (3.0 g, yield 67%) was obtained by performing the same process as in Synthesis Example 139, except that 2-(4-bromophenyl)-4,6-diphenylpyrimidine (3.1 g, 8.0 mmol) was used instead of 2-bromo-4,6-diphenylpyridine used in Synthesis Example 139.

Mass (theoretical value: 665.24, measured value: 665 g/mol)

[Synthesis Example 147] Synthesis of Compound G-9

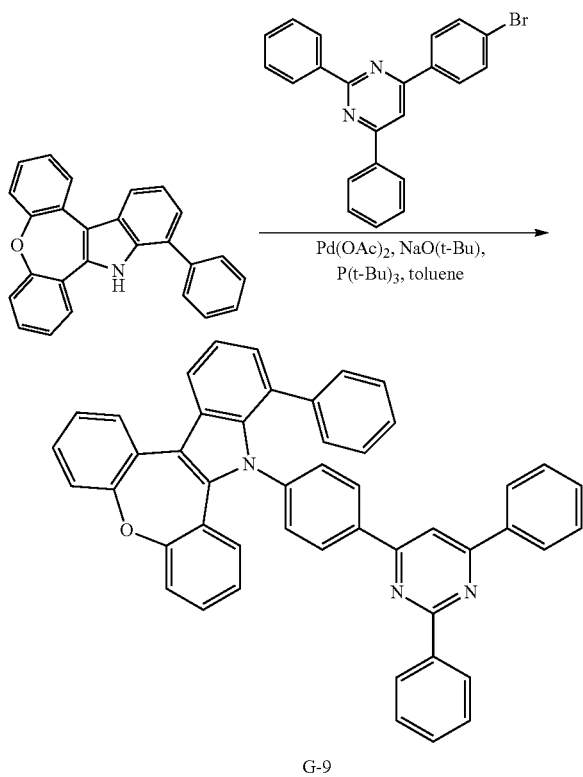

G-9

Compound G-9 (2.8 g, yield 63%) was obtained by performing the same process as in Synthesis Example 139, except that 4-(4-bromophenyl)-2,6-diphenylpyrimidine (3.1 g, 8.0 mmol) was used instead of 2-bromo-4,6-diphenylpyridine used in Synthesis Example 139.

Mass (theoretical value: 665.24, measured value: 665 g/mol)

[Synthesis Example 148] Synthesis of Compound G-10

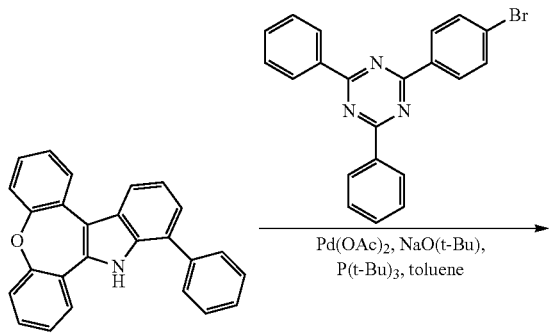

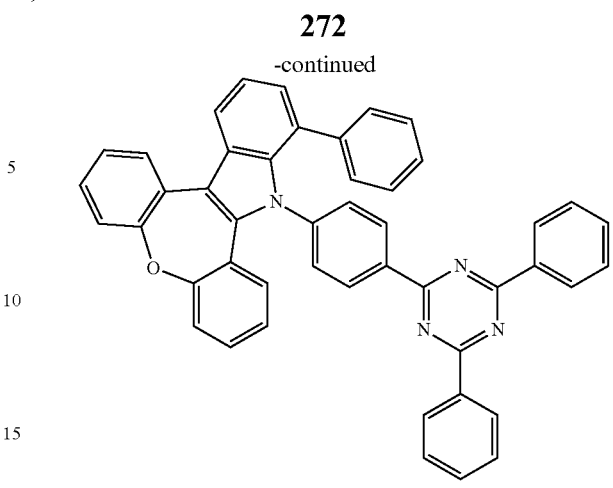

G-10

Compound G-10 (3.1 g, yield 70%) was obtained by performing the same process as in Synthesis Example 139, except that 2-(4-bromophenyl)-4,6-diphenyl-1,3,5-triazine (3.1 g, 8.0 mmol) was used instead of 2-bromo-4,6-diphenylpyridine used in Synthesis Example 139.

Mass (theoretical value: 666.24, measured value: 666 g/mol)

[Synthesis Example 149] Synthesis of Compound G-11

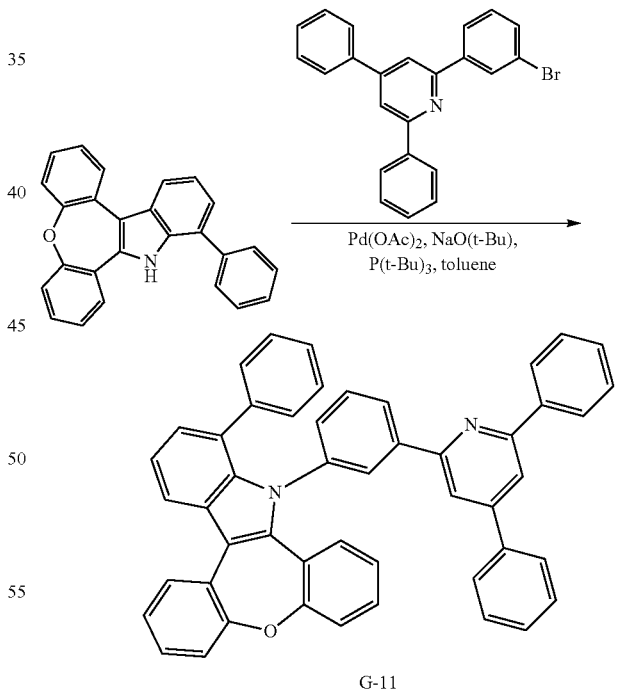

G-11

Compound G-11 (2.8 g, yield 62%) was obtained by performing the same process as in Synthesis Example 139, except that 2-(3-bromophenyl)-4,6-diphenylpyridine (3.1 g, 8.0 mmol) was used instead of 2-bromo-4,6-diphenylpyridine used in Synthesis Example 139.

Mass (theoretical value: 664.25, measured value: 664 g/mol)

[Synthesis Example 150] Synthesis of Compound G-12

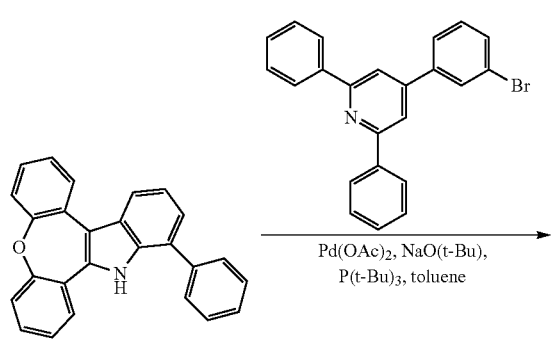

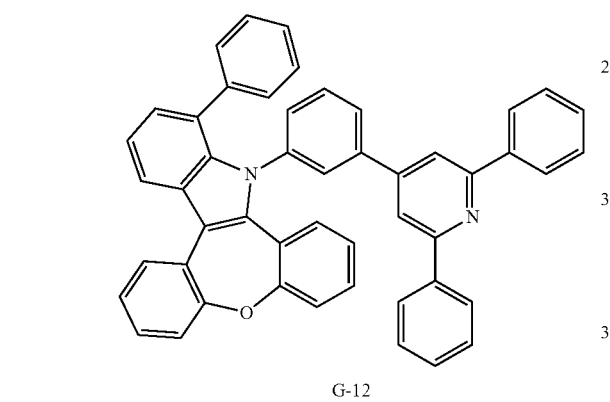

G-12

Compound G-12 (2.9 g, yield 66%) was obtained by performing the same process as in Synthesis Example 139, except that 4-(3-bromophenyl)-2,6-diphenylpyridine (3.1 g, 8.0 mmol) was used instead of 2-bromo-4,6-diphenylpyridine used in Synthesis Example 139.

Mass (theoretical value: 664.25, measured value: 664 g/mol)

[Synthesis Example 151] Synthesis of Compound G-13

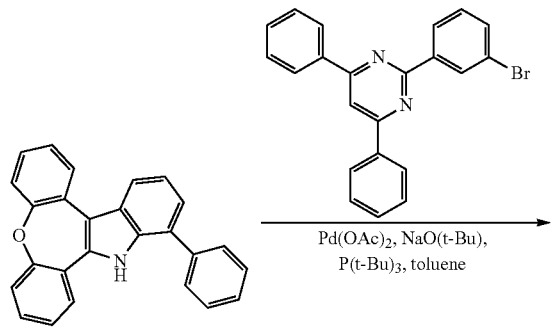

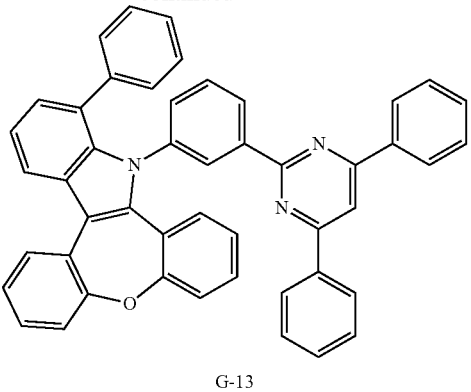

G-13

Compound G-13 (2.9 g, yield 65%) was obtained by performing the same process as in Synthesis Example 139, except that 2-(3-bromophenyl)-4,6-diphenylpyrimidine (3.1 g, 8.0 mmol) was used instead of 2-bromo-4,6-diphenylpyridine used in Synthesis Example 139.

Mass (theoretical value: 665.24, measured value: 665 g/mol)

[Synthesis Example 152] Synthesis of Compound G-14

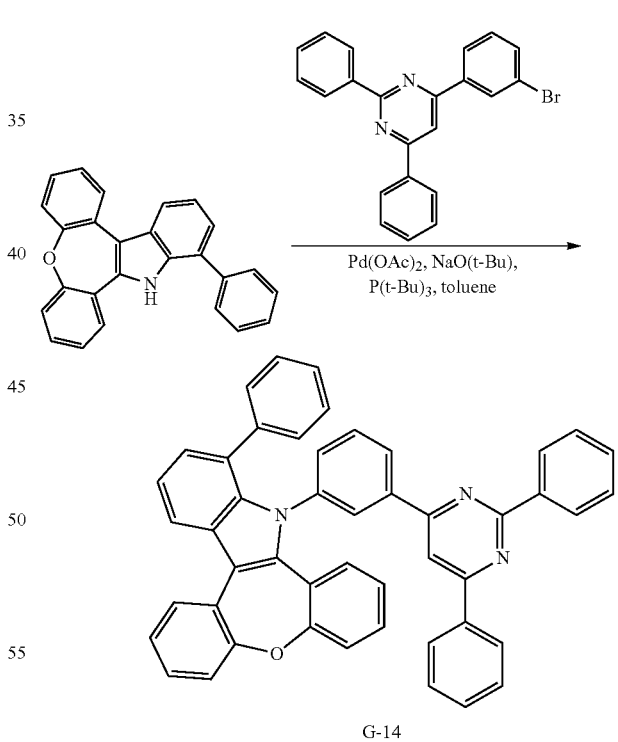

G-14

Compound G-14 (3.0 g, yield 68%) was obtained by performing the same process as in Synthesis Example 139, except that 4-(3-bromophenyl)-2,6-diphenylpyrimidine (3.1 g, 8.0 mmol) was used instead of 2-bromo-4,6-diphenylpyridine used in Synthesis Example 139.

Mass (theoretical value: 665.24, measured value: 665 g/mol)

[Synthesis Example 153] Synthesis of Compound G-15

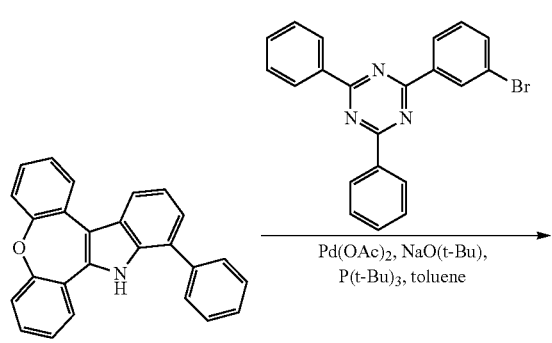

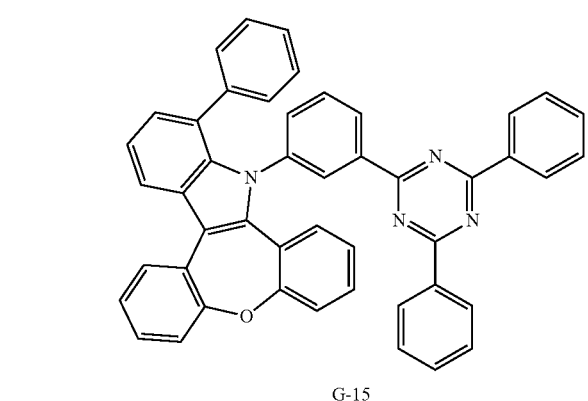

Compound G-15 (2.8 g, yield 63%) was obtained by performing the same process as in Synthesis Example 139, except that 2-(3-bromophenyl)-4,6-diphenyl-1,3,5-triazine (3.1 g, 8.0 mmol) was used instead of 2-bromo-4,6-diphenylpyridine used in Synthesis Example 139.

Mass (theoretical value: 666.24, measured value: 666 g/mol)

[Synthesis Example 154] Synthesis of Compound G-16

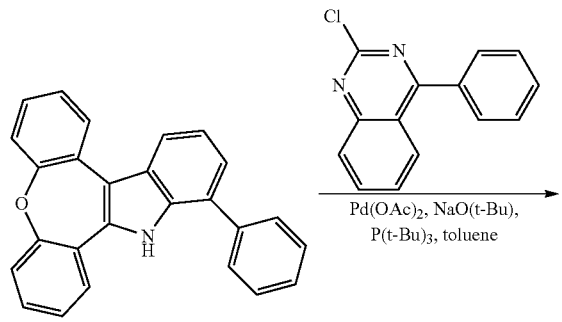

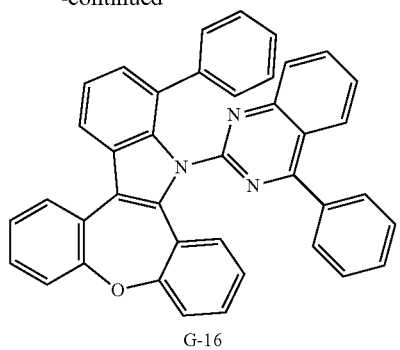

Compound G-16 (2.5 g, yield 65%) was obtained by performing the same process as in Synthesis Example 139, except that 2-chloro-4-phenylquinazoline (1.9 g, 8.0 mmol) was used instead of 2-bromo-4,6-diphenylpyridine used in Synthesis Example 139.

Mass (theoretical value: 563.20, measured value: 563 g/mol)

[Synthesis Example 155] Synthesis of Compound G-17

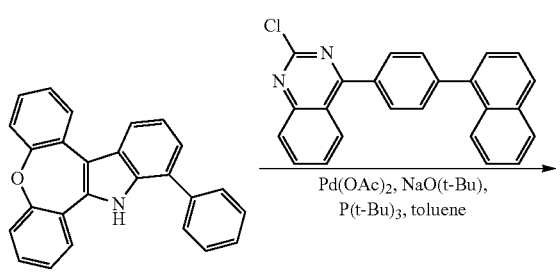

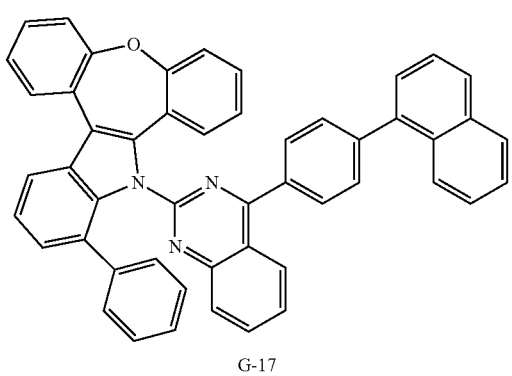

Compound G-17 (3.0 g, yield 65%) was obtained by performing the same process as in Synthesis Example 139, except that 2-chloro-4-(4-(naphthalen-1-yl)phenyl)quinazoline (2.9 g, 8.0 mmol) was used instead of 2-bromo-4,6-diphenylpyridine used in Synthesis Example 139.

Mass (theoretical value: 689.24, measured value: 689 g/mol)

[Synthesis Example 156] Synthesis of Compound G-18

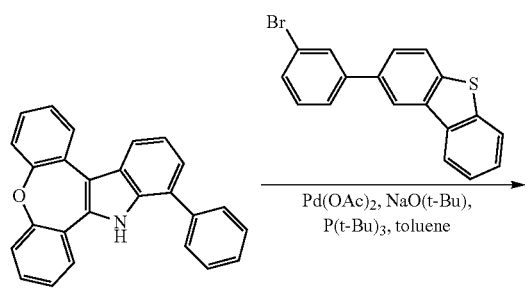

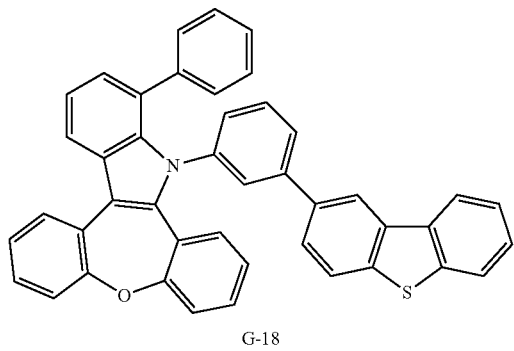

Compound G-18 (2.7 g, yield 68%) was obtained by performing the same process as in Synthesis Example 139, except that 2-(3-bromophenyl)dibenzo[b,d]thiophene (2.7 g, 8.0 mmol) was used instead of 2-bromo-4,6-diphenylpyridine used in Synthesis Example 139.

Mass (theoretical value: 617.18, measured value: 617 g/mol)

[Synthesis Example 157] Synthesis of Compound G-19

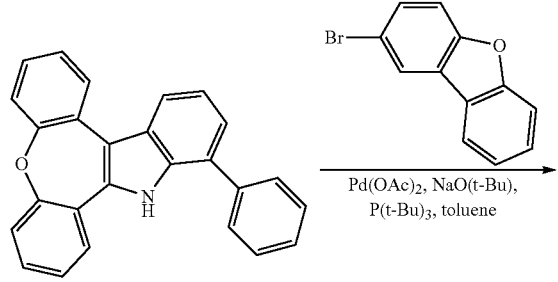

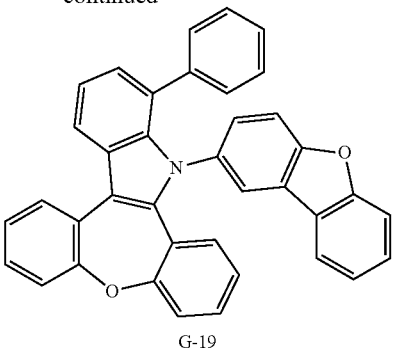

Compound G-19 (2.1 g, yield 60%) was obtained by performing the same process as in Synthesis Example 139, except that 2-bromodibenzo[b,d]furan (2.0 g, 8.0 mmol) was used instead of 2-bromo-4,6-diphenylpyridine used in Synthesis Example 139.

Mass (theoretical value: 525.17, measured value: 525 g/mol)

[Synthesis Example 158] Synthesis of Compound G-20

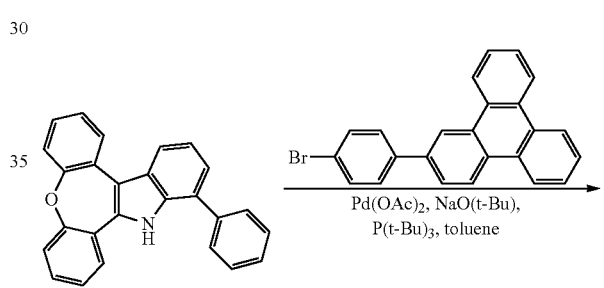

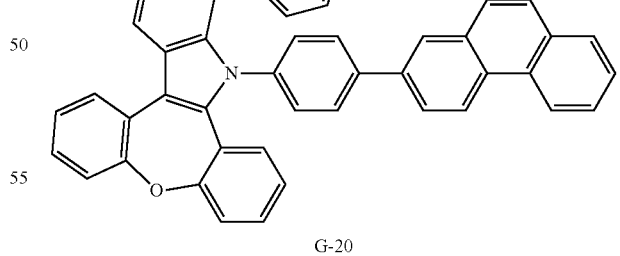

Compound G-20 (3.1 g, yield 70%) was obtained by performing the same process as in Synthesis Example 139, except that 2-(4-bromophenyl)triphenylene (3.1 g, 8.0 mmol) was used instead of 2-bromo-4,6-diphenylpyridine used in Synthesis Example 139.

Mass (theoretical value: 661.24, measured value: 661 g/mol)

[Synthesis Example 159] Synthesis of Compound G-21

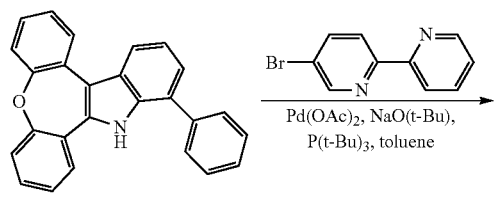

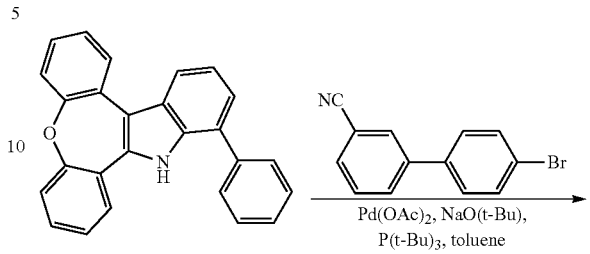

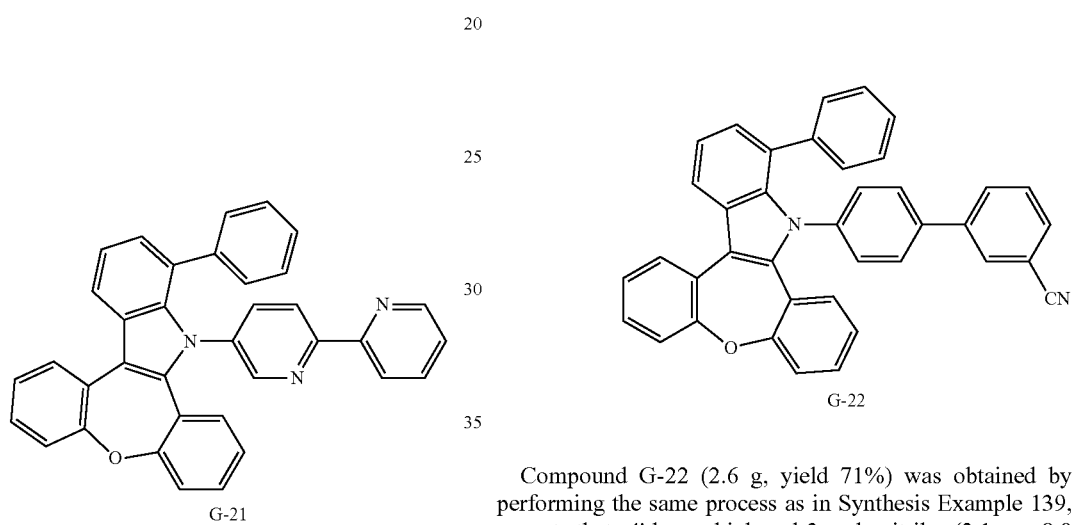

G-21

Compound G-21 (2.2 g, yield 65%) was obtained by performing the same process as in Synthesis Example 139, except that 5-bromo-2,2'-bipyridine (1.9 g, 8.0 mmol) was used instead of 2-bromo-4,6-diphenylpyridine used in Synthesis Example 139.

Mass (theoretical value: 513.18, measured value: 513 g/mol)

[Synthesis Example 160] Synthesis of Compound G-22

Compound G-22 (2.6 g, yield 71%) was obtained by performing the same process as in Synthesis Example 139, except that 4'-bromobiphenyl-3-carbonitrile (2.1 g, 8.0 mmol) was used instead of 2-bromo-4,6-diphenylpyridine used in Synthesis Example 139.

Mass (theoretical value: 536.19, measured value: 536 g/mol)

[Synthesis Example 161] Synthesis of Compound G-23

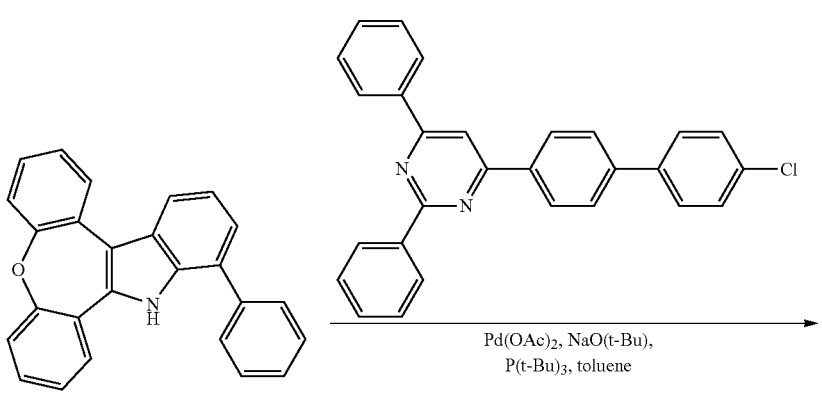

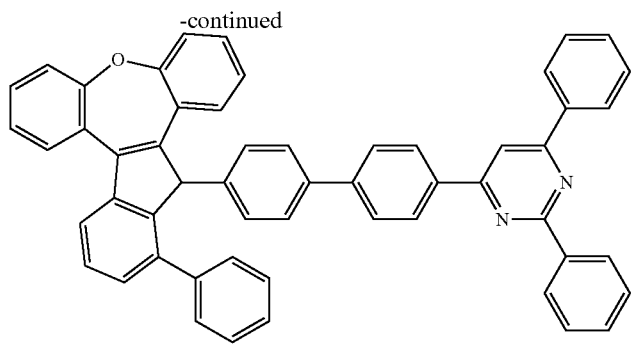

G-23

Compound G-23 (3.3 g, yield 66%) was obtained by performing the same process as in Synthesis Example 139, except that 4-(4'-chlorobiphenyl-4-yl)-2,6-diphenylpyrimidine (3.4 g, 8.0 mmol) was used instead of 2-bromo-4,6-diphenylpyridine used in Synthesis Example 139.

Mass (theoretical value: 741.27, measured value: 741 g/mol)

[Synthesis Example 162] Synthesis of Compound H-1

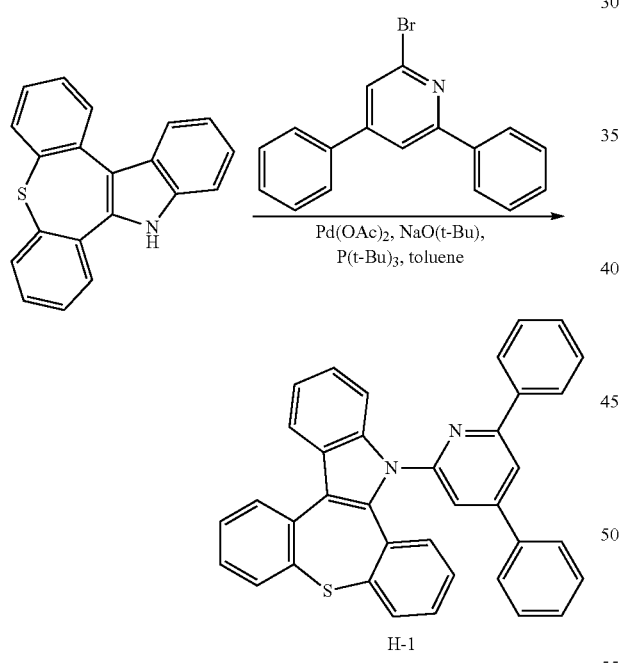

H-1

Compound IAz-8 (2.0 g, 6.7 mmol) synthesized in Preparation Example 8, 2-bromo-4,6-diphenylpyridine (2.5 g, 8.0 mmol), Pd(OAc)$_2$ (0.08 g, 0.34 mmol), P(t-Bu)$_3$ (0.16 ml, 0.67 mmol), NaO(t-Bu) (1.29 g, 13.4 mmol), and toluene (70 ml) were mixed under nitrogen flow, and the resulting mixture was stirred at 110° C. for 5 hours. After the reaction was terminated, toluene was concentrated, and a solid salt was filtered and then purified with recrystallization to obtain Compound H-1 (2.5 g, yield 71%).

Mass (theoretical value: 528.17, measured value: 528 g/mol)

[Synthesis Example 163] Synthesis of Compound H-2

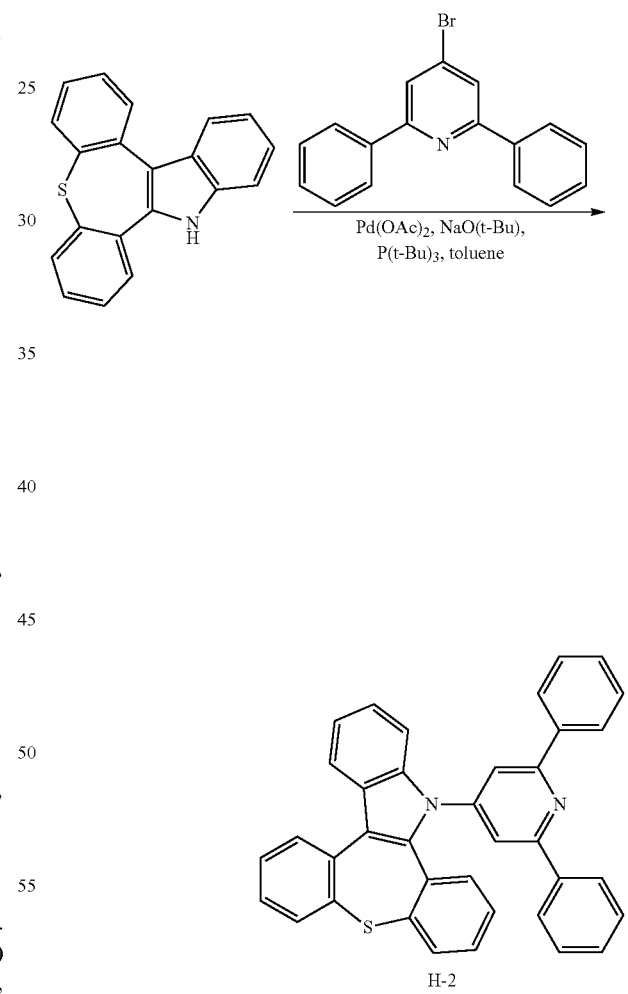

H-2

Compound H-2 (2.4 g, yield 69%) was obtained by performing the same process as in Synthesis Example 162, except that 4-bromo-2,6-diphenylpyridine (2.5 g, 8.0 mmol) was used instead of 2-bromo-4,6-diphenylpyridine used in Synthesis Example 162.

Mass (theoretical value: 528.17, measured value: 528 g/mol)

[Synthesis Example 164] Synthesis of Compound H-3

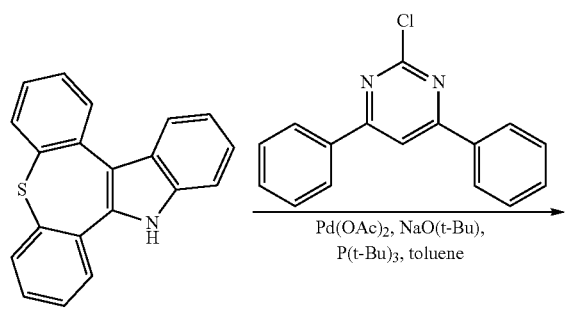

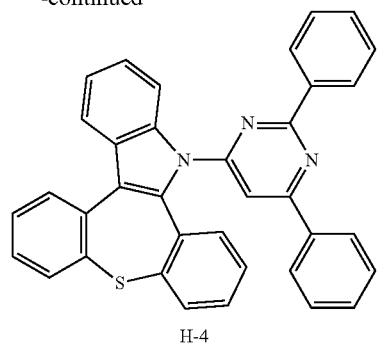

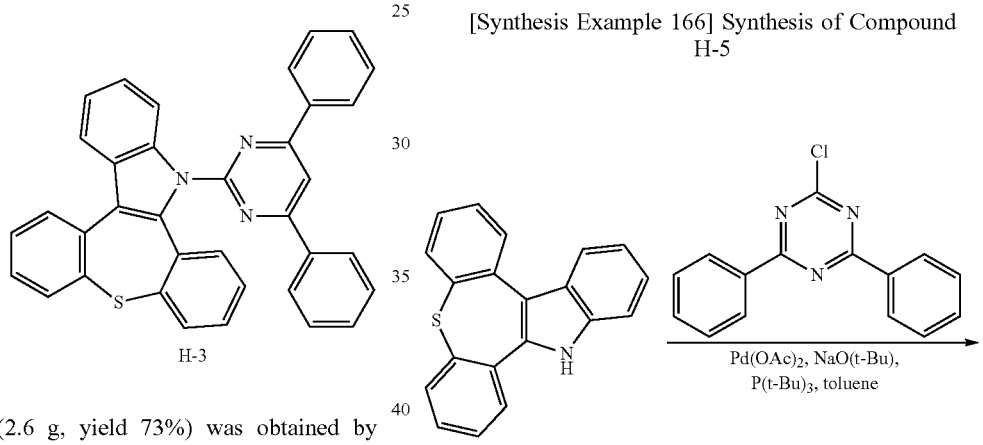

Compound H-3 (2.6 g, yield 73%) was obtained by performing the same process as in Synthesis Example 162, except that 2-chloro-4,6-diphenylpyrimidine (2.5 g, 8.0 mmol) was used instead of 2-bromo-4,6-diphenylpyridine used in Synthesis Example 162.

Mass (theoretical value: 529.16, measured value: 529 g/mol)

[Synthesis Example 165] Synthesis of Compound H-4

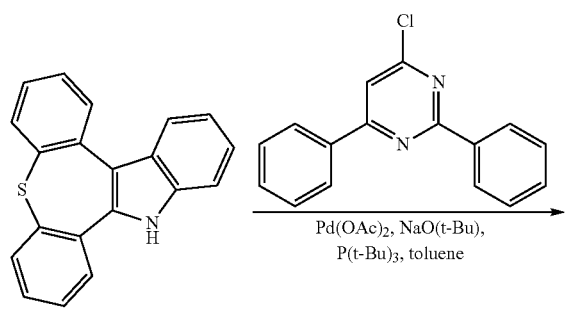

Compound H-4 (2.7 g, yield 76%) was obtained by performing the same process as in Synthesis Example 162, except that 4-chloro-2,6-diphenylpyrimidine (2.5 g, 8.0 mmol) was used instead of 2-bromo-4,6-diphenylpyridine used in Synthesis Example 162.

Mass (theoretical value: 529.16, measured value: 529 g/mol)

[Synthesis Example 166] Synthesis of Compound H-5

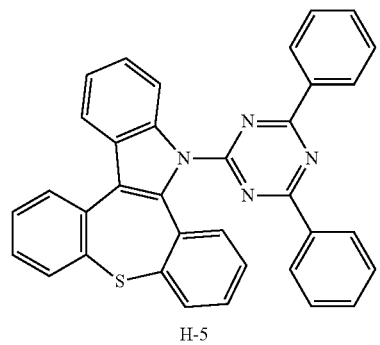

Compound H-5 (2.2 g, yield 63%) was obtained by performing the same process as in Synthesis Example 162, except that 2-chloro-4,6-diphenyl-1,3,5-triazine (2.1 g, 8.0 mmol) was used instead of 2-bromo-4,6-diphenylpyridine used in Synthesis Example 162.

Mass (theoretical value: 530.16, measured value: 530 g/mol)

[Synthesis Example 167] Synthesis of Compound H-6

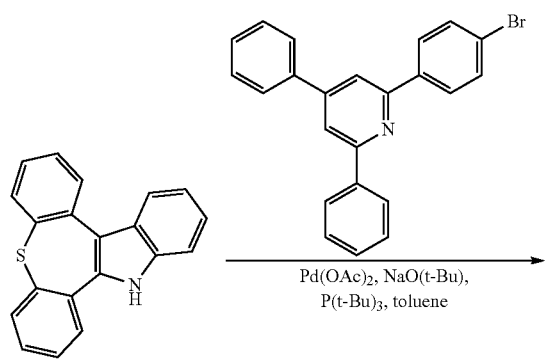

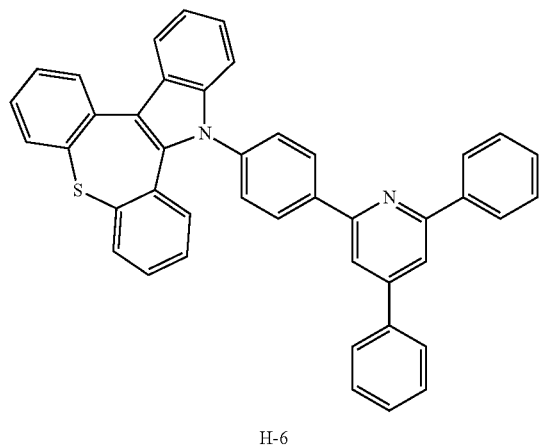

H-6

Compound H-6 (2.5 g, yield 62%) was obtained by performing the same process as in Synthesis Example 162, except that 2-(4-bromophenyl)-4,6-diphenylpyridine (3.1 g, 8.0 mmol) was used instead of 2-bromo-4,6-diphenylpyridine used in Synthesis Example 162.

Mass (theoretical value: 604.20, measured value: 604 g/mol)

[Synthesis Example 168] Synthesis of Compound H-7

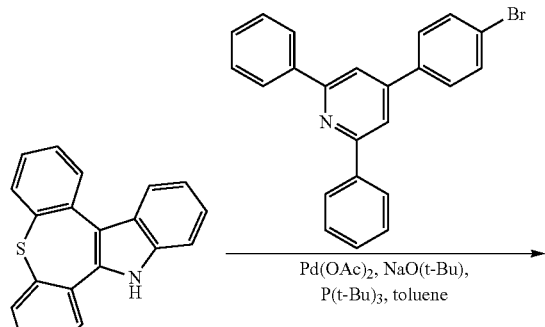

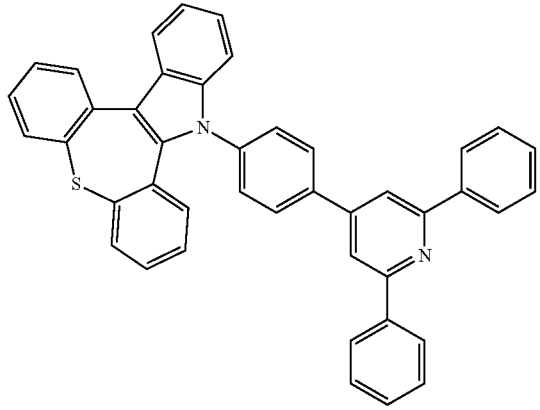

H-7

Compound H-7 (2.8 g, yield 68%) was obtained by performing the same process as in Synthesis Example 162, except that 4-(4-bromophenyl)-2,6-diphenylpyridine (3.1 g, 8.0 mmol) was used instead of 2-bromo-4,6-diphenylpyridine used in Synthesis Example 162.

Mass (theoretical value: 604.20, measured value: 604 g/mol)

[Synthesis Example 169] Synthesis of Compound H-8

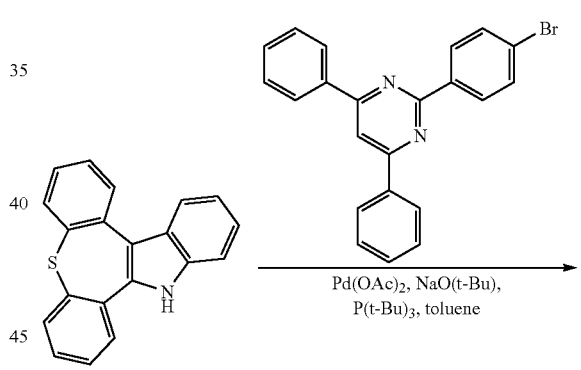

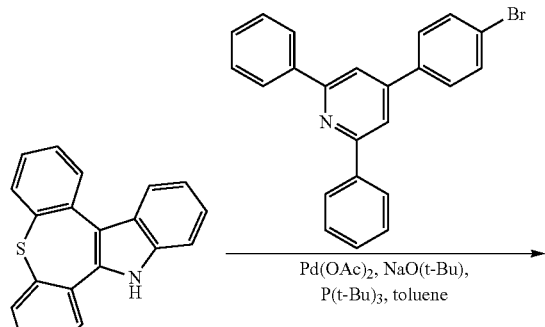

H-8

Compound H-8 (2.6 g, yield 64%) was obtained by performing the same process as in Synthesis Example 162, except that 2-(4-bromophenyl)-4,6-diphenylpyrimidine (3.1 g, 8.0 mmol) was used instead of 2-bromo-4,6-diphenylpyridine used in Synthesis Example 162.

Mass (theoretical value: 605.19, measured value: 605 g/mol)

[Synthesis Example 170] Synthesis of Compound H-9

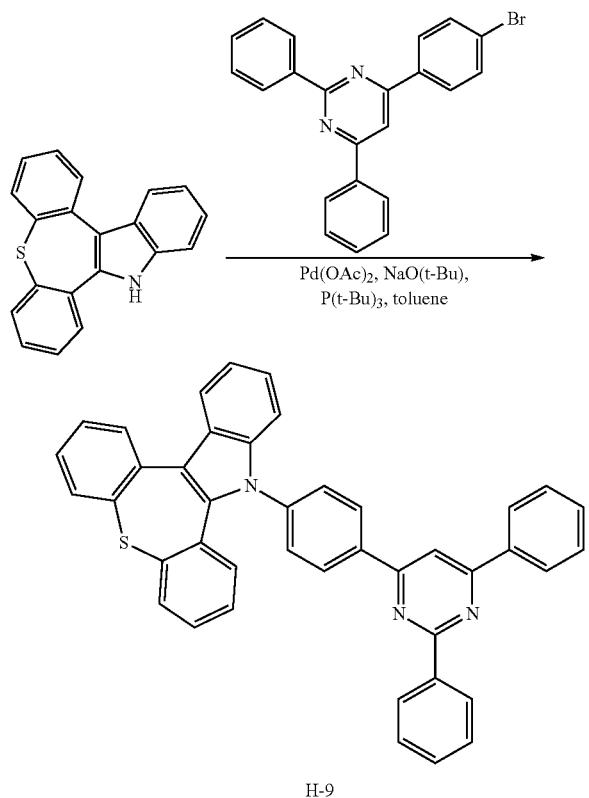

H-9

Compound H-9 (2.6 g, yield 64%) was obtained by performing the same process as in Synthesis Example 162, except that 4-(4-bromophenyl)-2,6-diphenylpyrimidine (3.1 g, 8.0 mmol) was used instead of 2-bromo-4,6-diphenylpyridine used in Synthesis Example 162.

Mass (theoretical value: 605.19, measured value: 605 g/mol)

[Synthesis Example 171] Synthesis of Compound H-10

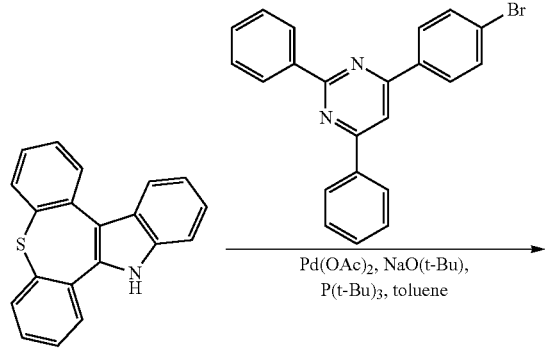

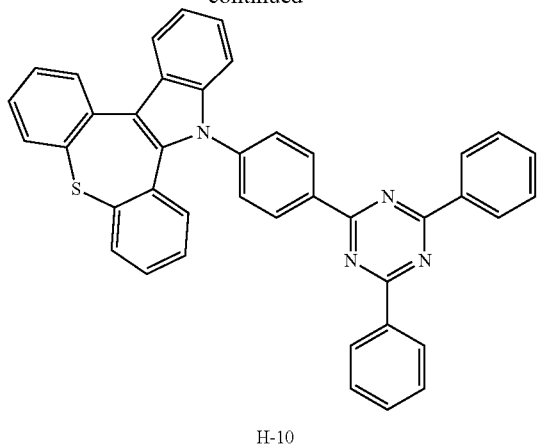

H-10

Compound H-10 (2.7 g, yield 66%) was obtained by performing the same process as in Synthesis Example 162, except that 2-(4-bromophenyl)-4,6-diphenyl-1,3,5-triazine (3.1 g, 8.0 mmol) was used instead of 2-bromo-4,6-diphenylpyridine used in Synthesis Example 162.

Mass (theoretical value: 606.19, measured value: 606 g/mol)

[Synthesis Example 172] Synthesis of Compound H-11

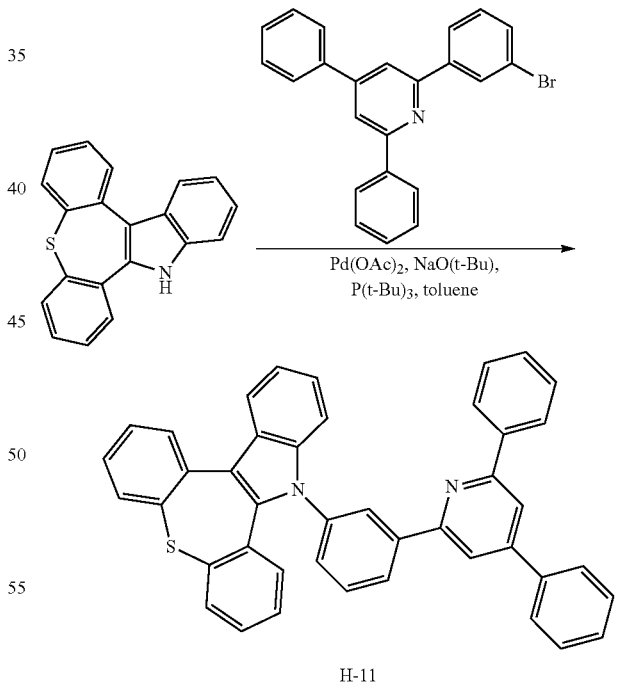

H-11

Compound H-11 (2.8 g, yield 68%) was obtained by performing the same process as in Synthesis Example 162, except that 2-(3-bromophenyl)-4,6-diphenylpyridine (3.1 g, 8.0 mmol) was used instead of 2-bromo-4,6-diphenylpyridine used in Synthesis Example 162.

Mass (theoretical value: 604.20, measured value: 604 g/mol)

[Synthesis Example 173] Synthesis of Compound H-12

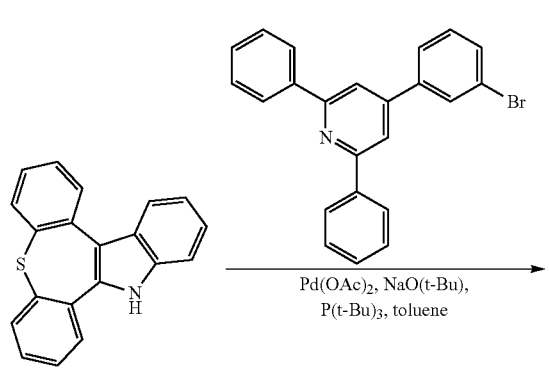

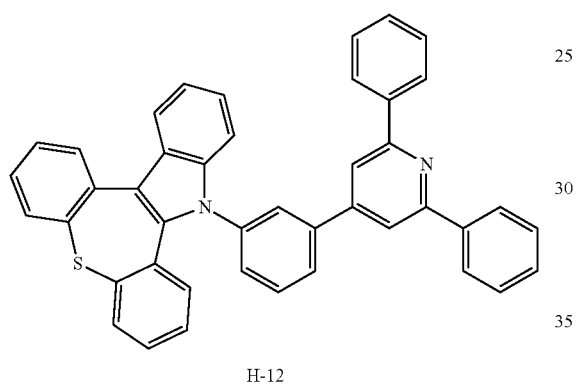

H-12

Compound H-12 (2.4 g, yield 60%) was obtained by performing the same process as in Synthesis Example 162, except that 4-(3-bromophenyl)-2,6-diphenylpyridine (3.1 g, 8.0 mmol) was used instead of 2-bromo-4,6-diphenylpyridine used in Synthesis Example 162.

Mass (theoretical value: 604.20, measured value: 604 g/mol)

[Synthesis Example 174] Synthesis of Compound H-13

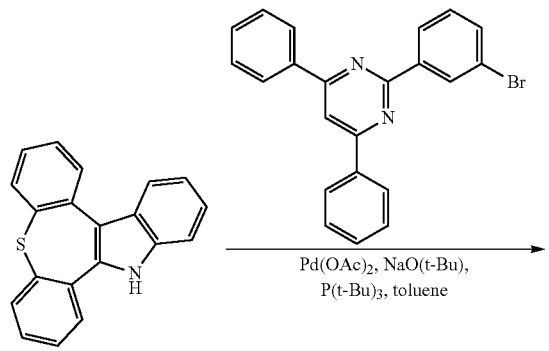

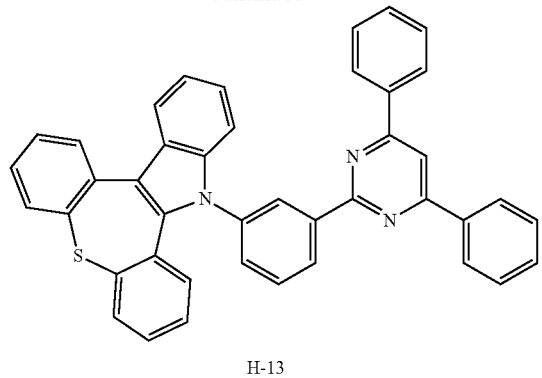

H-13

Compound H-13 (2.5 g, yield 62%) was obtained by performing the same process as in Synthesis Example 162, except that 2-(3-bromophenyl)-4,6-diphenylpyrimidine (3.1 g, 8.0 mmol) was used instead of 2-bromo-4,6-diphenylpyridine used in Synthesis Example 162.

Mass (theoretical value: 605.19, measured value: 605 g/mol)

[Synthesis Example 175] Synthesis of Compound H-14

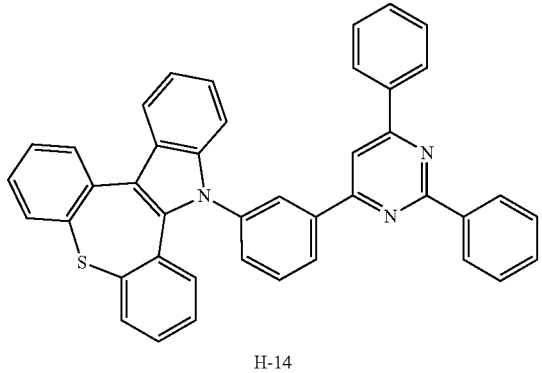

H-14

Compound H-14 (3.0 g, yield 73%) was obtained by performing the same process as in Synthesis Example 162, except that 4-(3-bromophenyl)-2,6-diphenylpyridine (3.1 g, 8.0 mmol) was used instead of 2-bromo-4,6-diphenylpyridine used in Synthesis Example 162.

Mass (theoretical value: 605.19, measured value: 605 g/mol)

[Synthesis Example 176] Synthesis of Compound H-15

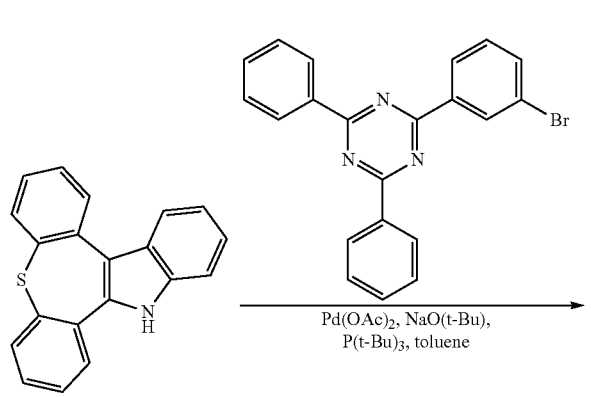

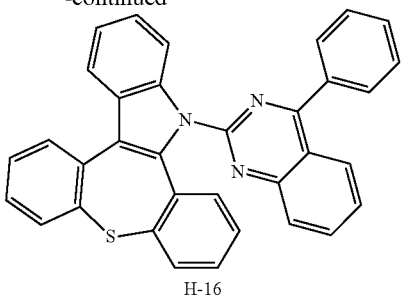

H-16

Compound H-16 (2.3 g, yield 69%) was obtained by performing the same process as in Synthesis Example 162, except that 2-chloro-4-phenylquinazoline (1.9 g, 8.0 mmol) was used instead of 2-bromo-4,6-diphenylpyridine used in Synthesis Example 162.

Mass (theoretical value: 503.15, measured value: 503 g/mol)

[Synthesis Example 178] Synthesis of Compound H-17

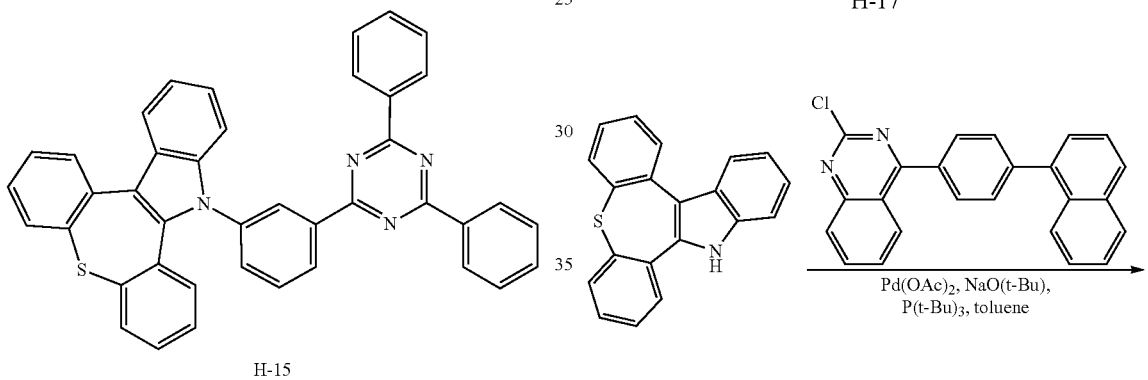

H-15

Compound H-15 (2.9 g, yield 71%) was obtained by performing the same process as in Synthesis Example 162, except that 2-(3-bromophenyl)-4,6-diphenyl-1,3,5-triazine (3.1 g, 8.0 mmol) was used instead of 2-bromo-4,6-diphenylpyridine used in Synthesis Example 162.

Mass (theoretical value: 606.19, measured value: 606 g/mol)

[Synthesis Example 177] Synthesis of Compound H-16

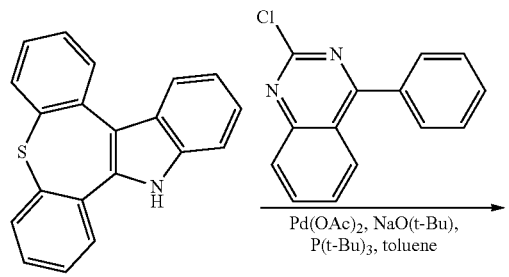

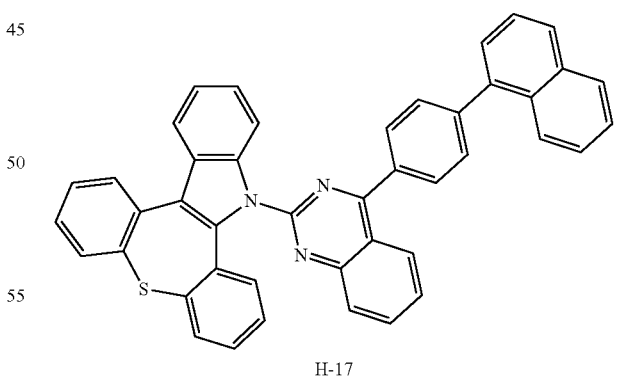

H-17

Compound H-17 (2.8 g, yield 67%) was obtained by performing the same process as in Synthesis Example 162, except that 2-chloro-4-(4-(naphthalen-1-yl)phenyl)quinazoline (2.9 g, 8.0 mmol) was used instead of 2-bromo-4,6-diphenylpyridine used in Synthesis Example 162.

Mass (theoretical value: 629.19, measured value: 629 g/mol)

[Synthesis Example 179] Synthesis of Compound H-18

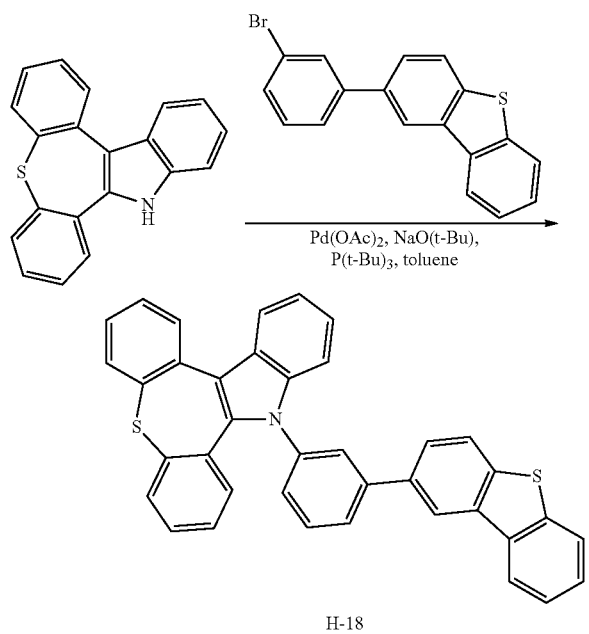

H-18

Compound H-18 (2.7 g, yield 71%) was obtained by performing the same process as in Synthesis Example 162, except that 2-(3-bromophenyl)dibenzo[b,d]thiophene (2.7 g, 8.0 mmol) was used instead of 2-bromo-4,6-diphenylpyridine used in Synthesis Example 162.

Mass (theoretical value: 557.13, measured value: 557 g/mol)

[Synthesis Example 180] Synthesis of Compound H-19

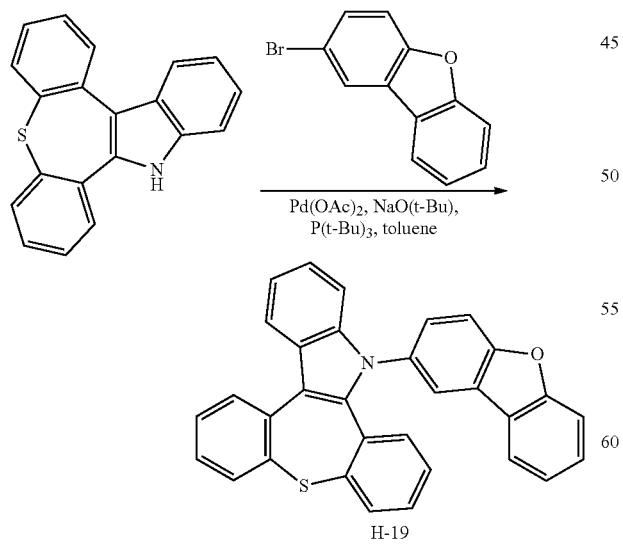

H-19

Compound H-19 (2.3 g, yield 75%) was obtained by performing the same process as in Synthesis Example 162, except that 2-bromodibenzo[b,d]furan (2.0 g, 8.0 mmol) was used instead of 2-bromo-4,6-diphenylpyridine used in Synthesis Example 162.

Mass (theoretical value: 465.12, measured value: 465 g/mol)

[Synthesis Example 181] Synthesis of Compound H-20

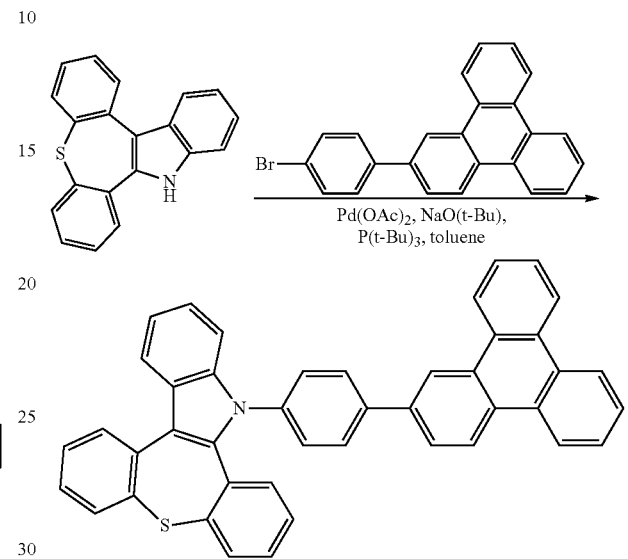

H-20

Compound H-20 (2.6 g, yield 65%) was obtained by performing the same process as in Synthesis Example 162, except that 2-(4-bromophenyl)triphenylene (3.1 g, 8.0 mmol) was used instead of 2-bromo-4,6-diphenylpyridine used in Synthesis Example 162.

Mass (theoretical value: 601.19, measured value: 601 g/mol)

[Synthesis Example 182] Synthesis of Compound H-21

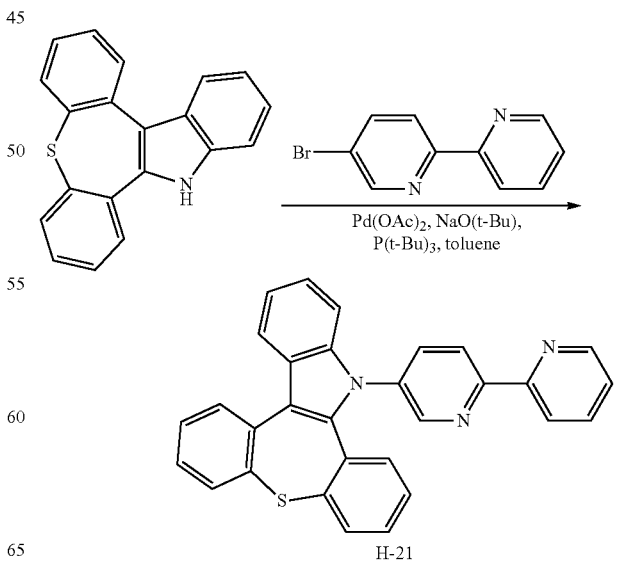

H-21

Compound H-21 (2.1 g, yield 68%) was obtained by performing the same process as in Synthesis Example 162, except that 5-bromo-2,2'-bipyridine (1.9 g, 8.0 mmol) was used instead of 2-bromo-4,6-diphenylpyridine used in Synthesis Example 162.

Mass (theoretical value: 453.13, measured value: 453 g/mol)

[Synthesis Example 183] Synthesis of Compound H-22

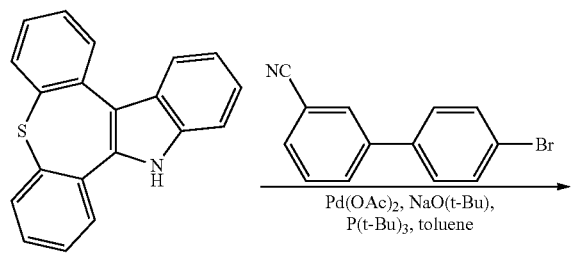

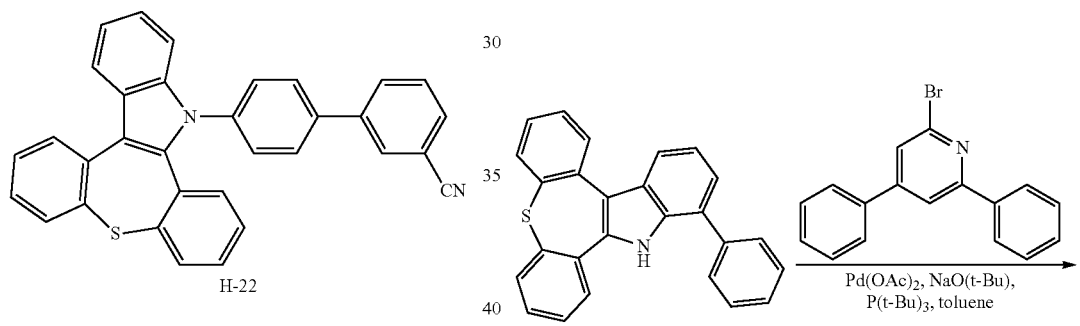

H-22

Compound H-22 (2.2 g, yield 69%) was obtained by performing the same process as in Synthesis Example 162, except that 4'-bromobiphenyl-3-carbonitrile (2.1 g, 8.0 mmol) was used instead of 2-bromo-4,6-diphenylpyridine used in Synthesis Example 162.

Mass (theoretical value: 476.14, measured value: 476 g/mol)

[Synthesis Example 184] Synthesis of Compound H-23

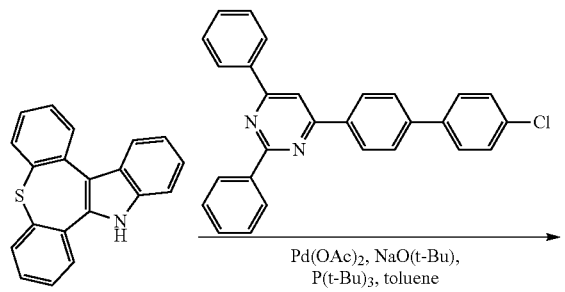

H-23

Compound H-23 (2.9 g, yield 63%) was obtained by performing the same process as in Synthesis Example 162, except that 4-(4'-chlorobiphenyl-4-yl)-2,6-diphenylpyrimidine (3.4 g, 8.0 mmol) was used instead of 2-bromo-4,6-diphenylpyridine used in Synthesis Example 162.

Mass (theoretical value: 681.22, measured value: 681 g/mol)

[Synthesis Example 185] Synthesis of Compound I-1

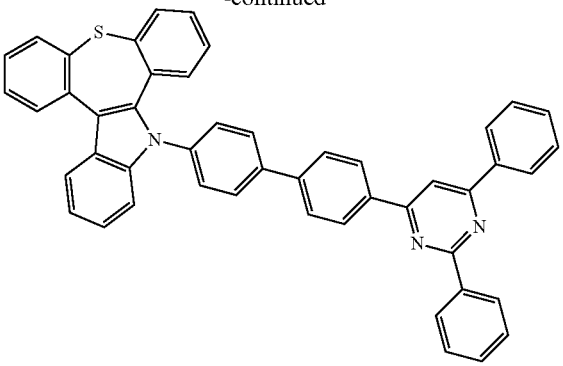

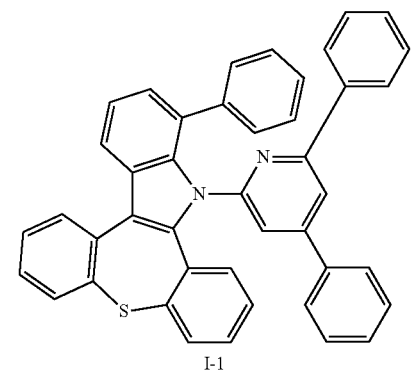

I-1

Compound IAz-9 (2.5 g, 6.7 mmol) synthesized in Preparation Example 9, 2-bromo-4,6-diphenylpyridine (2.5 g, 8.0 mmol), Pd(OAc)$_2$ (0.08 g, 0.34 mmol), P(t-Bu)$_3$ (0.16 ml, 0.67 mmol), NaO(t-Bu) (1.29 g, 13.4 mmol), and toluene (70 ml) were mixed under nitrogen flow, and the resulting mixture was stirred at 110° C. for 5 hours. After the reaction was terminated, toluene was concentrated, and a solid salt was filtered and then purified with recrystallization to obtain Compound I-1 (2.6 g, yield 65%).

Mass (theoretical value: 604.20, measured value: 604 g/mol)

[Synthesis Example 186] Synthesis of Compound I-2

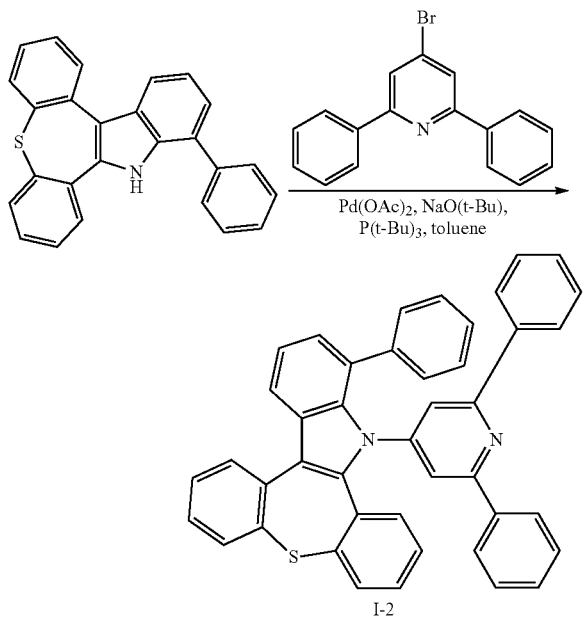

Compound I-2 (2.5 g, yield 61%) was obtained by performing the same process as in Synthesis Example 185, except that 4-bromo-2,6-diphenylpyridine (2.5 g, 8.0 mmol) was used instead of 2-bromo-4,6-diphenylpyridine used in Synthesis Example 185.

Mass (theoretical value: 604.20, measured value: 604 g/mol)

[Synthesis Example 187] Synthesis of Compound I-3

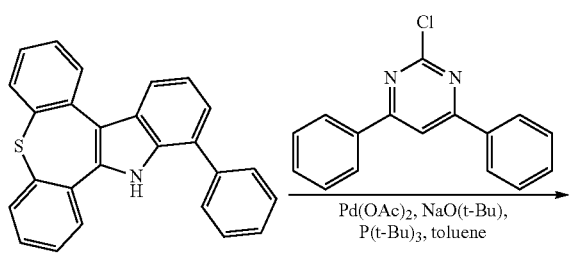

Compound I-3 (2.8 g, yield 68%) was obtained by performing the same process as in Synthesis Example 185, except that 2-chloro-4,6-diphenylpyrimidine (2.5 g, 8.0 mmol) was used instead of 2-bromo-4,6-diphenylpyridine used in Synthesis Example 185.

Mass (theoretical value: 605.19, measured value: 605 g/mol)

[Synthesis Example 188] Synthesis of Compound I-4

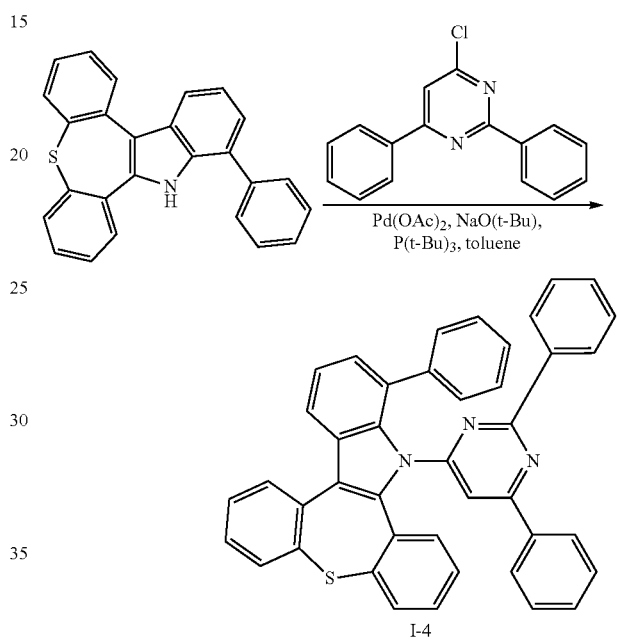

Compound I-4 (2.8 g, yield 70%) was obtained by performing the same process as in Synthesis Example 185, except that 4-chloro-2,6-diphenylpyrimidine (2.5 g, 8.0 mmol) was used instead of 2-bromo-4,6-diphenylpyridine used in Synthesis Example 185.

Mass (theoretical value: 605.19, measured value: 605 g/mol)

[Synthesis Example 189] Synthesis of Compound I-5

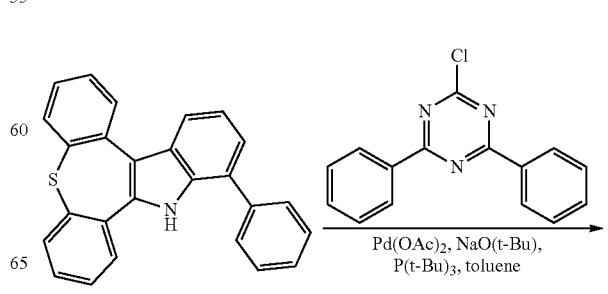

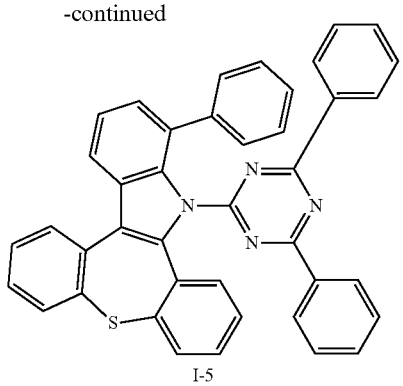

I-5

Compound I-5 (3.0 g, yield 74%) was obtained by performing the same process as in Synthesis Example 185, except that 2-chloro-4,6-diphenyl-1,3,5-triazine (2.1 g, 8.0 mmol) was used instead of 2-bromo-4,6-diphenylpyridine used in Synthesis Example 185.

Mass (theoretical value: 606.19, measured value: 606 g/mol)

[Synthesis Example 190] Synthesis of Compound I-6

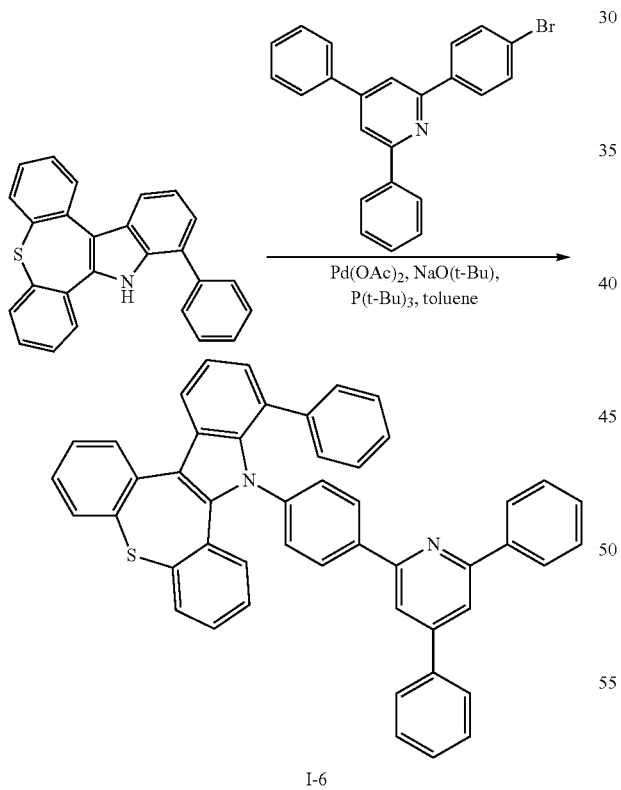

I-6

Compound I-6 (3.0 g, yield 65%) was obtained by performing the same process as in Synthesis Example 185, except that 2-(4-bromophenyl)-4,6-diphenylpyridine (3.1 g, 8.0 mmol) was used instead of 2-bromo-4,6-diphenylpyridine used in Synthesis Example 185.

Mass (theoretical value: 680.23, measured value: 680 g/mol)

[Synthesis Example 191] Synthesis of Compound I-7

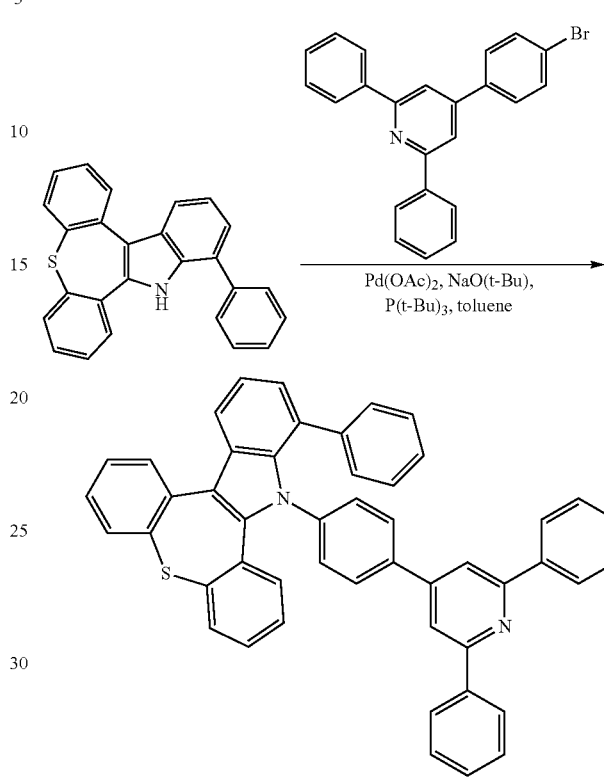

I-7

Compound I-7 (2.8 g, yield 61%) was obtained by performing the same process as in Synthesis Example 185, except that 4-(4-bromophenyl)-2,6-diphenylpyridine (3.1 g, 8.0 mmol) was used instead of 2-bromo-4,6-diphenylpyridine used in Synthesis Example 185.

Mass (theoretical value: 680.23, measured value: 680 g/mol)

[Synthesis Example 192] Synthesis of Compound I-8

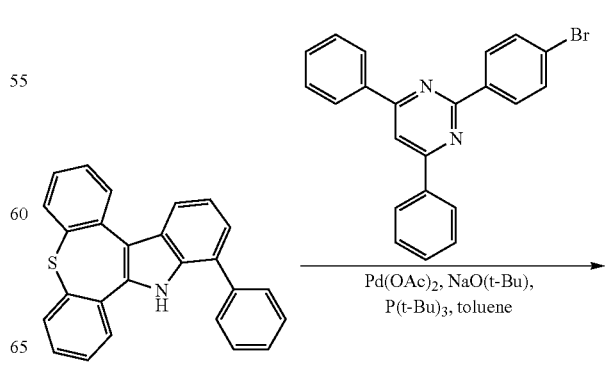

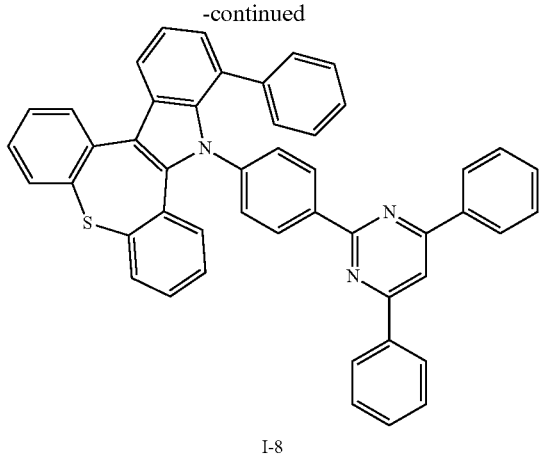

I-8

Compound I-8 (2.9 g, yield 63%) was obtained by performing the same process as in Synthesis Example 185, except that 2-(4-bromophenyl)-4,6-diphenylpyrimidine (3.1 g, 8.0 mmol) was used instead of 2-bromo-4,6-diphenylpyridine used in Synthesis Example 185.

Mass (theoretical value: 680.22, measured value: 680 g/mol)

[Synthesis Example 193] Synthesis of Compound I-9

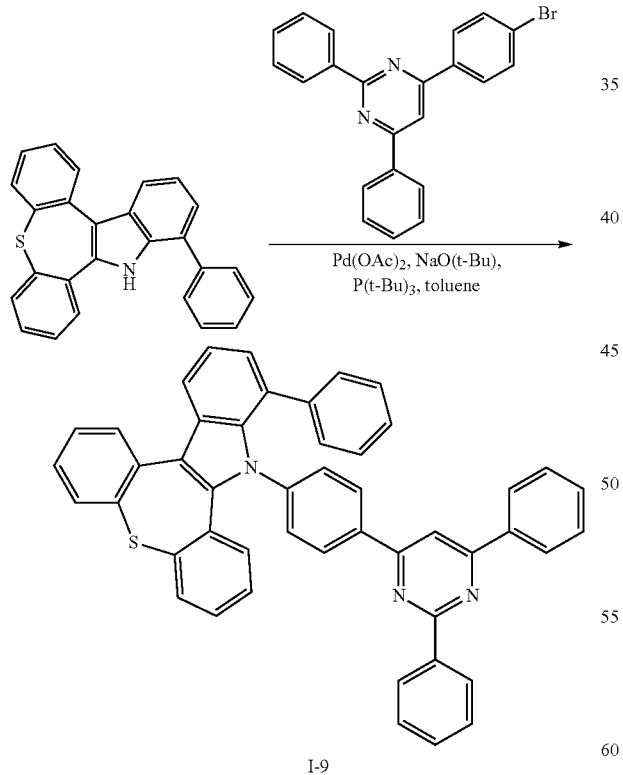

I-9

Compound I-9 (2.9 g, yield 64%) was obtained by performing the same process as in Synthesis Example 185, except that 4-(4-bromophenyl)-2,6-diphenylpyrimidine (3.1 g, 8.0 mmol) was used instead of 2-bromo-4,6-diphenylpyridine used in Synthesis Example 185.

Mass (theoretical value: 681.22, measured value: 681 g/mol)

[Synthesis Example 194] Synthesis of Compound I-10

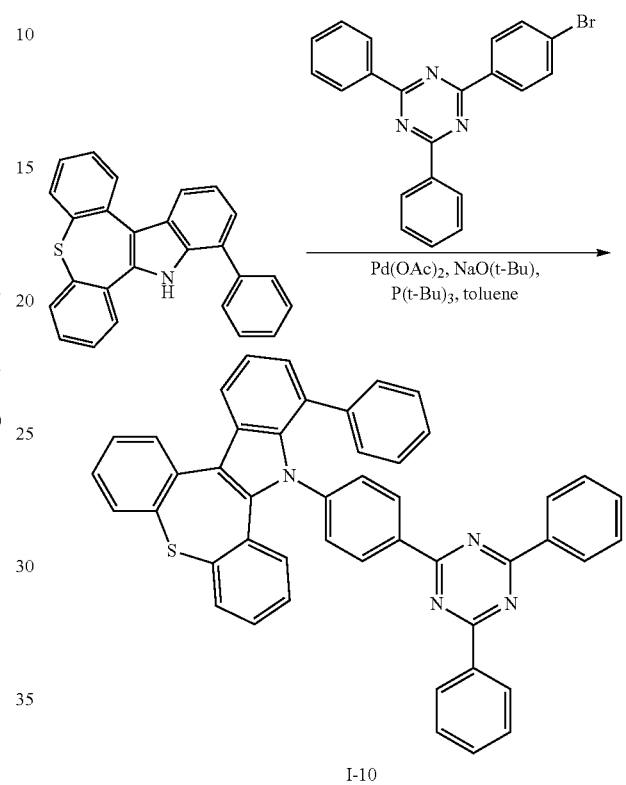

I-10

Compound I-10 (3.2 g, yield 70%) was obtained by performing the same process as in Synthesis Example 185, except that 2-(4-bromophenyl)-4,6-diphenyl-1,3,5-triazine (3.1 g, 8.0 mmol) was used instead of 2-bromo-4,6-diphenylpyridine used in Synthesis Example 185.

Mass (theoretical value: 682.22, measured value: 682 g/mol)

[Synthesis Example 195] Synthesis of Compound I-11

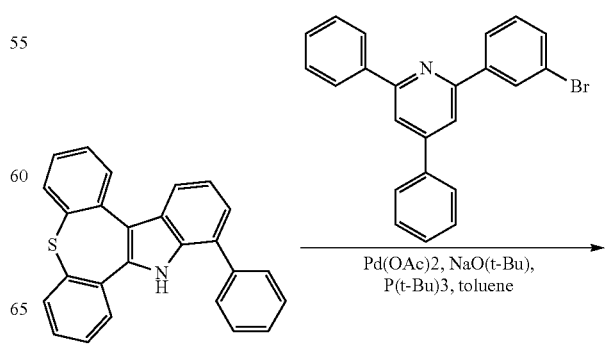

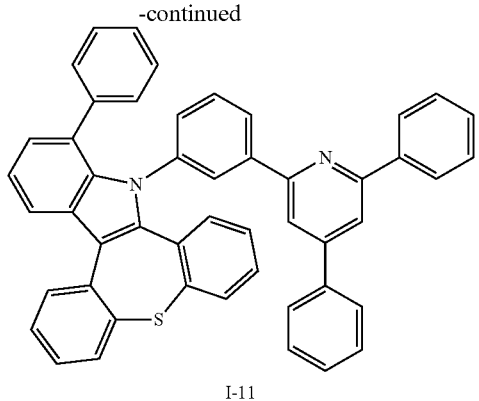

I-11

Compound I-11 (3.5 g, yield 76%) was obtained by performing the same process as in Synthesis Example 185, except that 2-(3-bromophenyl)-4,6-diphenylpyridine (3.1 g, 8.0 mmol) was used instead of 2-bromo-4,6-diphenylpyridine used in Synthesis Example 185.

Mass (theoretical value: 680.23, measured value: 680 g/mol)

[Synthesis Example 196] Synthesis of Compound I-12

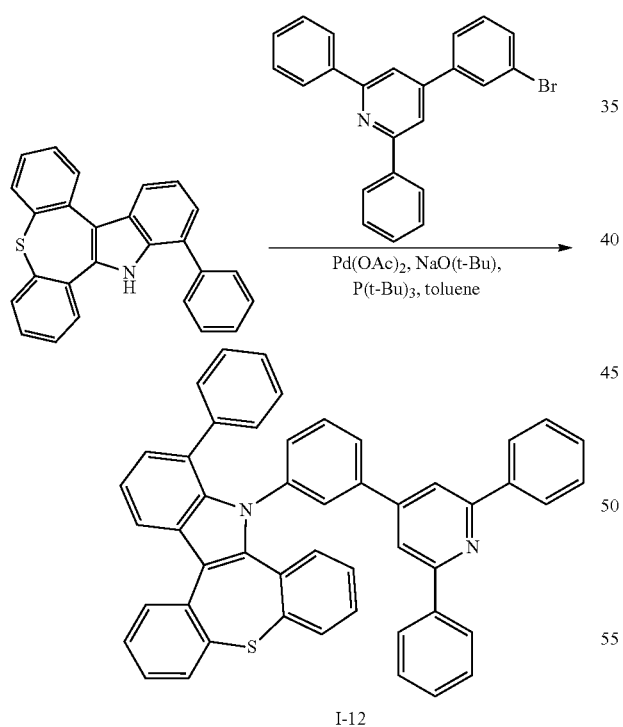

I-12

Compound I-12 (3.3 g, yield 73%) was obtained by performing the same process as in Synthesis Example 185, except that 4-(3-bromophenyl)-2,6-diphenylpyridine (3.1 g, 8.0 mmol) was used instead of 2-bromo-4,6-diphenylpyridine used in Synthesis Example 185.

Mass (theoretical value: 680.23, measured value: 680 g/mol)

[Synthesis Example 197] Synthesis of Compound I-13

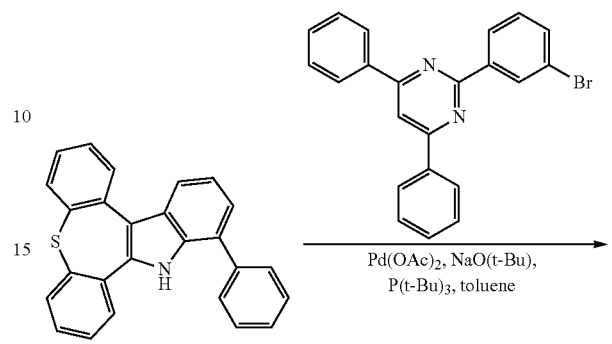

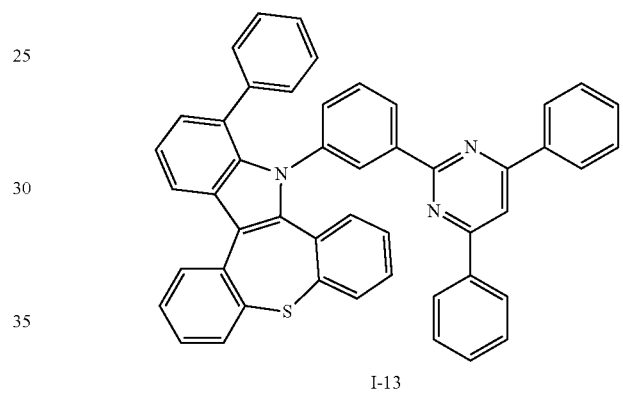

I-13

Compound I-13 (3.2 g, yield 71%) was obtained by performing the same process as in Synthesis Example 185, except that 2-(3-bromophenyl)-4,6-diphenylpyrimidine (3.1 g, 8.0 mmol) was used instead of 2-bromo-4,6-diphenylpyridine used in Synthesis Example 185.

Mass (theoretical value: 681.22, measured value: 681 g/mol)

[Synthesis Example 198] Synthesis of Compound I-14

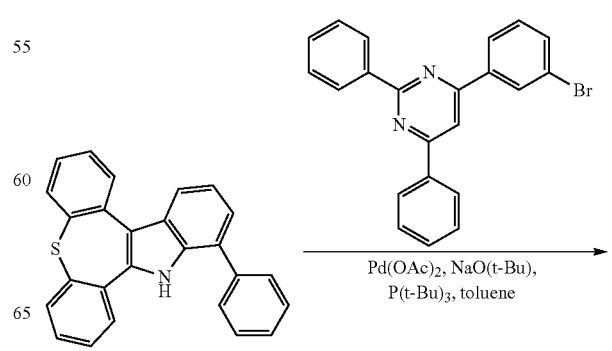

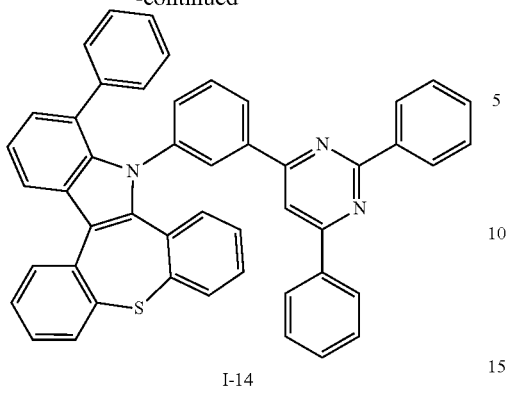

I-14

Compound I-14 (3.1 g, yield 68%) was obtained by performing the same process as in Synthesis Example 185, except that 4-(3-bromophenyl)-2,6-diphenylpyrimidine (3.1 g, 8.0 mmol) was used instead of 2-bromo-4,6-diphenylpyridine used in Synthesis Example 185.

Mass (theoretical value: 681.22, measured value: 681 g/mol)

[Synthesis Example 199] Synthesis of Compound I-15

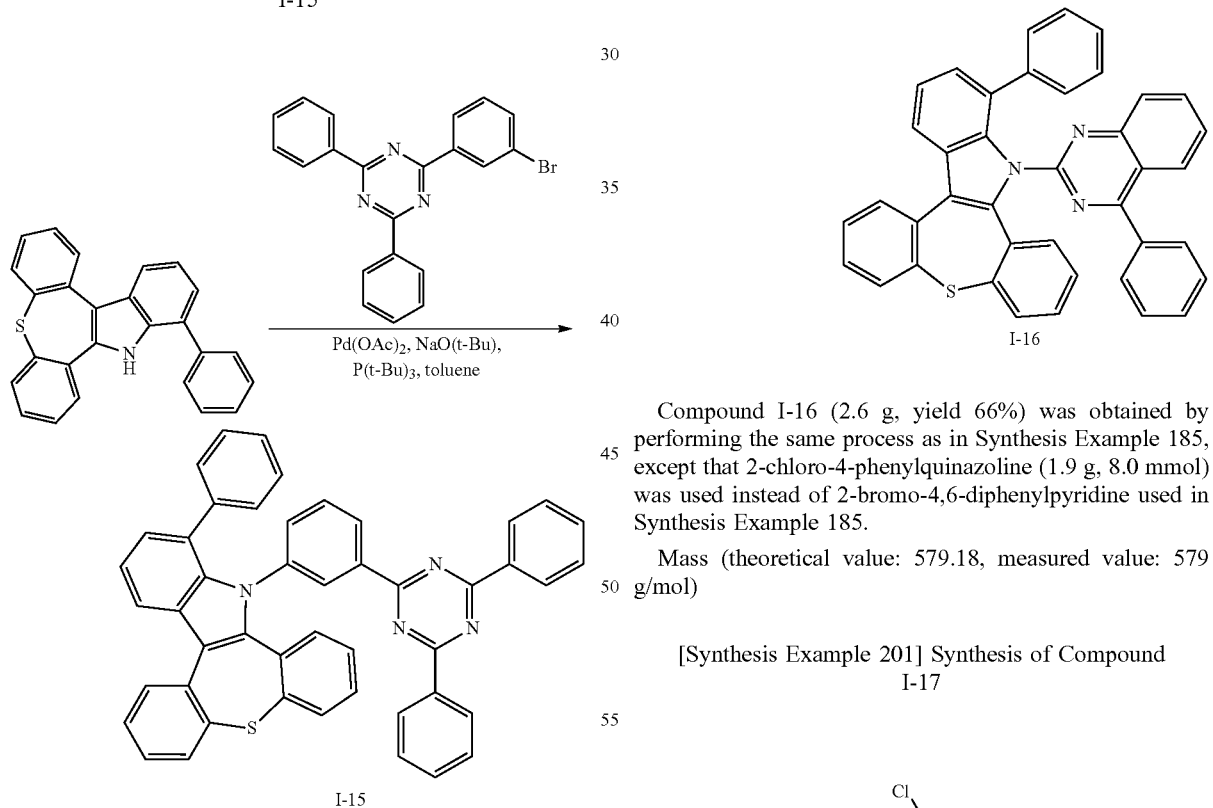

I-15

Compound I-15 (3.0 g, yield 65%) was obtained by performing the same process as in Synthesis Example 185, except that 2-(3-bromophenyl)-4,6-diphenyl-1,3,5-triazine (3.1 g, 8.0 mmol) was used instead of 2-bromo-4,6-diphenylpyridine used in Synthesis Example 185.

Mass (theoretical value: 682.22, measured value: 682 g/mol)

[Synthesis Example 200] Synthesis of Compound I-16

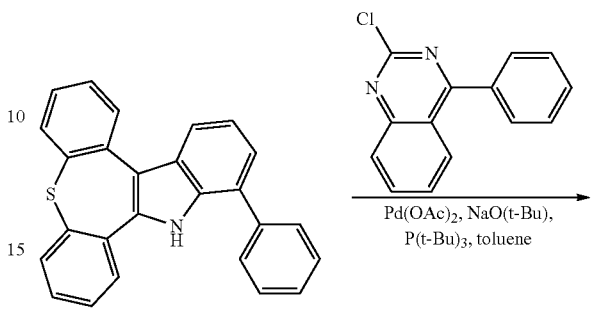

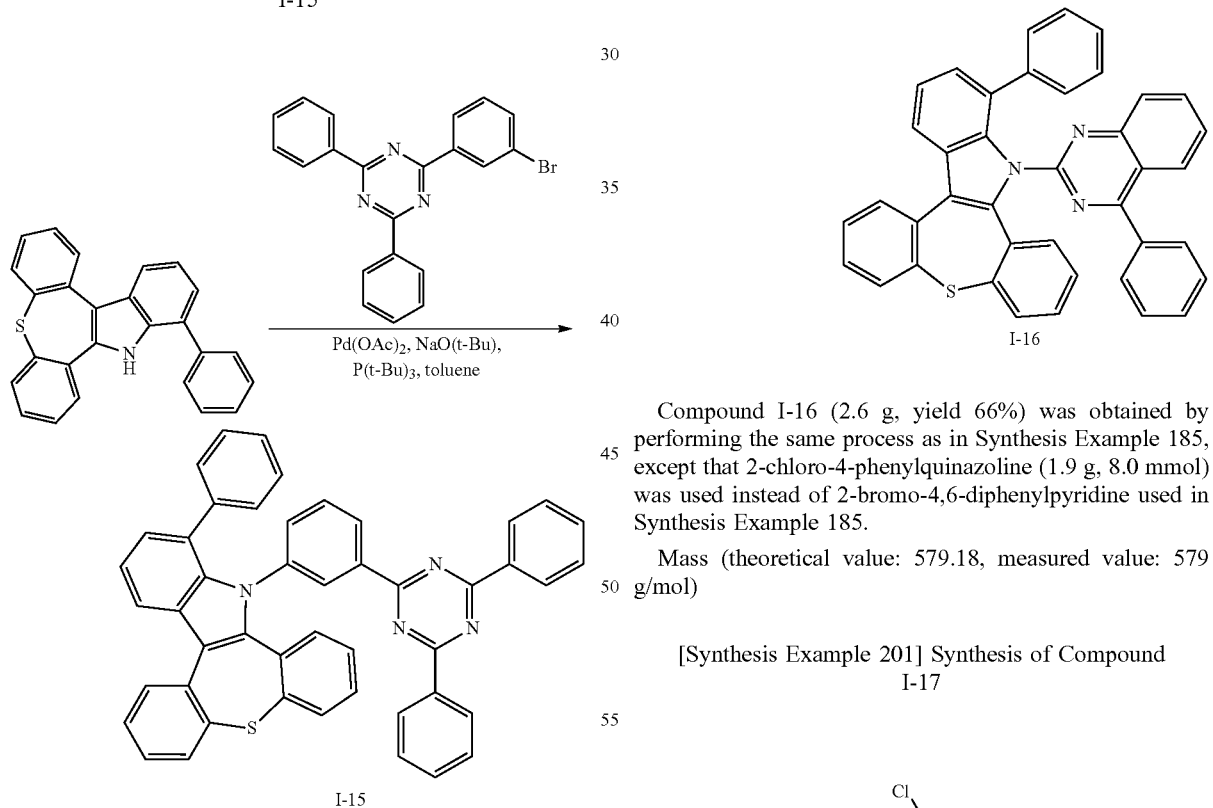

I-16

Compound I-16 (2.6 g, yield 66%) was obtained by performing the same process as in Synthesis Example 185, except that 2-chloro-4-phenylquinazoline (1.9 g, 8.0 mmol) was used instead of 2-bromo-4,6-diphenylpyridine used in Synthesis Example 185.

Mass (theoretical value: 579.18, measured value: 579 g/mol)

[Synthesis Example 201] Synthesis of Compound I-17

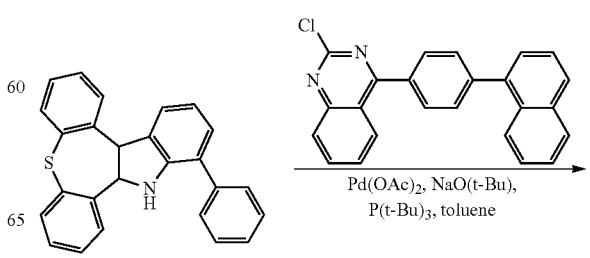

-continued

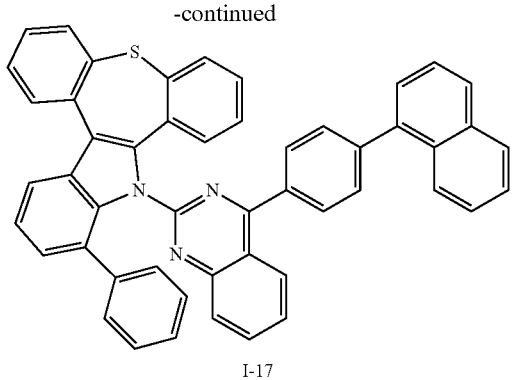

I-17

Compound I-17 (3.2 g, yield 67%) was obtained by performing the same process as in Synthesis Example 185, except that 2-chloro-4-(4-(naphthalen-1-yl)phenyl)quinazoline (2.9 g, 8.0 mmol) was used instead of 2-bromo-4,6-diphenylpyridine used in Synthesis Example 185.

Mass (theoretical value: 705.22, measured value: 705 g/mol)

[Synthesis Example 202] Synthesis of Compound I-18

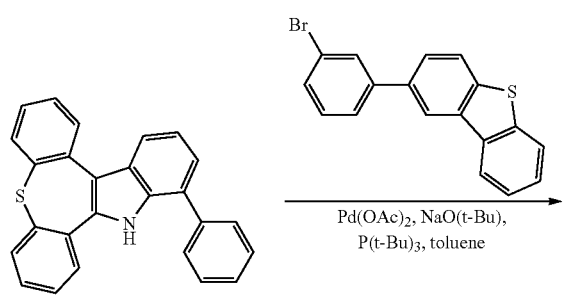

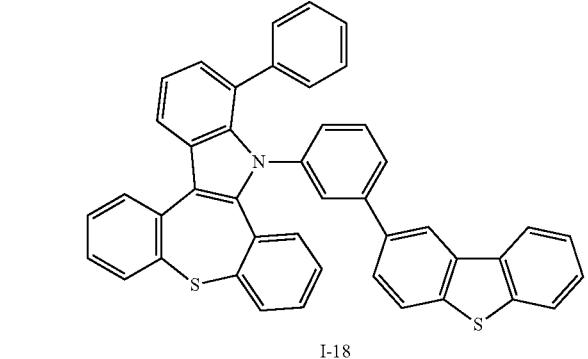

I-18

Compound I-18 (3.3 g, yield 77%) was obtained by performing the same process as in Synthesis Example 185, except that 2-(3-bromophenyl)dibenzo[b,d]thiophene (2.7 g, 8.0 mmol) was used instead of 2-bromo-4,6-diphenylpyridine used in Synthesis Example 185.

Mass (theoretical value: 633.16, measured value: 633 g/mol)

[Synthesis Example 203] Synthesis of Compound I-19

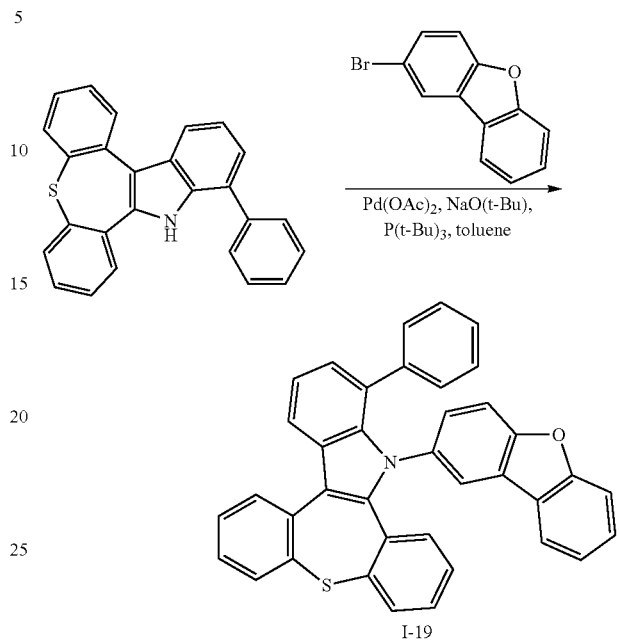

I-19

Compound I-19 (2.7 g, yield 74%) was obtained by performing the same process as in Synthesis Example 185, except that 2-bromodibenzo[b,d]furan (2.0 g, 8.0 mmol) was used instead of 2-bromo-4,6-diphenylpyridine used in Synthesis Example 185.

Mass (theoretical value: 541.15, measured value: 541 g/mol)

[Synthesis Example 204] Synthesis of Compound I-20

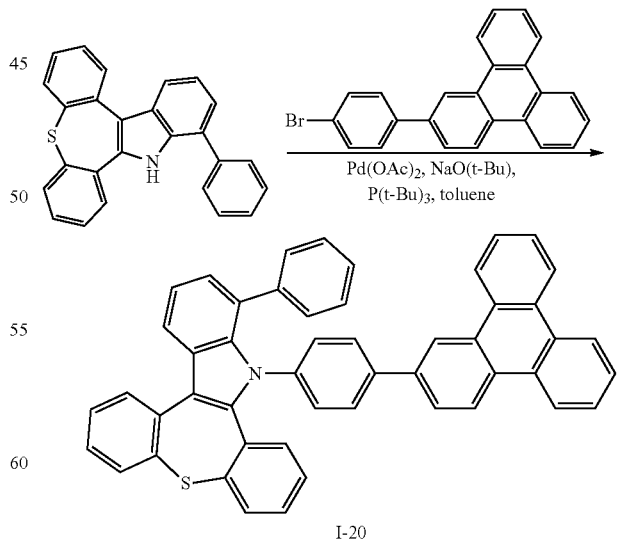

I-20

Compound I-20 (3.3 g, yield 72%) was obtained by performing the same process as in Synthesis Example 185, except that 2-(4-bromophenyl)triphenylene (3.1 g, 8.0 mmol) was used instead of 2-bromo-4,6-diphenylpyridine used in Synthesis Example 185.

Mass (theoretical value: 677.22, measured value: 677 g/mol)

[Synthesis Example 205] Synthesis of Compound I-21

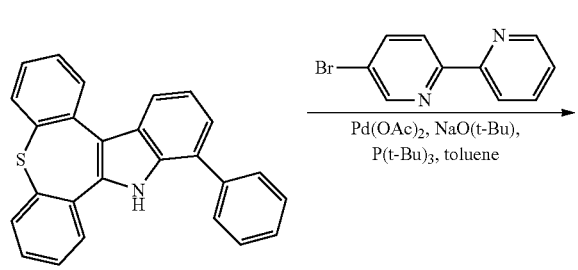

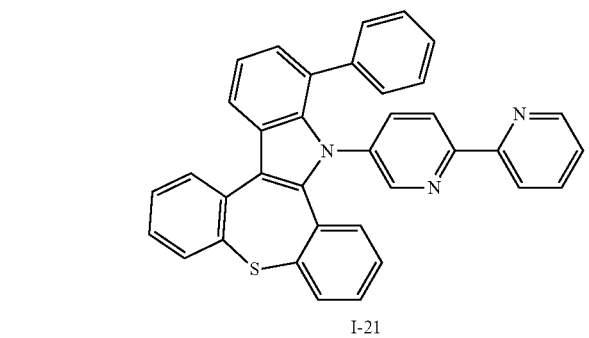

I-21

Compound I-21 (2.3 g, yield 65%) was obtained by performing the same process as in Synthesis Example 185, except that 5-bromo-2,2'-bipyridine (1.9 g, 8.0 mmol) was used instead of 2-bromo-4,6-diphenylpyridine used in Synthesis Example 185.

Mass (theoretical value: 529.16, measured value: 529 g/mol)

[Synthesis Example 206] Synthesis of Compound I-22

I-22

Compound I-22 (2.5 g, yield 68%) was obtained by performing the same process as in Synthesis Example 185, except that 4'-bromobiphenyl-3-carbonitrile (2.1 g, 8.0 mmol) was used instead of 2-bromo-4,6-diphenylpyridine used in Synthesis Example 185.

Mass (theoretical value: 552.17, measured value: 552 g/mol)

[Synthesis Example 207] Synthesis of Compound I-23

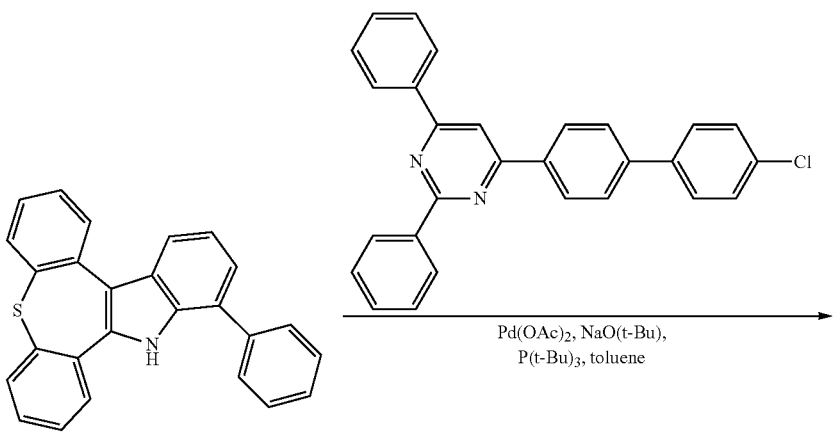

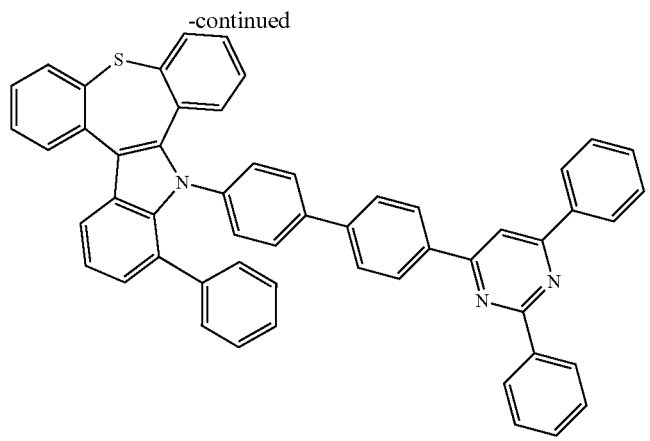

I-23

Compound I-23 (3.4 g, yield 67%) was obtained by performing the same process as in Synthesis Example 185, except that 4-(4'-chlorobiphenyl-4-yl)-2,6-diphenylpyrimidine (3.4 g, 8.0 mmol) was used instead of 2-bromo-4,6-diphenylpyridine used in Synthesis Example 185.

Mass (theoretical value: 757.25, measured value: 757 g/mol)

[Synthesis Example 208] Synthesis of Compound L-1

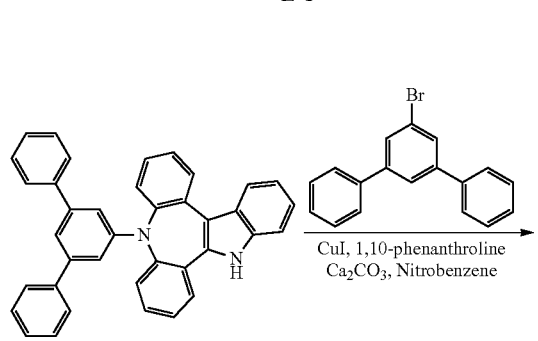

L-1

Compound IAz-3 (3.4 g, 6.7 mmol) synthesized in Preparation Example 3, 5'-bromo-(1,1',3',1")terphenyl (2.5 g, 8.0 mmol), CuI (0.13 g, 0.67 mmol), 1,10-phenanthroline (0.24 g, 1.34 mmol), $Cs_2CO_3$ (4.37 g, 13.4 mmol), and nitrobenzene (25 ml) were mixed under nitrogen flow, and the resulting mixture was stirred at 210° C. for 3 hours. After the reaction was terminated, a solid salt was filtered and then purified with column chromatography to obtain Compound L-1 (3.2 g, yield 65%).

Mass (theoretical value: 738.3, measured value: 738 g/mol)

[Synthesis Example 209] Synthesis of Compound L-2

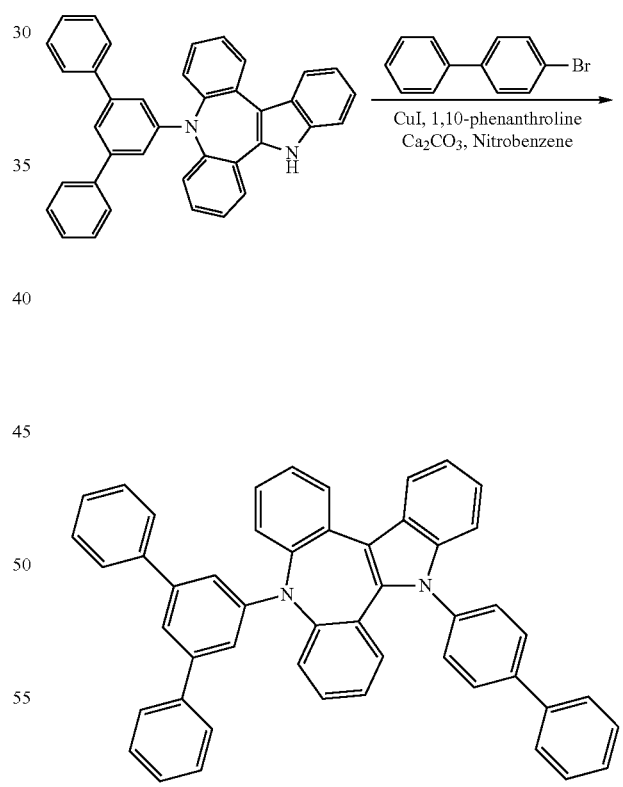

L2

Compound L-2 (3.0 g, yield 68%) was obtained by performing the same process as in Synthesis Example 208, except that 4-bromobiphenyl (1.90 g, 8.0 mmol) was used instead of 5'-bromo-(1,1',3',1")terphenyl used in Synthesis Example 208. Mass (theoretical value: 662.27, measured value: 662 g/mol)

[Synthesis Example 210] Synthesis of Compound L-3

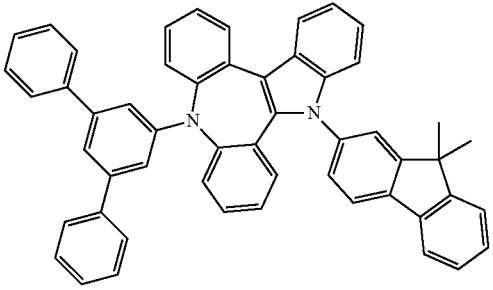

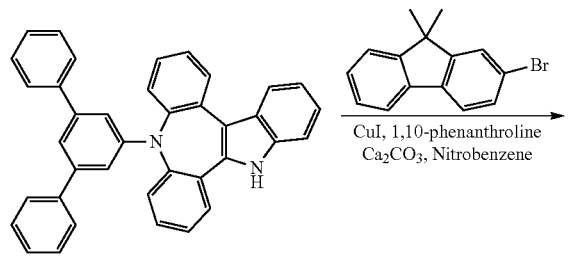

Compound L-3 (3.4 g, yield 72%) was obtained by performing the same process as in Synthesis Example 208, except that 2-bromo-9,9-dimethyl-9H-fluorene (2.18 g, 8.0 mmol) was used instead of 5'-bromo-(1,1',3',1")terphenyl used in Synthesis Example 208.

Mass (theoretical value: 702.3, measured value: 702 g/mol)

[Synthesis Example 211] Synthesis of Compound M-1

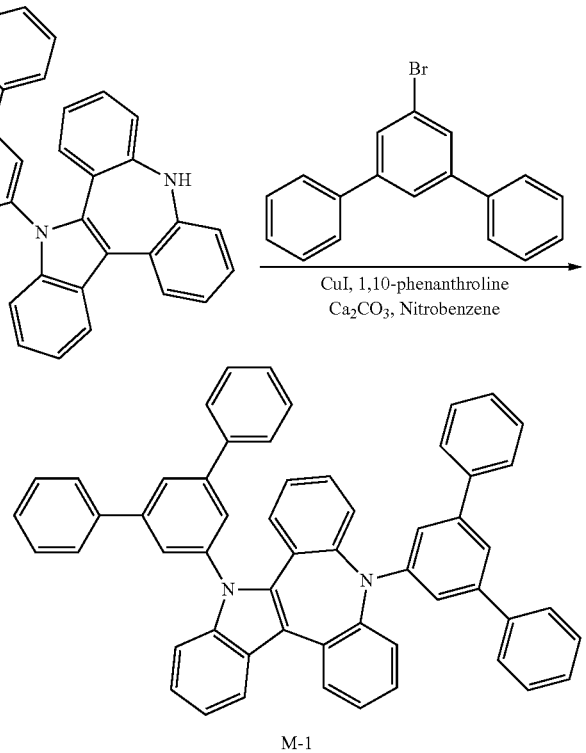

Compound IAz-4 (3.4 g, 6.7 mmol) synthesized in Preparation Example 4, 5'-bromo-(1,1',3',1")terphenyl (2.5 g, 8.0 mmol), CuI (0.13 g, 0.67 mmol), 1,10-phenanthroline (0.24 g, 1.34 mmol), Cs$_2$CO$_3$ (4.37 g, 13.4 mmol), and nitrobenzene (25 ml) were mixed under nitrogen flow, and the resulting mixture was stirred at 210° C. for 3 hours. After the reaction was terminated, a solid salt was filtered and then purified with column chromatography to obtain Compound M-1 (3.4 g, yield 68%).

Mass (theoretical value: 738.3, measured value: 738 g/mol)

[Synthesis Example 212] Synthesis of Compound M-2

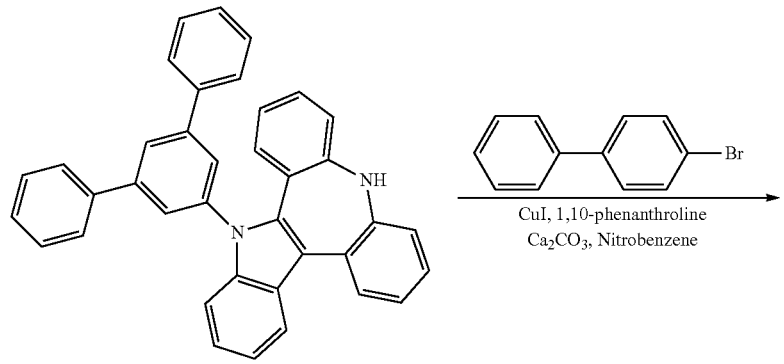

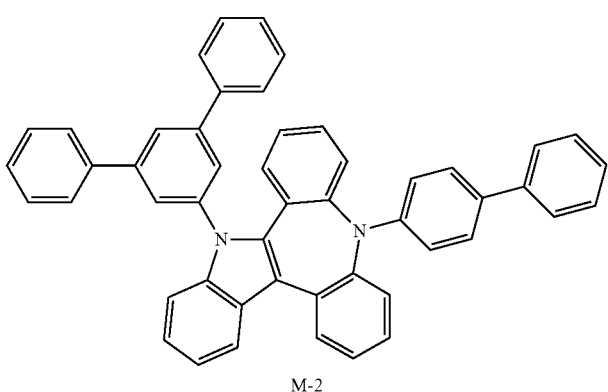

M-2

Compound M-2 (2.8 g, yield 63%) was obtained by performing the same process as in Synthesis Example 211, except that 4-bromobiphenyl (1.90 g, 8.0 mmol) was used instead of 5'-bromo-(1,1',3',1")terphenyl used in Synthesis Example 211. Mass (theoretical value: 622.27, measured value: 622 g/mol)

[Synthesis Example 213] Synthesis of Compound M-3

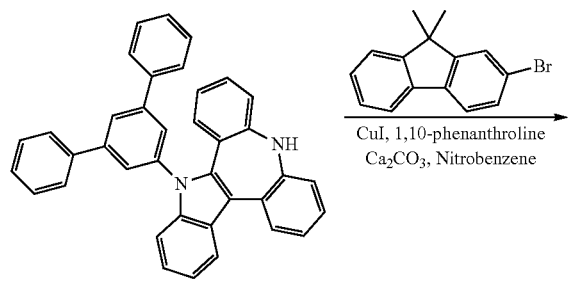

-continued

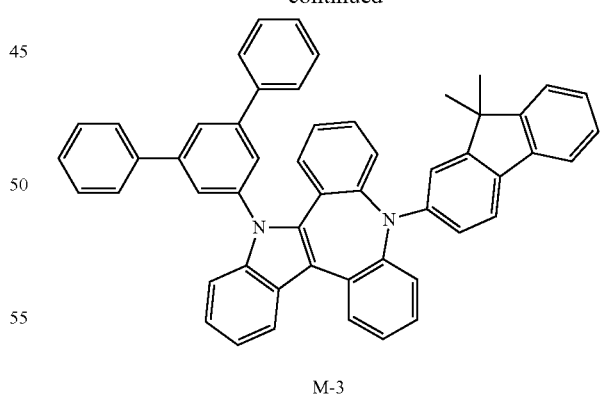

M-3

Compound M-3 (3.5 g, yield 75%) was obtained by performing the same process as in Synthesis Example 211, except that 2-bromo-9,9-dimethyl-9H-fluorene (2.18 g, 8.0 mmol) was used instead of 5'-bromo-(1,1',3',1")terphenyl used in Synthesis Example 211.

Mass (theoretical value: 702.3, measured value: 702 g/mol)

[Synthesis Example 214] Synthesis of Compound N-1

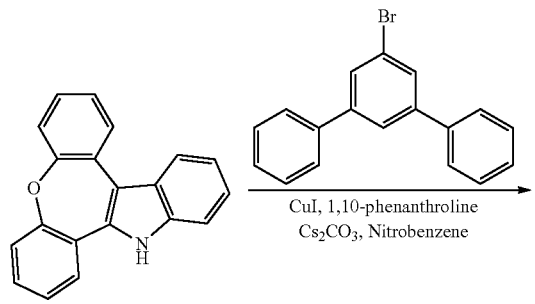

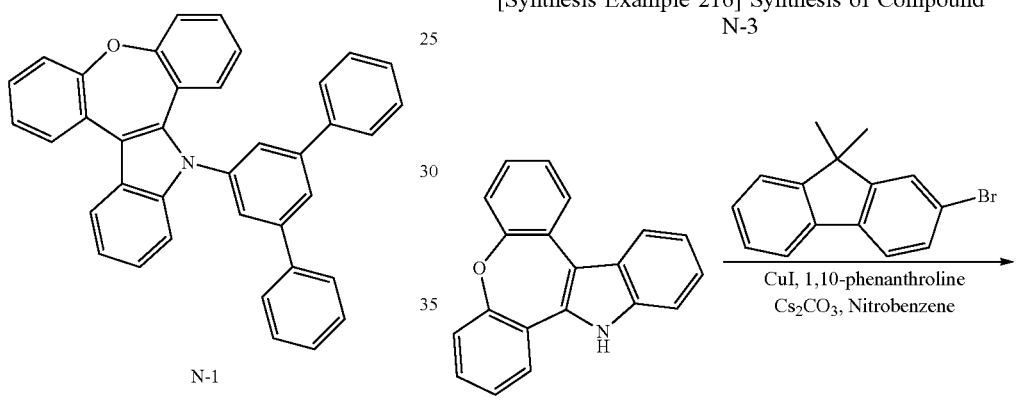

N-1

Compound IAz-6 (1.9 g, 6.7 mmol) synthesized in Preparation Example 6, 5'-bromo-(1,1',3',1")terphenyl (2.5 g, 8.0 mmol), CuI (0.13 g, 0.67 mmol), 1,10-phenanthroline (0.24 g, 1.34 mmol), Cs$_2$CO$_3$ (4.37 g, 13.4 mmol), and nitrobenzene (25 ml) were mixed under nitrogen flow, and the resulting mixture was stirred at 210° C. for 3 hours. After the reaction was terminated, a solid salt was filtered and then purified with column chromatography to obtain Compound N-1 (2.5 g, yield 73%).

Mass (theoretical value: 511.19, measured value: 511 g/mol)

[Synthesis Example 215] Synthesis of Compound N-2

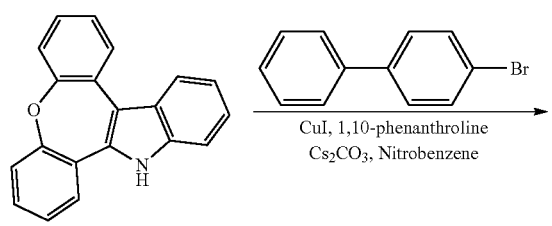

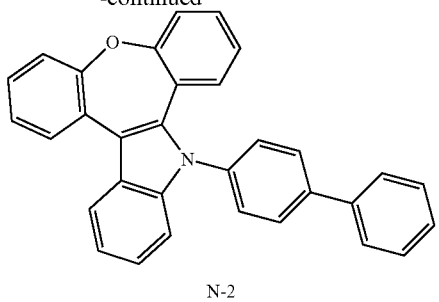

N-2

Compound N-2 (2.2 g, yield 77%) was obtained by performing the same process as in Synthesis Example 214, except that 4-bromobiphenyl (1.90 g, 8.0 mmol) was used instead of 5'-bromo-(1,1',3',1")terphenyl used in Synthesis Example 214.

Mass (theoretical value: 435.16, measured value: 435 g/mol)

[Synthesis Example 216] Synthesis of Compound N-3

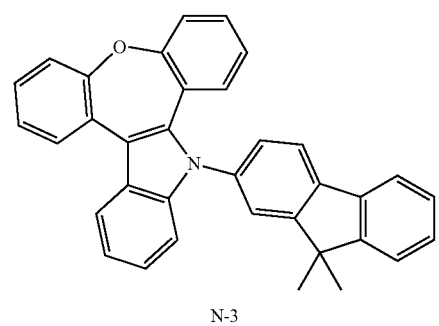

N-3

Compound N-3 (2.3 g, yield 72%) was obtained by performing the same process as in Synthesis Example 214, except that 2-bromo-9,9-dimethyl-9H-fluorene (2.18 g, 8.0 mmol) was used instead of 5'-bromo-(1,1',3',1")terphenyl used in Synthesis Example 214.

Mass (theoretical value: 475.19, measured value: 475 g/mol)

[Synthesis Example 217] Synthesis of Compound O-1

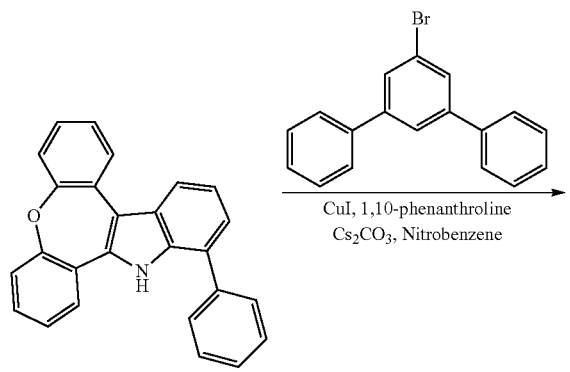

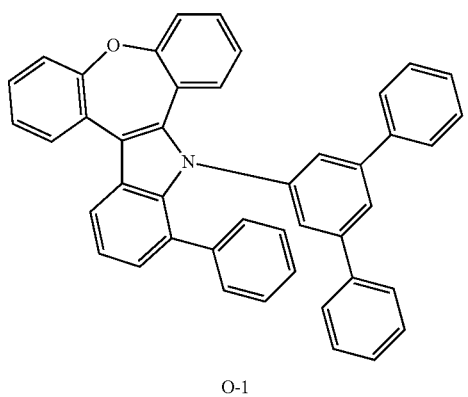

O-1

Compound IAz-7 (2.4 g, 6.7 mmol) synthesized in Preparation Example 7, 5'-bromo-(1,1',3',1")terphenyl (2.5 g, 8.0 mmol), CuI (0.13 g, 0.67 mmol), 1,10-phenanthroline (0.24 g, 1.34 mmol), Cs₂CO₃ (4.37 g, 13.4 mmol), and nitrobenzene (25 ml) were mixed under nitrogen flow, and the resulting mixture was stirred at 210° C. for 3 hours. After the reaction was terminated, a solid salt was filtered and then purified with column chromatography to obtain Compound O-1 (2.3 g, yield 66%).

Mass (theoretical value: 511.19, measured value: 511 g/mol)

[Synthesis Example 218] Synthesis of Compound O-2

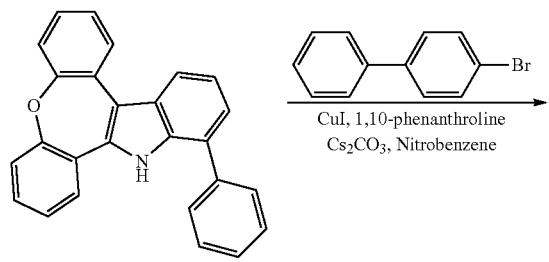

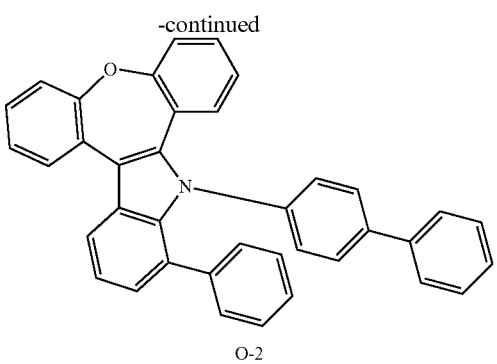

O-2

Compound O-2 (1.9 g, yield 64%) was obtained by performing the same process as in Synthesis Example 217, except that 4-bromobiphenyl (1.90 g, 8.0 mmol) was used instead of 5'-bromo-(1,1',3',1")terphenyl used in Synthesis Example 217.

Mass (theoretical value: 435.16, measured value: 435 g/mol)

[Synthesis Example 219] Synthesis of Compound O-3

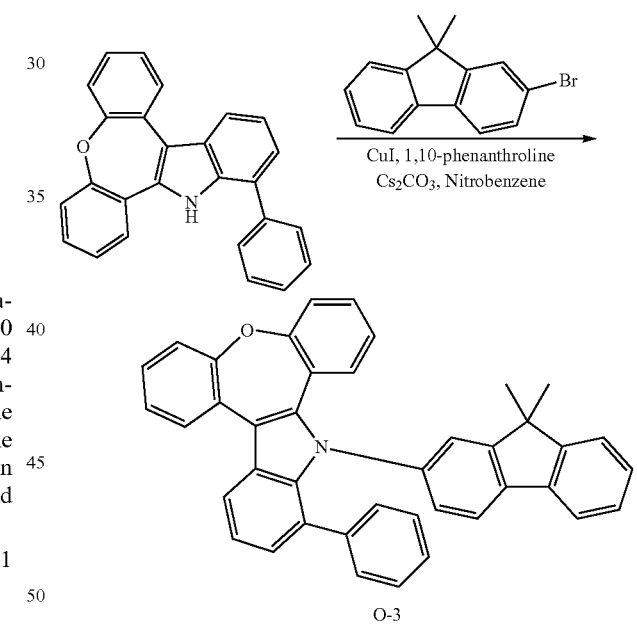

O-3

Compound O-3 (2.2 g, yield 69%) was obtained by performing the same process as in Synthesis Example 217, except that 2-bromo-9,9-dimethyl-9H-fluorene (2.18 g, 8.0 mmol) was used instead of 5'-bromo-(1,1',3',1")terphenyl used in Synthesis Example 217.

Mass (theoretical value: 475.19, measured value: 475 g/mol)

[Example 1] Manufacture of Green Organic EL Element

Compound A-1 synthesized in Synthesis Example 1 was subjected to highly pure sublimation purification by a typically known method, and then a green organic EL element was manufactured according to the following procedure.

First, a glass substrate thinly coated with indium tin oxide (ITO) to have a thickness of 1,500 Å was ultrasonically washed with distilled water. When the ultrasonic washing with distilled water was completed, the substrate was ultrasonically washed with a solvent such as isopropyl alcohol, acetone, and methanol, dried, transferred to a UV ozone cleaner (Power sonic 405, manufactured by Hwashin Tech), washed for 5 minutes by using UV, and then transferred to a vacuum evaporator.

An organic EL element was manufactured by laminating m-MTDATA (60 nm)/TCTA (80 nm)/90% Compound A-1+ 10% Ir(ppy)$_3$ (30 nm)/BCP (10 nm)/Alq$_3$ (30 nm)/LiF (1 nm)/Al (200 nm) in this order on the thus prepared ITO transparent electrode. The structures of m-MTDATA, TCTA, Ir(ppy)$_3$, and BCP are as follows.

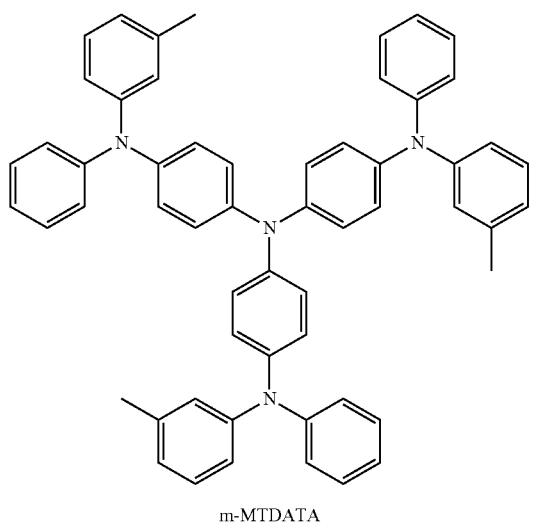

m-MTDATA

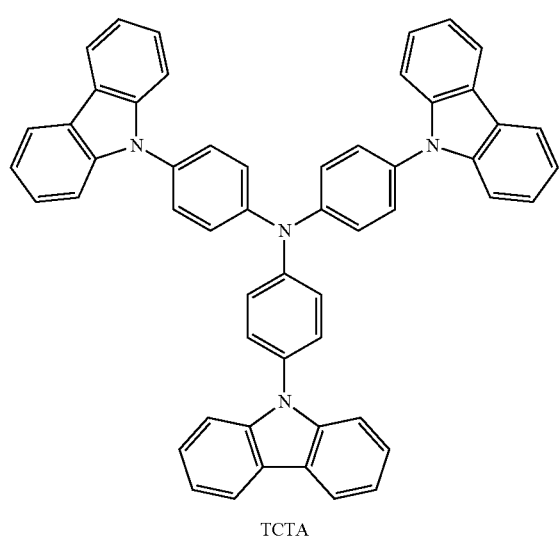

TCTA

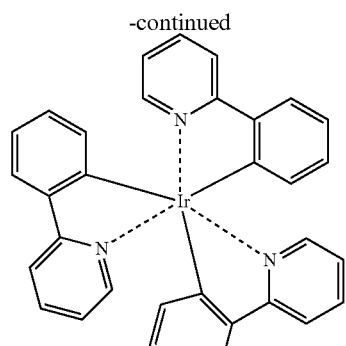

Ir(ppy)$_3$

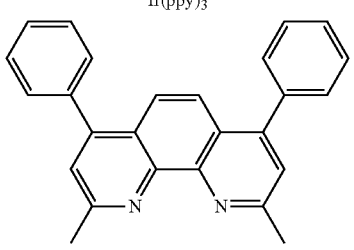

BCP

[Example 2] to [Example 189] Manufacture of Green Organic EL Element

A green organic EL element was manufactured by the same procedure as in Example 1, except that when a light emitting layer is formed in Example 1, Compounds A-2 to I-23 each synthesized in Synthesis Examples 2 to 189 were used instead of Compound A-1 used as a light emitting host material (see Table 1).

[Comparative Example 1] Manufacture of Green Organic EL Element

A green organic EL element was manufactured by the same procedure as in Example 1, except that when a light emitting layer is formed in Example 1, CBP was used instead of Compound A-1 used as a light emitting host material. The structure of CBP used is as follows.

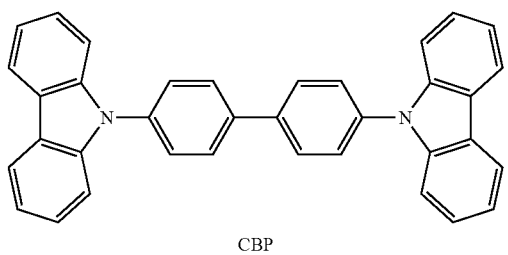 [SMILES: c1ccc2c(c1)c1ccccc1n2-c1ccc(-c2ccc(-n3c4ccccc4c4ccccc43)cc2)cc1 ; "CBP"]

CBP

Evaluation Example 1

For each of the green organic EL elements manufactured in Examples 1 to 189 and Comparative Example 1, the driving voltage, current efficiency, and light emitting peaks thereof were measured at a current density of 10 mA/cm$^2$, and the results are shown in the following Table 1.

TABLE 1

| Sample | Host | Driving voltage (V) | EL peak (nm) | Current efficiency (cd/A) |
|---|---|---|---|---|
| Example 1 | A-1 | 6.7 | 517 | 41.3 |
| Example 2 | A-2 | 6.7 | 515 | 43.1 |
| Example 3 | A-3 | 6.51 | 518 | 43.5 |
| Example 4 | A-4 | 6.77 | 518 | 41.4 |
| Example 5 | A-5 | 6.46 | 518 | 41.3 |
| Example 6 | A-6 | 6.81 | 517 | 41.2 |
| Example 7 | A-7 | 6.68 | 515 | 41.3 |
| Example 8 | A-8 | 6.66 | 518 | 39.7 |
| Example 9 | A-9 | 6.48 | 518 | 38.9 |
| Example 10 | A-10 | 6.86 | 517 | 41.3 |
| Example 11 | A-11 | 6.77 | 515 | 41.3 |
| Example 12 | A-12 | 6.66 | 518 | 43.1 |
| Example 13 | A-13 | 6.65 | 518 | 43.5 |
| Example 14 | A-14 | 6.71 | 517 | 41.4 |
| Example 15 | A-15 | 6.65 | 518 | 42.2 |
| Example 16 | A-18 | 6.71 | 517 | 42 |
| Example 17 | A-19 | 6.72 | 515 | 41.6 |
| Example 18 | A-20 | 6.72 | 518 | 41.5 |
| Example 19 | A-21 | 6.73 | 518 | 41.4 |
| Example 20 | A-22 | 6.73 | 518 | 41.9 |
| Example 21 | A-23 | 6.73 | 517 | 41.6 |
| Example 22 | B-1 | 6.48 | 515 | 41.5 |
| Example 23 | B-2 | 6.86 | 518 | 39.2 |
| Example 24 | B-3 | 6.77 | 518 | 41.3 |
| Example 25 | B-4 | 6.66 | 517 | 39.7 |
| Example 26 | B-5 | 6.65 | 518 | 38.9 |
| Example 27 | B-6 | 6.65 | 517 | 41.3 |
| Example 28 | B-7 | 6.64 | 515 | 41.3 |
| Example 29 | B-8 | 6.64 | 518 | 41.3 |
| Example 30 | B-9 | 6.64 | 518 | 41.2 |
| Example 31 | B-10 | 6.63 | 518 | 41.2 |
| Example 32 | B-11 | 6.72 | 518 | 41.3 |
| Example 33 | B-12 | 6.73 | 517 | 41.3 |
| Example 34 | B-13 | 6.73 | 515 | 41.2 |
| Example 35 | B-14 | 6.73 | 518 | 41.3 |
| Example 36 | B-15 | 6.48 | 518 | 39.7 |
| Example 37 | B-18 | 6.86 | 517 | 38.9 |
| Example 38 | B-19 | 6.77 | 518 | 41.3 |
| Example 39 | B-20 | 6.66 | 517 | 41.3 |
| Example 40 | B-21 | 6.77 | 515 | 43.1 |
| Example 41 | B-22 | 6.66 | 518 | 43.5 |
| Example 42 | B-23 | 6.66 | 518 | 41.4 |
| Example 43 | C-1 | 6.81 | 517 | 42.2 |
| Example 44 | C-2 | 6.66 | 515 | 42 |
| Example 45 | C-3 | 6.81 | 518 | 39.7 |
| Example 46 | C-4 | 6.68 | 518 | 38.9 |
| Example 47 | C-5 | 6.66 | 518 | 41.3 |
| Example 48 | C-6 | 6.7 | 517 | 41.3 |
| Example 49 | C-7 | 6.7 | 515 | 43.1 |
| Example 50 | C-8 | 6.51 | 518 | 43.5 |
| Example 51 | C-9 | 6.77 | 518 | 41.4 |
| Example 52 | C-10 | 6.46 | 518 | 42.2 |
| Example 53 | C-11 | 6.81 | 517 | 42 |
| Example 54 | C-12 | 6.68 | 515 | 41.8 |
| Example 55 | C-13 | 6.66 | 518 | 41.3 |
| Example 56 | C-14 | 6.48 | 518 | 41.2 |
| Example 57 | C-15 | 6.86 | 517 | 41.2 |
| Example 58 | C-18 | 6.77 | 515 | 41.4 |
| Example 59 | C-19 | 6.66 | 518 | 42.2 |
| Example 60 | C-20 | 6.81 | 518 | 39.7 |
| Example 61 | C-21 | 6.68 | 518 | 38.9 |
| Example 62 | C-22 | 6.66 | 518 | 41.3 |
| Example 63 | C-23 | 6.7 | 517 | 41.3 |
| Example 64 | D-1 | 6.7 | 515 | 43.1 |
| Example 65 | D-2 | 6.51 | 518 | 43.5 |
| Example 66 | D-3 | 6.77 | 518 | 41.4 |
| Example 67 | D-4 | 6.46 | 518 | 42.2 |
| Example 68 | D-5 | 6.81 | 517 | 42 |
| Example 69 | D-6 | 6.68 | 515 | 41.8 |
| Example 70 | D-7 | 6.66 | 515 | 41.3 |
| Example 71 | D-8 | 6.48 | 518 | 41.2 |
| Example 72 | D-9 | 6.66 | 518 | 41.3 |
| Example 73 | D-10 | 6.81 | 517 | 39.7 |
| Example 74 | D-11 | 6.68 | 515 | 38.9 |
| Example 75 | D-12 | 6.66 | 517 | 41.3 |
| Example 76 | D-13 | 6.7 | 515 | 41.3 |
| Example 77 | D-14 | 6.7 | 518 | 43.1 |
| Example 78 | D-15 | 6.51 | 518 | 43.5 |
| Example 79 | D-18 | 6.77 | 517 | 41.4 |
| Example 80 | D-19 | 6.46 | 515 | 42.2 |
| Example 81 | D-20 | 6.81 | 515 | 42 |
| Example 82 | D-21 | 6.68 | 515 | 41.8 |
| Example 83 | D-22 | 6.66 | 518 | 41.3 |
| Example 84 | D-23 | 6.48 | 518 | 41.2 |
| Example 85 | E-1 | 6.86 | 517 | 41.2 |
| Example 86 | E-2 | 6.77 | 515 | 41.4 |
| Example 87 | E-3 | 6.66 | 518 | 42.2 |
| Example 88 | E-4 | 6.81 | 518 | 39.7 |
| Example 89 | E-5 | 6.7 | 515 | 43.1 |
| Example 90 | E-6 | 6.51 | 518 | 43.5 |
| Example 91 | E-7 | 6.77 | 518 | 41.4 |
| Example 92 | E-8 | 6.46 | 518 | 42.2 |
| Example 93 | E-9 | 6.81 | 517 | 42 |
| Example 94 | E-10 | 6.68 | 515 | 41.8 |
| Example 95 | E-11 | 6.66 | 518 | 41.3 |
| Example 96 | E-12 | 6.48 | 518 | 41.2 |
| Example 97 | E-13 | 6.86 | 517 | 41.3 |
| Example 98 | E-14 | 6.77 | 515 | 41.2 |
| Example 99 | E-15 | 6.66 | 517 | 41.3 |
| Example 100 | E-18 | 6.65 | 515 | 39.7 |
| Example 101 | E-19 | 6.71 | 518 | 38.9 |
| Example 102 | E-20 | 6.65 | 518 | 41.3 |
| Example 103 | E-21 | 6.71 | 517 | 41.3 |
| Example 104 | E-22 | 6.72 | 515 | 43.1 |
| Example 105 | E-23 | 6.72 | 515 | 43.5 |
| Example 106 | F-1 | 6.73 | 518 | 41.4 |
| Example 107 | F-2 | 6.73 | 518 | 42.2 |
| Example 108 | F-3 | 6.73 | 517 | 42 |
| Example 109 | F-4 | 6.48 | 515 | 41.5 |
| Example 110 | F-5 | 6.86 | 518 | 39.2 |
| Example 111 | F-6 | 6.77 | 518 | 41.3 |
| Example 112 | F-7 | 6.66 | 517 | 39.7 |
| Example 113 | F-8 | 6.65 | 518 | 38.9 |
| Example 114 | F-9 | 6.65 | 517 | 41.3 |
| Example 115 | F-10 | 6.64 | 515 | 41.3 |
| Example 116 | F-11 | 6.64 | 518 | 41.3 |
| Example 117 | F-12 | 6.64 | 518 | 41.2 |
| Example 118 | F-13 | 6.63 | 517 | 41.2 |
| Example 119 | F-14 | 6.72 | 515 | 41.3 |
| Example 120 | F-15 | 6.73 | 517 | 41.3 |
| Example 121 | F-18 | 6.73 | 515 | 41.3 |
| Example 122 | F-19 | 6.73 | 518 | 41.2 |
| Example 123 | F-20 | 6.48 | 518 | 41.2 |
| Example 124 | F-21 | 6.86 | 517 | 41.4 |
| Example 125 | F-22 | 6.77 | 515 | 42.2 |
| Example 126 | F-23 | 6.66 | 515 | 42 |
| Example 127 | G-1 | 6.77 | 515 | 41.8 |
| Example 128 | G-2 | 6.66 | 518 | 42 |
| Example 129 | G-3 | 6.66 | 518 | 42.5 |
| Example 130 | G-4 | 6.81 | 517 | 41.3 |
| Example 131 | G-5 | 6.66 | 515 | 41.3 |
| Example 132 | G-6 | 6.81 | 518 | 41.2 |
| Example 133 | G-7 | 6.68 | 518 | 41.3 |
| Example 134 | G-8 | 6.66 | 518 | 39.7 |
| Example 135 | G-9 | 6.7 | 517 | 38.9 |
| Example 136 | G-10 | 6.7 | 515 | 41.3 |
| Example 137 | G-11 | 6.51 | 518 | 41.3 |
| Example 138 | G-12 | 6.77 | 518 | 43.1 |
| Example 139 | G-13 | 6.46 | 517 | 43.5 |
| Example 140 | G-14 | 6.81 | 515 | 41.4 |
| Example 141 | G-15 | 6.68 | 517 | 42.2 |
| Example 142 | G-18 | 6.66 | 515 | 42 |
| Example 143 | G-19 | 6.48 | 518 | 41.2 |
| Example 144 | G-20 | 6.86 | 518 | 41.2 |
| Example 145 | G-21 | 6.77 | 517 | 41.4 |
| Example 146 | G-22 | 6.66 | 515 | 42.2 |
| Example 147 | G-23 | 6.81 | 515 | 39.7 |
| Example 148 | H-1 | 6.68 | 518 | 38.9 |
| Example 149 | H-2 | 6.66 | 518 | 41.3 |
| Example 150 | H-3 | 6.7 | 517 | 41.3 |
| Example 151 | H-4 | 6.7 | 515 | 43.1 |
| Example 152 | H-5 | 6.51 | 518 | 43.5 |
| Example 153 | H-6 | 6.77 | 518 | 41.4 |
| Example 154 | H-7 | 6.46 | 518 | 42.2 |

TABLE 1-continued

| Sample | Host | Driving voltage (V) | EL peak (nm) | Current efficiency (cd/A) |
|---|---|---|---|---|
| Example 155 | H-8 | 6.81 | 517 | 42 |
| Example 156 | H-9 | 6.68 | 515 | 41.8 |
| Example 157 | H-10 | 6.66 | 515 | 41.3 |
| Example 158 | H-11 | 6.48 | 518 | 41.2 |
| Example 159 | H-12 | 6.66 | 518 | 41.3 |
| Example 160 | H-13 | 6.81 | 517 | 39.7 |
| Example 161 | H-14 | 6.68 | 515 | 38.9 |
| Example 162 | H-15 | 6.66 | 517 | 41.3 |
| Example 163 | H-18 | 6.7 | 515 | 41.3 |
| Example 164 | H-19 | 6.7 | 518 | 43.1 |
| Example 165 | H-20 | 6.51 | 518 | 43.5 |
| Example 166 | H-21 | 6.77 | 517 | 41.4 |
| Example 167 | H-22 | 6.46 | 515 | 42.2 |
| Example 168 | H-23 | 6.81 | 515 | 42 |
| Example 169 | I-1 | 6.68 | 515 | 41.8 |
| Example 170 | I-2 | 6.66 | 518 | 41.3 |
| Example 171 | I-3 | 6.48 | 518 | 41.2 |
| Example 172 | I-4 | 6.86 | 517 | 41.2 |
| Example 173 | I-5 | 6.77 | 515 | 41.4 |
| Example 174 | I-6 | 6.66 | 518 | 42.2 |
| Example 175 | I-7 | 6.81 | 518 | 39.7 |
| Example 176 | I-8 | 6.7 | 515 | 43.1 |
| Example 177 | I-9 | 6.51 | 518 | 43.5 |
| Example 178 | I-10 | 6.77 | 518 | 41.4 |
| Example 179 | I-11 | 6.61 | 517 | 41.1 |
| Example 180 | I-12 | 6.51 | 515 | 42.5 |
| Example 181 | I-13 | 6.77 | 517 | 39.2 |
| Example 182 | I-14 | 6.66 | 515 | 41.3 |
| Example 183 | I-15 | 6.65 | 518 | 39.7 |
| Example 184 | I-18 | 6.65 | 518 | 41.1 |
| Example 185 | I-19 | 6.77 | 517 | 41.3 |
| Example 186 | I-20 | 6.65 | 515 | 39.7 |
| Example 187 | I-21 | 6.77 | 515 | 41.1 |
| Example 188 | I-22 | 6.66 | 515 | 42.5 |
| Example 189 | I-23 | 6.65 | 515 | 42.5 |
| Comparative Example 1 | CBP | 6.93 | 516 | 38.2 |

As shown in Table 1, it could be confirmed that the green organic EL elements of Examples 1 to 189 in which the compounds (A-1 to I-23) according to the present disclosure are used as a material for the light emitting layer exhibit better performance in terms of efficiency and driving voltage than the green organic EL element of Comparative Example 1 in the related art in which the CBP is used.

[Example 190] Manufacture of Red Organic EL Element

Compound A-16 synthesized in Synthesis Example 16 was subjected to highly pure sublimation purification by a typically known method, and then a red organic electroluminescent element was manufactured according to the following procedure.

First, a glass substrate thinly coated with indium tin oxide (ITO) to have a thickness of 1,500 Å was ultrasonically washed with distilled water. When the ultrasonic washing with distilled water was completed, the substrate was ultrasonically washed with a solvent such as isopropyl alcohol, acetone, and methanol, dried, transferred to a UV ozone cleaner (Power sonic 405, manufactured by Hwashin Tech), washed for 5 minutes by using UV, and then transferred to a vacuum evaporator.

An organic electroluminescent element was manufactured by laminating m-MTDATA (60 nm)/TCTA (80 nm)/90% Compound A-16+10% (piq)$_2$Ir(acac) (30 nm)/BCP (10 nm)/Alq$_3$ (30 nm)/LiF (1 nm)/Al (200 nm) in this order on the thus prepared ITO transparent electrode. The structures of m-MTDATA, TCTA, and BCP used are the same as described in Example 1, and the structure of (piq)$_2$Ir(acac) is as follows.

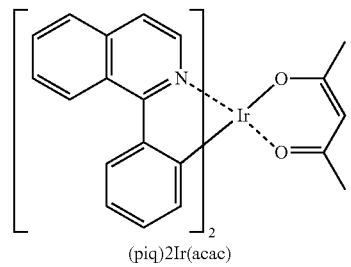

(piq)2Ir(acac)

[Example 191] to [Example 207] Manufacture of Red Organic EL Element

A red organic EL element was manufactured by the same procedure as in Example 190, except that when a light emitting layer is formed in Example 190, Compounds A-16 to I-17 each synthesized in Synthesis Examples 17 to 201 were used instead of Compound A-16 used as a light emitting host material (see Table 2).

Comparative Example 2

A red organic electroluminescent element was manufactured by the same procedure as in Example 190, except that when a light emitting layer is formed in Example 190, CBP was used instead of Compound A-16 used as a light emitting host material. The structure of CBP used is the same as described in Comparative Example 1.

Evaluation Example 2

For each of the organic electroluminescent elements manufactured in Examples 190 to 207 and Comparative Example 2, the driving voltage and current efficiency thereof were measured at a current density of 10 mA/cm$^2$, and the results are shown in the following Table 2.

TABLE 2

| Sample | Host | Driving voltage (V) | Current efficiency (cd/A) |
|---|---|---|---|
| Example 190 | A-16 | 4.76 | 10.1 |
| Example 191 | A-17 | 4.53 | 11.5 |
| Example 192 | B-16 | 4.65 | 11.8 |
| Example 193 | B-17 | 4.74 | 11.5 |
| Example 194 | C-16 | 4.87 | 11.8 |
| Example 195 | C-17 | 4.56 | 9.6 |
| Example 196 | D-16 | 4.64 | 9.7 |
| Example 197 | D-17 | 4.55 | 9.1 |
| Example 198 | E-16 | 4.68 | 9.2 |
| Example 199 | E-17 | 4.55 | 11.5 |
| Example 200 | F-16 | 4.32 | 11.8 |
| Example 201 | F-17 | 4.74 | 11.5 |
| Example 202 | G-16 | 4.87 | 11.8 |
| Example 203 | G-17 | 4.53 | 9.6 |
| Example 204 | H-16 | 4.65 | 9.7 |
| Example 205 | H-17 | 4.74 | 11.8 |
| Example 206 | I-16 | 4.87 | 9.6 |
| Example 207 | I-17 | 4.76 | 9.7 |
| Comparative Example 2 | CBP | 5.25 | 8.2 |

As shown in Table 2, it could be confirmed that the red organic EL elements of Examples 190 to 207 in which the compounds (A-16 to I-17) according to the present disclosure are used as a material for the light emitting layer exhibit better performance in terms of efficiency and driving voltage than the red organic electroluminescent element of Comparative Example 2 in the related art in which the CBP is used.

[Example 208] Manufacture of Green Organic EL Element

Compound L-1 synthesized in Synthesis Example 208 was subjected to highly pure sublimation purification by a typically known method, and then a green organic electroluminescent element was manufactured as follows.

A glass substrate thinly coated with indium tin oxide (ITO) to have a thickness of 1,500 Å was ultrasonically washed with distilled water. When the ultrasonic washing with distilled water was completed, the substrate was ultrasonically washed with a solvent such as isopropyl alcohol, acetone, and methanol, dried, transferred to a UV ozone cleaner (Power sonic 405, manufactured by Hwashin Tech), washed for 5 minutes by using UV, and then transferred to a vacuum evaporator.

An organic electroluminescent element was manufactured by laminating m-MTDATA (60 nm)/TCTA (80 nm)/Compound L-1 (40 nm)/CBP+10% Ir(ppy)$_3$ (30 nm)/BCP (10 nm)/Alq$_3$ (30 nm)/LiF (1 nm)/Al (200 nm) in this order on the thus prepared ITO transparent electrode.

[Example 209] to [Example 219] Manufacture of Green Organic EL Element

A green organic EL element was manufactured by the same procedure as in Example 208, except that when a light emitting layer is formed in Example 208, Compounds L-2 to O-3 each synthesized in Synthesis Examples 209 to 219 were used instead of Compound L-1 used as a light emitting auxiliary layer material.

Comparative Example 3

A green organic electroluminescent element was manufactured by the same procedure as in Example 208, except that Compound L-1 was not used as a light emitting auxiliary layer material in Example 208.

Evaluation Example 3

For each of the organic electroluminescent elements manufactured in Examples 208 to 219 and Comparative Example 3, the driving voltage and current efficiency thereof were measured at a current density of 10 mA/cm$^2$, and the results are shown in the following Table 3.

TABLE 3

| Sample | Light emitting auxiliary layer | Driving voltage (V) | Current efficiency (cd/A) |
|---|---|---|---|
| Example 208 | L-1 | 6.80 | 42.9 |
| Example 209 | L-2 | 6.85 | 42.6 |
| Example 210 | L-3 | 6.80 | 42.4 |
| Example 211 | M-1 | 6.80 | 42.0 |
| Example 212 | M-2 | 6.75 | 42.7 |
| Example 213 | M-3 | 6.90 | 42.7 |
| Example 214 | N-1 | 6.80 | 41.8 |
| Example 215 | N-2 | 6.80 | 42.5 |
| Example 216 | N-3 | 6.90 | 42.9 |
| Example 217 | O-1 | 6.85 | 41.9 |
| Example 218 | O-2 | 6.70 | 42.6 |
| Example 219 | O-3 | 6.85 | 42.9 |
| Comparative Example 2 | — | 6.93 | 38.2 |

As shown in Table 3, it could be seen that the green organic electroluminescent elements of Examples 208 to 219, in which the compounds (L-1 to O-3) represented by Chemical Formula 1 according to the present disclosure are used as a light emitting auxiliary layer material had a slightly lower driving voltage and a significantly improved light emitting efficiency than the green organic electroluminescent element of Comparative Example 3, in which the light emitting auxiliary layer material is not used.

[Example 220] Manufacture of Blue Organic EL Element

Compound A-9 synthesized in Synthesis Example 9 was subjected to highly pure sublimation purification by a typically known method, and then a blue organic electroluminescent element was manufactured as follows.

A glass substrate thinly coated with indium tin oxide (ITO) to have a thickness of 1,500 Å was ultrasonically washed with distilled water. When the ultrasonic washing with distilled water was completed, the substrate was ultrasonically washed with a solvent such as isopropyl alcohol, acetone, and methanol, dried, transferred to a UV ozone cleaner (Power sonic 405, manufactured by Hwashin Tech), washed for 5 minutes by using UV, and then transferred to a vacuum evaporator.

An organic electroluminescent element was manufactured by laminating DS-205 (80 nm)/NPB (15 nm)/AND+5% DS-405 (30 nm)/Compound A-9 (5 nm)/Alq$_3$ (25 nm)/LiF (1 nm)/Al (200 nm) in this order on the thus prepared ITO transparent electrode.

In this case, the structures of NPB, AND, and Alga used are as follows.

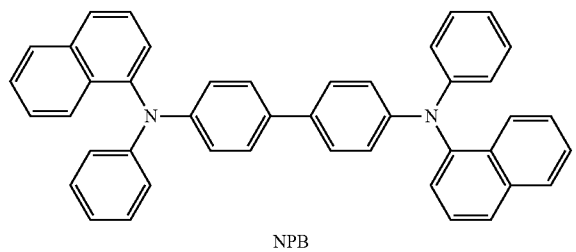

NPB

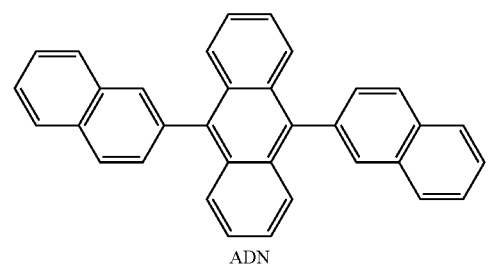

ADN

-continued

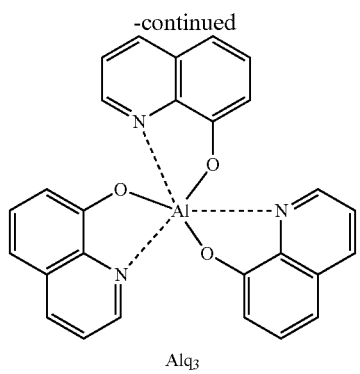

Alq3

[Example 221] to [Example 231] Manufacture of Blue Organic EL Element

A blue organic EL element was manufactured by the same procedure as in Example 220, except that each compound shown in Table 4 was used instead of Compound A-9 used as a lifetime enhancement layer material in Example 220.

[Example 232] Manufacture of Blue Organic EL Element

Compound A-3 synthesized in Synthesis Example 3 was subjected to highly pure sublimation purification by a typically known method, and then a blue organic electroluminescent element was manufactured as follows.

A glass substrate thinly coated with indium tin oxide (ITO) to have a thickness of 1,500 Å was ultrasonically washed with distilled water. When the ultrasonic washing with distilled water was completed, the substrate was ultrasonically washed with a solvent such as isopropyl alcohol, acetone, and methanol, dried, transferred to a UV ozone cleaner (Power sonic 405, manufactured by Hwashin Tech), washed for 5 minutes by using UV, and then transferred to a vacuum evaporator.

An organic electroluminescent element was manufactured by laminating DS-205 (80 nm)/NPB (15 nm)/AND+5% DS-405 (30 nm)/Compound A-3 (30 nm)/LiF (1 nm)/Al (200 nm) in this order on the thus prepared ITO transparent electrode.

[Example 233] to [Example 235] Manufacture of Blue Organic EL Element

A blue organic EL element was manufactured by the same procedure as in Example 232, except that each compound shown in Table 5 was used instead of Compound A-3 used as an electron transporting layer material in Example 232.

[Comparative Example 4] Manufacture of Blue Organic Electroluminescent Element

A blue organic electroluminescent element was manufactured by the same procedure as in Example 220, except that a lifetime enhancement layer was not included, and the electron transporting layer material Alq$_3$ was deposited to have a thickness of 30 nm instead of 25 nm.

[Comparative Example 5] Manufacture of Blue Organic Electroluminescent Element

An organic electroluminescent element was manufactured by the same procedure as in Example 1, except that BCP was used instead of using Compound A-9 used as a lifetime enhancement layer material in Example 220.

In this case, the structure of BCP used is as follows.

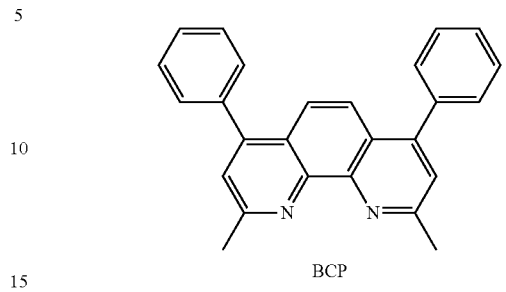

BCP

Evaluation Example 4

For each of the organic electroluminescent elements manufactured in Examples 220 to 235 and Comparative Examples 4 and 5, the driving voltage, current efficiency, light emitting peaks, and lifetime ($T_{97}$) thereof were measured at a current density of 10 mA/cm$^2$, and the results are shown in the following Tables 4 and 5.

TABLE 4

| Sample | Lifetime enhancement layer | Driving voltage (V) | Current efficiency (cd/A) | Light emitting peak (nm) | Lifetime (hr, $T_{97}$) |
|---|---|---|---|---|---|
| Example 220 | A-9 | 4.4 | 6.2 | 457 | 45 |
| Example 221 | A-10 | 4.1 | 6.3 | 458 | 62 |
| Example 222 | A-15 | 4.2 | 6.6 | 458 | 55 |
| Example 223 | B-10 | 4.5 | 6.2 | 458 | 75 |
| Example 224 | B-15 | 4.3 | 6.5 | 458 | 59 |
| Example 225 | F-9 | 4.3 | 6.1 | 458 | 78 |
| Example 226 | F-14 | 4.4 | 6.4 | 457 | 60 |
| Example 227 | H-9 | 4.1 | 6.2 | 458 | 64 |
| Example 228 | H-14 | 4.7 | 6.0 | 458 | 50 |
| Example 229 | K-6 | 4.7 | 6.4 | 457 | 85 |
| Example 230 | P-1 | 4.5 | 6.1 | 458 | 55 |
| Example 231 | P-5 | 4.2 | 6.0 | 458 | 75 |
| Comparative Example 4 | — | 4.7 | 5.6 | 458 | 32 |
| Comparative Example 5 | BCP | 5.3 | 5.9 | 458 | 28 |

TABLE 5

| Sample | Electron transporting layer | Driving voltage (V) | Current efficiency (cd/A) | Light emitting peak (nm) |
|---|---|---|---|---|
| Example 232 | A-3 | 4.5 | 6.3 | 458 |
| Example 233 | A-8 | 4.4 | 6.3 | 458 |
| Example 234 | A-21 | 4.3 | 6.1 | 458 |
| Example 235 | A-22 | 4.1 | 6.5 | 458 |
| Comparative Example 4 | — | 4.7 | 5.6 | 458 |

As can be seen from Table 4, the blue organic EL elements of Examples 220 to 231, in which Compounds A-9 to P-5 are used as a lifetime enhancement layer material, had a driving voltage which is similar to or slightly better than that of the blue organic EL element of Comparative Example 4 in which a lifetime enhancement layer was not used, but had the significantly improved current efficiency and lifetime.

Further, the blue organic EL elements of Examples 220 to 231 had better driving voltage and current efficiency than the blue organic EL element of Comparative Example 5, in which the CBP in the related art is used as a hole blocking layer material instead of the lifetime enhancement layer, and had the significantly improved lifetime.

As can be seen in Table 5, the blue organic EL elements of Examples 232 to 235, in which Compounds A-3 to A22 are used as an electron transporting layer material, had more improved driving voltage and current efficiency than the blue organic EL element of Comparative Example 4 in which Alga is used as an electron transporting layer material.

As described above, it could be confirmed that when the compound of Chemical Formula 1 according to the present disclosure is used as a lifetime enhancement layer material or an electron transporting layer material, the driving voltage and current efficiency are improved, and furthermore, lifetime characteristics may be significantly improved.

The invention claimed is:

1. A compound of the following Chemical Formula 1:

Chemical Formula 1

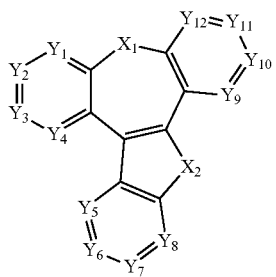

in Chemical Formula 1, $X_1$ and $X_2$ are the same as or different from each other, and are each independently selected from the group consisting of O, S, $N(Ar_1)$, $C(Ar_2)(Ar_3)$, and $Si(Ar_4)(Ar_5)$, wherein at least one of $X_1$ and $X_2$ is $N(Ar_1)$;

$Y_1$ to $Y_{12}$ are the same as or different from each other, and are each independently N or $C(R_1)$, wherein when $R_1$ is present in a plural number, these are the same as or different from each other;

$Ar_1$ to $Ar_5$ are the same as or different from each other, and are each independently selected from the group consisting of a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_6$ to $C_{60}$ arylphosphine group, a $C_6$ to $C_{60}$ arylphosphine oxide group, and a $C_6$ to $C_{60}$ arylamine group, or optionally combine with an adjacent group to form a fused ring, $R_1$ is selected from the group consisting of hydrogen, deuterium, halogen, a cyano group, a nitro group, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_6$ to $C_{60}$ arylphosphine group, a $C_6$ to $C_{60}$ arylphosphine oxide group, and a $C_6$ to $C_{60}$ arylamine group, or optionally combines with an adjacent group to form a fused ring, and the alkyl group, the cycloalkyl group, the heterocycloalkyl group, the aryl group, the heteroaryl group, the arylphosphine group, the arylphosphine oxide group, and the arylamine group of $Ar_1$ to $Ar_5$ and $R_1$ are optionally each independently unsubstituted or substituted with one or more substituents selected from the group consisting of deuterium, halogen, a cyano group, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_6$ to $C_{60}$ arylphosphine group, a $C_6$ to $C_{60}$ arylphosphine oxide group, and a $C_6$ to $C_{60}$ arylamine group, wherein the substituent optionally combines with an adjacent group to form a fused ring, provided that when the substituent is present in a plural number, these are optionally the same as or different from each other.

2. The compound of claim 1, wherein the compound of the Chemical Formula 1 is represented by any one of the following Chemical Formulae 2 to 10:

Chemical Formula 2

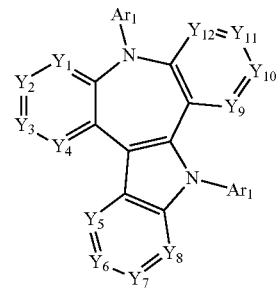

Chemical Formula 3

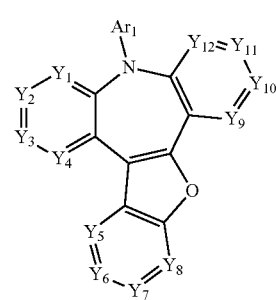

Chemical Formula 4

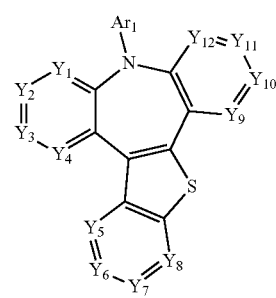

Chemical Formula 5

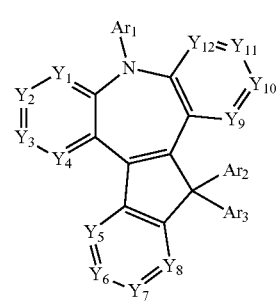

-continued

Chemical Formula 6

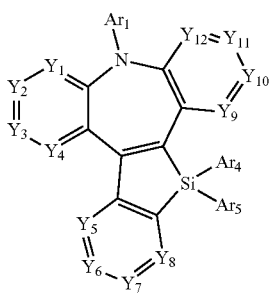

Chemical Formula 7

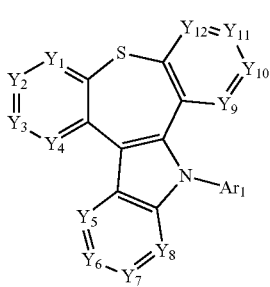

Chemical Formula 8

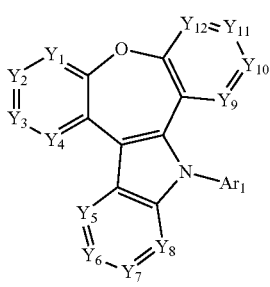

Chemical Formula 9

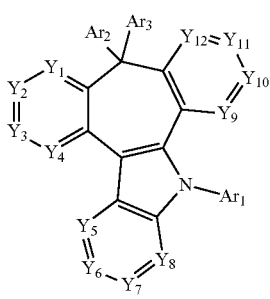

Chemical Formula 10

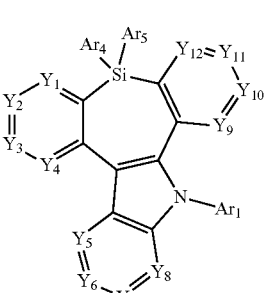

in Chemical Formulae 2 to 10, $Ar_1$ to $Ar_5$ and $Y_1$ to $Y_{12}$ are each the same as those defined in claim 1.

3. The compound of claim 1, wherein $X_1$ and $X_2$ are the same as or different from each other, and are each independently selected from the group consisting of O, S, and $N(Ar_1)$, and in this case, at least one of $X_1$ and $X_2$ is $N(Ar_1)$, and $Ar_1$ is the same as that defined in claim 1.

4. The compound of claim 1, wherein $Ar_1$ to $Ar_5$ and $R_1$ are the same as or different from each other, and are each independently selected from the group consisting of a $C_1$ to $C_{40}$ alkyl group, a $C_6$ to $C_{60}$ aryl group, and a heteroaryl group having 5 to 60 nuclear atoms, and the alkyl group, the aryl group, and the heteroaryl group of $Ar_1$ to $Ar_5$ and $R_1$ are optionally each independently unsubstituted or substituted with one or more substituents selected from the group consisting of deuterium, halogen, a cyano group, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_6$ to $C_{60}$ arylphosphine group, a $C_6$ to $C_{60}$ arylphosphine oxide group, and a $C_6$ to $C_{60}$ arylamine group, wherein the substituent optionally combines with an adjacent group to form a fused ring, provided that when the substituent is present in a plural number, these are optionally the same as or different from each other.

5. The compound of claim 1, wherein $Ar_1$ to $R_1$ are each independently a substituent of the following Chemical Formula 11, or a $C_6$ to $C_{60}$ aryl group, and the aryl group of $Ar_1$ and $R_1$ are optionally each independently unsubstituted or substituted with one or more substituents selected from the group consisting of deuterium, halogen, a cyano group, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_6$ to $C_{60}$ arylphosphine group, a $C_6$ to $C_{60}$ arylphosphine oxide group, and a $C_6$ to $C_{60}$ arylamine group, wherein the substituent optionally combines with an adjacent group to form a fused ring, provided that when the substituent is present in a plural number, these are optionally the same as or different from each other:

Chemical Formula 11

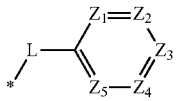

in Chemical Formula 11,

L is a single bond, or is selected from the group consisting of a $C_6$ to $C_{18}$ arylene group and a heteroarylene group having 5 to 18 nuclear atoms, $Z_1$ to $Z_5$ are the same as or different from each other, and are each independently N or $C(R_{11})$, provided that at least one of $Z_1$ to $Z_5$ is N, and in this case, when $C(R_{11})$ is present in a plural number, these are the same as or different from each other, and $R_{11}$ is selected from the group consisting of hydrogen, deuterium, halogen, a cyano group, a $C_1$ to $C_{40}$ alkyl group, a $C_6$ to $C_{40}$ aryl group, a heteroaryl group having 5 to 40 nuclear atoms, a $C_6$ to $C_{40}$ arylamine group, a $C_6$ to $C_{40}$ arylphosphine group, and a $C_6$ to $C_{40}$ arylphosphine oxide group, or optionally combines with an adjacent group to form a fused ring, wherein the alkyl group, the aryl group, the heteroaryl group, the arylamine group, the arylphosphine group, and the arylphospine oxide group of $R_{11}$ are optionally each independently unsubstituted or substituted with one or more substituents selected from the group consisting of deuterium, halogen, a cyano group, a $C_1$ to $C_{40}$ alkyl group, a $C_2$ to $C_{40}$ alkenyl group, a $C_2$ to $C_{40}$ alkynyl group, a $C_6$ to $C_{40}$ aryl group, a heteroaryl group having 5 to 40 nuclear atoms, a $C_6$ to $C_{40}$ arylamine group, a $C_3$ to $C_{40}$ cycloalkyl group, a heterocycloalkyl group having 3 to 40 nuclear atoms, a $C_6$ to $C_{40}$ arylphosphine group, and a $C_6$ to $C_{40}$ arylphosphine oxide group, wherein when the substituent is present in a plural number, these are optionally the same as or different from each other.

6. The compound of claim 1, wherein $Ar_1$ and $R_1$ are each independently a substituent represented by any one of the following Chemical Formulae A-1 to A-15:

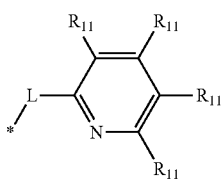
A-1

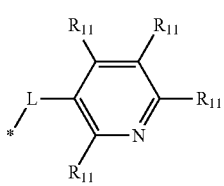
A-2

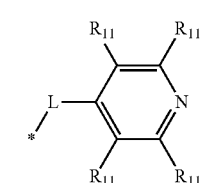
A-3

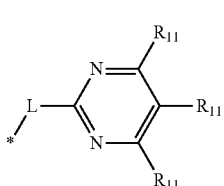
A-4

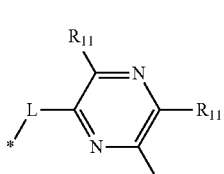
A-5

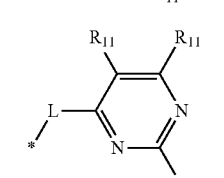
A-6

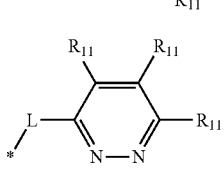
A-7

-continued

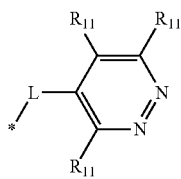
A-8

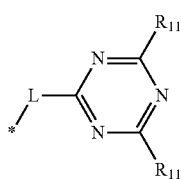
A-9

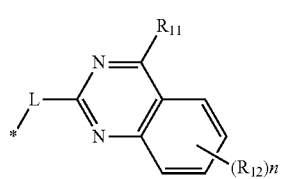
A-10

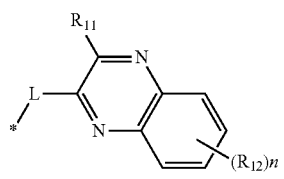
A-11

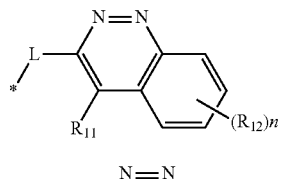
A-12

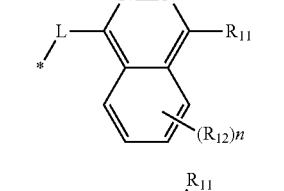
A-13

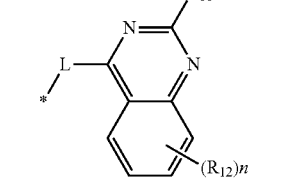
A-14

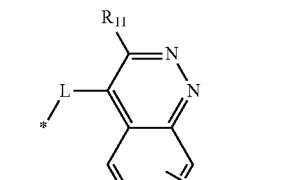
A-15 in Chemical Formulae A-1 to A-15,
L is a single bond, or is selected from the group consisting of a $C_6$ to $C_{18}$ arylene group and a heteroarylene group having 5 to 18 nuclear atoms,
a plurality of $R_{11}$ is the same as or different from each other, $R_{11}$ is selected from the group consisting of hydrogen, deuterium (D), halogen, a cyano group, a $C_1$ to $C_{40}$ alkyl group, a $C_6$ to $C_{40}$ aryl group, a heteroaryl group having 5 to 40 nuclear atoms, a $C_6$ to $C_{40}$ arylamine group, a $C_6$ to $C_{40}$ arylphosphine group, and a $C_6$ to $C_{40}$ arylphosphine oxide group, or optionally combines with an adjacent group to form a fused ring, a plurality of $R_{12}$ is the same as or different from each other, $R_{12}$ is selected from the group consisting of hydrogen, deuterium, halogen, a cyano group, a $C_1$ to $C_{40}$ alkyl group, a $C_6$ to $C_{40}$ aryl group, a heteroaryl group having 5 to 40 nuclear atoms, a $C_6$ to $C_{40}$ arylamine group, a $C_6$ to $C_{40}$ arylphosphine group, and a $C_6$ to $C_{40}$ arylphosphine oxide group, or optionally combines with an adjacent group to form a fused ring, and n is an integer of 1 to 4, wherein the alkyl group, the aryl group, the heteroaryl group, the arylamine group, the arylphosphine group, and the arylphospine oxide group of $R_{11}$ and $R_{12}$ are optionally each independently unsubstituted or substituted with one or more substituents selected from the group consisting of deuterium, halogen, a cyano group, a $C_1$ to $C_{40}$ alkyl group, a $C_2$ to $C_{40}$ alkenyl group, a $C_2$ to $C_{40}$ alkynyl group, a $C_6$ to $C_{40}$ aryl group, a heteroaryl group having 5 to 40 nuclear atoms, a $C_6$ to $C_{40}$ arylamine group, a $C_3$ to $C_{40}$ cycloalkyl group, a heterocycloalkyl group having 3 to 40 nuclear atoms, a $C_6$ to $C_{40}$ arylphosphine group, and a $C_6$ to $C_{40}$ arylphosphine oxide group, wherein when the substituent is present in a plural number, these are optionally the same as or different from each other.

7. An organic electroluminescent element comprising an anode, a cathode, and one or more organic material layers interposed between the anode and the cathode, wherein at least one of the organic material layers comprises the compound described in claim 1.

8. The organic electroluminescent element of claim 7, wherein the one or more organic material layers comprise a hole injection layer, a hole transporting layer, a light emitting layer, an electron transporting layer, and an electron injection layer, and the one or more organic material layers comprising the compound are a light emitting layer or an electron transporting layer.

9. The organic electroluminescent element of claim 7, wherein the one or more organic material layers comprise a hole injection layer, a hole transporting layer, a light emitting auxiliary layer, a light emitting layer, an electron transporting layer, and an electron injection layer, and the one or more organic material layers comprising the compound are a light emitting auxiliary layer.

10. The organic electroluminescent element of claim 7, wherein the one or more organic material layers comprise a hole injection layer, a hole transporting layer, a light emitting layer, a lifetime enhancement layer, an electron transporting layer, and an electron injection layer, and the one or more organic material layers comprising the compound are a lifetime enhancement layer.

11. The organic electroluminescent element of claim 7, wherein the compound of the Chemical Formula 1 is represented by any one of the following Chemical Formulae 2 to 10:

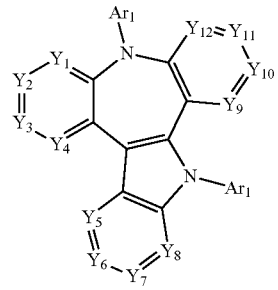

Chemical Formula 2

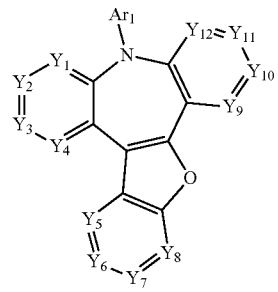

Chemical Formula 3

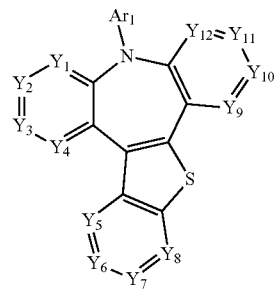

Chemical Formula 4

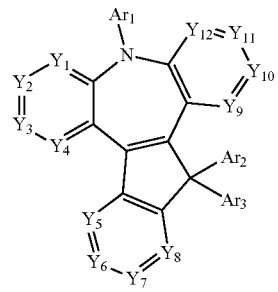

Chemical Formula 5

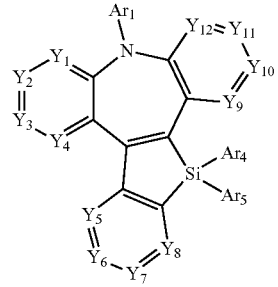

Chemical Formula 6

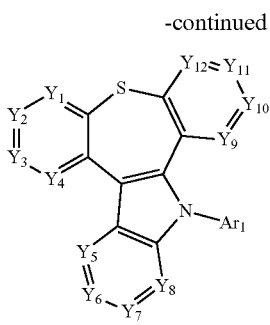

Chemical Formula 7

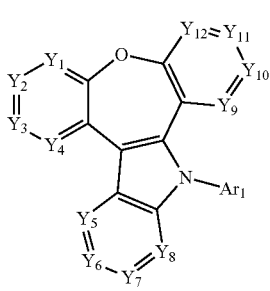

Chemical Formula 8

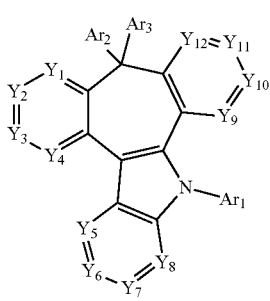

Chemical Formula 9

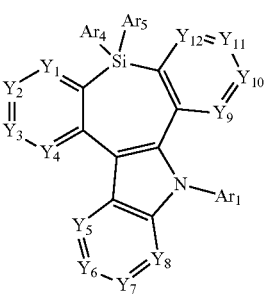

Chemical Formula 10 in Chemical Formulae 2 to 10,
$Ar_1$ to $Ar_5$ and $Y_1$ to $Y_{12}$ are each the same as those defined in claim 1.

12. The organic electroluminescent element of claim 7, wherein $X_1$ and $X_2$ are the same as or different from each other, and are each independently selected from the group consisting of O, S, and $N(Ar_1)$, and in this case, at least one of $X_1$ and $X_2$ is $N(Ar_1)$, and
$Ar_1$ is the same as that defined in claim 1.

13. The organic electroluminescent element of claim 7, wherein $Ar_1$ to $Ar_5$ and $R_1$ are the same as or different from each other, and are each independently selected from the group consisting of a $C_1$ to $C_{40}$ alkyl group, a $C_6$ to $C_{60}$ aryl group, and a heteroaryl group having 5 to 60 nuclear atoms, and
the alkyl group, the aryl group, and the heteroaryl group of $Ar_1$ to $Ar_5$ and $R_1$ are optionally each independently unsubstituted or substituted with one or more substituents selected from the group consisting of deuterium, halogen, a cyano group, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, $C_6$ to $C_{60}$ arylphosphine group, a $C_6$ to $C_{60}$ arylphosphine oxide group, and a $C_6$ to $C_{60}$ arylamine group, wherein the substituent optionally combines with an adjacent group to form a fused ring, provided that when the substituent is present in a plural number, these are optionally the same as or different from each other.

14. The organic electroluminescent element of claim 7, wherein $Ar_1$ to $R_1$ are each independently a substituent represented by the following Chemical Formula 11, or a $C_6$ to $C_{60}$ aryl group,
wherein the aryl group of $Ar_1$ and $R_1$ are optionally each independently unsubstituted or substituted with one or more substituents selected from the group consisting of deuterium, halogen, a cyano group, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_6$ to $C_{60}$ arylphosphine group, a $C_6$ to $C_{60}$ arylphosphine oxide group, and a $C_6$ to $C_{60}$ arylamine group, wherein the substituent optionally combines with an adjacent group to form a fused ring, provided that when the substituent is present in a plural number, these are optionally the same as or different from each other:

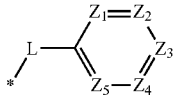

Chemical Formula 11 in Chemical Formula 11,
L is a single bond, or is selected from the group consisting of a $C_6$ to $C_{18}$ arylene group and a heteroarylene group having 5 to 18 nuclear atoms,
$Z_1$ to $Z_5$ are the same as or different from each other, and are each independently N or $C(R_{11})$, provided that at least one of $Z_1$ to $Z_5$ is N, and in this case, when $C(R_{11})$ is present in a plural number, these are the same as or different from each other, and
$R_{11}$ is selected from the group consisting of hydrogen, deuterium, halogen, a cyano group, a $C_1$ to $C_{40}$ alkyl group, a $C_6$ to $C_{40}$ aryl group, a heteroaryl group having 5 to 40 nuclear atoms, a $C_6$ to $C_{40}$ arylamine group, a $C_6$ to $C_{40}$ arylphosphine group, and a $C_6$ to $C_{40}$ arylphosphine oxide group, or optionally combines with an adjacent group to form a fused ring,
wherein the alkyl group, the aryl group, the heteroaryl group, the arylamine group, the arylphosphine group, and the arylphospine oxide group of $R_{11}$ are optionally each independently unsubstituted or substituted with one or more substituents selected from the group consisting of deuterium, halogen, a cyano group, a $C_1$ to $C_{40}$ alkyl group, a $C_2$ to $C_{40}$ alkenyl group, a $C_2$ to $C_{40}$ alkynyl group, a $C_6$ to $C_{40}$ aryl group, a heteroaryl group having 5 to 40 nuclear atoms, a $C_6$ to $C_{40}$ arylamine group, a $C_3$ to $C_{40}$ cycloalkyl group, a heterocycloalkyl group having 3 to 40 nuclear atoms, a $C_6$ to $C_{40}$ arylphosphine group, and a $C_6$ to $C_{40}$ arylphosphine oxide group, wherein when the substituent is present in a plural number, these are optionally the same as or different from each other.

15. The organic electroluminescent element of claim 7, wherein Ar$_1$ and R$_1$ are each independently a substituent represented by any one of the following Chemical Formulae A-1 to A-15:

A-1
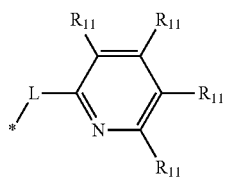

A-2
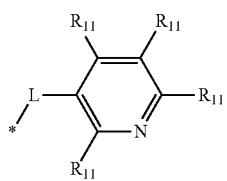

A-3
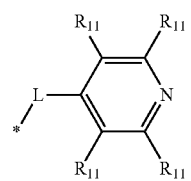

A-4
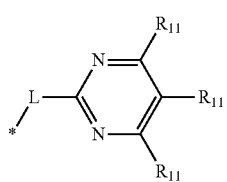

A-5
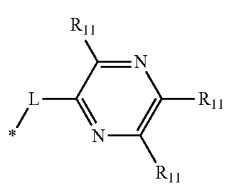

A-6
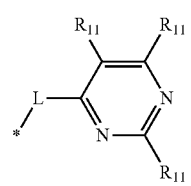

A-7
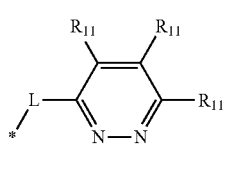

A-8
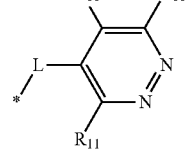

A-9
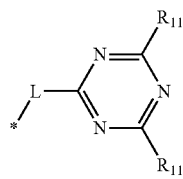

A-10
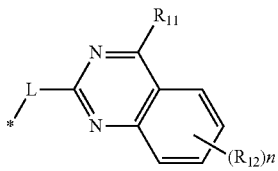

A-11
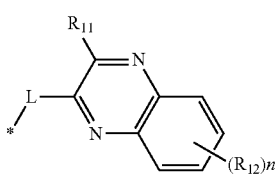

A-12
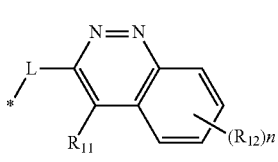

A-13
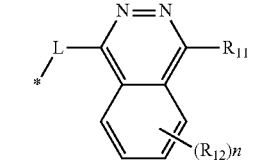

A-14
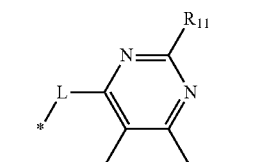

A-15
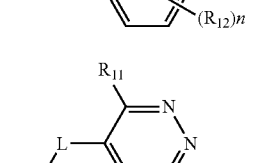

in Chemical Formulae A-1 to A-15,

L is a single bond, or is selected from the group consisting of a C$_6$ to C$_{18}$ arylene group and a heteroarylene group having 5 to 18 nuclear atoms, a plurality of R$_{11}$ is the same as or different from each other, R$_{11}$ is selected from the group consisting of hydrogen, deuterium, halogen, a cyano group, a C$_1$ to C$_{40}$ alkyl group, a C$_6$ to C$_{40}$ aryl group, a heteroaryl group having 5 to 40 nuclear atoms, a C$_6$ to C$_{40}$ arylamine group, a C$_6$ to C$_{40}$ arylphosphine group, and a C$_6$ to C$_{40}$ arylphosphine oxide group, or optionally combines with an adjacent group to form a fused ring, a plurality of $R_{12}$ is the same as or different from each other, $R_{12}$ is selected from the group consisting of hydrogen, deuterium, halogen, a cyano group, a $C_1$ to $C_{40}$ alkyl group, a $C_6$ to $C_{40}$ aryl group, a heteroaryl group having 5 to 40 nuclear atoms, a $C_6$ to $C_{40}$ arylamine group, a $C_6$ to $C_{40}$ arylphosphine group, and a $C_6$ to $C_{40}$ arylphosphine oxide group, or optionally combines with an adjacent group to form a fused ring, and n is an integer of 1 to 4, wherein the alkyl group, the aryl group, the heteroaryl group, the arylamine group, the arylphosphine group, and the arylphospine oxide group of $R_{11}$ and $R_{12}$ are optionally each independently unsubstituted or substituted with one or more substituents selected from the group consisting of deuterium (D), halogen, a cyano group, a $C_1$ to $C_{40}$ alkyl group, a $C_2$ to $C_{40}$ alkenyl group, a $C_2$ to $C_{40}$ alkynyl group, a $C_6$ to $C_{40}$ aryl group, a heteroaryl group having 5 to 40 nuclear atoms, a $C_6$ to $C_{40}$ arylamine group, a $C_3$ to $C_{40}$ cycloalkyl group, a heterocycloalkyl group having 3 to 40 nuclear atoms, a $C_6$ to $C_{40}$ arylphosphine group, and a $C_6$ to $C_{40}$ arylphosphine oxide group, wherein when the substituent is present in a plural number, these are optionally the same as or different from each other.

* * * * *